US009266892B2

(12) United States Patent
Zhuo et al.

(10) Patent No.: US 9,266,892 B2
(45) Date of Patent: Feb. 23, 2016

(54) FUSED PYRAZOLES AS FGFR INHIBITORS

(71) Applicants: Incyte Corporation, Wilmington, DE (US); Incyte Holdings Corporation, Wilmington, DE (US)

(72) Inventors: Jincong Zhuo, Garnet Valley, PA (US); Meizhong Xu, Hockessin, DE (US); Ding-Quan Qian, Newark, DE (US)

(73) Assignees: Incyte Holdings Corporation, Wilmington, DE (US); Incyte Corporation, Wilmington, DE (US)

( * ) Notice: Subject to any disclaimer, the term of this patent is extended or adjusted under 35 U.S.C. 154(b) by 0 days.

(21) Appl. No.: 14/132,653

(22) Filed: Dec. 18, 2013

(65) Prior Publication Data

US 2014/0171405 A1  Jun. 19, 2014

Related U.S. Application Data

(60) Provisional application No. 61/739,374, filed on Dec. 19, 2012.

(51) Int. Cl.
| | | |
|---|---|---|
| A61K 31/498 | (2006.01) | |
| C07D 487/04 | (2006.01) | |
| C07D 471/04 | (2006.01) | |
| A61K 31/519 | (2006.01) | |
| A61K 31/5025 | (2006.01) | |
| A61K 31/437 | (2006.01) | |

(52) U.S. Cl.
CPC ............ *C07D 487/04* (2013.01); *C07D 471/04* (2013.01); *A61K 31/437* (2013.01); *A61K 31/498* (2013.01); *A61K 31/5025* (2013.01); *A61K 31/519* (2013.01)

(58) Field of Classification Search
CPC . A61K 31/519; A61K 1/437; A61K 31/5025; A61K 31/49833; C07D 471/04; C07D 487/04
See application file for complete search history.

(56) References Cited

U.S. PATENT DOCUMENTS

| | | | |
|---|---|---|---|
| 850,370 A | 4/1907 | Hynes | |
| 3,894,021 A | 7/1975 | Denzel et al. | |
| 4,271,074 A | 6/1981 | Lohmann et al. | |
| 4,339,267 A | 7/1982 | Levitt | |
| 4,347,348 A | 8/1982 | Chernikhov et al. | |
| 4,402,878 A | 9/1983 | D'Alelio et al. | |
| 4,405,519 A | 9/1983 | D'Alelio et al. | |
| 4,405,520 A | 9/1983 | D'Alelio et al. | |
| 4,405,786 A | 9/1983 | D'Alelio et al. | |
| 4,460,773 A | 7/1984 | Suzuki et al. | |
| 4,874,803 A | 10/1989 | Baron et al. | |
| 4,940,705 A | 7/1990 | Boshagen et al. | |
| 5,159,054 A | 10/1992 | Keller | |
| 5,240,941 A | 8/1993 | Bruneau | |
| 5,480,887 A | 1/1996 | Hornback et al. | |
| 5,536,725 A | 7/1996 | Cullen et al. | |
| 5,541,324 A | 7/1996 | TenBrink et al. | |
| 5,783,577 A | 7/1998 | Houghten et al. | |
| 5,845,025 A | 12/1998 | Garito et al. | |
| 5,994,364 A | 11/1999 | Njoroge et al. | |
| 6,465,484 B1 | 10/2002 | Bilodeau et al. | |
| 6,998,408 B2 | 2/2006 | Pinto | |
| 7,074,801 B1 | 7/2006 | Yoshida et al. | |
| 7,125,880 B1 | 10/2006 | Chen | |
| 8,754,114 B2 * | 6/2014 | Yao ...................... | C07D 235/06 514/394 |
| 8,889,711 B2 * | 11/2014 | Bedjeguelal ......... | C07D 487/04 514/303 |
| 2003/0078255 A1 | 4/2003 | Pinto | |
| 2003/0078277 A1 | 4/2003 | Hibi et al. | |
| 2003/0181622 A1 | 9/2003 | Chiu et al. | |
| 2004/0044012 A1 | 3/2004 | Dobrusin et al. | |
| 2004/0067948 A1 | 4/2004 | Hallett | |
| 2004/0097493 A1 | 5/2004 | Chen et al. | |
| 2004/0122029 A1 | 6/2004 | Liu et al. | |
| 2004/0204427 A1 | 10/2004 | Chen et al. | |
| 2005/0070542 A1 | 3/2005 | Hodgetts et al. | |
| 2005/0148603 A1 | 7/2005 | Jimenez et al. | |
| 2005/0197340 A1 | 9/2005 | Arora et al. | |
| 2006/0222637 A1 | 10/2006 | Bamdad | |
| 2006/0270849 A1 | 11/2006 | Nishino et al. | |
| 2007/0116984 A1 | 5/2007 | Park et al. | |
| 2007/0197510 A1 | 8/2007 | Ohmoto et al. | |
| 2007/0280943 A1 | 12/2007 | Friedman et al. | |
| 2008/0249301 A1 | 10/2008 | Hornberger et al. | |
| 2009/0098086 A1 | 4/2009 | Zask et al. | |
| 2009/0099165 A1 | 4/2009 | Hurley et al. | |
| 2009/0099190 A1 | 4/2009 | Flynn et al. | |
| 2009/0105233 A1 | 4/2009 | Chua et al. | |
| 2009/0131467 A1 | 5/2009 | Kanazawa et al. | |
| 2009/0163545 A1 | 6/2009 | Goldfarb | |
| 2009/0246198 A1 | 10/2009 | Dong et al. | |

(Continued)

FOREIGN PATENT DOCUMENTS

| | | |
|---|---|---|
| CN | 101007778 | 8/2007 |
| CN | 102399220 | 4/2012 |
| CN | 102399233 | 4/2012 |
| CN | 103571502 | 2/2014 |
| CN | 103588771 | 2/2014 |
| CN | 104262330 | 1/2015 |
| DE | 2156720 | 5/1973 |
| DE | 2934578 | 3/1981 |
| DE | 3432983 | 4/1985 |
| DE | 280853 | 7/1990 |

(Continued)

OTHER PUBLICATIONS

M. Takeda et al., Clinical Cancer Research, 3051-3057 (2007).*
H. Huynh, 15 Expert Opinion Emerging Drugs, 13-26 (2010).*
Y. Wang, 3 Nature Medicine, 887-893 (1997).*
V. Knights et al., 125 Pharmacology & Therapeutics, 105-107 (2010).*

(Continued)

*Primary Examiner* — Alexander R Pagano
(74) *Attorney, Agent, or Firm* — Fish & Richardson P.C.

(57) ABSTRACT

The present invention relates to fused pyrazole derivatives, and pharmaceutical compositions including the same, that are inhibitors of one or more FGFR enzymes and are useful in the treatment of FGFR-associated diseases such as cancer.

40 Claims, No Drawings

(56) References Cited

U.S. PATENT DOCUMENTS

| | | |
|---|---|---|
| 2010/0032626 A1 | 2/2010 | Akino |
| 2010/0099684 A1 | 4/2010 | Cook, II et al. |
| 2010/0105661 A1 | 4/2010 | Shirakami et al. |
| 2010/0143547 A1 | 6/2010 | Kriegel et al. |
| 2010/0210636 A1 | 8/2010 | Ishikawa et al. |
| 2010/0239496 A1 | 9/2010 | Gangadharmath et al. |
| 2011/0045511 A1 | 2/2011 | Graus Porta et al. |
| 2011/0159604 A1 | 6/2011 | Fan et al. |
| 2011/0160203 A1 | 6/2011 | Liu et al. |
| 2011/0195968 A1 | 8/2011 | Greul et al. |
| 2011/0212077 A1 | 9/2011 | Noronha et al. |
| 2011/0224155 A1 | 9/2011 | Tachdjian et al. |
| 2011/0262525 A1 | 10/2011 | Wang et al. |
| 2011/0313003 A1 | 12/2011 | Shi et al. |
| 2012/0135997 A1 | 5/2012 | Kato et al. |
| 2012/0165305 A1 | 6/2012 | Yao et al. |
| 2012/0295881 A1 | 11/2012 | Lange et al. |
| 2012/0319095 A1 | 12/2012 | Tada et al. |
| 2013/0078731 A1 | 3/2013 | George et al. |
| 2013/0200356 A1 | 8/2013 | Jung et al. |
| 2013/0338134 A1 | 12/2013 | Wu et al. |
| 2014/0045814 A1 | 2/2014 | Lu et al. |
| 2014/0054564 A1 | 2/2014 | Kim et al. |
| 2014/0080892 A1 | 3/2014 | Bhanot et al. |
| 2014/0088100 A1 | 3/2014 | Bifulco, Jr. et al. |
| 2014/0103325 A1 | 4/2014 | Shin et al. |
| 2014/0117318 A1 | 5/2014 | Choi et al. |
| 2014/0148548 A1 | 5/2014 | Yamanaka et al. |
| 2014/0187559 A1 | 7/2014 | Miduturu |
| 2014/0243308 A1* | 8/2014 | Yao .................. C07D 235/06 514/210.18 |
| 2014/0315902 A1 | 10/2014 | Sun et al. |
| 2014/0374722 A1 | 12/2014 | Kim et al. |
| 2014/0378468 A1 | 12/2014 | Aichholz et al. |
| 2014/0378481 A1 | 12/2014 | Bifulco, Jr. et al. |
| 2014/0378483 A1 | 12/2014 | Benazet et al. |
| 2015/0011548 A1 | 1/2015 | Linnanen et al. |
| 2015/0011560 A1 | 1/2015 | Legeai-Mallet |
| 2015/0011579 A1 | 1/2015 | Clary-Ceccato et al. |

FOREIGN PATENT DOCUMENTS

| | | |
|---|---|---|
| DE | 3937633 | 5/1991 |
| DE | 4119767 | 12/1992 |
| DE | 19912638 | 9/2000 |
| EP | 0466452 | 1/1992 |
| EP | 0995751 | 4/2000 |
| EP | 1199070 | 4/2002 |
| EP | 1217000 | 6/2002 |
| EP | 1388541 | 2/2004 |
| FR | 2428654 | 1/1980 |
| FR | 2876582 | 4/2006 |
| FR | 2983196 | 5/2013 |
| FR | 2983199 | 5/2013 |
| FR | 2983200 | 5/2013 |
| JP | 62273979 | 11/1987 |
| JP | 63017882 | 1/1988 |
| JP | S6310630 | 1/1988 |
| JP | 02009895 | 1/1990 |
| JP | H0348656 | 3/1991 |
| JP | H03275669 | 12/1991 |
| JP | 04179576 | 6/1992 |
| JP | H04158084 | 6/1992 |
| JP | H04328121 | 11/1992 |
| JP | H05320173 | 12/1993 |
| JP | H05320515 | 12/1993 |
| JP | H09188812 | 7/1997 |
| JP | H1060426 | 3/1998 |
| JP | H11171865 | 6/1999 |
| JP | 2000123973 | 4/2000 |
| JP | 2001265031 | 9/2001 |
| JP | 2002-296731 | 10/2002 |
| JP | 2003-335788 | 11/2003 |
| JP | 2004-203749 | 7/2004 |
| JP | 2004-346145 | 12/2004 |
| JP | 2005-320288 | 11/2005 |
| JP | 2005-15395 | 8/2006 |
| JP | 2006-284843 | 10/2006 |
| JP | 2006-316054 | 11/2006 |
| JP | 2006-28027 | 8/2007 |
| JP | 2008-198769 | 8/2008 |
| JP | 2010-180147 | 8/2010 |
| JP | 2010-248429 | 11/2010 |
| JP | 2010-267847 | 11/2010 |
| JP | 2010-270245 | 12/2010 |
| JP | 2010-272618 | 12/2010 |
| JP | 2010-272727 | 12/2010 |
| JP | 2010-278114 | 12/2010 |
| JP | 2011-9348 | 1/2011 |
| JP | 2011-44637 | 3/2011 |
| JP | 2011-116840 | 6/2011 |
| JP | 2011-222650 | 11/2011 |
| JP | 2012-116825 | 6/2012 |
| JP | 2012-136476 | 7/2012 |
| JP | 5120580 | 1/2013 |
| JP | 2013-49251 | 3/2013 |
| JP | 2013-179181 | 9/2013 |
| KR | 20080045536 | 5/2008 |
| KR | 20110023190 | 3/2011 |
| KR | 20110043270 | 4/2011 |
| KR | 20120052034 | 5/2012 |
| KR | 20120078303 | 7/2012 |
| KR | 20130043460 | 4/2013 |
| KR | 20140090411 | 7/2014 |
| KR | 2014009105 | 8/2014 |
| WO | WO8803025 | 5/1988 |
| WO | WO9109835 | 7/1991 |
| WO | WO9110172 | 7/1991 |
| WO | WO9206078 | 4/1992 |
| WO | WO9222552 | 12/1992 |
| WO | WO9324488 | 12/1993 |
| WO | WO9413669 | 6/1994 |
| WO | WO9415995 | 7/1994 |
| WO | WO9425438 | 11/1994 |
| WO | WO9520965 | 8/1995 |
| WO | WO9615128 | 5/1996 |
| WO | WO9640707 | 12/1996 |
| WO | WO9747601 | 12/1997 |
| WO | WO9805661 | 2/1998 |
| WO | WO9806703 | 2/1998 |
| WO | WO9811438 | 3/1998 |
| WO | WO9818781 | 5/1998 |
| WO | WO9828281 | 7/1998 |
| WO | WO9833798 | 8/1998 |
| WO | WO9846609 | 10/1998 |
| WO | WO9854156 | 12/1998 |
| WO | WO9906422 | 2/1999 |
| WO | WO9907732 | 2/1999 |
| WO | WO9909030 | 2/1999 |
| WO | WO9942442 | 8/1999 |
| WO | WO9959975 | 11/1999 |
| WO | WO 99/61444 | 12/1999 |
| WO | WO9961444 | 12/1999 |
| WO | WO9964400 | 12/1999 |
| WO | WO0024744 | 5/2000 |
| WO | WO0068186 | 11/2000 |
| WO | WO0102369 | 1/2001 |
| WO | WO0122938 | 4/2001 |
| WO | WO0123386 | 4/2001 |
| WO | WO0129041 | 4/2001 |
| WO | WO0129042 | 4/2001 |
| WO | WO 01/42247 | 6/2001 |
| WO | WO0142247 | 6/2001 |
| WO | WO0153273 | 7/2001 |
| WO | WO0155148 | 8/2001 |
| WO | WO0157037 | 8/2001 |
| WO | WO0157038 | 8/2001 |
| WO | WO0158899 | 8/2001 |
| WO | WO0166099 | 9/2001 |
| WO | WO0168647 | 9/2001 |
| WO | WO 01/85722 | 11/2001 |
| WO | WO0183472 | 11/2001 |
| WO | WO0200655 | 1/2002 |

(56) References Cited

FOREIGN PATENT DOCUMENTS

| | | |
|---|---|---|
| WO | WO0212442 | 2/2002 |
| WO | WO0214315 | 2/2002 |
| WO | WO0220011 | 3/2002 |
| WO | WO02055082 | 7/2002 |
| WO | WO02066481 | 8/2002 |
| WO | WO02074754 | 9/2002 |
| WO | WO02076953 | 10/2002 |
| WO | WO02088095 | 11/2002 |
| WO | WO02094825 | 11/2002 |
| WO | WO 02/096873 | 12/2002 |
| WO | WO02102793 | 12/2002 |
| WO | WO03000187 | 1/2003 |
| WO | WO03000688 | 1/2003 |
| WO | WO03000690 | 1/2003 |
| WO | WO03009852 | 2/2003 |
| WO | WO03014083 | 2/2003 |
| WO | WO03037891 | 5/2003 |
| WO | WO03040131 | 5/2003 |
| WO | WO03049542 | 6/2003 |
| WO | WO03062236 | 7/2003 |
| WO | WO03075836 | 9/2003 |
| WO | WO03082871 | 10/2003 |
| WO | WO03097609 | 11/2003 |
| WO | WO 03/099818 | 12/2003 |
| WO | WO03099818 | 12/2003 |
| WO | WO03101985 | 12/2003 |
| WO | WO2004002986 | 1/2004 |
| WO | WO2004011465 | 2/2004 |
| WO | WO2004014382 | 2/2004 |
| WO | WO2004014907 | 2/2004 |
| WO | WO2004018472 | 3/2004 |
| WO | WO2004020441 | 3/2004 |
| WO | WO2004041821 | 5/2004 |
| WO | WO2004041822 | 5/2004 |
| WO | WO2004041823 | 5/2004 |
| WO | WO2004043367 | 5/2004 |
| WO | WO2004048343 | 6/2004 |
| WO | WO2004052291 | 6/2004 |
| WO | WO2004052862 | 6/2004 |
| WO | WO2004056822 | 7/2004 |
| WO | WO2004056830 | 7/2004 |
| WO | WO2004065378 | 8/2004 |
| WO | WO 2004/083177 | 9/2004 |
| WO | WO2004087053 | 10/2004 |
| WO | WO2004089955 | 10/2004 |
| WO | WO2004094420 | 11/2004 |
| WO | WO2004099209 | 11/2004 |
| WO | WO2004108139 | 11/2004 |
| WO | WO2004110487 | 12/2004 |
| WO | WO2004112793 | 12/2004 |
| WO | WO2004113307 | 12/2004 |
| WO | WO2005007653 | 1/2005 |
| WO | WO2005011597 | 2/2005 |
| WO | WO 2004/112793 | 3/2005 |
| WO | WO2005021533 | 3/2005 |
| WO | WO2005028434 | 3/2005 |
| WO | WO2005028478 | 3/2005 |
| WO | WO2005028480 | 3/2005 |
| WO | WO2005040119 | 5/2005 |
| WO | WO2005047289 | 5/2005 |
| WO | WO2005056524 | 6/2005 |
| WO | WO2005063768 | 6/2005 |
| WO | WO2005066162 | 7/2005 |
| WO | WO2005070430 | 8/2005 |
| WO | WO2005070929 | 8/2005 |
| WO | WO2005072412 | 8/2005 |
| WO | WO2005073232 | 8/2005 |
| WO | WO2005080393 | 9/2005 |
| WO | WO2005082903 | 9/2005 |
| WO | WO2005085210 | 9/2005 |
| WO | WO2005085248 | 9/2005 |
| WO | WO2005085249 | 9/2005 |
| WO | WO2005087765 | 9/2005 |
| WO | WO2005092901 | 10/2005 |
| WO | WO2005113536 | 12/2005 |
| WO | WO2005116035 | 12/2005 |
| WO | WO2005121130 | 12/2005 |
| WO | WO2005121142 | 12/2005 |
| WO | WO 2006/000420 | 1/2006 |
| WO | WO 2006/024834 | 3/2006 |
| WO | WO 2006/030031 | 3/2006 |
| WO | WO2006024486 | 3/2006 |
| WO | WO2006024487 | 3/2006 |
| WO | WO2006024834 | 3/2006 |
| WO | WO2006028289 | 3/2006 |
| WO | WO2006030031 | 3/2006 |
| WO | WO2006038112 | 4/2006 |
| WO | WO 2006/050162 | 5/2006 |
| WO | WO 2006/052712 | 5/2006 |
| WO | WO2006050076 | 5/2006 |
| WO | WO2006052712 | 5/2006 |
| WO | WO2006055752 | 5/2006 |
| WO | WO 2006/024524 | 6/2006 |
| WO | WO2006058120 | 6/2006 |
| WO | WO2006062465 | 6/2006 |
| WO | WO2006065703 | 6/2006 |
| WO | WO2006074293 | 7/2006 |
| WO | WO2006087230 | 8/2006 |
| WO | WO2006092691 | 9/2006 |
| WO | WO2006102588 | 9/2006 |
| WO | WO2006102610 | 9/2006 |
| WO | WO2006105448 | 10/2006 |
| WO | WO2006107644 | 10/2006 |
| WO | WO2006112666 | 10/2006 |
| WO | WO 2006/124731 | 11/2006 |
| WO | WO2006119504 | 11/2006 |
| WO | WO2006124462 | 11/2006 |
| WO | WO2006124731 | 11/2006 |
| WO | WO2006135821 | 12/2006 |
| WO | WO2006136442 | 12/2006 |
| WO | WO2007013964 | 2/2007 |
| WO | WO2007017096 | 2/2007 |
| WO | WO2007021795 | 2/2007 |
| WO | WO2007022268 | 2/2007 |
| WO | WO 2007/030366 | 3/2007 |
| WO | WO2007023105 | 3/2007 |
| WO | WO2007025949 | 3/2007 |
| WO | WO2007032466 | 3/2007 |
| WO | WO2007033780 | 3/2007 |
| WO | WO2007038209 | 4/2007 |
| WO | WO2007044698 | 4/2007 |
| WO | WO2007044729 | 4/2007 |
| WO | WO2007048802 | 5/2007 |
| WO | WO2007053135 | 5/2007 |
| WO | WO2007053452 | 5/2007 |
| WO | WO2007053498 | 5/2007 |
| WO | WO2007055418 | 5/2007 |
| WO | WO2007056023 | 5/2007 |
| WO | WO2007056075 | 5/2007 |
| WO | WO2007056170 | 5/2007 |
| WO | WO2007058392 | 5/2007 |
| WO | WO2007058626 | 5/2007 |
| WO | WO2007059108 | 5/2007 |
| WO | WO2007061554 | 5/2007 |
| WO | WO2007064883 | 6/2007 |
| WO | WO2007064931 | 6/2007 |
| WO | WO2007066189 | 6/2007 |
| WO | WO2007067444 | 6/2007 |
| WO | WO2007071752 | 6/2007 |
| WO | WO2007084314 | 7/2007 |
| WO | WO 2007/088999 | 8/2007 |
| WO | WO2007092879 | 8/2007 |
| WO | WO2007093901 | 8/2007 |
| WO | WO2007109334 | 9/2007 |
| WO | WO2007110868 | 10/2007 |
| WO | WO2007112347 | 10/2007 |
| WO | WO2007120097 | 10/2007 |
| WO | WO2007120339 | 10/2007 |
| WO | WO 2007/125405 | 11/2007 |
| WO | WO 2007/134259 | 11/2007 |
| WO | WO 2007/136465 | 11/2007 |
| WO | WO2007125351 | 11/2007 |
| WO | WO2007126841 | 11/2007 |
| WO | WO2007134259 | 11/2007 |

(56) References Cited

FOREIGN PATENT DOCUMENTS

| | | |
|---|---|---|
| WO | WO2007136465 | 11/2007 |
| WO | WO 2007/147217 | 12/2007 |
| WO | WO2007140957 | 12/2007 |
| WO | WO2007143600 | 12/2007 |
| WO | WO2007147217 | 12/2007 |
| WO | WO2008001070 | 1/2008 |
| WO | WO2008003766 | 1/2008 |
| WO | WO2008005877 | 1/2008 |
| WO | WO2008008234 | 1/2008 |
| WO | WO2008008747 | 1/2008 |
| WO | WO2008012635 | 1/2008 |
| WO | WO2008021389 | 2/2008 |
| WO | WO2008021851 | 2/2008 |
| WO | WO 2008/033999 | 3/2008 |
| WO | WO2008025556 | 3/2008 |
| WO | WO2008033858 | 3/2008 |
| WO | WO2008033999 | 3/2008 |
| WO | WO2008034859 | 3/2008 |
| WO | WO2008034860 | 3/2008 |
| WO | WO2008042639 | 4/2008 |
| WO | WO 2008/060907 | 5/2008 |
| WO | WO2008052898 | 5/2008 |
| WO | WO2008052934 | 5/2008 |
| WO | WO2008060907 | 5/2008 |
| WO | WO2008063583 | 5/2008 |
| WO | WO2008063609 | 5/2008 |
| WO | WO 2008/074068 | 6/2008 |
| WO | WO2008071455 | 6/2008 |
| WO | WO2008074068 | 6/2008 |
| WO | WO2008075068 | 6/2008 |
| WO | WO2008076278 | 6/2008 |
| WO | WO 2008/078091 | 7/2008 |
| WO | WO 2008/078100 | 7/2008 |
| WO | WO2008078091 | 7/2008 |
| WO | WO2008078100 | 7/2008 |
| WO | WO2008079460 | 7/2008 |
| WO | WO2008079933 | 7/2008 |
| WO | WO2008085942 | 7/2008 |
| WO | WO2008089105 | 7/2008 |
| WO | WO2008099075 | 8/2008 |
| WO | WO 2008/109181 | 9/2008 |
| WO | WO2008107436 | 9/2008 |
| WO | WO2008107544 | 9/2008 |
| WO | WO2008109943 | 9/2008 |
| WO | WO2008115974 | 9/2008 |
| WO | WO2008117269 | 10/2008 |
| WO | WO2008118454 | 10/2008 |
| WO | WO2008123755 | 10/2008 |
| WO | WO2008128141 | 10/2008 |
| WO | WO2008130584 | 10/2008 |
| WO | WO2008131972 | 11/2008 |
| WO | WO2008141065 | 11/2008 |
| WO | WO2008142720 | 11/2008 |
| WO | WO2008144253 | 11/2008 |
| WO | WO2008151184 | 12/2008 |
| WO | WO2008153207 | 12/2008 |
| WO | WO2008153852 | 12/2008 |
| WO | WO2008154221 | 12/2008 |
| WO | WO 2009/013335 | 1/2009 |
| WO | WO2009013335 | 1/2009 |
| WO | WO2009013354 | 1/2009 |
| WO | WO2009097446 | 1/2009 |
| WO | WO2009016253 | 2/2009 |
| WO | WO2009019518 | 2/2009 |
| WO | WO2009021083 | 2/2009 |
| WO | WO 2009/030871 | 3/2009 |
| WO | WO 2009/032861 | 3/2009 |
| WO | WO 2009/036012 | 3/2009 |
| WO | WO2009029625 | 3/2009 |
| WO | WO 2009/044788 | 4/2009 |
| WO | WO 2009/046606 | 4/2009 |
| WO | WO 2009/047255 | 4/2009 |
| WO | WO 2009/047993 | 4/2009 |
| WO | WO 2009/049018 | 4/2009 |
| WO | WO 2009/053737 | 4/2009 |
| WO | WO 2009/055828 | 4/2009 |
| WO | WO2009047506 | 4/2009 |
| WO | WO2009047522 | 4/2009 |
| WO | WO2009056886 | 5/2009 |
| WO | WO 2009/071535 | 6/2009 |
| WO | WO 2009/073153 | 6/2009 |
| WO | WO 2009/086509 | 7/2009 |
| WO | WO 2009/087238 | 7/2009 |
| WO | WO 2009/092764 | 7/2009 |
| WO | WO 2009/093209 | 7/2009 |
| WO | WO 2009/093210 | 7/2009 |
| WO | WO 2009/094528 | 7/2009 |
| WO | WO2009086130 | 7/2009 |
| WO | WO2009099982 | 8/2009 |
| WO | WO2009103652 | 8/2009 |
| WO | WO2009105717 | 8/2009 |
| WO | WO 2009/044788 | 9/2009 |
| WO | WO2009108332 | 9/2009 |
| WO | WO2009108827 | 9/2009 |
| WO | WO2009112826 | 9/2009 |
| WO | WO2009114870 | 9/2009 |
| WO | WO2009114874 | 9/2009 |
| WO | WO2009122180 | 10/2009 |
| WO | WO2009123967 | 10/2009 |
| WO | WO2009125808 | 10/2009 |
| WO | WO2009125809 | 10/2009 |
| WO | WO2009126584 | 10/2009 |
| WO | WO2009128520 | 10/2009 |
| WO | WO2009131687 | 10/2009 |
| WO | WO2009131926 | 10/2009 |
| WO | WO2009132980 | 11/2009 |
| WO | WO2009133127 | 11/2009 |
| WO | WO2009141386 | 11/2009 |
| WO | WO2009144205 | 12/2009 |
| WO | WO2009144302 | 12/2009 |
| WO | WO2009146034 | 12/2009 |
| WO | WO2009150150 | 12/2009 |
| WO | WO2009150240 | 12/2009 |
| WO | WO2009151997 | 12/2009 |
| WO | WO2009153592 | 12/2009 |
| WO | WO2009157423 | 12/2009 |
| WO | WO2010006947 | 1/2010 |
| WO | WO2010007099 | 1/2010 |
| WO | WO2010007116 | 1/2010 |
| WO | WO2010009155 | 1/2010 |
| WO | WO2010009195 | 1/2010 |
| WO | WO2010009207 | 1/2010 |
| WO | WO2010015643 | 2/2010 |
| WO | WO2010017047 | 2/2010 |
| WO | WO2010019210 | 2/2010 |
| WO | WO2010019899 | 2/2010 |
| WO | WO2010030027 | 3/2010 |
| WO | WO 2010/038081 | 4/2010 |
| WO | WO2010045371 | 4/2010 |
| WO | WO2010049731 | 5/2010 |
| WO | WO2010051043 | 5/2010 |
| WO | WO2010052448 | 5/2010 |
| WO | WO2010059552 | 5/2010 |
| WO | WO2010059658 | 5/2010 |
| WO | WO2010064621 | 6/2010 |
| WO | WO2010064875 | 6/2010 |
| WO | WO2010067886 | 6/2010 |
| WO | WO2010067888 | 6/2010 |
| WO | WO 2010/077680 | 7/2010 |
| WO | WO 2010/083145 | 7/2010 |
| WO | WO2010077647 | 7/2010 |
| WO | WO2010078421 | 7/2010 |
| WO | WO2010078427 | 7/2010 |
| WO | WO2010080503 | 7/2010 |
| WO | WO2010080712 | 7/2010 |
| WO | WO2010083145 | 7/2010 |
| WO | WO2010083283 | 7/2010 |
| WO | WO 2010/086089 | 8/2010 |
| WO | WO2010086089 | 8/2010 |
| WO | WO2010092181 | 8/2010 |
| WO | WO2010001033 | 9/2010 |
| WO | WO2010099938 | 9/2010 |
| WO | WO2010104047 | 9/2010 |
| WO | WO2010107765 | 9/2010 |

(56) References Cited

FOREIGN PATENT DOCUMENTS

| | | |
|---|---|---|
| WO | WO2010107768 | 9/2010 |
| WO | WO2010111303 | 9/2010 |
| WO | WO2010111573 | 9/2010 |
| WO | WO2010115279 | 10/2010 |
| WO | WO2010117323 | 10/2010 |
| WO | WO2010117425 | 10/2010 |
| WO | WO2010119284 | 10/2010 |
| WO | WO2010119285 | 10/2010 |
| WO | WO 2010/117323 | 11/2010 |
| WO | WO 2010/126960 | 11/2010 |
| WO | WO 2010/127212 | 11/2010 |
| WO | WO2010125216 | 11/2010 |
| WO | WO2010126960 | 11/2010 |
| WO | WO2010127212 | 11/2010 |
| WO | WO2010129509 | 11/2010 |
| WO | WO 2010/151689 | 12/2010 |
| WO | WO2010136031 | 12/2010 |
| WO | WO2010142801 | 12/2010 |
| WO | WO2011002038 | 1/2011 |
| WO | WO2011007819 | 1/2011 |
| WO | WO2011011597 | 1/2011 |
| WO | WO2011012816 | 2/2011 |
| WO | WO2011014535 | 2/2011 |
| WO | WO2011015037 | 2/2011 |
| WO | WO2011016472 | 2/2011 |
| WO | WO2011016528 | 2/2011 |
| WO | WO2011018894 | 2/2011 |
| WO | WO2011022439 | 2/2011 |
| WO | WO2011026579 | 3/2011 |
| WO | WO2011028947 | 3/2011 |
| WO | WO2011031740 | 3/2011 |
| WO | WO2011032050 | 3/2011 |
| WO | WO2011039344 | 4/2011 |
| WO | WO2011041143 | 4/2011 |
| WO | WO2011042389 | 4/2011 |
| WO | WO2011042474 | 4/2011 |
| WO | WO2011045344 | 4/2011 |
| WO | WO2011049825 | 4/2011 |
| WO | WO2011049988 | 4/2011 |
| WO | WO2011050245 | 4/2011 |
| WO | WO2011051425 | 5/2011 |
| WO | WO2011054843 | 5/2011 |
| WO | WO2011055911 | 5/2011 |
| WO | WO2011057022 | 5/2011 |
| WO | WO2011060295 | 5/2011 |
| WO | WO2011062253 | 5/2011 |
| WO | WO2011062885 | 5/2011 |
| WO | WO2011063159 | 5/2011 |
| WO | WO2011068899 | 6/2011 |
| WO | WO2011071821 | 6/2011 |
| WO | WO2011075515 | 6/2011 |
| WO | WO2011075620 | 6/2011 |
| WO | WO2011077043 | 6/2011 |
| WO | WO2011077044 | 6/2011 |
| WO | WO2011079231 | 6/2011 |
| WO | WO 2011/080755 | 7/2011 |
| WO | WO2011082234 | 7/2011 |
| WO | WO2011082266 | 7/2011 |
| WO | WO2011082267 | 7/2011 |
| WO | WO2011082488 | 7/2011 |
| WO | WO2011087776 | 7/2011 |
| WO | WO2011090666 | 7/2011 |
| WO | WO2011090738 | 7/2011 |
| WO | WO2011090760 | 7/2011 |
| WO | WO 2011/093672 | 8/2011 |
| WO | WO 2011/103557 | 8/2011 |
| WO | WO2011093672 | 8/2011 |
| WO | WO2011094890 | 8/2011 |
| WO | WO2011097717 | 8/2011 |
| WO | WO2011101806 | 8/2011 |
| WO | WO2011102441 | 8/2011 |
| WO | WO2011103196 | 8/2011 |
| WO | WO2011103441 | 8/2011 |
| WO | WO2011103460 | 8/2011 |
| WO | WO2011103557 | 8/2011 |
| WO | WO 2011/112687 | 9/2011 |
| WO | WO2011105161 | 9/2011 |
| WO | WO2011109237 | 9/2011 |
| WO | WO2011111880 | 9/2011 |
| WO | WO2011112687 | 9/2011 |
| WO | WO2011112995 | 9/2011 |
| WO | WO2011115725 | 9/2011 |
| WO | WO2011119894 | 9/2011 |
| WO | WO2011120327 | 10/2011 |
| WO | WO2011123493 | 10/2011 |
| WO | WO2011128403 | 10/2011 |
| WO | WO2011130390 | 10/2011 |
| WO | WO2011133722 | 10/2011 |
| WO | WO2011133750 | 10/2011 |
| WO | WO2011133888 | 10/2011 |
| WO | WO2011135376 | 11/2011 |
| WO | WO2011137313 | 11/2011 |
| WO | WO2011140338 | 11/2011 |
| WO | WO2011141756 | 11/2011 |
| WO | WO2011141848 | 11/2011 |
| WO | WO2011143033 | 11/2011 |
| WO | WO2011143318 | 11/2011 |
| WO | WO2011143430 | 11/2011 |
| WO | WO2011147198 | 12/2011 |
| WO | WO2011147199 | 12/2011 |
| WO | WO2011151360 | 12/2011 |
| WO | WO2011153553 | 12/2011 |
| WO | WO2011155983 | 12/2011 |
| WO | WO2011156610 | 12/2011 |
| WO | WO2012000103 | 1/2012 |
| WO | WO2012003544 | 1/2012 |
| WO | WO2012004217 | 1/2012 |
| WO | WO2012004731 | 1/2012 |
| WO | WO2012004732 | 1/2012 |
| WO | WO2012008563 | 1/2012 |
| WO | WO2012008564 | 1/2012 |
| WO | WO2012008999 | 1/2012 |
| WO | WO2012009258 | 1/2012 |
| WO | WO2012009309 | 1/2012 |
| WO | WO 2012/019093 | 2/2012 |
| WO | WO2012013619 | 2/2012 |
| WO | WO2012015274 | 2/2012 |
| WO | WO2012019093 | 2/2012 |
| WO | WO2012020133 | 2/2012 |
| WO | WO2012027236 | 3/2012 |
| WO | WO2012027239 | 3/2012 |
| WO | WO2012030990 | 3/2012 |
| WO | WO2012031004 | 3/2012 |
| WO | WO2012032031 | 3/2012 |
| WO | WO2012032065 | 3/2012 |
| WO | WO2012032067 | 3/2012 |
| WO | WO2012032334 | 3/2012 |
| WO | WO2012035996 | 3/2012 |
| WO | WO2012036233 | 3/2012 |
| WO | WO2012038743 | 3/2012 |
| WO | WO2012047699 | 4/2012 |
| WO | WO2012054364 | 4/2012 |
| WO | WO 2012/062462 | 5/2012 |
| WO | WO 2012/064715 | 5/2012 |
| WO | WO2012057260 | 5/2012 |
| WO | WO2012058211 | 5/2012 |
| WO | WO2012061337 | 5/2012 |
| WO | WO2012063207 | 5/2012 |
| WO | WO2012065297 | 5/2012 |
| WO | WO2012065546 | 5/2012 |
| WO | WO2012066578 | 5/2012 |
| WO | WO2012068343 | 5/2012 |
| WO | WO 2012/080727 | 6/2012 |
| WO | WO 2012/080729 | 6/2012 |
| WO | WO 2012/088266 | 6/2012 |
| WO | WO2012073017 | 6/2012 |
| WO | WO2012083866 | 6/2012 |
| WO | WO2012083953 | 6/2012 |
| WO | WO2012083954 | 6/2012 |
| WO | WO2012087784 | 6/2012 |
| WO | WO2012091240 | 7/2012 |
| WO | WO2012093731 | 7/2012 |
| WO | WO2012098068 | 7/2012 |
| WO | WO 2012/101239 | 8/2012 |

(56) References Cited

FOREIGN PATENT DOCUMENTS

| | | |
|---|---|---|
| WO | WO2012106995 | 8/2012 |
| WO | WO2012112961 | 8/2012 |
| WO | WO2012112965 | 8/2012 |
| WO | WO2012116237 | 8/2012 |
| WO | WO2012125812 | 9/2012 |
| WO | WO2012127012 | 9/2012 |
| WO | WO2012134943 | 10/2012 |
| WO | WO2012138975 | 10/2012 |
| WO | WO2012140114 | 10/2012 |
| WO | WO2012158704 | 11/2012 |
| WO | WO2012158795 | 11/2012 |
| WO | WO2012158994 | 11/2012 |
| WO | WO2012161812 | 11/2012 |
| WO | WO2012167247 | 12/2012 |
| WO | WO2012173370 | 12/2012 |
| WO | WO2013016197 | 1/2013 |
| WO | WO2013024002 | 2/2013 |
| WO | WO2013024895 | 2/2013 |
| WO | WO2013033981 | 3/2013 |
| WO | WO2013039854 | 3/2013 |
| WO | WO2013049352 | 4/2013 |
| WO | WO 2013/063000 | 5/2013 |
| WO | WO 2013/063003 | 5/2013 |
| WO | WO2013108809 | 7/2013 |
| WO | WO2013109027 | 7/2013 |
| WO | WO2013124316 | 8/2013 |
| WO | WO2013136249 | 9/2013 |
| WO | WO2013144339 | 10/2013 |
| WO | WO 2014/007951 | 1/2014 |
| WO | WO 2014/011284 | 1/2014 |
| WO | WO 2014/011900 | 1/2014 |
| WO | WO2014011284 | 1/2014 |
| WO | WO2014011900 | 1/2014 |
| WO | WO 2014/026125 | 2/2014 |
| WO | WO2014019186 | 2/2014 |
| WO | WO2014022528 | 2/2014 |
| WO | WO 2014/044846 | 3/2014 |
| WO | WO 2014/048878 | 4/2014 |
| WO | WO2014048878 | 4/2014 |
| WO | WO2014062454 | 4/2014 |
| WO | WO2014085216 | 5/2014 |
| WO | WO2014089913 | 6/2014 |
| WO | WO2014105849 | 7/2014 |
| WO | WO2014113191 | 7/2014 |
| WO | WO2014136972 | 9/2014 |
| WO | WO2014138485 | 9/2014 |
| WO | WO2014140184 | 9/2014 |
| WO | WO2014144737 | 9/2014 |
| WO | WO 2014/162039 | 10/2014 |
| WO | WO 2014/174307 | 10/2014 |
| WO | WO2014160160 | 10/2014 |
| WO | WO2014160478 | 10/2014 |
| WO | WO2014160521 | 10/2014 |
| WO | WO2014171755 | 10/2014 |
| WO | WO2014172644 | 10/2014 |
| WO | WO 2014/182829 | 11/2014 |
| WO | WO2014182829 | 11/2014 |
| WO | WO2014198942 | 12/2014 |
| WO | WO2014206343 | 12/2014 |
| WO | WO2014206344 | 12/2014 |
| WO | WO 2015/006754 | 1/2015 |
| WO | WO2015000715 | 1/2015 |
| WO | WO2015006492 | 1/2015 |
| WO | WO2015030021 | 3/2015 |

OTHER PUBLICATIONS

H. Greulich, 17 Trends in Molecular Medicine, 283-292 (2011).*
J. Bonaventure et al., 6 Clinical Pediatric Endocrinology, 105-113 (1997).*
L. Tan et al., PNAS E4869-E4877 (2014).*
O Segev et al., 9 Human Molecular Genetics, 249-258 (2000).*
International Search Report and Written Opinion in International Application No. PCT/US2014/034662, mailed Oct. 24, 2014, 18 pages.
International Search Report and Written Opinion in International Application No. PCT/US2013/045309, mailed on Jan. 22, 2014, 19 pages.
Eissa, "Synthesis and evaluation of some surface active agents from long chain fatty amine," Spanish National Research Council, Jan. 2007, 58(4):379-389.
Ghorab et al., "Synthesis of some sulfur containing Tetrahydrobenzoabuthieno[b]Thieno(Pyridines, Quinolines, Oxazines and Pyrimidines) as possible radioprotective and Antineoplastic agents," Phosphorus, Sulfur and Silicon, Jan. 1998, 134/135:57-76.
International Search Report dated Jun. 19, 2012 for International Appln. No. PCT/US2011/066473 (15 pgs.)
International Preliminary Report on Patentability and Written Opinion in International Application No. PCT/US2011/066473, issued Jun. 25, 2013, 10 pages.
International Search Report and Written Opinion in International Application No. PCT/US2013/054361, dated Oct. 16, 2013, 12 pages.
Invitation to Pay Additional Fees and, Where Applicable, Protest Fee in International Application No. PCT/US2013/045309, mailed Nov. 25, 2013, 5 pages.
Berge et al., "Pharmaceutical Salts", Journal of Pharmaceutical Science, 66(2):1-19 (1977).
Blom et al., "Optimizing Preparative LC-MS Configurations and Methods for Parallel Synthesis Purification", *J. Combi Chem.*, 5, 670 (2003).
Blom et al., Preparative LC-MS Purification: Improved Compound Specific Method Optimization, J. Combi. Chem. 2004, 6(6), 874-883.
Blom, K., "Two-Pump At Column Dilution Configuration for Preparative LC-MS", *J. Combi Chem.*, 4, 295 (2002).
Chase et al., "Activity of TKI258 against primary cells and cell lines with FGFR1 fusion genes associated with the 8p11 myeloproliferative syndryome," Blood, 2007, 110:3729-3734.
Chesi et al., "Activated fibroblast growth factor receptor 3 is an oncogene that contributes to tumor progression in multiple myeloma," Blood, 2001, 97:729-736.
Cole et al, "Inhibition of FGFR2 and FGFR1 increases cisplatin sensitivity in ovarian cancer," Cancer Biol. Therapy, Sep. 1, 2010, 10(5):495-504.
Crose et al., "FGFR4 Blockade Exerts Distinct Antitumorigenic Effects in Human Embryonal versus Alveolar Rhabdomyosarcoma," Clin Cancer Res., 2012, 18:3780-3790.
Dutt et al., "Drug-sensitive FGFR2 mutations in endometrial carcinoma," PNAS, Jun. 24, 2008, 105(25):8713-8717.
Eswarakumar et al., "Cellular signaling by fibroblast growth factor receptors," Cytokine & Growth Factor Reviews, 2005, 16:139-149.
French et al., "Targeting FGFR4 Inhibits Hepatocellular Carcinoma in Preclinical Mouse Models," PLoS ONE, 2012, 7(5):e36713, 1-12.
Greene, T. W. and Wuts, P. G. M., "Protective Groups in Organic Synthesis", 3rd Ed., Wiley & Sons, Inc., New York (1999).
Gu et al., "Phosphotyrosine profiling identifies the KG-1 cell line as a model for the study of FGFR1 fusions in acute myeloid leukemia," Blood, Dec. 15, 2006, 108(13):4202-42040.
Knights and Cook, "De-regulated FGF receptors as therapeutic targets in cancer," Pharmacology & Therapeutics, 2010, 125:105-117.
Koziczak et al., "Blocking of FGFR signaling inhibits breast cancer cell proliferation through downregulation of D-type cyclins," Oncogene, 2004, 23:3501-3508.
Kunii et al., "FGFR2-Amplified Gastric Cancer Cell Lines Require FGFR2 and Erbb3 Signaling for Growth and Survival," Cancer Res., Apr. 1, 2008, 68(7):2340-2348.
Lamont et al., "Small molecule FGF receptor inhibitors block FGFR-dependent urothelial carcinoma growth in vitro and in vivo," Br. J Cancer, 2011, 104:75-82.
Marshall et al., "Fibroblast Growth Factor Receptors are Components of Autocrine Signaling Networks in Head and Neck Squamous Cell Carcinoma Cells," Clin Cancer Res., 2011, 17:5016-5025.
Matsuda et al., "Fibroblast Growth Factor Receptor 2 IIIc as a Therapeutic Target for Colorectal Cancer Cells," Mol Cancer Ther., 2012, 52 pages.

(56) References Cited

OTHER PUBLICATIONS

McMahon, "VEGF Receptor Signaling in Tumor Angiogenesis," Oncologist, 2000, 5(suppl 1):3-10.
Metzner, "Fibroblast Growth Factor Receptors as Therapeutic Targets in Human Melanoma: Synergism with BRAF Inhibition," J Investigative Dermatol., 2011, 131:2087-2095.
Murphy et al., "Evidence for distinct alterations in the FGF axis in prostate cancer progression to an aggressive clinical phenotype," J Pathol., 2010, 220:452-460.
Nomura et al., "FGF10/FGFR20 signal induces cell migration and invasion in pancreatic cancer," Br. J Cancer, 2008, 99:305-313.
Norman et al., "Protein-Ligand Crystal Structures Can Guide the Design of Selective Inhibitors of the FGFR Tyrosine Kinase," J. Med. Chem., 2012, 55(11):5003-5012.
Pinedo and Slamon, "Translational Research: The Role of VEGF in Tumor Angiogenesis," Oncologist, 2000, 5(suppl 1):1-2.
Remington's Pharmaceutical Sciences, 17th ed., Mack Publishing Company, Easton, Pa., 1985, p. 1418.
Singh et al., "Transforming Fusions of FGFR and TACC Genes in Human Glioblastoma," Science, Sep. 2012, 337:1231-1235.
Turner and Grose, "Fibroblast growth factor signalling: from development to cancer," Nature Reviews Cancer, 2010, 10:116-129.
Weiss et al., Frequent and Focal FGFR1 Amplification Associates with Therapeutically Tractable FGFR1 Dependency in Squamous Cell Lung Cancer, Sci. Transl. Med., 2010, 2(62):62ra93, pp. 1-7.
International Preliminary Report on Patentability in International Application No. PCT/US2013/045309, mailed Dec. 24, 2014, 11 pages.
"Sabiosciences.com" [online]. "FGF Pathway," 2000-2012, [retrieved on Jun. 23, 2015]. Retrieved from the Internet: URL <http://www.sabiosciences.com/pathway.php?sn=FGF_Signaling>, 3 pages.
Acevedo et al., "Inducible FGFR-1 Activation Leads to Irreversible Prostate Adenocarcinoma and an Epithelial-to-Mesenchymal Transition," Cancer Cell, Dec. 2007, 12: 559-571.
Antonios-McCrea et al., "LHMDS mediated tandem acylation-cyclization of 2-aminobenzenecarbonitriles with 2-benzymidazol-2-ylacetates: a short and efficient route to the synthesis of 4-amino-3-benzimidazol-2-ylhydroquinolin-2-ones," Tetrahedron Letters, 2006, 657-660.
Avet-Loiseau et al., "Impact of high-risk cytogenetics and prior therapy on outcomes in patients with advanced relapsed or refractory multiple myeloma treated with lenalidomide plus dexamethasone," Leukemia, 2010, 623-628.
Bai et al., "GP369, an FGFR2-IIIb specific antibody, exhibits potent antitumor activity against human cancers driven by activated FGFR2 signaling," Am. Assoc. for Cancer Research, Aug. 17, 2010, 30 pages.
Bansal et al., "Specific inhibitor of FGF receptor signaling: FGF-2-mediated effects on proliferation, differentiation, and MAPK activation are inhibited by PD173074 in oligodendrocyte-lineage cells," J. Neurosci. Res., 2003, 74: 486.
Beekman et al., "New Molecular Targets and Novel Agents in the Treatment of Advanced Urothelial Cancer," Semin Oncol, 2007, 34: 154-164.
Bello et al., "E-3810 is a potent dual inhibitor of VEGFR and FGFR that exerts antitumor activity in multiple preclinical models," Cancer Res, 2011.
Bello et al., "E-3810 is a potent dual inhibitor of VEGFR and FGFR that exerts antitumor activity in multiple preclinical models," Cancer Res, 2011, Supplemental figures, 4 pages.
Bello et al., "E-3810 is a potent dual inhibitor of VEGFR and FGFR that exerts antitumor activity in multiple preclinical models," Cancer Res, 2011, Supplemental table, 3 pages.
Bello et al., "E-3810 is a potent dual inhibitor of VEGFR and FGFR that exerts antitumor activity in multiple preclinical models," Cancer Res, 2011, Supplementary data, 4 pages.
Benet-Pages et al., "An FGF23 missense mutation causes familial tumoral calcinosis with hyperphosphatemia," Human Molecular Genetics, 2005, 14(3):385-390.
Bergwitz and Juppner, "Regulation of Phosphate Homeostasis by PHT, Vitamin D, and FGF23," Annu. Rev. Med., 2010, 61:91-104.
Bhide et al., "Discovery and Preclinical Studies of (R )-1-(4-(4-Fluoro-2-methyl-1H-indol-5-yloxy)-5-methylpyrrolo[2,1-f][1,2,4]triazin-6-yloxy)propan-2-ol (BMS-540215), an In Vivo Active Potent VEGFR-2 Inhibitor," Journal of Medicinal Chemistry, 2006, 49(7): 2143-2146.
Billottet et al., "Targets of Fibroblast Growth Factor 1 (FGF-1) and FGF-2 Signaling Involved in the Invasive and Tumorigenic Behavior of Carchinoma Cells," Molecular Biology of the Cell, Oct. 2004, 15: 4725-4734.
BioCentury, Week of Nov. 10, 2014, 52 pages.
Bisping et al., "Bortezomib, Dexamethasone, and Fibroblast Growth Factor Receptor 3-Specific Tyrosine Kinase Inhibitor in t(4;14) Myeloma," Clin Cancer Res, Jan. 2009, 15(2):520-531.
Black et al., "Targeted therapies in bladder cancer—an update," Urologic Oncology: Seminars and Original Investigations, 2007, 433-438.
Bono et al., "Inhibition of Tumor Angiogenesis and Growth by a Small-Molecule Multi-FGF Receptor Blocker with Allosteric Properties," Cancer Cell, Apr. 2013, 477-488.
Brooks et al., "Fibroblast growth factor signaling: a new therapeutic opportunity in cancer," Clinical Cancer Research, 2012, 1-23.
Cappellen et al., "Frequent activating mutations of FGFR3 in human bladder and cervix carcinomas," Nature Genetics, Sep. 1999, 23: 18-20.
Carmichael et al., "Familial Tumoral Calcinosis: A Forty-Year Follow-up on One Family," The Journal of Bone & Joint Surgery, 2009, 664-671.
Cha et al., "Aberrant Receptor Internalization and Enhanced FRS2-dependent Signaling Contribute to the Transforming Activity of the Fibroblast Growth Factor Receptor 2 IIIb C3 Isoform," The Journal of Biological Chemistry, Mar. 2009, 284(10): 6227-6240.
Chefetz and Sprecher, "Familial tumoral calcinosis and the role of O-glycosylation in the maintenance of phosphate homeostasis," Biochimica et Biophysica Acta, 2009, 847-852.
Chefetz et al., "A novel homozygous missense mutation in FGF23 causes Familial Tumoral Calcinosis associated with disseminated visceral calcification," Hum Genet, 2005, 118:261-266.
Chell et al., "Tumour cell responses to new fibroblast growth factor receptor tyrosine kinase inhibitors and identification of a gatekeeper mutation in FGFR3 as a mechanism of acquired resistance," Oncogene, 2012, 1-12.
Chen et al., "Acenaphtho[1,2-b]pyrrole-Based Selective Fibroblast Growth Factor Receptors 1 (FRGR1) Inhibitors: Design, Synthesis, and Biological Activity," Jounal of Medicinal Chemistry, 2011, 54: 3732-3745.
Chen et al., "FGFR3 as a therapeutic target of the small molecule inhibitor PKC412 in hematopoietic malignancies," Oncogene, 2005, 24: 8259-8267.
Chesi et al., "Frequent translocation t(4;14)(p16.3;q32.3) in multiple myeloma is associated with increased expression and activating mutations of fibroblast growth factor receptor 3," Nature Genetics, 1997, 260-264.
Chng et al., "Translocation t(4;14) retains prognostic significance even in the setting of high-risk molecular signature," Leukemia, 2008, 2: 459-461.
Chuaqui et al., "Interaction Profiles of Protein Kinase—Inhibitor Complexes and Their Application to Virtual Screening," J. Med. Chem., 2005, 48: 121-133.
Coleman, "Positive and negative regulation of cellular sensitivity to anti-cancer drugs by FGF-2," Drug Resistance Updates, 2003, 85-94.
Cone et al., "Synthesis and biological evaluation of a triazole-based library of pyrido[2,3-d]pyrimidines as FGFR3 tyrosine kinase inhibitors," Organic & Biomolecular Chemistry, 2010, 8:2164-2173.
Covic et al., "Vascular calcification in chronic kidney disease," Clinical Science, 2010, 119: 111-121.
Dailey et al., "Mechanisms underlying differential responses to FGF signaling," Cytokine & Growth Factor Reviews, 2005, 233-247.
Damia, "Antitumor activity of E-3810, a new, potent and selective dual inhibitor of VEGF and FGF receptors," Mol Cancer Ther, Dec. 2009 8:A257, 1 page.

(56) References Cited

OTHER PUBLICATIONS

Dash et al., "A Role for Neoadjuvant Gemcitabine Plus Cisplatin in Muscle-Invasive Urothelial Carcinoma o the Bladder: A Retrospective Experience," Cancer, 2008, 113(9): 2471-2477.
Dey et al., "Targeting Fibroblast Growth Factor Receptors Blocks PI3K/AKT Signaling, Induces Apoptosis, and Impairs Mammary Tumor Outgrowth and Metastasis," Cancer Research, 2010, 4151-4162.
Dieci et al., "Fibroblast Growth Factor Receptor Inhibitors as a Cancer Treatment: From a Biologic Rationale to Medical Perspectives," Cancer Discovery, 2013, 1-16.
Dienstmann et al., "Genomic aberrations in the FGFR pathway: opportunities for targeted therapies in solid tumors," Annals of Oncology, 2013, 1-12.
Diller and Li, "Kinases, Homology Models, and High Throughput Docking," J. Med. Chem., 2003, 46: 4638-4647.
Dimopoulos et al., "Lenalidomide plus Dexamethasone for Relapsed or Refractory Multiple Myeloma," The New England Journal of Medicine, 2007, 357:2123-2132.
Dovedi and Davies, "Emerging targeted therapies for bladder cancer: a disease waiting for a drug," Cancer Metastasis Rev, 2009, 28:355-367.
Dring et al., "A Global Expression-based Analysis of the Consequences of the t(4;14) Translocation in Myeloma," Clinical Cancer Research, Sep. 2004, 10: 5692-5701.
Dutt et al., "Drug-sensitive FGFR2 mutations in endometrial carcinoma," Supporting Information, 8 pages.
Elsheikh et al., "FGFR1 amplification in breast carcinomas: a chromogenic in situ hybridisation analysis," Breast Cancer Research, Mar. 2007, 9(2): 1-12.
Eskens and Verweij, "The clinical toxicity profile of vascular endothelial growth factor (VEGF) and vascular endothelial growth factor receptor (VEGFR) targeting angiogenesis inhibitors; A review," European Journal of Cancer, 2006, 3127-3139.
Eswarakumar and Schlessinger, "Cellular signaling by fibroblast growth factor receptors," Cytokine & Growth Factor Reviews, 2005, 139-149.
Faul et al., "FGF23 induces left ventricular hypertrophy," The Journal of Clinical Investigation, 2010, 1-16.
Feng et al., "Targeting Fibroblast Growth Factor Receptor Signaling Inhibits Prostate Cancer Progression," Clinical Cancer Research, 2012, 1-9.
Ferrera et al., "Bevacizumab (Avastin), a humanized anti-VEGF monoclonal antibody for cancer therapy," Biochemical and Biophysical Research Communications, 2005, 328-335.
Fillmore et al., "Estrogen expands breast cancer stem-like cells through paracrine FGF/Tbx3 signaling," PNAS, 2010, 1-6.
Fischer et al., "Fibroblast growth factor receptor-mediated signals contribute to the malignant phenotype of non-small cel lung cancer cells: therapeutic implications and synergism with epidermal growth factor receptor inhibition," Mol Cancer Therapy, 2008, 3408-3419.
Frishberg et al., "Hypertosis-Hyperphosphatemia Syndrome: A Congenital Disorder of O-Glycosylation Associated With Augmented Processing of Fibroblast Growth Factor 23," Journal of Bone and Mineral Research, 2007, 22(2): 235-242.
Frishberg et al., "Identification of a recurrent mutation in GALNT3 demonstrates that hyperostosis-hyperphosphatemia syndrome and familial tumoral calcinosis are allelic disorders," J Mol Med, 2005, 83:33-38.
Fukumoto and Yamashita, "FGF23 is a hormone-regulating phophate metabolism—Unique biological characteristics of FGF23," Bone, 2007, 1190-1195.
Galdemard et al., "Regulation of FGF-3 Gene Expression in Tumorigenic and Non-tumorigenic Clones of a Human Colon Carcinoma Cell Line," The Journal of Biological Chemistry, 2000, 275(23): 17364-17373.
Garringer et al., "Molecular genetic and biochemical analyses of FGF23 mutations in familial tumoral calcinosis," Am J Physiol Endocrinol Metab, 2008, 929-937.

Gattineni et al., "FGF23 decreases renal NaPi-2a and NaPi-2c expression and induces hypophosphatemia in vivo predominantly via FGF receptor 1," Am J Physiol Renal Physiol, 2009, 297: 282-291.
Gavine et al., "AZD4547: An Orally Bioavailable, Potent, and Selective Inhibitor of the Fibroblast Growth Factor Receptor Tyrosine Kinase Family," American Association for Cancer Research, Apr. 2012, 72(8): 2045-2056.
Gerby et al., "2-Arylidenedihydroindole-3-ones: Design, synthesis, and biological activity on bladder carcinoma cell lines," Bioorganic & Medicinal Chemistry Letters, 2007, 208-213.
Goetz et al., "Isolated C-terminal tail of FGF23 alleviates hypophosphatemia by inhibiting FGF23-FGFR-Klotho complex formation," PNAS, Jan. 2010, 107(1): 407-412.
Gomez-Rivera et al., "The Tyrosine Kinase Inhibitor, AZD2171, Inhibits Vascular Endothelial Growth Factor Receptor Signaling and Growth of Anaplastic Thyroid Cancer in an Orthotopic Nude Mouse Model," Clin Cancer Res, Aug. 2007, 4519-4527.
Govindan, "Summary of Presentations from the Ninth Annual Targeted Therapies in Lung Cancer Symposium," Journal of Thoracic Oncology, Nov. 2009, 4(11): 1045-1089.
Gozgit et al., "Ponatinib (AP24534), a Multitargeted Pan-FGFR Inhibitor with Activity in Multiple FGFR-Amplified or Mutated Cancer Models," Mol Cancer Ther, 2012, 11: 690-699.
Grand et al., "Targeting FGFR3 in multiple myeloma: inhibition of t(4;14)-positive cells by SU5402 and PD173074," Leukemia, 2004, 18: 962-966.
Grose and Dickson, "Fibroblast growth factor signaling in tumorigenesis," Cytokine & Growth Factor Reviews, 2005, 179-186.
Guagnano et al., "Discovery of 3-(2,6-Dichloro-3,5-dimethoxyphenyl)-1-{6-[(4-ethyl-piperazin-1-yl)-phenylamino]-pyrimidin-4-yl}-1-methyl-urea (NVP-BGJ398), A Potent and Selective Inhibitor of the Fibroblast Growth Factor Receptor Family of Receptor Tyrosine Kinase," J. Med. Chem., 2011, 54: 7066-7083.
Guan et al., "Design and synthesis of aminopropyl tetrahydroindole-based indolin-2-ones as selective and potent inhibitors of Src and Yes tyrosine kinase," Bioorganic & Medicinal Chemistry Letters, 2004, 187-190.
Hafner et al., "High Frequency of FGFR3 Mutations in Adenoid Seborrheic Keratoses," Journal of Investigative Dermatology, 2006, 126: 2404-2407.
Hafner, "Seborrheic keratoses and epidermal nevi: new pathogenetic insights and therapeutic implications," Expert Rev Dermatol, 2006, 1(6): 759-761.
Hagel et al., "First Selective Small Molecule Inhibitor of FGFR4 for the Treatment of Hepatocellular Carcinomas with an Activated FGFR4 Signaling Pathway," Cancer Discovery, Apr. 2015, 1-14.
Hara and Saito, "CARD9 versus CARMA1 in innate and adaptive immunity," Cell Press, 2009, 234-242.
Hideshima and Anderson, "Preclinical Studies of Novel Targeted Therapies," Hematol Oncol Clin N Am, 2007, 1071-1091.
Honigberg et al., "The Bruton tyrosine kinase inhibitor PCI-32765 blocks B-cell activation and is efficacious in models of autoimmune disease and B-cell malignancy," Supporting Information, PNAS, Jul. 20, 2010, 107:29.
Hruska et al., "The Pathogenesis of Vascular Calcification in the Chronic Kidney Disease Mineral Bone Disorder (CKD-MBD): The Links Between Bone and Vasculature," Semin Nephrol, Mar. 2009, 29(2): 156-165.
Hynes and Dey, "Potential for Targeting the Fibroblast Growth Factor Receptors in Breast Cancer," Cancer Res, 2010, 70:5199-5202.
Ichikawa et al., "A homozygous missense mutation in human KLOTHO causes severe tumoral calcinosis," The Journal of Clinical Investigation, Sep. 2007, 117(9): 2684-2691.
Ichikawa et al., "A Novel GALNT3 Mutation in a Pseudoautosomal Dominant Form of Tumoral Calcinosis: Evidence That the Disorder Is Autosomal Recessive," J. Clin. Endocrinol. Metab., 2005, 90:2420-2423.
Ichikawa et al., "Clinical Variability of Familial Tumoral Calcinosis Caused by Novel GALNT3 Mutations," American Journal of Medical Genetics, 2009, 896-903.

(56) References Cited

OTHER PUBLICATIONS

Ichikawa et al., "Novel GALNT3 Mutations Causing Hyperostosis-Hyperphosphatemia Syndrome Result in Low Intact Fibroblast Growth Factor 23 Concentrations," J. Clin. Endocrinol. Metab., 2007, 92:1943-1947.
Ichikawa et al., "Tumoral Calcinosis Presenting with Eyelid Calcifications due to Novel Missense Mutations in the Glycosyl Transferase Domain of the GALNT3 Gene," J. Clin. Endocrinol. Metab., 2006, 91: 4472-4475.
International Preliminary Report on Patentability in International Application No. PCT/US2013/054361, mailed Feb. 19, 2015, 7 pages.
Isakova et al., "Fibroblast Growth Factor 23 and Risks of Mortality and End-Stage Renal Disease in Patients With Chronic Kidney Disease," JAMA, Jun. 15, 2011, 305:23, 2432-2439.
Ishikawa et al., "Accelerated proliferation of myeloma cells by interleukin-6 cooperating with fibroblast growth factor receptor 3-mediated signals," Oncogene, 2005, 24:6328-6332.
Jan de Beur, "Tumoral Calcinosis: A Look into the Metabolic Mirror of Phosphate Homeostasis," The Journal of Clinical Endocrinology & Metabolism, 2005, 90: 2469-2471.
Jebar et al., "FGFR3 and Ras gene mutations are mutually exclusive genetic events in urothelial cell carcinoma," Oncogene, 2005, 24: 5218-5225.
Johnson et al., "Pharmacological and Functional Comparison of the Polo-like Kinase Family: Insight into Inhibitor and Substrate Specificity," Biochemistry, 2007, 46: 9551-9563.
Jonker et al., "A phase I study to determine the safety, pharmacokinetics and pharmacodynamics of a dual VEGFR and FGFR inhibitor, brivanib, in patients with advanced or metastatic solid tumors," Annals of Oncology, 2010, 1-7.
Kang et al., FGFR3 Activates RSK2 to Mediate Hematopoietic Transformation through Tyrosine Phosphorylation of RSK2 and Activation of the MEK/ERK Pathway, Cancer Cell, Sep. 2007, 12:201-214.
Kassack et al., "Structure-activity relationships of analogues of NF449 confirm NF449 as the most potent and selective known $P2X_1$ receptor antagonist," European Journal of Medicinal Chemisty, 2004, 345-357.
Katoh and Katoh, "FGF signaling network in the gastrointestinal tract (Review)," International Journal of Oncology, 2006, 29: 163-168.
Keats et al., "Ten years and counting: so what do we know about t(4;14)(p16;q32) multiple myeloma," Leukemia & Lymphoma, Nov. 2006, 47(11): 2289-2300.
Keer et al., "Enrolling a Rare Patient Population: Establishing Proof of Concept for FP-1039, an FGF "Trap," in Endometrial Cancer Patients with the S252W FGFR2 Mutation," Journal of Clinical Oncology, 2010 ASCO Annual Meeting Abstracts, 28:15, May 20 Supplement, 1 page.
Kim et al., "Phase I/II and Pharmacodynamic Study of Dovitinib (TKI258), an Inhibitor of Fibroblast Growth Factor Receptors and VEGF Receptors, in Patients with Advanced Melanoma," Clin Cancer Res, 2011, 17: 7451-7461.
Kim et al., "The design, synthesis, and biological evaluation of potent receptor tyrosine kinase inhibitors," Bioorganic & Medicinal Chemistry Letters, 2012, 4979-4985.
Klein et al., "FGFR1 Kinase Inhibitors: Close Regioisomers Adopt Divergent Binding Modes and Display Distinct Biophysical Signatures," American Chemical Society, 2014, 166-171.
Kompier et al., "Bladder cancer: Novel molecular characteristics, diagnostic, and therapeutic implications," Urologic Oncology: Seminars and Original Investigations, 2010, 91-96.
Kompier et al., "FGFR3, HRAS, KRAS, NRAS and PIK3CA Mutations in Bladder Cancer and Their Potential as Biomarkers for Surveillance and Therapy," PLoS ONE, Nov. 2010, 5(11): 1-13.
Kono et al., "The fibroblast growth factor receptor signaling pathway as a mediator of intrinsic resistance to EGFR-specific tyrosine kinase inhibitors in non-small cell lung cancer," Drug Resistance Updates, 2009, 95-102.

Koziczak and Hynes, "Cooperation between Fibroblast Growth Factor Receptor-4 and ErbB2 in Regulation of Cyclin D1 Translation," The Journal of Biological Chemistry, 2004, 279(48): 50004-50011.
Krejci et al., "Molecular pathology of the fibroblast growth factor family," Hum Mutat, Sep. 2009, 30(9): 1245-1255.
Krejci et al., "NF449 Is a Novel Inhibitor of Fibroblast Growth Factor Receptor 3 (FGFR3) Signaling Active in Chondrocytes and Multiple Myeloma Cells," The Journal of Biological Chemistry, Jul. 2010, 285(27): 20644-20653.
Krejci et al., "NF449 is a novel inhibitor of fibroblast growth factor receptor 3 (FGFR3) signaling active in chondrocytes and multiple myeloma cells," The American Society for Biochemistry and Molecular Biology, 2010, 1-20.
Kunii et al., "FGFR2-Amplified Gastric Cancer Cell Lines Require FGFR2 and Erbb3 Signaling for Growth and Survival," Cancer Res., Apr. 1, 2008, Supplemental figures, 11 pages.
Kurosu et al., "Regulation of Fibroblast Growth Factor-23 Signaling by Klotho," The Journal of Biological Chemistry, Mar. 2006, 281(10): 6120-6123.
Lammoglia and Mericq, "Familial Tumoral Calcinosis Caused by a Novel FGF23 Mutation: Response to Induction of Tubular Renal Acidosis with Acetazolamide and the Non-Calcium Phosphate Binder Sevelamer," Horm Res, 2009, 71:178-184.
Lamont et al., "Small molecule FGF receptor inhibitors block FGFR-dependent urothelial carcinoma growth in vitro and in vivo," Br. J Cancer, 2010, 1-8.
Le Corre et al., "Synthesis and biological evaluation of a triazole-based library of pyrido[2,3-d]pyrimidines as FGFR3 tyrosine kinase inhibitors," Org. Biomol. Chem., 2010, 8, 2164-2173.
Lee et al., "In vivo Target Modulation and Biological Activity of CHIR-258, a Multitargeted Growth Factor Receptor Kinase Inhibitor, in Colon Cancer Models," Clin Cancer Res, May 2005, 3633-3641.
L'Hote and Knowles, "Cell responses to FGFR3 signalling: growth, differentiation and apoptosis," Experimental Cell Research, 2005, 417-431.
Li et al., "Compound deletion of Fgfr3 and Fgfr4 partially rescues the Hyp mouse phenotype," Am. J. Physiology—Endocrinol Metab, Dec. 7, 2010, 300:3, 29 pages.
Liu et al., "Developing Irreversible Inhibitors of the Protein Kinase Cysteinome," Chemistry & Biology, Feb. 2013, 146-159.
Liu et al., "FRFR3 and FRFR4 Do not Mediate Renal Effects of FGF23," J Am Soc Nephrol, 2008, 19:2342-2350.
Liu et al., "Pathogenic role of Fgf23 in Hyp mice," Am J Physiol Endocrinol Metab 291, Jan. 31, 2006, E38-E49.
Lopes de Menezes et al., "CHIR-258: A Potent Inhibitor of FLT3 Kinase in Experimental Tumor Xenograft Models of Human Acute Myelogenous Leukemia," Clin Cancer Res, Jul. 2005, 5281-5291.
Marek et al., "Fibroblast Growth Factor (FGF) and FGF Receptor-Mediated Autocrine Signaling in Non-Small-Cell Lung Cancer Cells," Molecular Pharmacology, 2009, 75:196-207.
Marfe and Stefano, "in vitro Anti-leukaemia Activity of Pyrrolo[1,2-b][1,2,5]benzothiadiaze-pines (PBTDs)," Recent Patents on Anti-Cancer Drug Discovery, 2010, 58-68.
Martinez-Torrecuadrada et al., "Targeting the Extracellular Domain of Fibroblast Growth Factor Receptor 3 with Human Single-Chain Fv Antibodies Inhibits Bladder Carcinoma Cell Line Proliferation," Clin Cancer Res, Sep. 2005, 6280-6290.
McConkey et al., "Molecular genetics of bladder cancer: Emerging mechanisms of tumor initiation and progression," Urologic Oncology: Seminars and Original Investigations, 2010, 429-440.
Meijer et al., "Fibroblast growth factor receptor 4 predicts failure on tamoxifen therapy in patients with recurrent breast cancer," Endocrine-Related Cancer, 2008, 15:101-111.
Mellor, "Targeted inhibition of the FGF19-FGFR4 pathway in hepatocellular carcinoma; translational safety considerations," Liver International, 2013, 1-9.
Memon et al., "Does Fgf23-klotho activity influence vascular and soft tissue calcification through regulating phosphate homeostasis," Kidney Int., 2008, 74(5): 566-570.

(56) References Cited

OTHER PUBLICATIONS

Miyake et al., "1-tert-Butyl-3-[6-(3,5-dimethoxy-phenyl)-2-(4-diethylamino-butylamino)-pyrido[2,3-d]pyrimidin-7-yl]-urea (PD173074), a Selective Tyrosine Kinase Inhibitor of Fibroblast Growth Factor Receptor-3 (FGFR3), Inhibits Cell Proliferation of Bladder Cancer Carrying the FGFR3 Gene Mutation along with Up-Regulation of p27/Kipl and $G_1/G_0$ Arrest," The Journal of Pharmacology and Experimental Therapeutics, 2010, 332(3):795-802.

Mohammadi et al., "Crystal structure of an angiogenesis inhibitor bound to the FGF receptor tyrosine kinase domain," The EMBO Journal, 1998, 5896-5904.

Mohammadi et al., "Structures of the Tyrosine Kinase Domain of Fibroblast Growth Factor Receptor in Complex with Inhibitors," Science, May 1997, 276:955-960.

Naito et al., "Progressive tumoral calcinosis as the presenting feature of sarcoidosis in a patient on haemodialysis treatment," Nephrol Dial Transplant, 1999, 14:2716-2719.

Nakatani et al., "In vivo genetic evidence for klotho-dependent, fibroblast growth factor 23 (Fgf23)—mediated regulation of systemic phosphate homeostasis," The FASEB Journal, Feb. 2009, 23:433-441.

Natajaran et al., "p38 MAP kinase inhibitors. Part 3: SAR on 3,4-dihydropyrimido-[4,5-d]pyrimidin-2-ones and 3,4-dihydropyrido[4,3-d]-pyrimidin-2-ones," Bioorgan. Med. Chem. Lett., 2006, 4400-4404.

Nitta, "Relationship between Fibroblast Growth Factor-23 and Mineral Metabolism in Chronic Kidney Disease," International Journal of Nephrology, 2010, 1-7.

Ornitz et al., "Receptor Specificity of the Fibroblast Growth Factor Family," The Journal of Biological Chemistry, 1996, 271(25): 15292-15297.

Pai et al., "Antibody-Mediated Inhibition of Fibroblast Growth Factor 19 Results in Increased Bile Acids Synthesis and Ileal Malabsortion of Bile Acides in Cynomolgus Monkeys," Toxicological Sciences, 2012, 126(2): 446-456.

Pan et al., "Mk-2461, a Novel Multitargeted Kinase Inhibitor, Preferentially Inhibits the Activated c-Met Receptor," Cancer Res, Feb. 2010, 1524-1533.

Pandith et al., "Oncogenic role of fibroblast growth factor receptor 3 in tumorigenesis of urinary bladder cancer," Urologic Oncology: Seminars and Original Investigations, 2010, 1-9.

Pardo et al., "The Fibroblast Growth Factor Receptor Inhibitor PD173074 Blocks Small Cell Lung Cancer Growth In vitro and In vivo," Cancer Res, Nov. 2009, 8645-8651.

Paterson et al., "Preclinical studies of fibroblast growth factor receptor 3 as a therapeutic target in multiple myeloma," British Journal of Haematology, 2004, 124:595-603.

Piazza et al., "Towards a new age in the treatment of multiple myeloma," Ann Hematol, 2007, 86:159-172.

Platt et al., "Spectrum of Phosphatidylinositol 3-Kinase Pathway Gene Alterations in Bladder Cancer," Clin Cancer Res, Oct. 2009, 6008-6017.

Pliarchopoulou et al., "Current chemotherapeutic options for the treatment of advanced bladder cancer: A review," Urologic Oncology: Seminars and Original Investigations, 2010, 1-9.

Plowright et al., "Ectopic expression of fibroblast growth factor receptor 3 promotes myeloma cell proliferation and prevents apoptosis," Blood, Feb. 2000, 95(3): 992-998.

Podar et al., "Emerging therapies for multiple myeloma," Expert Opin. Emerging Drugs, 2009, 14(1):9-127.

Podar et al., "Targeting signalling pathways for the treatment of multiple myeloma," Expert Opin. Ther. Targets, 2005, 359-381.

Pollett et al., "Overexpression of the myeloma-associated oncogene fibroblast growth factor receptor 3 confers dexamethasone resistance," Blood, Nov. 2002, 100(10): 3819-3821.

Pollock et al., "Frequent activating FGFR2 mutations in endometrial carcinomas parallel germline mutations associated with craniosynostosis and skeletal dysplasia syndromes," Oncogene, 2007, 26:7158-7162.

Propper et al., "Phase I and Pharmacokinetic Study of PKC412, an Inhibitor of Protein Kinase C," J Clin Oncol, 2001, 19(5):1485-1492.

Qian et al., "Targeting Tumor Angiogenesis with Histone Deacetylase Inhibitors: the Hydroxamic Acid Derivative LBH589," Clin Cancer Res, Jan. 2006, 634-642.

Qing et al., "Antibody-based targeting of FGFR3 in bladder carcinoma and t(4;14)-positive multiple myeloma in mice," The Journal of Clinical Investigation, May 2009, 119(5): 1216-1229.

Qing et al., "Antibody-based targeting of FGFR3 in bladder carcinoma and t(4;14)-positive multiple myeloma in mice," The Journal of Clinical Investigation, May 2009, Supplemental Table 1: Summary of crystallographic analysis, 21 pages.

Raab et al., "Multiple myeloma," Lancet, 2009, 374: 324-339.

Ravindranathan et al., "Discovery of Novel Fibroblast Growth Factor Receptor 1 Kinase Inhibitors by Structure-Based Virtual Screening," J. Med. Chem., 2010, 53: 1662-1672.

Razzaque, "FGF23-mediated regulation of systemic phosphate homeostasis: is Klotho an essential player?," Am J Physiol Renal Physiol, 2009, 470-476.

Reimers et al., "NoBP, a Nuclear Fibroblast Growth Factor 3 Binding Protein, Is Cell Cycle Regulated and Promotes Cell Growth," Molecular and Cellular Biology, Aug. 2001, 21(15): 4996-5007.

Reis-Filho et al., "FGFR1 Emerges as a Potential Therapeutic Target for Lobular Breast Carcinomas," Clin Cancer Res, Nov. 2006, 6652-6662.

Renhowe et al., "Design, Structure—Activity Relationships and in Vivo Characterization of 4-Amino-3-benzimidazol-2-ylhydroquinolin-2-ones: A Novel Class of Receptor Tyrosine Kinase Inhibitors," J. Med. Chem., 2009, 52: 278-292.

Ribatti et al., "The discovery of basic fibroblast growth factor/fibroblast growth factor-2 and its role in haematological malignancies," Cytokine & Growth Factor Reviews, 2007, 18: 327-334.

Ribatti, "Tyrosine Kinase Inhibitors as Antiangiogenic Drugs in Multiple Myeloma," Pharmaceuticals, 2010, 3: 1225-1231.

Roidl et al., "Resistance to Chemotherapy Is Associated with Fibroblast Growth Factor Receptor 4 Up-Regulation," Clin Cancer Res, Mar. 2009, 2058-2066.

Ronchetti et al., "Deregulated FGFR3 mutants in multiple myeloma cell lines with t(4;14): comparative analysis of Y373C, K650E and the novel G384D mutations," Oncogene, 2001, 20: 3553-3562.

Roumiantsev et al., "Distinct stem cell myeloproliferative/T lymphoma syndromes induced by ZNF198-FGFR1 and BCR-FGFR1 fusion genes from 8p11 translocations," Cancer Cell, Mar. 2004, 5: 287-298.

Ryan et al., "Toxicologic Pathology of Unique Biotechnology Agents and Biotherapies," Toxicologic Pathology, 1999, 27(1): 78-86.

Sakurai et al., "A novel angiogenesis inhibitor, Ki23057, is useful for preventing the progression of colon cancer and the spreading of cancer cells to the liver," European Journal of Cancer, 2007, 2612-2620.

Sarker et al., "A Phase I Pharmacokinetic and Pharmacodynamic Study of TKI258, an Oral, Multitargeted Receptor Tyrosine Kinase Inhibitor in Patients with Advanced Solid Tumors," Clin Cancer Res, Apr. 2008, 2075-2081.

Saxty et al., "Fragment-based drug discovery of selective inhibitors of fibroblast growth factor receptor (FGFr)," Cancer Res, Apr. 15, 2010, 70, 5778.

Schenone et al., "Small Molecules ATP-Comptetitive Inhibitors of FLT3: A Chemical Overview," Current Medicinal Chemistry, 2008, 15(29): 3113-3132.

Schlapbach et al., "A novel Pd-catalyzed cyclization rection of ureas for the synthesis of dihydroquinazolinone p38 kinase inhibitors," Bioorg. Med. Chem. Lett., 2004, 357-360.

Science IP Order 3032627, Chemical Structure Search , Science IP, Apr. 2012, 78 pages.

Science IP Order 3101926, Chemical Structure Search , Science IP, Jan. 2015, 50 pages.

Science IP Order 3101983, Chemical Structure Search , Science IP, Jan. 2015, 70 pages.

Science IP Order 3104564, Patent Chemical Structure Search , Science IP, Mar. 2015, 90 pages.

Science IP Order 3104565, Patent Chemical Structure Search , Science IP, Mar. 2015, 521 pages.

(56) References Cited

OTHER PUBLICATIONS

Shariat et al., "Association of Angiogenesis Related Markers With Bladder Cancer Outcomes and Other Molecular Markers," The Journal of Urology, May 2010, 183: 1744-1750.
Sharkey et al., "PKC412 demonstrates JNK-dependent activity against human multiple myeloma cells," Blood, Feb. 2007, 109(4): 1712-1719.
Slavin et al., "Familial Tumoral Calcinosis," The American Journal of Surgican Pathology, 1993, 17(8): 188-802.
Smith et al., "Circulating αKlotho influences phosphate handling by controlling FGF23 production," The Journal of Clinical Investigation, Dec. 2012, 122(12): 4710-4715.
Song et al., "Fibroblast growth factors: An epigenetic mechanism of broad spectrum resistance to anticancer drugs," PNAS, Jul. 2000, 97(15): 8658-8663.
Sonvilla et al., "Fibroblast growth factor receptor 3-111c mediates colorectal cancer growth and migration," British Journal of Cancer, 2010, 1-12.
Soria, "FGFR inhibition overview of clinical development programs," Presentation.
Soverini et al., "Novel mutation and RNA splice variant of fibroblast growth factor receptor 3 in multiple myeloma patients at diagnosis," Haematologica, 2002, 87: 1036-1040.
Specktor et al., "Hyperphosphatemic familial tumoral calcinosis caused by a mutation in GALNT3 in a European kindred," J Hum Genet, 2006, 51:487-490.
Squires et al., "Development of inhibitors of the fibroblast growth factor receptor (FGFR) kinase using a fragment based approach," Cancer Res 70, Apr. 15, 2010, 3626.
Squires et al., "Development of inhibitors of the fibroblast growth factor receptor (FGFR) kinase using a fragment based approach," Cancer Res, 2008 , 1 page.
Sun et al., "Design, Synthesis, and Evaluations of Substituted 3-[(3- or 4-Carboxyethylpyrrol-2-yl)methylidenyl]indolin-2-ones as Inhibitors of VEGF, FGF, and PDGF Receptor Tyrosine Kinases," J. Med. Chem., 1999, 42: 5120-5130.
Sun et al., "Identification of Substituted 3-[(4,5,6,7-Tetrahydro-1H-indol-2-yl)methylene]-1,3-dihydroindol-2-ones as Growth Factor Receptor Inhibitors for VEGF-R2 (Flk-1/KDR), FGF-R1, and PDGF-Rβ Tyrosine Kinases," J. Med. Chem., 2000, 43: 2655-2663.
Sun et al., "Synthesis and Biological Evaluations of 3-Substituated Indolin-2-ones: A Novel Class of Tyrosine Kinase Inhibitors That Exhibit Selectivity toward Particular Receptor Tyrosine Kinases," J. Med. Chem., 1998, 41: 2588-2603.
Takeda et al., "AZD2171 Shows Potent Antitumor Activity Against Gastric Cancer Over-Expressing Fibroblast Growth Factor Receptor 2/Keratinocyte Growth Factor Receptor," Clin Cancer Res, May 2007, 3051-3057.
Taylor, "Inhibitor PD-173074 Bound to the Tyrosine Kinase Domain of FGFR 1," Molecular & Behavioral Neuroscience Institute, 5 pages.
Taylor, "Inhibitor SU-5402 Bound to the Tyrosine Kinase Domain of FGFR 1," Molecular & Behavioral Neuroscience Institute, 6 pages.
Terai et al., "Vascular calcification and secondary hyperparathyroidism of severe chronic kidney disease and its relation to serum phosphate and calcium levels," British Journal of Pharmacology, 2009, 156: 1267-1278.
Thome and Weil, "Post-translational modifications regulate distinct functions of CARMA1 and BCL10," TRENDS in Immunology, 2007, 28(6): 281-288.
Thompson et al., "3-(3,5-Dimethoxyphenyl)-1,6-naphthyridine-2,7-diamines and Related 2-Urea Derivatives Are Potent and Selective Inhibitors of the FGF Receptor-1 Tyrosine Kinase," J. Med. Chem., 2000, 43: 4200-4211.
Thompson et al., "Synthesis and Structure—Activity Relationships of Soluble 7-Substituted 3-(3,5-Dimethoxyphenyl)-1,6-naphthyridin-2-amines and Related Ureas as Dual Inhibitors of the Fibroblast Growth Factor Receptor-1 and Vascular Endothelial Growth Factor Receptor-2 Tyrosine Kinases," J. Med. Chem., 2005, 48: 4628-2653.
Tolcher et al., "381 Preliminary results of a dose escalation study of the Fibroblast Growth Factor (FGF) "trap" FP-1039 (FGFR1:Fc) in patients with advanced malignancies," EJC Supplements, Nov. 2010, 8:7, p. 121.
Tomlinson et al., "FGFR3 protein expression and its relationship to mutation status and prognostic variables in bladder cancer," J Pathol, Sep. 2007, 213(1): 91-98.
Tomlinson et al., "Fibroblast Growth Factor Receptor 1 Promotes Proliferation and Survival via Activation of the Mitogen-Activated Protein Kinase Pathway in Bladder Cancer," Cancer Res, 2009, 4613-4620.
Tomlinson et al., "Knockdown by shRNA identifies S249C mutant FGFR3 as a potential therapeutic target in bladder cancer," Oncogene, 2007, 26: 5889-5899.
Topaz et al., "Mutations in GALNT3, encoding a protein involved in O-linked glycosylation, cause familial tumoral calcinosis," Nature Genetics, 2004, 1-3.
Traxler and Furet, "Strategies toward the Design of Novel and Selective Protein Tyrosine Kinase Inhibitors," Pharmacol. Ther., 1999, 82(2-3): 195-206.
Trudel et al., "CHIR-258, a novel, multitargeted tyrosine kinase inhibitor for the potential treatment of t(4;14) multiple myeloma," Blood, Apr. 2005, 105(7): 2941-2948.
Trudel et al , "Inhibition of fibroblast growth factor receptor 3 induces differentiation and apoptosis in t(4;14) myeloma," Blood, May 2004, 103(9):3521-3528.
Trudel, "CHIR-258, a Novel Multi-targeted Tyrosine KinaseInhibitor, for the Treatment of t(4;14) Multiple Myeloma," Presentation at Princess Margaret Hospital, 18 pages.
Turner et al., "FGFR1 Amplification Drives Endocrine Therapy Resistance and Is a Therapeutic Target in Breast Cancer," Cancer Res., Mar. 2010, 2085-2094.
Tvorogov et al., "Effective Suppression of Vascular Network Formation by Combination of Antibodies Blocking VEGFR Ligand Binding and Receptor Dimerization," Cancer Cell, Dec. 2010, 18: 630-640.
Urakawa et al., "Klotho converts canonical FGF receptor into a specific receptor for FGF23," Nature, Dec. 2006, 444: 770-774.
Uzawa et al., "Targeting fibroblast growth factor receptor 3 enhances radiosensitivity in human squamous cancer cells," Oncogene, 2011, 1-6.
van Oers et al., "FGFR3 Mutations Indicate Better Survival in Invasive Upper Urinary Tract and Bladder Tumours," European Urology, 2009, 650-658.
Våtsveen et al., "FGFR3 is expressed and is important for survival in INA-6, a human myeloma cell line without a t(4;14)," Eur. J. Haematol., 83:5, Jul. 6, 2009, 471-476.
Wu, "Urothelial Tumorigenesis: A Tale of Divergent Pathways," Nature Reviews, Sep. 2005, 5: 713-725.
Wöhrle et al., "FGF Receptors Control Vitamin D and Phosphate Homeostasis by Mediating Renal FGF-23 Signaling and Regulating FGF-23 Expression in Bone," Journal of Bone and Mineral Research, Oct. 2011, 26(10): 2486-2497.
Wöhrle et al., "Pharmacological inhibition of FGFR signaling ameliorates FGF23-mediated hypophosphatemic rickets," Journal of Bone and Mineral Research, 2012, 1-36.
Xian et al., "Pleiotropic effects of FGFR1 on cell proliferation, survival, and migration in a 3D mammary epithelial cell model," JCB, 2005, 171(4): 663-673.
Xin et al., "CHIR-258 Is Efficacious in a Newly Developed Fibroblast Growth Factor Receptor 3-Expressing Orthotopic Multiple Myeloma Model in Mice," Clin Cancer Res, Aug. 2006, 4908-4915.
Yu et al., "Analysis of the Biochemical Mechanisms for the Endocrine Actions of Firbroblast Growth Factor-23," Endocrinology, Nov. 2005, 146(11): 4647-4656.
Zaid et al., "Identification of FGFR4 as a Potential Therapeutic Target for Advanced-Stage, High-Grade Serous Ovarian Cancer," Clin Cancer Res, 2013, 19(4): 809-820.
Zhang et al., "AZD4547, a potent and selective FGF-receptor inhibitor induces tumor regressions in a human primary model of FGF-receptor 2 amplified gastric cancer and is efficacious in combination with chemotherapy," 2012.

(56) References Cited

OTHER PUBLICATIONS

Zhang et al., "Direct Cell Cycle Regulation by the Fibroblast Growth Factor Receptor (FGFR) Kinase through Phosphorylation-dependent Release of Cks1 from FGFR Substrate 2," The Journal of Biological Chemistry, 2004, 279(53): 55348-55354.

Zhang et al., "FP-1039 (FGFR1:Fc), A Soluble FGFR1 Receptor Antagonist, Inhibits Tumor Growth and Angiogenesis," Mol Cancer Ther, 6, Nov. 2007, B55, 1 page.

Zhang et al., "Receptor Specificity of the Fibroblast Growth Factor Family," Journal of Biological Chemistry, Jun. 2006, 281(23): 15694-15700.

Zhang et al., "Translating the therapeutic potential of AZD4547 in FGFR1-amplified non-small cell lung cancer through the use of patient derived tumor xenograft (PDTX) models," Clin cancer Res, Oct. 18, 2012, 40 pages.

Zhao et al., "A Novel, Selective Inhibitor of Fibroblast Growth Factor Receptors That Shows a Potent Broad Spectrum of Antitumor Activity in Several Tumor Xenograft Models," Mol Cancer Ther, Nov. 2011, 2200-2210.

Zhao et al., "Homozygous Deletions and Chromosome Amplifications in Human Lung Carcinomas Revealed by Single Nucleotide Polymorphism Array Analysis," Cancer Res, Jul. 2005, 5561-5570.

Zhou et al., "A Structure-Guided Approach to Creating Covalent FGFR Inhibitors," Chemistry and Biology, Mar. 2010, 285-295.

Zhu et al., "Fibroblast growth factor receptor 3 inhibition by short hairpin RNAs leads to apoptosis in multiple myeloma," Mol Cancer Ther, May 2005, 787-798.

Zieger et al., "Role of Activating Fibroblast Growth Factor Receptor 3 Mutations in the Development of Bladder Tumors," Clin Cancer Res, Nov. 2005, 7709-7719.

Zingone et al., "Ectopic expression of wild-type FGFR3 cooperates with MYC to accelerate development of B-cell lineage neoplasms," Leukemia, 2010, 1171-1178.

"FGF Receptor Tyrosine Kinase Inhibitor," Calbiochem diagram, 341608, date- prior to filing of U.S. Appl. No. 14/132,653, 1 page.

\* cited by examiner

FUSED PYRAZOLES AS FGFR INHIBITORS

FIELD OF THE INVENTION

The present invention relates to fused pyrazole derivatives, and pharmaceutical compositions including the same, that are inhibitors of one or more FGFR enzymes and are useful in the treatment of FGFR-associated diseases such as cancer.

BACKGROUND OF THE INVENTION

The Fibroblast Growth Factor Receptors (FGFR) are receptor tyrosine kinases that bind to fibroblast growth factor (FGF) ligands. There are four FGFR proteins (FGFR1-4) that are capable of binding ligands and are involved in the regulation of many physiological processes including tissue development, angiogenesis, wound healing, and metabolic regulation. Upon ligand binding, the receptors undergo dimerization and phosphorylation leading to stimulation of the protein kinase activity and recruitment of many intracellular docking proteins. These interactions facilitate the activation of an array of intracellular signaling pathways including Ras-MAPK, AKT-PI3K, and phospholipase C that are important for cellular growth, proliferation and survival (Reviewed in Eswarakumar et al. Cytokine & Growth Factor Reviews, 16, 139-149 (2005)). Aberrant activation of this pathway either through overexpression of FGF ligands or FGFR or activating mutations in the FGFRs can lead to tumor development, progression, and resistance to conventional cancer therapies. In human cancer, genetic alterations including gene amplification, chromosomal translocations and somatic mutations that lead to ligand-independent receptor activation have been described. Large scale DNA sequencing of thousands of tumor samples has revealed that components of the FGFR pathway are among the most frequently mutated in human cancer. Many of these activating mutations are identical to germline mutations that lead to skeletal dysplasia syndromes. Mechanisms that lead to aberrant ligand-dependent signaling in human disease include overexpression of FGFs and changes in FGFR splicing that lead to receptors with more promiscuous ligand binding abilities (Reviewed in Knights and Cook, Pharmacology & Therapeutics, 125, 105-117 (2010); Turner and Grose, Nature Reviews Cancer, 10, 116-129 (2010)). Therefore, development of inhibitors targeting FGFR may be useful in the clinical treatment of diseases that have elevated FGF or FGFR activity.

The cancer types in which FGF/FGFRs are implicated include, but are not limited to: carcinomas (e.g., bladder, breast, cervical, colorectal, endometrial, gastric, head and neck, kidney, liver, lung, ovarian, prostate); hematopoietic malignancies (e.g., multiple myeloma, chronic lymphocytic lymphoma, adult T cell leukemia, acute myelogenous leukemia, non-Hodgkin lymphoma, myeloproliferative neoplasms, and Waldenstrom's Macroglubulinemia); and other neoplasms (e.g., glioblastoma, melanoma, and rhabdosarcoma). In addition to a role in oncogenic neoplasms, FGFR activation has also been implicated in skeletal and chondrocyte disorders including, but not limited to, achrondroplasia and craniosynostosis syndromes.

There is a continuing need for the development of new drugs for the treatment of cancer and other diseases, and the FGFR inhibitors described herein help address this need.

SUMMARY OF THE INVENTION

The present invention provides, inter alia, a compound of Formula I:

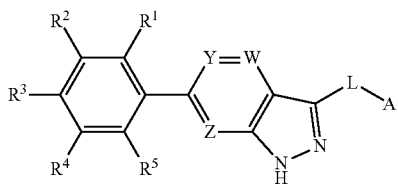

or a pharmaceutically acceptable salt thereof, wherein constituent variables are defined herein.

The present invention further provides a pharmaceutical composition comprising a compound of Formula I and at least one pharmaceutically acceptable carrier.

The present invention further provides a method of treating cancer in a patient comprising administering to the patient a therapeutically effective amount of a compound of Formula I, or a pharmaceutically acceptable salt thereof.

The present invention further provides a method of treating a myeloproliferative disorder in a patient comprising administering to the patient a therapeutically effective amount of a compound of Formula I, or a pharmaceutically acceptable salt thereof.

The present invention further provides a skeletal or chondrocyte disorder in a patient comprising administering to the patient a therapeutically effective amount of Formula I, or a pharmaceutically acceptable salt thereof.

The present invention further provides a compound of Formula I for use in therapy.

The present invention further provides use of a compound of Formula I in therapy.

The present invention further provides the use of a compound of Formula I for the preparation of a medicament for use in therapy.

DETAILED DESCRIPTION

The present invention provides an FGFR inhibitor of Formula I:

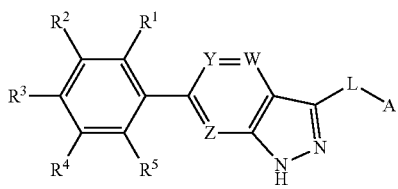

or a pharmaceutically acceptable salt thereof, wherein:
  W is N or $CR^6$;
  Y is N or $CR^7$;
  Z is N or $CR^8$;
  wherein one or two of W, Y, and Z is N;
  L is absent or selected from $C_{2-6}$ alkenylene, $C_{3-6}$ heteroalkenylene, $C_{2-6}$ alkynylene, and $C_{3-6}$ heteroalkynylene, wherein said $C_{2-6}$ alkenylene, $C_{3-6}$ heteroalkenylene, $C_{2-6}$ alkynylene, and $C_{3-6}$ heteroalkynylene are each optionally substituted with 1, 2, or 3 substituents independently selected from halo, CN, $NO_2$, $OR^a$, $C_{1-4}$ alkyl, $C_{1-4}$ haloalkyl, $C_{1-4}$ cyanoalkyl, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

A is selected from Formulas [aa], [bb], and [cc]:

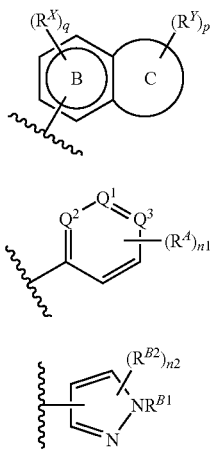

rings B and C in Formula [aa] together form a fused bicyclic heterocycle, wherein ring B is a six-membered aromatic ring selected from phenyl, pyridyl, pyrimidinyl, pyrazinyl, pyridazinyl, and triazinyl, wherein ring C is a 5- or 6-membered carbocycle or a 5- or 6-membered heterocycle, wherein 0, 1, or 2 ring-forming carbon or nitrogen atoms in ring C can be substituted by oxo, and wherein the fused bicyclic heterocycle comprising rings B and C is attached to L in Formula I via a ring atom in ring B;

$Q^1$, $Q^2$, and $Q^3$ are each independently selected from N and CH, wherein at least one of $Q^1$, $Q^2$, and $Q^3$ is CH;

each $R^X$ is a substituent on ring B and is independently selected from halo, $C_{1-4}$ alkyl, $C_{1-4}$ haloalkyl, and $C_{1-4}$ cyanoalkyl;

each $R^Y$ is a substituent on ring C and is independently selected from $C_{1-6}$ alkyl, $C_{1-6}$ haloalkyl, $Cy^1$, $OR^{a1}$, $C(O)R^{b1}$, $C(O)NR^{c1}R^{d1}$, $C(O)OR^{a1}$, $C(=NR^{e1})R^{b1}$, $NR^{e1})NR^{c1}R^{d1}$, $S(O)R^{b1}$, $S(O)NR^{c1}R^{d1}$, $S(O)_2R^{b1}$, and $S(O)_2NR^{c1}R^{d1}$, wherein said $C_{1-6}$ alkyl, is optionally substituted with 1, 2, 3, 4, or 5 substituents independently selected from $R^{Ya}$;

each $R^{Ya}$ is independently selected from $Cy^1$, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl of $R^{Ya}$ are each optionally substituted with 1, 2, or 3 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

each $R^A$ is independently selected from halo, $C_{1-6}$ alkyl, $C_{2-6}$ alkenyl, $C_{2-6}$ alkynyl, $Cy^2$, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(=NR^{e2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{2-6}$ alkenyl, and $C_{2-6}$ alkynyl are each optionally substituted with 1, 2, 3, 4, or 5 substituents independently selected from $R^{AZ}$;

each $R^{AZ}$ is independently selected from $Cy^2$, halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$, wherein said $C_{1-6}$ alkyl, $C_{2-6}$ alkenyl, and $C_{2-6}$ alkynyl of $R^{AZ}$ are each optionally substituted with 1, 2, or 3 substituents independently selected from $Cy^2$, halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

$R^{B1}$ is H, $C_{1-6}$ alkyl, $Cy^3$, $C(O)R^{b3}$, $C(O)NR^{c3}R^{d3}$, $C(O)OR^{a3}$, $C(=NR^{e3})R^{b3}$, or $C(=NR^{e3})NR^{c3}R^{d3}$; wherein said $C_{1-6}$ alkyl, is optionally substituted with 1, 2, 3, 4, or 5 substituents independently selected from $R^{BZ}$;

each $R^{BZ}$ is independently selected from $Cy^3$, halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$, wherein said $C_{1-6}$ alkyl, $C_{2-6}$ alkenyl, and $C_{2-6}$ alkynyl of $R^{BZ}$ are each optionally substituted with 1, 2, or 3 substituents independently selected from $Cy^3$, halo, CN, $NO_2$, $OR^{a3}$, $SR^{a3}$, $C(O)R^{b3}$, $C(O)NR^{c3}R^{d3}$, $c(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

each $R^{B2}$ is independently selected from halo, $C_{1-6}$ alkyl, $C_{2-6}$ alkenyl, $C_{2-6}$ alkynyl, $Cy^3$, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, and $C_{2-6}$ alkynyl are each optionally substituted with 1, 2, 3, 4, or 5 substituents independently selected from $R^{BZ}$;

$R^1$, $R^2$, $R^4$, and $R^5$ are each independently selected from halo, $C_{1-4}$ alkyl, $C_{1-4}$ haloalkyl, CN, $OR^{a4}$, $SR^{a4}$, $C(O)NR^{c4}R^{d4}$, $NR^{c4}R^{d4}$, $NR^{c4}C(O)R^{b4}$, $NR^{c4}S(O)R^{b4}$, $NR^{c4}S(O)_2R^{b4}$, $S(O)R^{b4}$, $S(O)NR^{c4}R^{d4}$, $S(O)_2R^{b4}$, and $S(O)_2NR^{c4}R^{d4}$; wherein said $C_{1-4}$ alkyl is optionally substituted with 1, 2, or 3 substituents independently selected from halo, CN, $OR^{a4}$, $SR^{a4}$, $C(O)NR^{c4}R^{d4}$, $NR^{c4}R^{d4}$, $NR^{c4}C(O)R^{b4}$, $NR^{c4}S(O)R^{b4}$, $NR^{c4}S(O)_2R^{b4}$, $S(O)R^{b4}$, $S(O)NR^{c4}R^{d4}$, $S(O)_2R^{b4}$, and $S(O)_2NR^{c4}R^{d4}$;

$R^3$ is H, halo, $C_{1-4}$ alkyl, $C_{1-4}$ haloalkyl, CN, $OR^{a4}$, $SR^{a4}$, $C(O)NR^{c4}R^{d4}$, $NR^{c4}R^{d4}$, $NR^{c4}C(O)R^{b4}$, $NR^{c4}S(O)R^{b4}$, $NR^{c4}S(O)_2R^{b4}$, $S(O)R^{b4}$, $S(O)NR^{c4}R^{d4}$, $S(O)_2R^{b4}$, and $S(O)_2NR^{c4}R^{d4}$; wherein said $C_{1-4}$ alkyl is optionally substituted with 1, 2, or 3 substituents independently selected from halo, CN, $OR^{a4}$, $SR^{a4}$, $C(O)NR^{c4}R^{d4}$, $NR^{c4}R^{d4}$, $NR^{c4}C(O)R^{b4}$, $NR^{c4}S(O)R^{b4}$, $NR^{c4}S(O)_2R^{b4}$, $S(O)R^{b4}$, $S(O)NR^{c4}R^{d4}$, $S(O)_2R^{b4}$, and $S(O)_2NR^{c4}R^{d4}$;

$R^6$, $R^7$, and $R^8$ are each independently selected from H, halo, $C_{1-4}$ alkyl, $C_{1-4}$ haloalkyl, and $C_{1-4}$ cyanoalkyl;

$Cy^1$, $Cy^2$, and $Cy^3$ are each independently selected from $C_{6-10}$ aryl, $C_{3-10}$ cycloalkyl, 5-10 membered heteroaryl, 4-10 membered heterocycloalkyl, each of which is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$, wherein said $C_{1-6}$ alkyl, $C_{2-6}$ alkenyl, $C_{2-6}$ alkynyl, $C_{3-10}$ cycloalkyl, 5-10 membered heteroaryl, and 4-10 membered heterocycloalkyl are each optionally substituted with 1, 2, or 3 substituents independently selected from halo, $C_{1-4}$ haloalkyl, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $C(=NR^{e5})NR^{c5}R^{d5}$, $NR^{c5}C(=NR^{e5})NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$;

each $R^a$, $R^b$, $R^c$, $R^d$, $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, $R^{d3}$, $R^{a5}$, $R^{b5}$, $R^{c5}$, and $R^{d5}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, or (4-10 membered heterocycloalkyl)-$C_{1-4}$ alkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl is optionally substituted with 1, 2, 3, 4, or 5 substituents independently selected from $C_{1-4}$ alkyl, $C_{1-4}$ haloalkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

each $R^{a4}$, $R^{b4}$, $R^{c4}$, and $R^{d4}$ is independently selected from H, $C_{1-4}$ alkyl, $C_{1-4}$ haloalkyl, $C_{1-4}$ hydroxyalkyl, and $C_{1-4}$ cyanoalkyl;

or any $R^c$ and $R^d$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, $C_{1-4}$ alkyl, $C_{1-4}$ haloalkyl, $C_{1-4}$ cyanoalkyl, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

or any $R^{c1}$ and $R^{d1}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 3-7 membered heterocycloalkyl, $C_{6-10}$ aryl, 5-6 membered heteroaryl, $C_{1-6}$ haloalkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, $C_{1-4}$ alkyl, $C_{1-4}$ haloalkyl, $C_{1-4}$ cyanoalkyl, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

or any $R^{c2}$ and $R^{d2}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, and 5-6 membered heteroaryl, $C_{1-6}$ haloalkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, $C_{1-4}$ alkyl, $C_{1-4}$ haloalkyl, $C_{1-4}$ cyanoalkyl, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

or any $R^{c3}$ and $R^{d3}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, $C_{1-4}$ alkyl, $C_{1-4}$ haloalkyl, $C_{1-4}$ cyanoalkyl, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

or any $R^{c5}$ and $R^{d5}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2$ NR$^{c6}$R$^{d6}$, and S(O)$_2$NR$^{c6}$R$^{d6}$, wherein said C$_{1-6}$ alkyl, C$_{3-7}$ cycloalkyl, 4-7 membered heterocycloalkyl, C$_{6-10}$ aryl, and 5-6 membered heteroaryl are optionally substituted by 1, 2, or 3 substituents independently selected from halo, C$_{1-4}$ alkyl, C$_{1-4}$ haloalkyl, C$_{1-4}$ cyanoalkyl, CN, OR$^{a6}$, SR$^{a6}$, C(O)R$^{b6}$, C(O)NR$^{c6}$R$^{d6}$, C(O)OR$^{a6}$, OC(O)R$^{b6}$, OC(O)NR$^{c6}$R$^{d6}$, NR$^{c6}$R$^{d6}$, NR$^{c6}$C(O)R$^{b6}$, NR$^{c6}$C(O)NR$^{c6}$R$^{d6}$, NR$^{c6}$C(O)OR$^{a6}$, C(=NR$^{e6}$)NR$^{c6}$R$^{d6}$, NR$^{c6}$C(=NR$^{e6}$)NR$^{c6}$R$^{d6}$, S(O)R$^{b6}$, S(O)NR$^{c6}$R$^{d6}$, S(O)$_2$R$^{b6}$, NR$^{c6}$S(O)$_2$R$^{b6}$, NR$^{c6}$S(O)$_2$NR$^{c6}$R$^{d6}$, and S(O)$_2$NR$^{c6}$R$^{d6}$;

each R$^{a6}$, R$^{b6}$, R$^{c6}$, and R$^{d6}$ is independently selected from H, C$_{1-4}$ alkyl, C$_{1-4}$ haloalkyl, C$_{2-4}$ alkenyl, and C$_{2-4}$ alkynyl, wherein said C$_{1-4}$ alkyl, C$_{2-4}$ alkenyl, and C$_{2-4}$ alkynyl, is optionally substituted with 1, 2, or 3 substituents independently selected from OH, CN, amino, halo, C$_{1-4}$ alkyl, C$_{1-4}$ alkoxy, C$_{1-4}$ alkylthio, C$_{1-4}$ alkylamino, di(C$_{1-4}$ alkyl)amino, C$_{1-4}$ haloalkyl, and C$_{1-4}$ haloalkoxy;

or any R$^{c6}$ and R$^{d6}$ together with the N atom to which they are attached form a 3-, 4-, 5-, 6-, or 7-membered heterocycloalkyl group optionally substituted with 1, 2, or 3 substituents independently selected from OH, CN, amino, halo, C$_{1-6}$ alkyl, C$_{1-4}$ alkoxy, C$_{1-4}$ alkylthio, C$_{1-4}$ alkylamino, di(C$_{1-4}$ alkyl)amino, C$_{1-4}$ haloalkyl, and C$_{1-4}$ haloalkoxy; and each R$^e$, R$^{e1}$, R$^{e2}$, R$^{e3}$, R$^{e5}$, and R$^{e6}$ is independently selected from H, C$_{1-4}$ alkyl, and CN;

n1 is 0, 1, 2, 3, 4, or 5;

n2 is 0, 1, or 2;

p is 0, 1, 2, or 3; and q is 0, 1, 2, or 3.

In some embodiments: W is CR$^6$; Y is N; and Z is N.

In some embodiments: W is CR$^6$; Y is N; and Z is CR$^8$.

In some embodiments: W is CR$^6$; Y is CR$^7$; and Z is N.

In some embodiments: W is N; Y is CR$^7$; and Z is CR$^8$.

In some embodiments, L is absent.

In some embodiments, L is selected from C$_{2-6}$ alkenylene, C$_{3-6}$ heteroalkenylene, C$_{2-6}$ alkynylene, and C$_{3-6}$ heteroalkynylene, wherein said C$_{2-6}$ alkenylene, C$_{3-6}$ heteroalkenylene, C$_{2-6}$ alkynylene, and C$_{3-6}$ heteroalkynylene are each optionally substituted with 1, 2, or 3 substituents independently selected from halo, CN, NO$_2$, OR$^a$, C$_{1-4}$ alkyl, C$_{1-4}$ haloalkyl, C$_{1-4}$ cyanoalkyl, C(O)NR$^c$R$^d$, C(O)OR$^a$, OC(O)R$^b$, OC(O)NR$^c$R$^d$, NR$^c$R$^d$, NR$^c$(O)R$^b$, NR$^c$(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$.

In some embodiments, L is selected from C$_{2-6}$ alkenylene and C$_{2-6}$ alkynylene, wherein said C$_{2-6}$ alkenylene and C$_{2-6}$ alkynylene are each optionally substituted with 1, 2, or 3 substituents independently selected from halo, CN, NO$_2$, OR$^a$, C$_{1-4}$ alkyl, C$_{1-4}$ haloalkyl, C$_{1-4}$ cyanoalkyl, C(O)NR$^c$R$^d$, C(O)OR$^a$, OC(O)R$^b$, OC(O)NR$^c$R$^d$, NR$^c$R$^d$, NR$^c$(O)R$^b$, NR$^c$(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$.

In some embodiments, L is selected from C$_{2-6}$ alkenylene and C$_{2-6}$ alkynylene.

In some embodiments, R$^3$ is H.

In some embodiments, R$^1$, R$^2$, R$^4$, and R$^5$ are each independently selected from halo, C$_{1-6}$ alkyl, C$_{1-6}$ haloalkyl, CN, and OR$^{a4}$.

In some embodiments, R$^1$, R$^2$, R$^4$, and R$^5$ are each independently selected from F, Cl, and methoxy.

In some embodiments, R$^1$ and R$^5$ are each independently selected from F and Cl, and R$^2$ and R$^4$ are each methoxy.

In some embodiments, R$^6$, R$^7$, and R$^8$ are each independently selected from H and halo.

In some embodiments, R$^6$, R$^7$, and R$^8$ are each H.

In some embodiments, A is a group represented by Formula [aa].

In some embodiments, Ring B is phenyl or pyridyl.

In some embodiments, Ring C is a 5-membered carbocycle or a 5-membered heterocycle.

In some embodiments, Ring C is a 6-membered carbocycle or a 6-membered heterocycle.

In some embodiments, Formula [aa] is a group having a structure selected from:

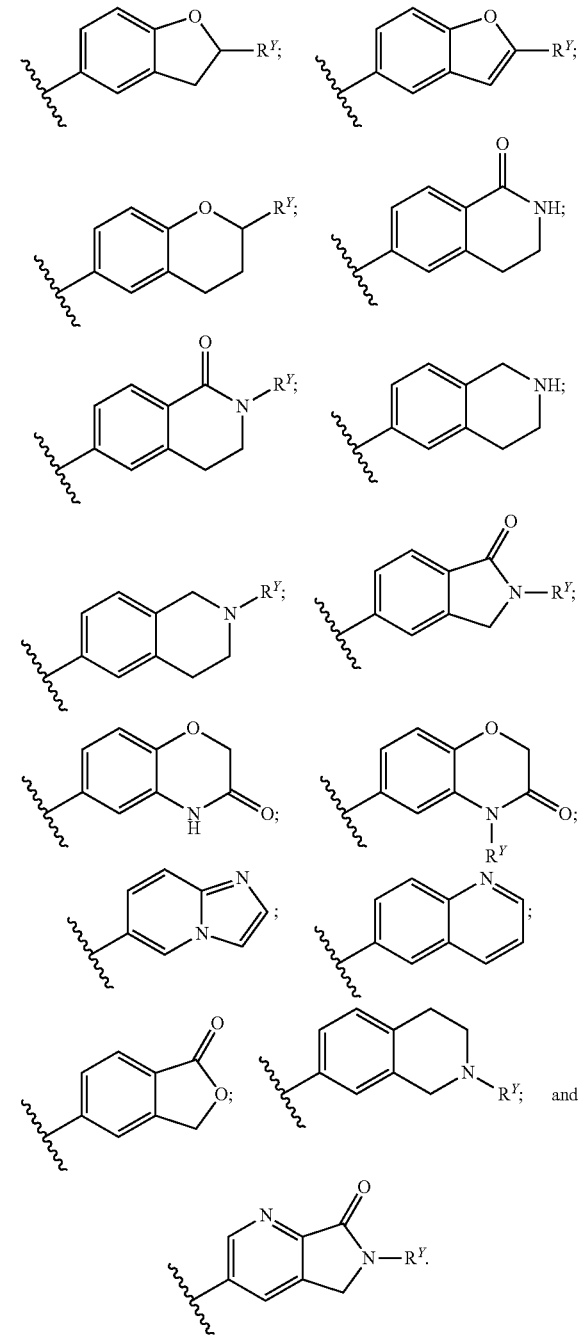

In some embodiments, each R$^Y$ is independently selected from C$_{1-6}$ alkyl, C$_{1-6}$ haloalkyl, Cy$^1$, C(O)NR$^{c1}$R$^{d1}$, C(O)

$OR^{a1}$, and $S(O)_2R^{b1}$, wherein said $C_{1-6}$ alkyl is optionally substituted with halo, CN, $OR^{a1}$, $NR^{c1}R^{d1}$, or $Cy^1$.

In some embodiments, each $R^Y$ is independently selected from $C_{1-6}$ alkyl, $Cy^1$, $C(O)NR^{c1}R^{d1}$, $C(O)OR^{a1}$, and $S(O)_2R^{b1}$, wherein said $C_{1-6}$ alkyl is optionally substituted with halo, $OR^{a1}$, $NR^{c1}R^{d1}$, or $Cy^1$.

In some embodiments:

each $R^Y$ is independently selected from $C_{1-6}$ alkyl, $C_{1-6}$ haloalkyl, $Cy^1$, $C(O)NR^{c1}R^{d1}$, $C(O)OR^{a1}$, and $S(O)_2R^{b1}$, wherein said $C_{1-6}$ alkyl is optionally substituted with halo, —CN, $OR^{a1}$, $NR^{c1}R^{d1}$, or $Cy^1$;

$Cy^1$ is $C_{3-6}$ cycloalkyl or 4-7 membered heterocycloalkyl, each of which is optionally substituted by 1 or 2 substituents independently selected from halo, $C_{1-6}$ alkyl, $C_{1-6}$ haloalkyl, hydroxy or $C_{1-6}$ alkoxy; and each $R^{a1}$, $R^{b1}$, $R^{c1}$, and $R^{d1}$ is independently selected from H, $C_{1-6}$ alkyl, and $C_{1-4}$ haloalkyl;

or any $R^{c1}$ and $R^{d1}$ together with the N atom to which they are attached form a 4-, 5-, 6-, or 7-membered heterocycloalkyl group optionally substituted with $C_{1-6}$ alkyl.

In some embodiments, each $R^Y$ is independently selected from dimethylaminocarbonyl, (4-methylpiperazinyl)carbonyl, methyl, ethyl, 2-propyl, methylsulfonyl, 4-hydroxycyclohexyl, cyclopropyl, methoxyethyl, tetrahydro-2H-pyran-4-yl, 2,2,2-trifluoroethyl, 2-hydroxy-1-methylethyl, 2-hydroxypropyl, 1-methylpiperidin-4-yl, dimethylaminoethyl, (1-methylpyrolidin-2-yl)ethyl, 1-cyanoethyl, and methoxycarbonyl.

In some embodiments, p is 0, 1, or 2.
In some embodiments, p is 0 or 1.
In some embodiments, p is 1.
In some embodiments, each $R^X$ is halo.
In some embodiments, each $R^X$ if F.
In some embodiments, q is 0.
In some embodiments, A is a group represented by Formula [bb].
In some embodiments, $Q^1$, $Q^2$, and $Q^3$ are each CH.
In some embodiments, $Q^1$ is N and $Q^2$, and $Q^3$ are each CH.
In some embodiments, $Q^1$ and $Q^2$ are both CH and $Q^3$ is N.

In some embodiments, each $R^4$ is independently selected from halo, $C_{1-6}$ alkyl, $Cy^2$, and $OR^{a2}$; wherein said $C_{1-6}$ alkyl is optionally substituted with 1, 2, or 3 substituents independently selected from R.

In some embodiments:

each $R^4$ is independently selected from halo, $C_{1-6}$ alkyl, $Cy^2$, and $OR^{a2}$, wherein said $C_{1-6}$ alkyl is optionally substituted with 1, 2, or 3 substituents independently selected from $R^{AZ}$;

$Cy^2$ is 4-7 membered heterocycloalkyl optionally substituted $C_{1-6}$ alkyl;

$R^{a2}$ is H or $C_{1-6}$ alkyl, wherein said $C_{1-6}$ alkyl is optionally substituted with 1 or 2 substituents independently selected from halo, CN, OH, $C_{1-4}$ alkyl, —$C(O)NH_2$, —$C(O)NH(C_{1-4}$ alkyl), —$C(O)N(C_{1-4}$ alkyl)$_2$, —$NH_2$, —$NH(C_{1-4}$ alkyl), —$N(C_{1-4}$ alkyl)$_2$; and $R^{AZ}$ is independently selected from halo, CN, OH, $C_{1-4}$ alkyl, —$C(O)NH_2$, —$C(O)NH(C_{1-4}$ alkyl), —$C(O)N(C_{1-4}$ alkyl)$_2$, —$NH_2$, —$NH(C_{1-4}$ alkyl), —$N(C_{1-4}$ alkyl)$_2$.

In some embodiments, each $R^4$ is independently selected from methoxy, 4-methylpiperazinyl, dimethylaminoethyloxy, methyl, dimethylaminocarbonylmethyloxy, fluoro, and 2-hydroxy-N,N-dimethylacetamide.

In some embodiments, n1 is 0, 1, or 2.
In some embodiments, A is a group represented by Formula [cc].
In some embodiments, A is a group represented by Formula [cc1]:

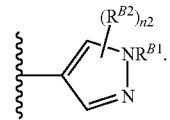

In some embodiments, $R^{B1}$ is $C_{1-6}$ alkyl optionally substituted with 1 or 2 substituents independently selected from $R^{BZ}$.

In some embodiments:

$R^{B1}$ is $C_{1-6}$ alkyl optionally substituted with 1 or 2 substituents independently selected from $R^{BZ}$;

$R^{BZ}$ is independently selected from halo, CN, —OH, $C_{1-4}$ alkoxy, and $C(O)NR^{c3}R^{d3}$; and each $R^{c3}$ and $R^{d3}$ is independently selected from H, $C_{1-6}$ alkyl, $C_{1-4}$ haloalkyl, $C_{1-3}$ alkoxy-$C_{1-6}$ alkyl, $C_{3-6}$ cycloalkyl, 1-methylpiperidinyl, and tetrahydro-2H-pyranyl;

or any $R^{c3}$ and $R^{d3}$ together with the N atom to which they are attached form a 4-, 5-, or 6-membered heterocycloalkyl group optionally substituted with 1 or 2 substituents independently selected from $C_{1-4}$ alkyl, halo, CN, —OH, $C_{1-4}$ alkoxy, —$NH_2$, —$NH(C_{1-4}$ alkyl), and —$N(C_{1-4}$ alkyl)$_2$.

In some embodiments, $R^{B1}$ is 1-cyanoethyl, methyl, methylaminocarbonylmethyl, dimethylaminocarbonylmethyl, cyclopropylaminocarbonylmethyl, (3-hydroxyazeditinyl)carbonylmethyl, morpholinocarbonylmethyl, (4-methylpyrazinyl)carbonylmethyl, (1-methylpiperidin-4-yl)aminocarbonylmethyl, (3-hydroxypyrolidinyl)carbonylmethyl, (3-dimethylaminopyrolidinyl)carbonylmethyl, (3-methoxypyrolidinyl)carbonylmethyl, methoxyethylaminocarbonylmethyl, (3-cyanopyrolidinyl)carbonylmethyl, (3-fluoropyrolidinyl)carbonylmethyl, hydroxyethyl, (tetrahydro-2H-pyran-2-yl)oxyethyl, 2-hydroxypropyl, 3-hydroxypropyl, or 2-hydroxyethyl.

In some embodiments, each $R^{BZ}$ is independently selected from CN, $OR^{a3}$, and $C(O)NR^{c3}R^{d3}$.

In some embodiments, n2 is 0.

In some embodiments, the compounds of the invention have Formula IIa, IIb, IIc, or IId:

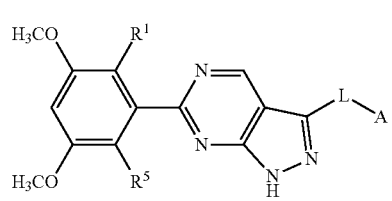

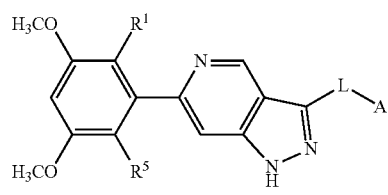

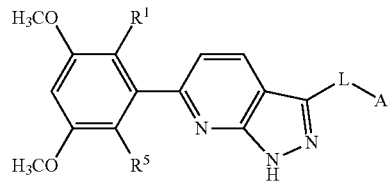

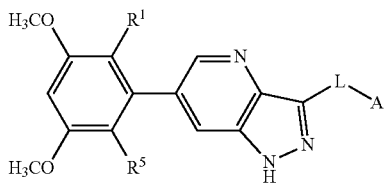

IId wherein R¹ and R⁵ are independently selected from F and Cl.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present specification various aryl, heteroaryl, cycloalkyl, and heterocycloalkyl rings are described. Unless otherwise specified, these rings can be attached to the rest of the molecule at any ring member as permitted by valency. For example, the term "pyridyl," "pyridinyl," or "a pyridine ring" may refer to a pyridin-2-yl, pyridin-3-yl, or pyridin-4-yl ring.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

For compounds of the invention in which a variable appears more than once, each variable can be a different moiety independently selected from the group defining the variable. For example, where a structure is described having two R groups that are simultaneously present on the same compound, the two R groups can represent different moieties independently selected from the group defined for R.

As used herein, the phrase "optionally substituted" means unsubstituted or substituted.

As used herein, the term "substituted" means that a hydrogen atom is replaced by a non-hydrogen group. It is to be understood that substitution at a given atom is limited by valency.

As used herein, the term "$C_{i-j}$", where i and j are integers, employed in combination with a chemical group, designates a range of the number of carbon atoms in the chemical group with i-j defining the range. For example, $C_{1-6}$ alkyl refers to an alkyl group having 1, 2, 3, 4, 5, or 6 carbon atoms.

As used herein, the term "alkyl", employed alone or in combination with other terms, refers to a saturated hydrocarbon group that may be straight-chain or branched. In some embodiments, the alkyl group contains 1 to 6, 1 to 4, or 1 to 3 carbon atoms. Examples of alkyl moieties include, but are not limited to, chemical groups such as methyl, ethyl, n-propyl, isopropyl, n-butyl, isobutyl, sec-butyl, tert-butyl, n-pentyl, 2-methyl-1-butyl, 3-pentyl, n-hexyl, 1,2,2-trimethylpropyl, and the like. In some embodiments, the alkyl group is methyl, ethyl, or propyl.

As used herein, "alkenyl", employed alone or in combination with other terms, refers to an alkyl group having one or more carbon-carbon double bonds. In some embodiments, the alkenyl moiety contains 2 to 6 or 2 to 4 carbon atoms. Example alkenyl groups include, but are not limited to, ethenyl, n-propenyl, isopropenyl, n-butenyl, sec-butenyl, and the like.

As used herein, "alkenylene", refers to a linking alkenyl group.

As used herein, "alkynyl", employed alone or in combination with other terms, refers to an alkyl group having one or more carbon-carbon triple bonds. Example alkynyl groups include, but are not limited to, ethynyl, propyn-1-yl, propyn-2-yl, and the like. In some embodiments, the alkynyl moiety contains 2 to 6 or 2 to 4 carbon atoms.

As used herein, "alkynylene" refers to a linking alkynyl group.

As used herein, "heteroalkenylene" refers to an alkenylene group wherein a methylene group in the alkenylene group is replaced with O, S, C(O), S(O), S(O)₂, NR, C(O)—O, C(O)—NR, S(O)—NR, or S(O)₂—NR group, wherein R is H, $C_{1-4}$ alkyl, $C_{1-4}$ haloalkyl, $C_{1-4}$ hydroxyalkyl, cyano-$C_{1-4}$ alkyl, cyclopropyl, or cyclopropyl-$C_{1-4}$ alkyl.

As used herein, "heteroalkynylene" refers to an alkynylene group wherein a methylene group in the alkynylene group is replaced with O, S, C(O), S(O), S(O)₂, NR, C(O)—O, C(O)—NR, S(O)—NR, or S(O)₂—NR group, wherein R is H, $C_{1-4}$ alkyl, $C_{1-4}$ haloalkyl, $C_{1-4}$ hydroxyalkyl, cyano-$C_{1-4}$ alkyl, cyclopropyl, or cyclopropyl-$C_{1-4}$ alkyl. An example heteroalkynylene group is —C≡C—CH₂—NH—C(O)—.

As used herein, "halo" or "halogen", employed alone or in combination with other terms, includes fluoro, chloro, bromo, and iodo. In some embodiments, halo is F or Cl.

As used herein, the term "haloalkyl", employed alone or in combination with other terms, refers to an alkyl group having up to the full valency of halogen atom substituents, which may either be the same or different. In some embodiments, the halogen atoms are fluoro atoms. In some embodiments, the alkyl group has 1 to 6 or 1 to 4 carbon atoms. Example haloalkyl groups include $CF_3$, $C_2F_5$, $CHF_2$, $CCl_3$, $CHCl_2$, $C_2Cl_5$, and the like.

As used herein, the term "cyanoalkyl", employed alone or in combination with other terms, refers to an alkyl group substituted by a cyano group.

As used herein, the term "alkoxy", employed alone or in combination with other terms, refers to a group of formula —O-alkyl. Example alkoxy groups include methoxy, ethoxy, propoxy (e.g., n-propoxy and isopropoxy), t-butoxy, and the like. In some embodiments, the alkyl group has 1 to 6 or 1 to 4 carbon atoms.

As used herein, "haloalkoxy", employed alone or in combination with other terms, refers to a group of formula —O-(haloalkyl). In some embodiments, the alkyl group has 1 to 6 or 1 to 4 carbon atoms. An example haloalkoxy group is —OCF₃.

As used herein, "amino", employed alone or in combination with other terms, refers to NH₂.

As used herein, the term "alkylamino", employed alone or in combination with other terms, refers to a group of formula —). In some embodiments, the alkylamino group has 1 to 6 or 1 to 4 carbon atoms. Example alkylamino groups include methylamino, ethylamino, propylamino (e.g., n-propylamino and isopropylamino), and the like.

As used herein, the term "dialkylamino", employed alone or in combination with other terms, refers to a group of formula —N(alkyl)$_2$. Example dialkylamino groups include dimethylamino, diethylamino, dipropylamino (e.g., di(n-propyl)amino and di(isopropyl)amino), and the like. In some embodiments, each alkyl group independently has 1 to 6 or 1 to 4 carbon atoms.

As used herein, the term "alkylthio", employed alone or in combination with other terms, refers to a group of formula —S-alkyl. In some embodiments, the alkyl group has 1 to 6 or 1 to 4 carbon atoms.

As used herein, the term "cycloalkyl", employed alone or in combination with other terms, refers to a non-aromatic cyclic hydrocarbon including cyclized alkyl and alkenyl groups. Cycloalkyl groups can include mono- or polycyclic (e.g., having 2, 3, or 4 fused, bridged, or spiro rings) ring systems. Also included in the definition of cycloalkyl are moieties that have one or more aromatic rings (e.g., aryl or heteroaryl rings) fused (i.e., having a bond in common with) to the cycloalkyl ring, for example, benzo derivatives of cyclopentane, cyclohexene, cyclohexane, and the like, or pyrido derivatives of cyclopentane or cyclohexane. Ring-forming carbon atoms of a cycloalkyl group can be optionally substituted by oxo. Cycloalkyl groups also include cycloalkylidenes. The term "cycloalkyl" also includes bridgehead cycloalkyl groups (e.g., non-aromatic cyclic hydrocarbon moieties containing at least one bridgehead carbon, such as admantan-1-yl) and spirocycloalkyl groups (e.g., non-aromatic hydrocarbon moieties containing at least two rings fused at a single carbon atom, such as spiro[2.5]octane and the like). In some embodiments, the cycloalkyl group has 3 to 10 ring members, or 3 to 7 ring members. In some embodiments, the cycloalkyl group is monocyclic or bicyclic. In some embodiments, the cycloalkyl group is monocyclic. In some embodiments, the cycloalkyl group is a $C_{3-7}$ monocyclic cycloalkyl group. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, tetrahydronaphtalenyl, octahydronaphthalenyl, indanyl, and the like. In some embodiments, the cycloalkyl group is cyclopropyl, cyclobutyl, cyclopentyl, or cyclohexyl.

As used herein, the term "cycloalkylalkyl", employed alone or in combination with other terms, refers to a group of formula cycloalkyl-alkyl-. In some embodiments, the alkyl portion has 1 to 4, 1 to 3, 1 to 2, or 1 carbon atom(s). In some embodiments, the alkyl portion is methylene. In some embodiments, the cycloalkyl portion has 3 to 10 ring members or 3 to 7 ring members. In some embodiments, the cycloalkyl group is monocyclic or bicyclic. In some embodiments, the cycloalkyl portion is monocyclic. In some embodiments, the cycloalkyl portion is a $C_{3-7}$ monocyclic cycloalkyl group.

As used herein, the term "heterocycloalkyl", employed alone or in combination with other terms, refers to a non-aromatic ring or ring system, which may optionally contain one or more alkenylene or alkynylene groups as part of the ring structure, which has at least one heteroatom ring member independently selected from nitrogen, sulfur, oxygen, and phosphorus. Heterocycloalkyl groups can include mono- or polycyclic (e.g., having 2, 3 or 4 fused, bridged, or spiro rings) ring systems. In some embodiments, the heterocycloalkyl group is a monocyclic or bicyclic group having 1, 2, 3, or 4 heteroatoms independently selected from nitrogen, sulfur and oxygen. Also included in the definition of heterocycloalkyl are moieties that have one or more aromatic rings (e.g., aryl or heteroaryl rings) fused (i.e., having a bond in common with) to the non-aromatic heterocycloalkyl ring, for example, 1,2,3,4-tetrahydro-quinoline and the like. Heterocycloalkyl groups can also include bridgehead heterocycloalkyl groups (e.g., a heterocycloalkyl moiety containing at least one bridgehead atom, such as azaadmantan-1-yl and the like) and spiroheterocycloalkyl groups (e.g., a heterocycloalkyl moiety containing at least two rings fused at a single atom, such as [1,4-dioxa-8-aza-spiro[4.5]decan-N-yl] and the like). In some embodiments, the heterocycloalkyl group has 3 to 10 ring-forming atoms, or about 3 to 8 ring forming atoms. In some embodiments, the heterocycloalkyl group has 2 to 20 carbon atoms, 2 to 15 carbon atoms, 2 to 10 carbon atoms, or about 2 to 8 carbon atoms. In some embodiments, the heterocycloalkyl group has 1 to 5 heteroatoms, 1 to 4 heteroatoms, 1 to 3 heteroatoms, or 1 to 2 heteroatoms. The carbon atoms or heteroatoms in the ring(s) of the heterocycloalkyl group can be oxidized to form a carbonyl, an N-oxide, or a sulfonyl group (or other oxidized linkage) or a nitrogen atom can be quaternized. In some embodiments, the heterocycloalkyl portion is a $C_{2-7}$ monocyclic heterocycloalkyl group. In some embodiments, the heterocycloalkyl group is a morpholine ring, pyrrolidine ring, piperazine ring, piperidine ring, tetrahydropyran ring, tetrahyropyridine, azetidine ring, tetrahydrofuran ring, indoline ring, pyrrolidinone ring, piperazinone ring, piperidinone ring, or indolinone ring.

As used herein, the term "heterocycloalkylalkyl", employed alone or in combination with other terms, refers to a group of formula heterocycloalkyl-alkyl-. In some embodiments, the alkyl portion has 1 to 4, 1 to 3, 1 to 2, or 1 carbon atom(s). In some embodiments, the alkyl portion is methylene. In some embodiments, the heterocycloalkyl portion has 3 to 10 ring members or 3 to 7 ring members. In some embodiments, the heterocycloalkyl group is monocyclic or bicyclic. In some embodiments, the heterocycloalkyl portion is monocyclic. In some embodiments, the heterocycloalkyl portion is a $C_{2-7}$ monocyclic heterocycloalkyl group.

As used herein, the term "aryl", employed alone or in combination with other terms, refers to a monocyclic or polycyclic (e.g., having 2 fused rings) aromatic hydrocarbon moiety, such as, but not limited to, phenyl, 1-naphthyl, 2-naphthyl, and the like. In some embodiments, aryl groups have from 6 to 10 carbon atoms or 6 carbon atoms. In some embodiments, the aryl group is a monocyclic or bicyclic group. In some embodiments, the aryl group is phenyl or naphthyl.

As used herein, the term "arylalkyl", employed alone or in combination with other terms, refers to a group of formula aryl-alkyl-. In some embodiments, the alkyl portion has 1 to 4, 1 to 3, 1 to 2, or 1 carbon atom(s). In some embodiments, the alkyl portion is methylene. In some embodiments, the aryl portion is phenyl. In some embodiments, the aryl group is a monocyclic or bicyclic group. In some embodiments, the arylalkyl group is benzyl.

As used herein, the term "heteroaryl", employed alone or in combination with other terms, refers to a monocyclic or polycyclic (e.g., having 2 or 3 fused rings) aromatic hydrocarbon moiety, having one or more heteroatom ring members independently selected from nitrogen, sulfur and oxygen. In some embodiments, the heteroaryl group is a monocyclic or bicyclic group having 1, 2, 3, or 4 heteroatoms independently selected from nitrogen, sulfur and oxygen. Example heteroaryl groups include, but are not limited to, pyridyl, pyrimidinyl, pyrazinyl, pyridazinyl, triazinyl, furyl, thienyl, imidazolyl, thiazolyl, indolyl, pyrryl, oxazolyl, benzofuryl, benzothienyl, benzthiazolyl, benzodioxolyl, isoxazolyl, pyrazolyl, triazolyl, tetrazolyl, indazolyl, 1,2,4-thiadiazolyl, isothiazolyl, purinyl, carbazolyl, benzimidazolyl, pyrrolyl, azolyl, quinolinyl, isoquinolinyl, benzisoxazolyl, imidazo[1,2-b]thiazolyl, pyridopyrazinyl, or the like. The carbon atoms or heteroatoms in the ring(s) of the heteroaryl group can be oxidized to form a carbonyl, an N-oxide, or a sulfonyl group (or other oxidized linkage) or a nitrogen atom can be quaternized, provided the aromatic nature of the ring is preserved. In some embodiments, the heteroaryl group has from 3 to 10 carbon atoms, from 3 to 8 carbon atoms, from 3 to 5 carbon atoms, from 1 to 5 carbon atoms, or from 5 to 10 carbon atoms. In some embodiments, the heteroaryl group contains 3 to 14, 4 to 12, 4 to 8, 9 to 10, or 5 to 6 ring-forming atoms. In some embodiments, the heteroaryl group has 1 to 4, 1 to 3, or 1 to 2 heteroatoms.

As used herein, the term "heteroarylalkyl", employed alone or in combination with other terms, refers to a group of formula heteroaryl-alkyl-. In some embodiments, the alkyl portion has 1 to 4, 1 to 3, 1 to 2, or 1 carbon atom(s). In some embodiments, the alkyl portion is methylene. In some embodiments, the heteroaryl portion is a monocyclic or bicyclic group having 1, 2, 3, or 4 heteroatoms independently selected from nitrogen, sulfur and oxygen. In some embodiments, the heteroaryl portion has 5 to 10 carbon atoms.

As used herein, the term "carbocycle" refers to an aryl group or a cycloalkyl group.

As used herein, the term "heterocycle" refers to a heteroaryl group or a heterocycloalkyl group.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Other resolving agents suitable for fractional crystallization methods include stereoisomerically pure forms of methylbenzyl-amine (e.g., S and R forms, or diastereomerically pure forms), 2-phenylglycinol, norephedrine, ephedrine, N-methylephedrine, cyclohexylethylamine, 1,2-diaminocyclohexane, and the like. Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention also include all isotopes of atoms occurring in the intermediates or final compounds. Isotopes include those atoms having the same atomic number but different mass numbers. For example, isotopes of hydrogen include tritium and deuterium.

The term, "compound," as used herein is meant to include all stereoisomers, geometric isomers, tautomers, and isotopes of the structures depicted.

All compounds, and pharmaceutically acceptable salts thereof, can be found together with other substances such as water and solvents (e.g., in the form of hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences*, 17th ed., Mack Publishing Company, Easton, Pa., 1985, p. 1418 and Berge et al., *Journal of Pharmaceutical Science*, 66, 2 (1977), each of which is incorporated herein by reference in its entirety.

Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in P. G. M. Wuts and T. W. Greene, *Greene's Protective Groups in Organic Synthesis,* 4rd. Ed., Wiley & Sons, Inc., New Jersey (2007), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), or mass spectrometry, or by chromatography such as high performance liquid chromatography (HPLC) or thin layer chromatography.

Compounds of the invention can be prepared according to numerous preparatory routes known in the literature. Example synthetic methods for preparing compounds of the invention are provided in the Schemes below.

A series of bicyclic pyrazole derivatives 6 can be prepared by the methods outlined in Scheme 1. Introduction of a protecting group PG (PG=THP, Boc or Cbz etc. . . . ) to compound 1 can provide the corresponding compound 2. Suzuki coupling of 2 with a boronic acid or ester ArB(OR')$_2$ (R'=H or alkyl and Ar=aryl or heteroaryl, such as phenyl substituted by R$^1$-R$^5$ as in Formula I) can provide the pyrazole derivative 3. Removal of the protecting group in 3 (PG=THP or Boc) under acid conditions or (PG=Cbz) catalytic hydrogenation in the presence of a catalyst such as Pd/C or Pd(OH)$_2$/C affords the compound 4. Halogenation of the compound 4 with NIS (N-iodosuccinimide), NBS (N-bromosuccinimide) or NCS (N-chlorosuccinimide) can yield the corresponding pyrazole halide 5 (X=I, Br or Cl), which can be further converted to the desired pyrazole derivatives 6 by Suzuki coupling with a boronic acid or ester CyB(OR")$_2$ (R"=H or alkyl, Cy=cyclic moiety such as A in Formula I).

Scheme 1

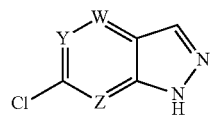

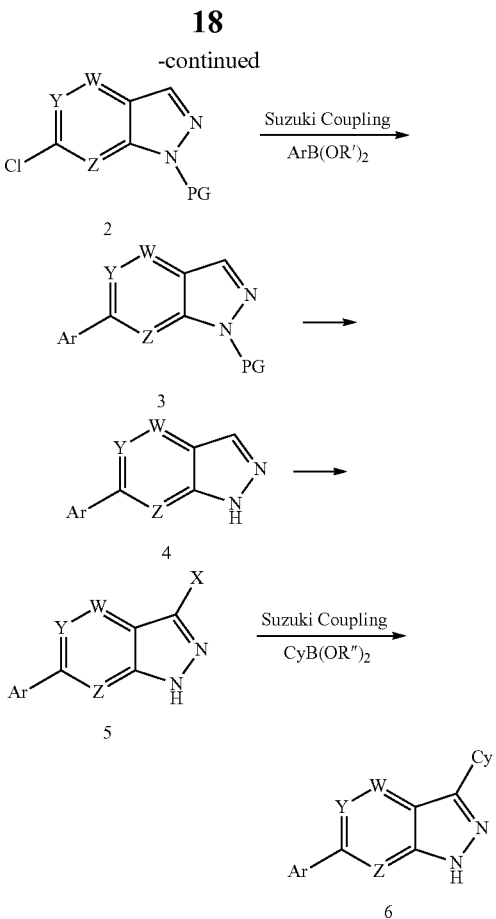

Alternatively, a series of bicyclic pyrazole derivatives 3 can be prepared according to the procedure outlined in Scheme 2. The pyrazole derivatives 3 can be obtained by Stille coupling of ArX (X=I, Br, Cl or OTf) with tributyltin compound 7 can be prepared by palladium catalyzed reaction with Bu$_3$SnSnBu$_3$.

Scheme 2

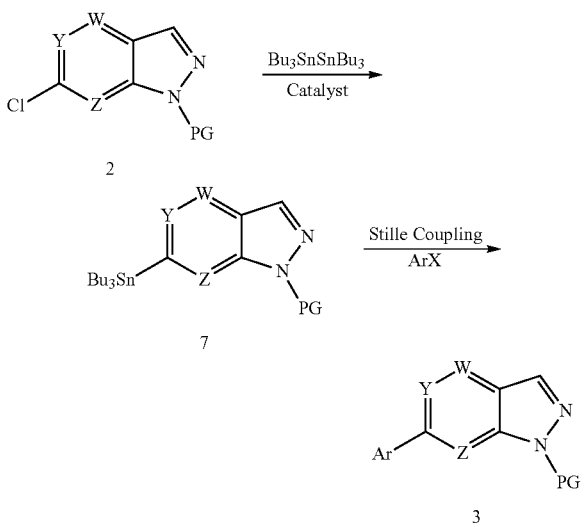

A series of aryl halide ArX (X=I, Br, Cl) 13 or aryl boronic acid or ester ArB(OR')$_2$ (R'=H or alkyl) derivatives 14 can be prepared according to the procedures described in Scheme 3. Displacement of fluorine in compound 8 with benzylamine provides the aniline 9 which can be converted to bis-ether by reacting with a suitable sodium alkoxide (NaOR where R is, e.g., methyl, alkyl). The following saponification can provide acid 10. Decarboxylation of benzoic acid 10, followed by hydrogenation using Pd(OH)$_2$/C can afford aniline 12. Aniline derivatives 12 can be converted to the corresponding halide ArX (X=I, Br, Cl) 13 under standard Sandmeyer reaction conditions (e. g., aniline 13 reacts with sodium nitrite and hydrogen chloride to form an aryl diazonium salt, which was substituted by an halide ion in the presence of copper (I) bromide or potassium iodide to form the desired aryl halide). The halide 13 can be transferred to the corresponding aryl boronic acid or ester 14.

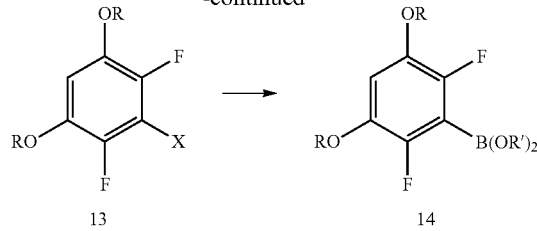

A series of aniline derivatives 18 can be prepared according to the procedures outlined in Scheme 4. Compound 16 can be obtained by treatment of the aniline 15 (where R=methyl or alkyl) with acetic anhydride or acetyl chloride at low temperature. Treatment of compound 16 with sulfuryl chloride can afford compound 17 which can be then converted to the aniline derivatives 18 by removal of the acetyl group under basic conditions.

Scheme 3

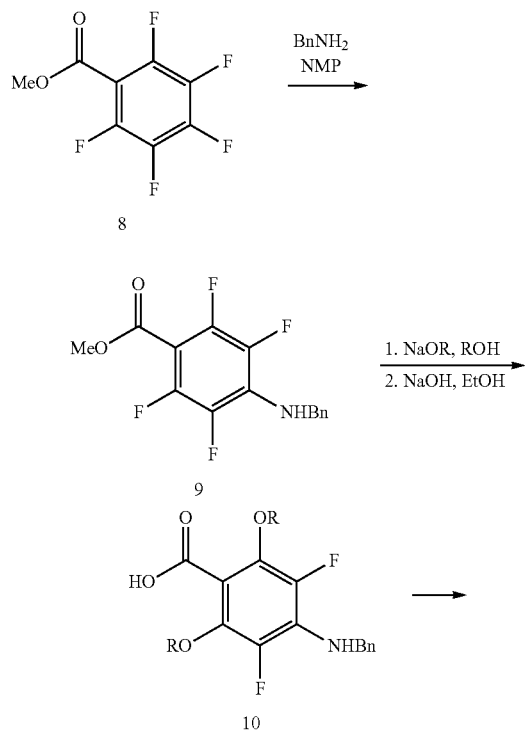

Scheme 4

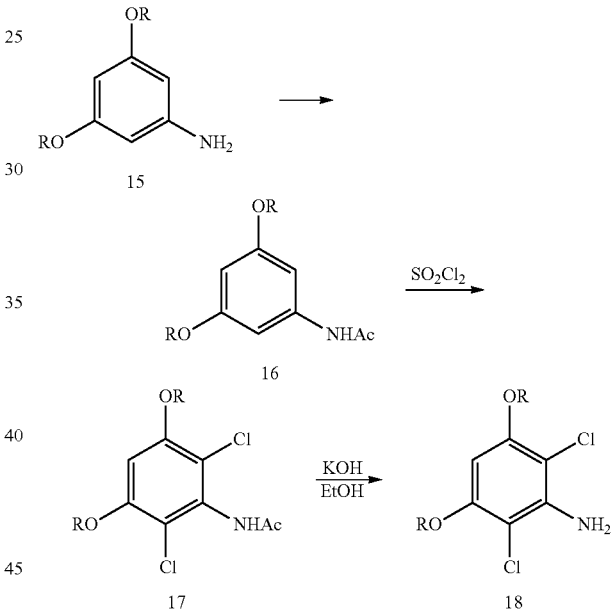

A series of aniline derivatives 21 can be prepared according to the procedures outlined in Scheme 5. Treatment of compound 16 with Selectfluor® can provide the desired monofluoride 19 which can then be converted to compound 20 by treating with sulfuryl chloride. The acetyl group of 20 can be removed under basic conditions to give the aniline derivatives 21.

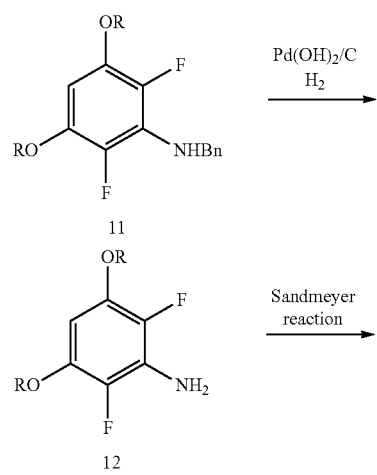

Scheme 5

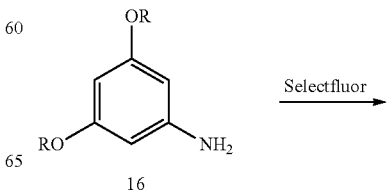

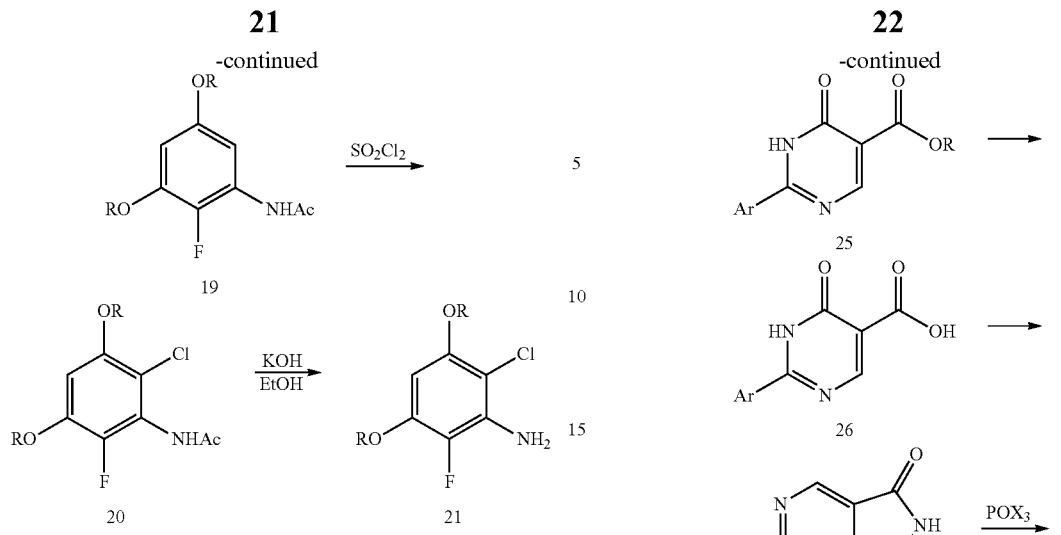

A series of aryl boronic ester derivatives 23 can be prepared according to the procedures outlined in Scheme 6. Treatment of aryl boronic ester 22 with sulfuryl chloride can afford the corresponding aryl boronic ester 23.

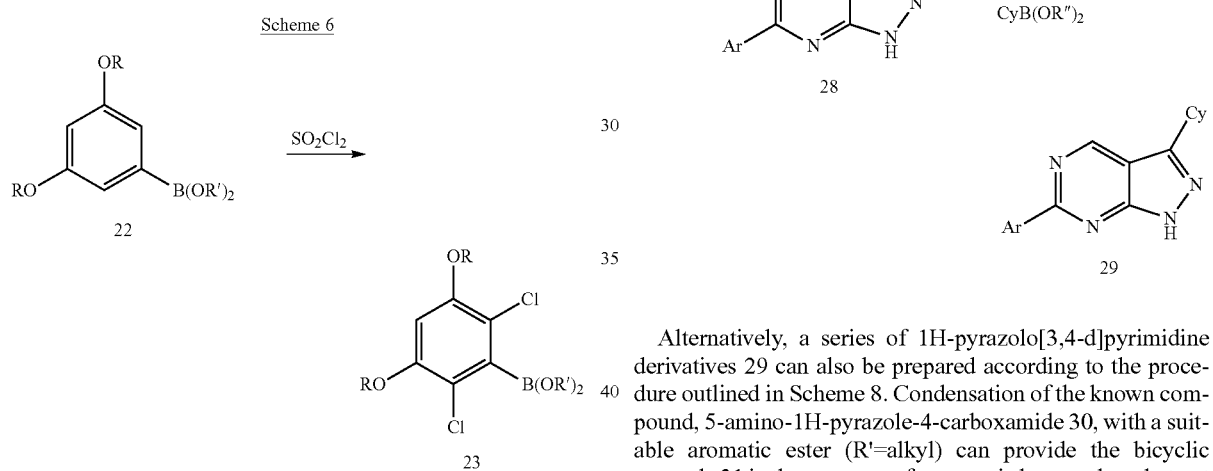

A series of 1H-pyrazolo[3,4-d]pyrimidine derivatives 29 can be prepared according to the procedure outlined in Scheme 7. Cycloaddition of aryl carboximidamide with dialkyl 2-(alkoxymethylene)malonate 24 (R=alkyl) can give the pyrimidinone carboxylate 25 which can be transferred to the corresponding acid 26 by saponification. Treatment of 26 with a chlorinating agent such as $POCl_3$, $PCl_5$ or $SOCl_2$ followed by reaction with hydrazine can provide the bicyclic derivative 27 which can be converted to the corresponding halide 28 upon treatment with $POX_3$ (X=Br or Cl) or $SOCl_2$. Suzuki coupling of 28 with a boronic acid or ester $CyB(OR'')_2$ can afford the compound 29.

Alternatively, a series of 1H-pyrazolo[3,4-d]pyrimidine derivatives 29 can also be prepared according to the procedure outlined in Scheme 8. Condensation of the known compound, 5-amino-1H-pyrazole-4-carboxamide 30, with a suitable aromatic ester (R'=alkyl) can provide the bicyclic pyrazole 31 in the presence of an organic base such as, but not limited to, NaH, NaOBu-t, NaOEt, KOBu-t in an appropriate solvent such as, but not limited to, ethanol, isopropyl alcohol, n-butanol. Treatment of compound 31 with a chlorinating agent such as $POCl_3$, $PCl_5$ or $SOCl_2$ can afford the corresponding chloride 32 which can be converted to the 1H-pyrazolo[3,4-d]pyrimidine derivative 33 by using a reducing agent such as Sn or Zn. Compound 33 can be transferred to the desired 1H-pyrazolo[3,4-d]pyrimidine derivative 29 by reaction with a suitable halogenating agent such as NIS, NBS or NCS followed by the Suzuki coupling with a suitable boronic acid or ester as described in Scheme 1.

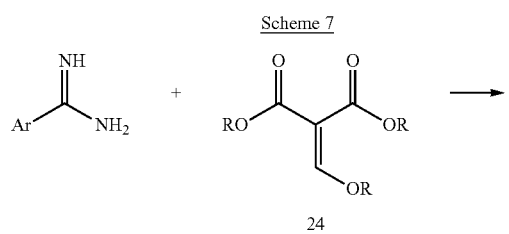

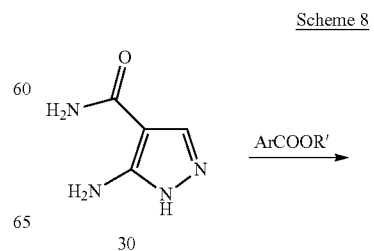

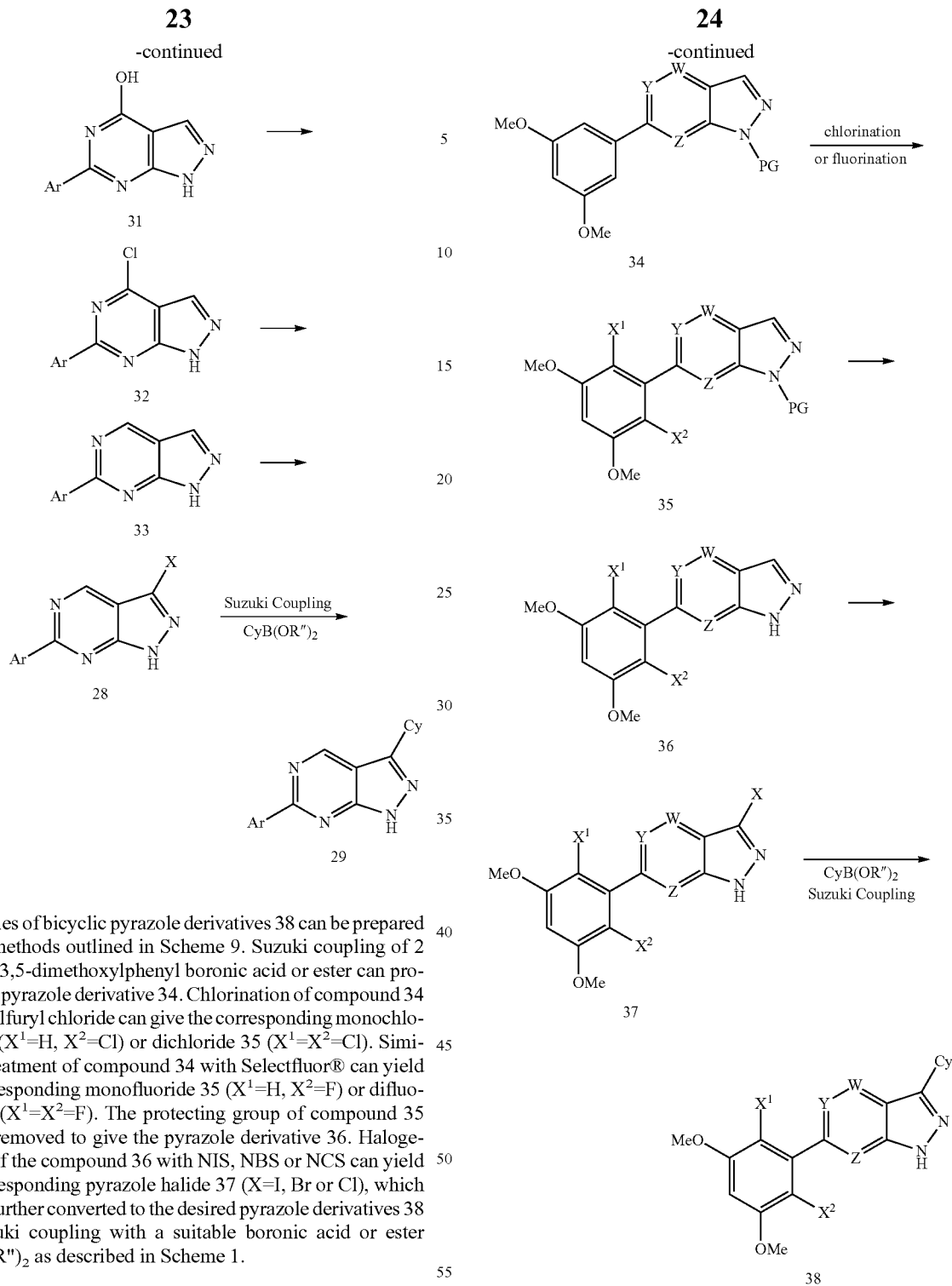

A series of bicyclic pyrazole derivatives 38 can be prepared by the methods outlined in Scheme 9. Suzuki coupling of 2 with an 3,5-dimethoxylphenyl boronic acid or ester can provide the pyrazole derivative 34. Chlorination of compound 34 using sulfuryl chloride can give the corresponding monochloride 35 ($X^1$=H, $X^2$=Cl) or dichloride 35 ($X^1$=$X^2$=Cl). Similarly, treatment of compound 34 with Selectfluor® can yield the corresponding monofluoride 35 ($X^1$=H, $X^2$=F) or difluoride 35 ($X^1$=$X^2$=F). The protecting group of compound 35 can be removed to give the pyrazole derivative 36. Halogenation of the compound 36 with NIS, NBS or NCS can yield the corresponding pyrazole halide 37 (X=I, Br or Cl), which can be further converted to the desired pyrazole derivatives 38 by Suzuki coupling with a suitable boronic acid or ester CyB(OR")$_2$ as described in Scheme 1.

Scheme 9

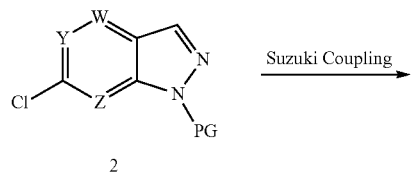

Alternatively, a series of bicyclic pyrazole derivatives 43 can be prepared by the methods outlined in Scheme 10. Compound 34 can be prepared using procedures as described in the Scheme 9. As described above, treatment of compound 34 with Selectfluor® can yield the corresponding monofluoride 39. Chlorination of the fluoride 39 with sulfuryl chloride, followed by the removal of the protecting group PG can afford the pyrazole derivatives 41 which can be transferred to the final product 43 by halogenation and Suzuki coupling reactions as described in Schemes 1 and 9.

Scheme 10

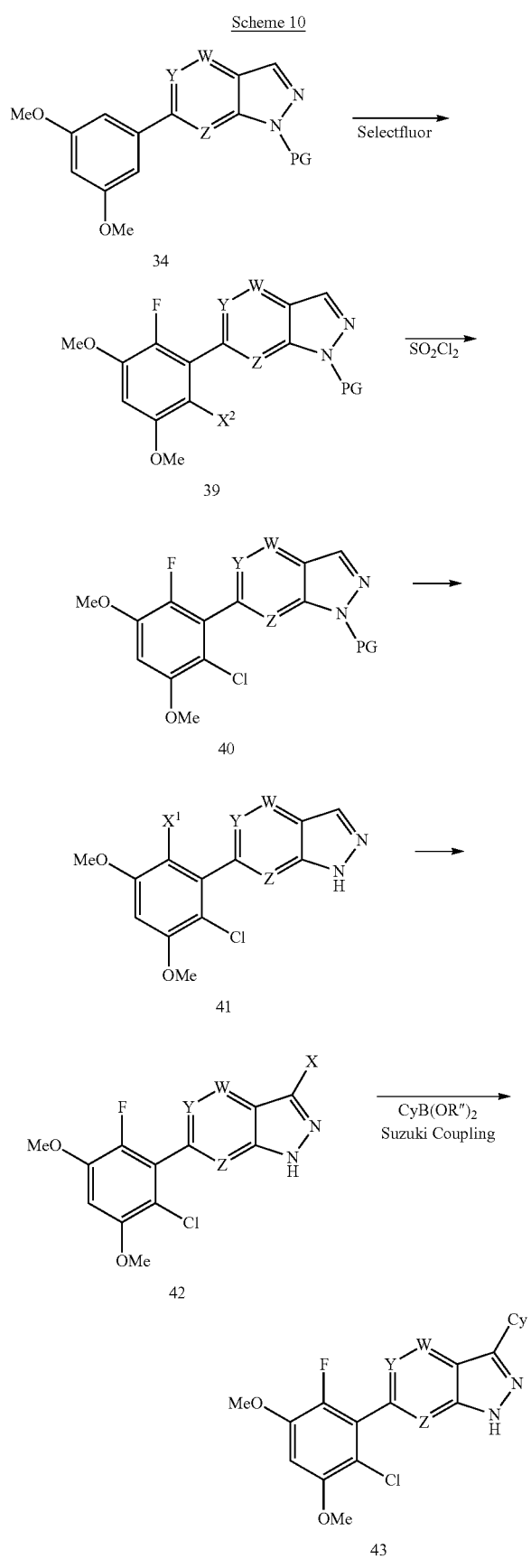

A series of bicyclic pyrazole derivatives 46 can be prepared by the methods outlined in Scheme 11. Cross coupling of a suitable substituted vinyl derivative 44 (L' is absent or selected from $C_{1-4}$ alkylene and $C_{1-4}$ heteroalkylene; A is selected from Formulas [aa], [bb], and [cc]) with pyrazole halide 43 (X=I, Br or Cl; PG=THP, Boc or Cbz etc. . . . ) in the presence of a suitable transition metal catalyst and a suitable base under Heck reaction conditions can afford the corresponding product 45. Removal of the protecting group in 45 (PG=THP or Boc or trityl) under acid conditions affords the compound 46.

Scheme 11

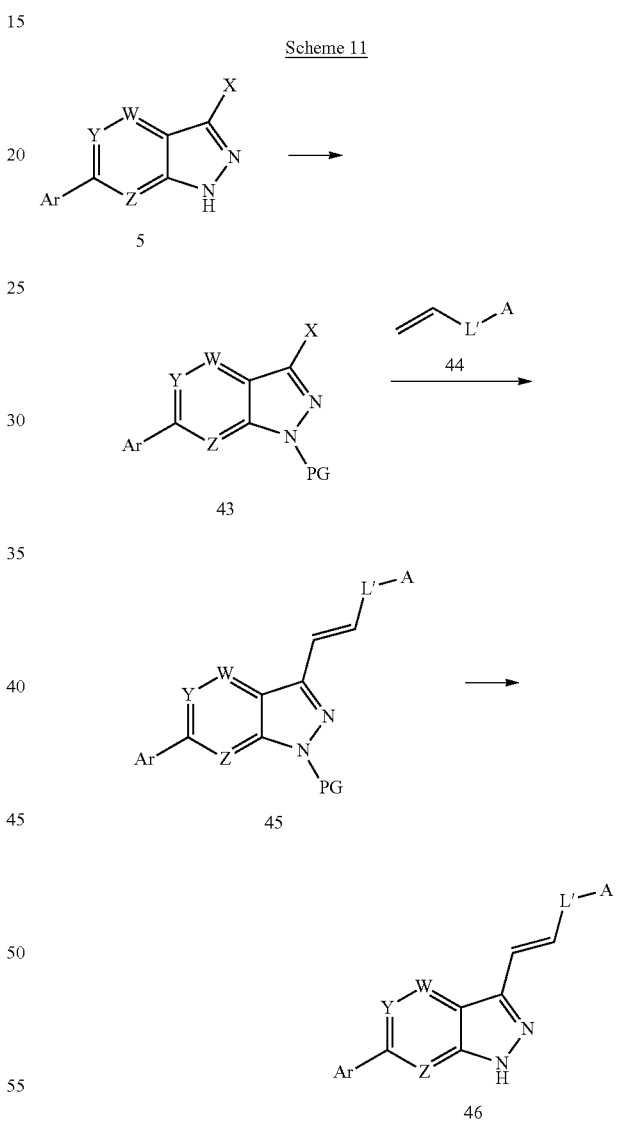

A series of bicyclic pyrazole derivatives 50 can be prepared by the methods outlined in Scheme 12. Suzuki coupling of 43 with a vinyl boronic ester 47 can provide the vinyl pyrazole derivative 48. Heck reaction of 48 with a suitable halide CyX (X=I or Br) under Heck reaction conditions can yield compound 49 which can be transferred to the pyrazole derivative 50 by removal of the protecting group under the conditions as described previously.

Scheme 12

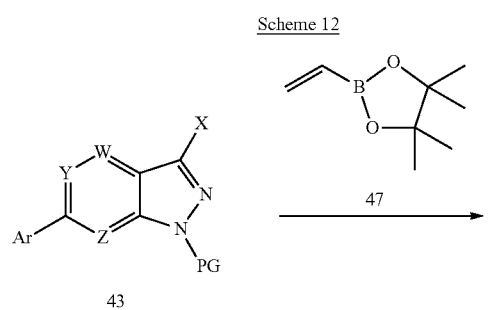

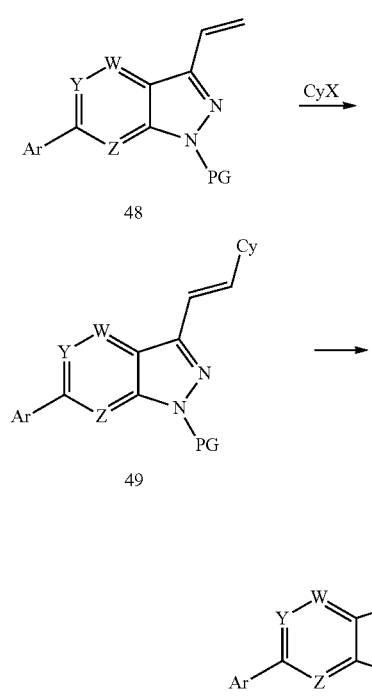

Similarly, a series of alkynylene pyrazole derivatives 53 can be prepared by the methods outlined in Scheme 13. Cross coupling of a suitable substituted ethynyl derivative 51 (L' is absent or selected from $C_{1-4}$ alkylene and $C_{1-4}$ heteroalkylene; A is selected from Formulas [aa], [bb], and [cc]) with pyrazole halide 43 (X=I, Br or Cl; PG=THP, Boc or Cbz etc. . . . ) in the presence of a suitable transition metal catalyst, CuI and a suitable base under Sonogashira reaction conditions can afford the corresponding compound 52 which can be transformed to the pyrazole derivative 53 by removal of the protecting group under the conditions as described previously.

Scheme 13

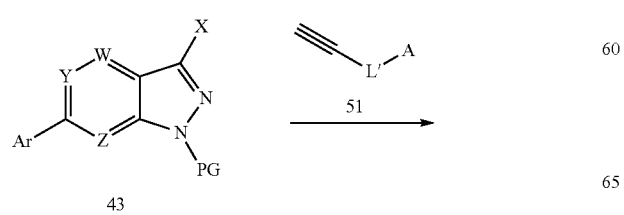

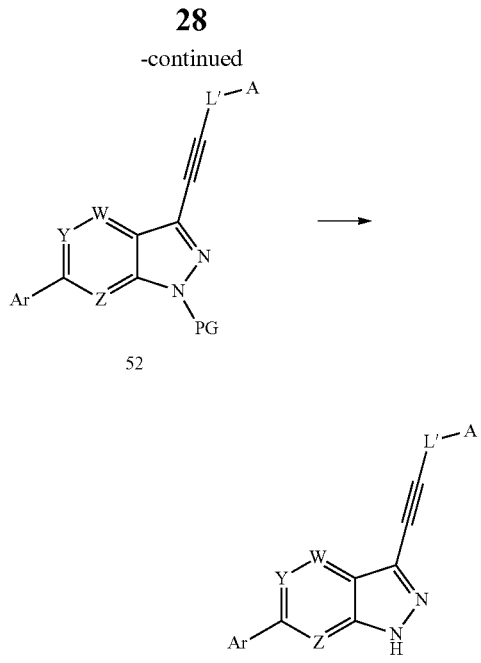

A series of ethynylene pyrazole derivatives 56 can be prepared by the methods outlined in Scheme 14. Suzuki coupling of 43 with ethynyltrimethylsilane can provide the ethynyl pyrazole derivative 54. Coupling of 54 with a suitable halide CyX (X=I or Br) under Sonogashira reaction conditions can yield compound 55 which can be transferred to the pyrazole derivative 56 by removal of the protecting group under the conditions as described previously.

Scheme 14

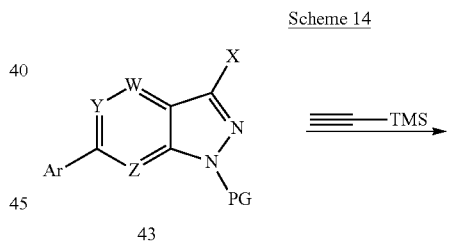

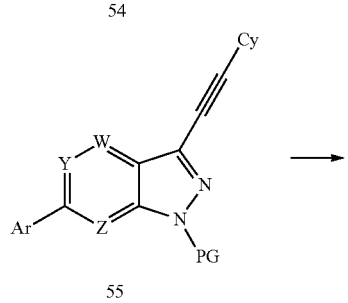

-continued

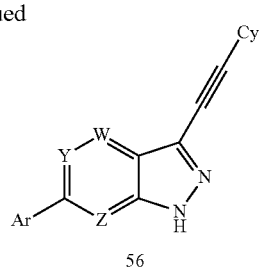

56

Methods of Use

Compounds of the invention can inhibit activity of one or more FGFR enzymes. For example, the compounds of the invention can be used to inhibit activity of an FGFR enzyme in a cell or in an individual or patient in need of inhibition of the enzyme by administering an inhibiting amount of a compound of the invention to the cell, individual, or patient.

In some embodiments, the compounds of the invention are inhibitors of one or more of FGFR1, FGFR2, FGFR3, and FGFR4. In some embodiments, the compounds of the invention inhibit each of FGFR1, FGFR2, and FGFR3. In some embodiments, the compounds of the invention are selective for one or more FGFR enzymes. In some embodiments, the compounds of the invention are selective for one or more FGFR enzymes over VEGFR2. In some embodiments, the selectivity is 2-fold or more, 3-fold or more, 5-fold or more, 10-fold or more, 50-fold or more, or 100-fold or more.

As FGFR inhibitors, the compounds of the invention are useful in the treatment of various diseases associated with abnormal expression or activity of FGFR enzymes or FGFR ligands.

For example, the compounds of the invention are useful in the treatment of cancer. Example cancers include bladder cancer, breast cancer, cervical cancer, colorectal cancer, endometrial cancer, gastric cancer, head and neck cancer, kidney cancer, liver cancer, lung cancer (e.g., adenocarcinoma, small cell lung cancer and non-small cell lung carcinomas), ovarian cancer, prostate cancer, esophageal cancer, gall bladder cancer, pancreatic cancer (e.g. exocrine pancreatic carcinoma), stomach cancer, thyroid cancer, skin cancer (e.g., squamous cell carcinoma).

Further example cancers include hematopoietic malignancies such as leukemia, multiple myeloma, chronic lymphocytic lymphoma, adult T cell leukemia, B-cell lymphoma, acute myelogenous leukemia, Hodgkin's or non-Hodgkin's lymphoma, myeloproliferative neoplasms (e.g., polycythemia vera, essential thrombocythemia, and primary myelofibrosis), Waldenstrom's Macroglubulinemia, hairy cell lymphoma, and Burkett's lymphoma.

Other cancers treatable with the compounds of the invention include glioblastoma, melanoma, and rhabdosarcoma.

In addition to oncogenic neoplasms, the compounds of the invention can be useful in the treatment of skeletal and chondrocyte disorders including, but not limited to, achrondroplasia, hypochondroplasia, dwarfism, thanatophoric dysplasia (TD) (clinical forms TD I and TD II), Apert syndrome, Crouzon syndrome, Jackson-Weiss syndrome, Beare-Stevenson cutis gyrate syndrome, Pfeiffer syndrome, and craniosynostosis syndromes.

The compounds of the invention may further be useful in the treatment of fibrotic diseases, such as where a disease symptom or disorder is characterized by fibrosis. Example fibrotic diseases include liver cirrhosis, glomerulonephritis, pulmonary fibrosis, systemic fibrosis, rheumatoid arthritis, and wound healing.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the FGFR enzyme with a compound of the invention includes the administration of a compound of the present invention to an individual or patient, such as a human, having FGFR, as well as, for example, introducing a compound of the invention into a sample containing a cellular or purified preparation containing the FGFR enzyme.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein the term "treating" or "treatment" refers to 1) preventing the disease; for example, preventing a disease, condition or disorder in an individual who may be predisposed to the disease, condition or disorder but does not yet experience or display the pathology or symptomatology of the disease; 2) inhibiting the disease; for example, inhibiting a disease, condition or disorder in an individual who is experiencing or displaying the pathology or symptomatology of the disease, condition or disorder (i.e., arresting further development of the pathology and/or symptomatology), or 3) ameliorating the disease; for example, ameliorating a disease, condition or disorder in an individual who is experiencing or displaying the pathology or symptomatology of the disease, condition or disorder (i.e., reversing the pathology and/or symptomatology).

Combination Therapy

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2, GM-CSF, etc.), and/or tyrosine kinase inhibitors can be used in combination with the compounds of the present invention for treatment of FGFR-associated diseases, disorders or conditions. The agents can be combined with the present compounds in a single dosage form, or the agents can be administered simultaneously or sequentially as separate dosage forms.

Suitable antiviral agents contemplated for use in combination with the compounds of the present invention can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(−)-FTC]; beta-L-FD4 (also called beta-L-D4C and named beta-L-2',3'-dicleoxy-5-fluoro-cytidene); DAPD, ((−)-beta-D-2,6-diamino-purine dioxolane); and lodenosine (FddA). Typical suitable NNRTIs include nevirapine (BI-RG-587); delaviradine (BHAP, U-90152);

efavirenz (DMP-266); PNU-142721; AG-1549; MKC-442 (1-(ethoxy-methyl)-5-(1-methylethyl)-6-(phenylmethyl)-(2,4(1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549. Other antiviral agents include hydroxyurea, ribavirin, IL-2, IL-12, pentafuside and Yissum Project No. 11607.

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylenemelamine, triethylenethiophosphoramine, busulfan, carmustine, lomustine, streptozocin, dacarbazine, and temozolomide.

Other suitable agents for use in combination with the compounds of the present invention include: dacarbazine (DTIC), optionally, along with other chemotherapy drugs such as carmustine (BCNU) and cisplatin; the "Dartmouth regimen," which consists of DTIC, BCNU, cisplatin and tamoxifen; a combination of cisplatin, vinblastine, and DTIC; or temozolomide. Compounds according to the invention may also be combined with immunotherapy drugs, including cytokines such as interferon alpha, interleukin 2, and tumor necrosis factor (TNF) in.

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (TAXOL™), mithramycin, deoxycoformycin, mitomycin-C, L-asparaginase, interferons (especially IFN-a), etoposide, and teniposide.

Other cytotoxic agents include navelbene, CPT-11, anastrazole, letrazole, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB and PD-1, or antibodies to cytokines (IL-10, TGF-β, etc.).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

Pharmaceutical Formulations and Dosage Forms

When employed as pharmaceuticals, the compounds of the invention can be administered in the form of pharmaceutical compositions which refers to a combination of a compound of the invention, or its pharmaceutically acceptable salt, and at least one pharmaceutically acceptable carrier. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal, or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, one or more of the compounds of the invention above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid pre-formulation composition containing a homogeneous mixture of a compound of the present invention. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds of the invention can also be formulated in combination with one or more additional active ingredients which can include any pharmaceutical agent such as antiviral agents, vaccines, antibodies, immune enhancers, immune suppressants, anti-inflammatory agents and the like.

Labeled Compounds and Assay Methods

Another aspect of the present invention relates to fluorescent dye, spin label, heavy metal or radio-labeled compounds of the invention that would be useful not only in imaging but also in assays, both in vitro and in vivo, for localizing and quantitating the FGFR enzyme in tissue samples, including human, and for identifying FGFR enzyme ligands by inhibition binding of a labeled compound. Accordingly, the present invention includes FGFR enzyme assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro FGFR enzyme labeling and competition assays, compounds that incorporate $^3$H, $^{14}$C, $^{82}$Br, $^{125}$I, $^{131}$I, or $^{35}$S will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled" or "labeled compound" is a compound that has incorporated at least one radionuclide. In some embodiments the radionuclide is selected from the group consisting of $^3$H, $^{14}$C, $^{125}$I, $^{35}$S and $^{82}$Br.

Synthetic methods for incorporating radio-isotopes into organic compounds are applicable to compounds of the invention and are well known in the art.

A radio-labeled compound of the invention can be used in a screening assay to identify/evaluate compounds. In general terms, a newly synthesized or identified compound (i.e., test compound) can be evaluated for its ability to reduce binding of the radio-labeled compound of the invention to the FGFR enzyme. Accordingly, the ability of a test compound to compete with the radio-labeled compound for binding to the FGFR enzyme directly correlates to its binding affinity.

Kits

The present invention also includes pharmaceutical kits useful, for example, in the treatment or prevention of FGFR-associated diseases or disorders, obesity, diabetes and other diseases referred to herein which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples were found to be inhibitors of one or more FGFR enzymes as described below.

EXAMPLES

Experimental procedures for compounds of the invention are provided below. Open Access Prep LC-MS Purifications of some of the compounds prepared were performed on Waters mass directed fractionation systems. The basic equipment setup, protocols, and control software for the operation of these systems have been described in detail in the literature. See e.g. "Two-Pump at Column Dilution Configuration for Preparative LC-MS", K. Blom, J. Combi. Chem., 4, 295 (2002); "Optimizing Preparative LC-MS Configurations and Methods for Parallel Synthesis Purification", K. Blom, R. Sparks, J. Doughty, G. Everlof, T. Hague, A. Combs, J. Combi. Chem., 5, 670 (2003); and "Preparative LC-MS Purification: Improved Compound Specific Method Optimization", K. Blom, B. Glass, R. Sparks, A. Combs, J. Combi. Chem., 6, 874-883 (2004). The compounds separated were typically subjected to analytical liquid chromatography mass spectrometry (LCMS) for purity under the following conditions: Instrument; Agilent 1100 series, LC/MSD, Column: Waters Sunfire™ $C_{18}$ 5 μm, 2.1×5.0 mm, Buffers: mobile phase A: 0.025% TFA in water and mobile phase B: 0.025% TFA in acetonitrile; gradient 2% to 80% of B in 3 minutes with flow rate 1.5 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 μm, 19×100 mm column, eluting with mobile phase A: 0.1% TFA (trifluoroacetic acid) in water and mobile phase B: 0.1% TFA in acetonitrile; the flow rate was 30 mL/minute, the separating gradient was optimized for each compound using the Compound Specific Method Optimization protocol as described in the literature [see "Preparative LCMS Purification: Improved Compound Specific Method Optimization", K. Blom, B. Glass, R. Sparks, A. Combs, J. Comb. Chem., 6, 874-883 (2004)]. Typically, the flow rate used with 30×100 mm column was 60 mL/minute;

pH=10 purifications: Waters XBridge $C_{18}$ 5 μm, 19×100 mm column, eluting with mobile phase A: 0.15% NH$_4$OH in water and mobile phase B: 0.15% NH$_4$OH in acetonitrile; the flow rate was 30 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, J. Comb. Chem., 6, 874-883 (2004)]. Typically, the flow rate used with 30×100 mm column was 60 mL/minute.

Example 1

5-[6-(2,6-Dichloro-3,5-dimethoxyphenyl)-1H-pyrazolo[3,4-d]pyrimidin-3-yl]-N,N-dimethyl-2,3-dihydro-1-benzofuran-2-carboxamide

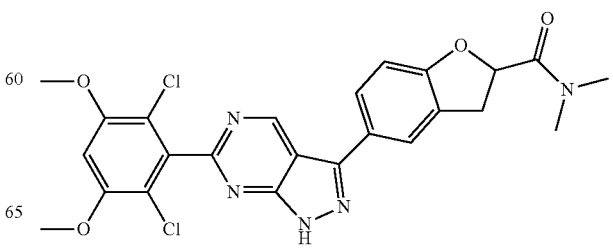

Step 1: 5-bromo-N,N-dimethyl-2,3-dihydro-1-benzofuran-2-carboxamide

A mixture of 5-bromo-2,3-dihydro-1-benzofuran-2-carboxylic acid (0.243 g, 1.00 mmol) (ParkWay, Cat. No. YB-162), benzotriazol-1-yloxytris(dimethylamino)phosphonium hexafluorophosphate (0.464 g, 1.05 mmol) and 2.0 M dimethylamine in tetrahydrofuran (THF) (2.00 mL, 4.00 mmol) was stirred at r.t. for 2 h. The volatiles were removed under reduced pressure. The residue was purified by flash chromatography on a silica gel column with ethyl acetate in hexanes (gradient: 0-50%) to afford the desired product (0.235 g, 87%). LCMS (M+H)$^+$=270.0/272.0.

Step 2: N,N-dimethyl-5-(4,4,5,5-tetramethyl-1,3,2-dioxaborolan-2-yl)-2,3-dihydro-1-benzofuran-2-carboxamide A mixture of 5-bromo-N,N-dimethyl-2,3-dihydro-1-benzofuran-2-carboxamide (0.235 g, 0.870 mmol), 4,4,5,5,4',4',5',5'-octamethyl-[2,2']bi[[1,3,2]dioxaborolanyl] (0.243 g, 0.957 mmol) (Aldrich Cat. No. 473294), potassium acetate (0.213 g, 2.17 mmol), [1,1'-bis(diphenylphosphino)ferrocene]dichloropalladium(II) complexed with dichloromethane (1:1) (36 mg, 0.043 mmol); and 1,1'-bis(diphenylphosphino)ferrocene (0.024 g, 0.043 mmol) in 1,4-dioxane (4.3 mL) was degassed and stirred at 100° C. for 3 h. After cooling the mixture was concentrated under reduced pressure. The residue was purified by flash chromatography on a silica gel column with ethyl acetate in hexanes (gradient: 0-50%) to afford the desired product (0.27 g, 98%). LCMS (M+H)$^+$=318.1.

Step 3: 6-chloro-1-(tetrahydro-2H-pyran-2-yl)-1H-pyrazolo[3,4-d]pyrimidine

To a suspension of 6-chloro-1H-pyrazolo[3,4-d]pyrimidine (1.00 g, 6.47 mmol) (Ark, Cat. No. AK-30782) in THF (10 mL) at r.t. was added methanesulfonic acid (84 µL, 1.3 mmol), followed by dihydropyran (1.77 mL, 19.4 mmol). The mixture was stirred at r.t. over weekend. The reaction mixture was quenched with saturated aqueous NaHCO$_3$, and extracted with ethyl acetate (3×20 mL). The combined organic layers were washed with brine, dried over MgSO$_4$, filtered and concentrated under reduced pressure to afford the crude product which was directly used in the next step reaction without further purification. LCMS (M-84+H)$^+$: m/z=155.1/157.0.

Step 4: 6-(3,5-dimethoxyphenyl)-1-(tetrahydro-2H-pyran-2-yl)-1H-pyrazolo[3,4-d]pyrimidine A mixture of 6-chloro-1-(tetrahydro-2H-pyran-2-yl)-1H-pyrazolo[3,4-d]pyrimidine (5.2 mmol), (3,5-dimethoxyphenyl)boronic acid (1.0 g, 5.7 mmol), [1,1'-bis(diphenylphosphino)ferrocene]dichloropalladium(II) complexed with dichloromethane (1:1) (0.3 g, 0.4 mmol) and potassium phosphate (2.2 g) in 1,4-dioxane (10 mL) and water (2 mL) in a reaction vial was degassed and sealed. The mixture was stirred at 100° C. for 3 h. After cooling, the reaction mixture was extracted with ethyl acetate (3×20 mL). The combined organic layers were washed with brine, dried over MgSO$_4$, filtered and concentrated under reduced pressure. The residue was purified by flash chromatography on a silica gel column with ethyl acetate in hexanes (0-35%) to afford the desired product. LCMS (M+H)$^+$=341.1.

Step 5: 6-(2,6-dichloro-3,5-dimethoxyphenyl)-1H-pyrazolo[3,4-d]pyrimidine

Sulfuryl chloride (0.24 mL, 2.9 mmol) was added to a solution of 6-(3,5-dimethoxyphenyl)-1-(tetrahydro-2H-pyran-2-yl)-1H-pyrazolo[3,4-d]pyrimidine (0.50 g, 1.5 mmol) in acetonitrile (5 mL) at 0° C. under nitrogen atmosphere. The reaction mixture was stirred at r.t. for 30 min, and 2 mL of water was added. The mixture was stirred at 40° C. overnight. The reaction mixture was quenched with saturated aqueous NaHCO$_3$. The precipitates formed were filtered, washed with water then ether, and dried under vacuum to afford the desired product (0.30 g). LCMS (M+H)$^+$=325.0/327.0.

Step 6: 6-(2,6-dichloro-3,5-dimethoxyphenyl)-3-iodo-1H-pyrazolo[3,4-d]pyrimidine N-Iodosuccinimide (0.23 g, 1.0 mmol) was added to a solution of 6-(2,6-dichloro-3,5-dimethoxyphenyl)-1H-pyrazolo[3,4-d]pyrimidine (0.30 g) in N,N-dimethylformamide (5.0 mL). The reaction mixture was stirred at 40° C. overnight. The reaction mixture was diluted with water and quenched with aqueous Na$_2$S$_2$O$_3$. The precipitates formed were filtered, washed with water, ether, and dried in vacuum to afford the desired product (0.33 g). LCMS (M+H)$^+$=450.8/452.8.

Step 7: 5-[6-(2,6-dichloro-3,5-dimethoxyphenyl)-1H-pyrazolo[3,4-d]pyrimidin-3-yl]-N,N-dimethyl-2,3-dihydro-1-benzofuran-2-carboxamide A mixture of 6-(2,6-dichloro-3,5-dimethoxyphenyl)-3-iodo-1H-pyrazolo[3,4-d]pyrimidine (18.0 mg, 0.0400 mmol), N,N-dimethyl-5-(4,4,5,5-tetramethyl-1,3,2-dioxaborolan-2-yl)-2,3-dihydro-1-benzofuran-2-carboxamide (19.0 mg, 0.0600 mmol), tetrakis(triphenylphosphine)palladium(0) (2.77 mg, 0.00240 mmol), and sodium carbonate (12.7 mg, 0.120 mmol) in 1,4-dioxane (0.42 mL) and water (0.14 mL) in a reaction vial was sealed, and degassed and recharged with nitrogen for three times. The mixture was stirred at 120° C. for 3 h. After cooling, the mixture was diluted with methanol, and purified by RP-HPLC (pH=10) to afford the desired product. LCMS (M+H)$^+$=514.0/516.0. $^1$H NMR (300 MHz, DMSO-d$_6$) δ: 9.77 (s, 1H), 8.02 (s, 1H), 7.92 (d, J=8.4 Hz, 1H), 7.06 (s, 1H), 6.97 (d, J=8.4 Hz, 1H), 5.76 (d, J=9.1, 7.4 Hz, 1H), 3.99 (s, 6H), 3.55-3.49 (m, 2H), 3.13 (s, 3H), 2.90 (s, 3H).

Example 2

6-[6-(2,6-Dichloro-3,5-dimethoxyphenyl)-1H-pyrazolo[3,4-d]pyrimidin-3-yl]-N,N-dimethylchromane-2-carboxamide

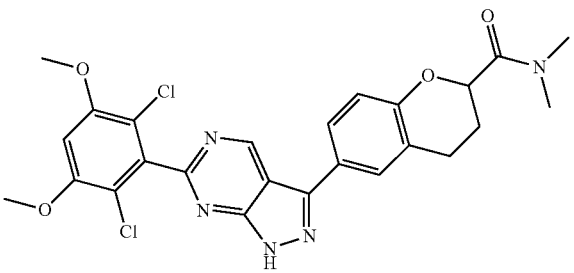

Step 1: N,N-dimethyl-6-(4,4,5,5-tetramethyl-1,3,2-dioxaborolan-2-yl)chromane-2-carboxamide This compound was prepared by using procedures analogous to those described for the synthesis of Example 1, Steps 1-2 starting with 6-bromochromane-2-carboxylic acid (Princeton Bio, Cat. No. PBMR006932). LCMS (M+H)$^+$=332.1.

Step 2: 6-[6-(2,6-dichloro-3,5-dimethoxyphenyl)-1H-pyrazolo[3,4-d]pyrimidin-3-yl]-N,N-dimethyl-chromane-2-carboxamide This compound was prepared by using procedures analogous to those described for the synthesis of Example 1, Step 7 starting from 6-(2,6-dichloro-3,5-dimethoxyphenyl)-3-iodo-1H-pyrazolo[3,4-d]pyrimidine and N,N-dimethyl-6-(4,4,5,5-tetramethyl-1,3,2-dioxaborolan-2-yl)chromane-2-carboxamide. LCMS (M+H)$^+$=528.0/530.0. $^1$H NMR (300 MHz, DMSO-d$_6$) δ: 9.77 (s, 1H), 7.87 (s, 1H), 7.85 (d, J=9.1 Hz, 1H), 7.06 (s, 1H), 6.95 (d, J=9.1 Hz, 1H), 5.19-5.14 (m, 1H), 3.99 (s, 6H), 3.12 (s, 3H), 2.89 (s, 3H), 2.15-1.95 (m, 4H).

Example 3

5-[6-(2,6-Difluoro-3,5-dimethoxyphenyl)-1H-pyrazolo[3,4-d]pyrimidin-3-yl]-N,N-dimethyl-2,3-dihydro-1-benzofuran-2-carboxamide

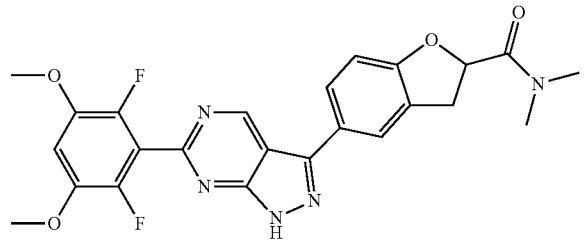

Step 1: 2,4-difluoro-3-iodo-1,5-dimethoxybenzene

To a stirred slurry of 2,6-difluoro-3,5-dimethoxyaniline (6.00 g, 31.7 mmol) in 6.0 M hydrogen chloride in water (54 mL, 324 mmol), a solution of sodium nitrite (2.30 g, 33.3 mmol) in water (12 mL) was added drop-wise over 15 min. at 0° C. After an additional 15 min., the result orange-red slurry was added to a solution of potassium iodide (21.0 g, 126 mmol) in water (30 mL) in small-portion at 0° C. The mixture was then allowed to stir at r.t. for 1 h. The precipitates were collected by filtration, washed with water, and dried under reduced pressure. The filtrate was neutralized with 6 N NaOH to pH~7, and extracted with ethyl acetate (3×20 mL). The combined organic layers were washed with saturated Na$_2$S$_2$O$_3$ aqueous solution, dried over MgSO$_4$, filtered and concentrated under reduced pressure. The residue combined with the precipitates collected previously was purified by flash chromatography on a silica gel column with ethyl acetate in hexanes (gradient: 0-50%) to afford the desired product (6.1 g, 64%). $^1$H-NMR (300 MHz, CDCl$_3$): 6.68 (t, J=8.0 Hz, 1H), 3.88 (s, 6H).

Step 2: 2-(2,6-difluoro-3,5-dimethoxyphenyl)-4,4,5,5-tetramethyl-1,3,2-dioxaborolane To a solution of 2,4-difluoro-3-iodo-1,5-dimethoxybenzene (1.50 g, 5.00 mmol) in tetrahedrofuran (THF, 20 mL) was slowly added 2.0 M isopropyl magnesium chloride in THF (2.87 mL, 5.75 mmol) at −10° C. under an atmosphere of nitrogen. After 10 min., 2-isopropoxy-4,4,5,5-tetramethyl-1,3,2-dioxaborolane (1.27 mL, 6.25 mmol)(Aldrich, Cat. No. 417149) was added. The reaction mixture was then stirred at ambient temperature for 2 h. The mixture was quenched with sat. NH$_4$Cl, and extracted with ethyl acetate. The combined organic layers were washed with water and brine, dried over Na$_2$SO$_4$, filtered and concentrated under reduced pressure. The residue (solid) was treated with ethyl ether, filtered, and dried under reduced pressure to afford the desired product (1.20 g, 80%). $^1$H-NMR (400 MHz, CDCl$_3$): 6.70 (t, J=8.2 Hz, 1H), 3.85 (s, 6H), 1.38 (s, 12H). LCMS (M+H)+=301.1.

Step 3: 6-(2,6-difluoro-3,5-dimethoxyphenyl)-1-(tetrahydro-2H-pyran-2-yl)-1H-pyrazolo[3,4-d]pyrimidine A mixture of 6-chloro-1-(tetrahydro-2H-pyran-2-yl)-1H-pyrazolo[3,4-d]pyrimidine (477 mg, 2.00 mmol), 2-(2,6-difluoro-3,5-dimethoxyphenyl)-4,4,5,5-tetramethyl-1,3,2-dioxaborolane (600. mg, 2.00 mmol), bis(tri-t-butylphosphine) palladium (150.0 mg, 0.300 mmol) and diisopropylethylamine (0.700 mL, 4.02 mmol) in 1,4-dioxane (20 mL) was degassed and recharged with nitrogen for three times. The mixture was stirred at 125° C. overnight. The solvent was removed under reduced pressure. The residue was purified by flash chromatography on a silica gel column with ethyl acetate in hexanes (gradient: 0-50%) to afford the desired product (0.30 g, 40%). LCMS (M+H)$^+$=377.2.

Step 4: 6-(2,6-difluoro-3,5-dimethoxyphenyl)-3-iodo-1H-pyrazolo[3,4-d]pyrimidine To a solution of 6-(2,6-difluoro-3,5-dimethoxyphenyl)-1-(tetrahydro-2H-pyran-2-yl)-1H-pyrazolo[3,4-d]pyrimidine (0.380 g, 1.01 mmol) in THF (5 mL) and methanol (3 mL) was added HCl solution previously prepared from acetyl chloride (2 mL) in methanol (3 mL) at 0° C. The mixture was stirred at r.t. for 2 h. The volatiles were evaporated under reduced pressure. The residue was diluted with water (5 mL), and neutralized with NaOH (2N) to pH~5. The precipitates (desired product) were collected by filtration and washed with water. The filtrate was extracted with ethyl acetate (3×5 mL). The combined organic layers were dried over Na$_2$SO$_4$, filtered and concentrated under reduced pressure. The residue (desired product) was combined with the precipitates collected above to afford the desired product (0.295 g), 6-(2,6-difluoro-3,5-dimethoxyphenyl)-1H-pyrazolo[3,4-d]pyrimidine, which was directly used in the next step reaction without further purification. LCMS (M+H)$^+$=293.0.

The above 6-(2,6-difluoro-3,5-dimethoxyphenyl)-1H-pyrazolo[3,4-d]pyrimidine was dissolved in DMF (10 mL). To the solution was added N-iodosuccinimide (0.269 g, 1.20 mmol). The mixture was stirred at 50° C. for 24 h. The mixture was diluted with ethyl acetate, washed with aqueous Na$_2$S$_2$O$_3$ solution and brine. The organic layer was dried over MgSO$_4$, filtered and concentrated under reduced pressure. The residue was purified by flash chromatography on a silica gel column with ethyl acetate in hexanes (gradient: 0-50%) to afford the desired product (0.285 g, 67.5%). LCMS (M+H)$^+$=418.9

Step 5: 5-[6-(2,6-difluoro-3,5-dimethoxyphenyl)-1H-pyrazolo[3,4-d]pyrimidin-3-yl]-N,N-dimethyl-2,3-dihydro-1-benzofuran-2-carboxamide A mixture of 6-(2,6-difluoro-3,5-dimethoxyphenyl)-3-iodo-1H-pyrazolo[3,4-d]pyrimidine (16.7 mg, 0.0400 mmol), N,N-dimethyl-5-(4,4,5,5-tetramethyl-1,3,2-dioxaborolan-2-yl)-2,3-dihydro-1-benzofuran-2-carboxamide (19.0 mg, 0.0600 mmol) (Example 1, Step 2), tetrakis(triphenylphosphine)palladium(0) (2.77 mg, 0.00240 mmol) and sodium carbonate (12.7 mg, 0.120 mmol) in 1,4-dioxane (0.42 mL) and water (0.14 mL) in a reaction vial was sealed, and degassed and recharged with nitrogen for three times. The mixture was stirred at 115° C. for 5 h. After cooling, the mixture was diluted with methanol, and purified by RP-HPLC (pH=10) to afford the desired product. LCMS (M+H)⁺=482.0.

Example 4

5-[6-(2,6-Difluoro-3,5-dimethoxyphenyl)-1H-pyrazolo[3,4-d]pyrimidin-3-yl]-N,N-dimethyl-2,3-dihydro-1-benzofuran-2-carboxamide (Enantiomer I)

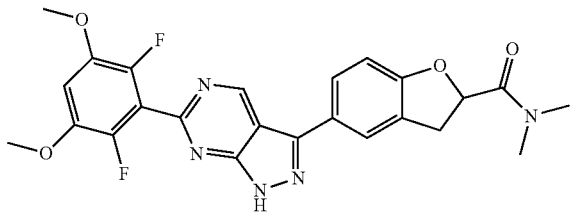

Step 1: N,N-dimethyl-5-(4,4,5,5-tetramethyl-1,3,2-dioxaborolan-2-yl)-2,3-dihydro-1-benzofuran-2-carboxamide The racemic N,N-dimethyl-5-(4,4,5,5-tetramethyl-1,3,2-dioxaborolan-2-yl)-2,3-dihydro-1-benzofuran-2-carboxamide (Example 1, Step 2) was separated by chiral purification using the following conditions: Column: Chiralcel AD-H, 5 µm, 20×250 mm; mobil phase: 20% ethanol in hexanes; gradient: 16 mL/min isoc.; Loading: about 25 mg (500 µL) injection); Instrument: Agilent 1100 Preparative HPLC. Two peaks were separated well: peak I: t=9.14 min. peak II: t=14.39 min. LCMS (M+H)⁺=318.1.

Step 2: 5-[6-(2,6-Difluoro-3,5-dimethoxyphenyl)-1H-pyrazolo[3,4-d]pyrimidin-3-yl]-N,N-dimethyl-2,3-dihydro-1-benzofuran-2-carboxamide (Enantiomer I)

A mixture of 6-(2,6-difluoro-3,5-dimethoxyphenyl)-3-iodo-1H-pyrazolo[3,4-d]pyrimidine (15.0 mg, 0.0359 mmol), N,N-dimethyl-5-(4,4,5,5-tetramethyl-1,3,2-dioxaborolan-2-yl)-2,3-dihydro-1-benzofuran-2-carboxamide (13.6 mg, 0.0430 mmol) (Peak 1), [1,1'-bis(diphenylphosphino)ferrocene]dichloropalladium(II) complex with dichloromethane (1:1) (1.8 mg, 0.0022 mmol) and potassium phosphate (22.8 mg, 0.108 mmol) in 1,4-dioxane (0.48 mL) and water (0.24 mL) in a reaction vial was sealed, and degassed and recharged with nitrogen for three times. The mixture was stirred at 100° C. overnight. After cooling, the mixture was diluted with methanol, and purified by RP-HPLC (pH=10) to afford the desired product. LCMS (M+H)⁺=482.1.

Example 5

5-[6-(2,6-Difluoro-3,5-dimethoxyphenyl)-1H-pyrazolo[3,4-d]pyrimidin-3-yl]-N,N-dimethyl-2,3-dihydro-1-benzofuran-2-carboxamide (Enantiomer II)

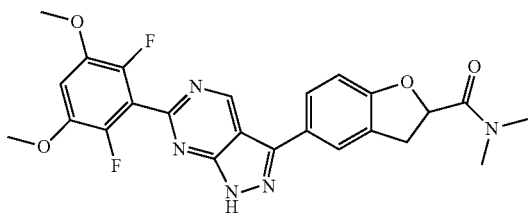

This compound was prepared by using procedures analogous to those described for the synthesis of Example 4, Step 2 starting from 6-(2,6-difluoro-3,5-dimethoxyphenyl)-3-iodo-1H-pyrazolo[3,4-d]pyrimidine and N,N-dimethyl-5-(4,4,5,5-tetramethyl-1,3,2-dioxaborolan-2-yl)-2,3-dihydro-1-benzofuran-2-carboxamide (Peak II from chiral separation, Example 4, Step 1). LCMS (M+H)⁺=482.1. ¹H NMR (300 MHz, DMSO-d₆) δ: 14.25 (s, 1H), 9.77 (s, 1H), 8.01 (s, 1H), 7.91 (d, J=8.5 Hz, 1H), 7.18 (t, J=8.4 Hz, 1H), 6.97 (d, J=8.5 Hz, 1H), 5.83-5.70 (m, 1H), 3.94 (s, 6H), 3.55-3.49 (m, 2H), 3.13 (s, 3H), 2.90 (s, 3H).

Example 6

6-[6-(2,6-Difluoro-3,5-dimethoxyphenyl)-1H-pyrazolo[3,4-d]pyrimidin-3-yl]-N,N-dimethylchromane-2-carboxamide

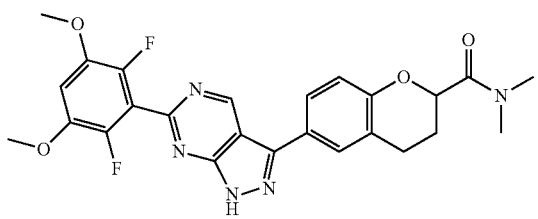

This compound was prepared by using procedures analogous to those described for the synthesis of Example 1, Step 7 starting from 6-(2,6-difluoro-3,5-dimethoxyphenyl)-3-iodo-1H-pyrazolo[3,4-d]pyrimidine and N,N-dimethyl-6-(4,4,5,5-tetramethyl-1,3,2-dioxaborolan-2-yl)chromane-2-carboxamide. LCMS (M+H)⁺=496.0.

Example 7

6-(2,6-Difluoro-3,5-dimethoxyphenyl)-3-{2-[(4-methylpiperazin-1-yl)carbonyl]-2,3-dihydro-1-benzofuran-5-yl}-1H-pyrazolo[3,4-d]pyrimidine

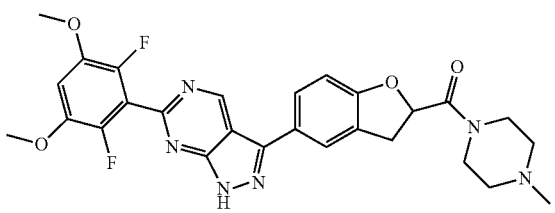

Step 1: 1[(5-bromo-2,3-dihydro-1-benzofuran-2-yl) carbonyl]-4-methylpiperazine A mixture of 5-bromo-2,3-dihydro-1-benzofuran-2-carboxylic acid (0.243 g, 1.00 mmol), benzotriazol-1-yloxytris (dimethylamino)phosphonium hexafluorophosphate (0.464 g, 1.05 mmol), 1-methyl-piperazine (116 μL, 1.05 mmol) and N,N-diisopropylethylamine (696 μL, 4.00 mmol) was stirred at r.t. for 2 h. The volatiles were removed under reduced pressure. The residue was purified by flash chromatography on a silica gel column with ethyl acetate in hexanes (gradient: 0-50%) to afford the desired product (0.325 g, 95%). LCMS $(M+H)^+=324.9/327.0$.

Step 2: 1-methyl-4-{[5-(4,4,5,5-tetramethyl-1,3,2-dioxaborolan-2-yl)-2,3-dihydro-1-benzofuran-2-yl]carbonyl}piperazine A mixture of 1-[(5-bromo-2,3-dihydro-1-benzofuran-2-yl)carbonyl]-4-methylpiperazine (0.325 g, 1.00 mmol), 4,4,5,5,4',4',5',5'-octamethyl-[2,2']bi[[1,3,2]dioxaborolanyl] (0.279 g, 1.10 mmol), potassium acetate (0.245 g, 2.50 mmol) and [1,1'-bis(diphenylphosphino)ferrocene]dichloropalladium(II) complex with dichloromethane (1:1) (41 mg, 0.050 mmol) and 1,1'-bis(diphenylphosphino)ferrocene (28 mg, 0.050 mmol) in 1,4-dioxane (5.0 mL) was degassed and stirred at 105° C. overnight. After cooling the mixture was concentrated, the residue was purified by flash chromatography on a silica gel column with ethyl acetate in hexanes (gradient: 0-50%) to afford the desired product (0.32 g, 86%). LCMS $(M+H-56)^+=373.2$.

Step 3: 6-(2,6-difluoro-3,5-dimethoxyphenyl)-3-{2[(4-methylpiperazin-1-yl)carbonyl]-2,3-dihydro-1-benzofuran-5-yl}-1H-pyrazolo[3,4-c]pyrimidine A mixture of 6-(2,6-difluoro-3,5-dimethoxyphenyl)-3-iodo-1H-pyrazolo[3,4-d]pyrimidine (20.0 mg, 0.0478 mmol), 1-methyl-4-{[5-(4,4,5,5-tetramethyl-1,3,2-dioxaborolan-2-yl)-2,3-dihydro-1-benzofuran-2-yl]carbonyl}piperazine (21.4 mg, 0.0574 mmol), [1,1'-bis(diphenylphosphino)ferrocene]dichloropalladium(II) complexed with dichloromethane (1:1) (0.0023 g, 0.0029 mmol), and potassium phosphate (0.0304 g, 0.143 mmol) in 1,4-dioxane (0.64 mL) and water (0.32 mL) in a reaction vial was sealed, and degassed and recharged with nitrogen for three times. The mixture was stirred at 100° C. overnight. After cooling, the mixture was diluted with methanol, and purified by RP-HPLC (pH=2) to afford the desired product as TFA salt. LCMS $(M+H)^+=537.1$.

Example 8

6-[6-(2,6-Dichloro-3,5-dimethoxyphenyl)-1H-pyrazolo[3,4-d]pyrimidin-3-yl]-3,4-dihydroisoquinolin-1(2H)-one

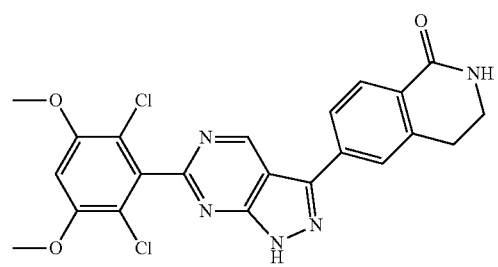 [SMILES: COc1cc(OC)c(Cl)c(-c2ncc3c(-c4ccc5c(c4)CCNC5=O)n[nH]c3n2)c1Cl]

Step 1: 6-(4,4,5,5-tetramethyl-1,3,2-dioxaborolan-2-yl)-3,4-dihydroisoquinolin-1(2H)-one A mixture of 6-bromo-3,4-dihydroisoquinolin-1(2H)-one (904 mg, 4.00 mmol), 4,4,5,5,4',4',5',5'-octamethyl-[2,2']bi[[1,3,2]dioxaborolanyl] (559 mg, 2.20 mmol), potassium acetate (491 mg, 5.00 mmol), and [1,1'-bis(diphenylphosphino)ferrocene]dichloropalladium(II) complex with dichloromethane (1:1) (82 mg, 0.10 mmol) in 1,4-dioxane (10 mL) and 1,1'-bis(diphenylphosphino)ferrocene (55 mg, 0.10 mmol) was degassed and stirred at 100° C. for 3 h. After cooling it was concentrated. The residue was purified by flash chromatography on a silica gel column with ethyl acetate in hexanes (gradient: 0-50%) to afford the desired product (1.03 g, 94%). LCMS $(M+H)^+=274.1$.

Step 2: 6-[6-(2,6-dichloro-3,5-dimethoxyphenyl)-1H-pyrazolo[3,4-d]pyrimidin-3-yl]-3,4-dihydroisoquinolin-1(2H)-one A mixture of 6-(2,6-dichloro-3,5-dimethoxyphenyl)-3-iodo-1H-pyrazolo[3,4-d]pyrimidine (18.0 mg, 0.0400 mmol), 6-(4,4,5,5-tetramethyl-1,3,2-dioxaborolan-2-yl)-3,4-dihydroisoquinolin-1(2H)-one (16.4 mg, 0.0600 mmol), tetrakis(triphenylphosphine)palladium(0) (2.77 mg, 0.00240 mmol), and sodium carbonate (12.7 mg, 0.120 mmol) in 1,4-dioxane (0.42 mL) and water (0.14 mL) in a reaction vial was sealed, and degassed and recharged with nitrogen for three times. The mixture was stirred at 120° C. for 3 h. After cooling, the mixture was diluted with methanol, and purified by RP-HPLC (pH=10) to afford the desired product. LCMS $(M+H)^+=470.0/471.9$. $^1H$ NMR (300 MHz, DMSO-$d_6$) δ: 9.90 (s, 1H), 8.16-7.97 (m, 3H), 7.07 (s, 1H), 4.00 (s, 6H), 3.49-3.40 (m, 2H), 3.07 (t, J=6.5 Hz, 3H).

Example 9

6-[6-(2,6-Dichloro-3,5-dimethoxyphenyl)-1H-pyrazolo[3,4-d]pyrimidin-3-yl]-2-methyl-3,4-dihydroisoquinolin-1(2H)-one

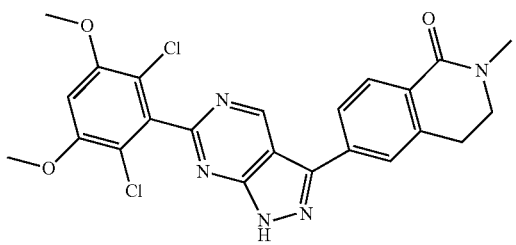

Step 1: 2-methyl-6-(4,4,5,5-tetramethyl-1,3,2-dioxaborolan-2-yl)-3,4-dihydroisoquinolin-1(2H)-one Sodium hydride (29.3 mg, 0.732 mmol) was added to a solution of 6-(4,4,5,5-tetramethyl-1,3,2-dioxaborolan-2-yl)-3,4-dihydroisoquinolin-1(2H)-one (100 mg, 0.366 mmol) in DMF (1.0 mL). The mixture was stirred at r.t. for 5 min, and then methyl iodide (57.0 μL, 0.915 mmol) was added. The mixture was stirred at 50° C. for 6 h, then diluted with ethyl acetate, and washed with water and brine. The organic layer was dried over $MgSO_4$, filtered and concentrated under reduced pressure. The residue was purified by flash chromatography on a silica gel column with ethyl acetate in hexanes (gradient: 0-50%) to afford the desired product (0.038 g, 36%). LCMS $(M+H)^+=274.2$.

Step 2: 6-[6-(2,6-dichloro-3,5-dimethoxyphenyl)-1H-pyrazolo[3,4-d]pyrimidin-3-yl]-2-methyl-3,4-dihydroisoquinolin-1(2H)-one This compound was prepared by using procedures analogous to those described for the synthesis of Example 8, Step 2 starting from 6-(2,6-dichloro-3,5-dimethoxyphenyl)-3-iodo-1H-pyrazolo[3,4-d]pyrimidine and 2-methyl-6-(4,4,5,5-tetramethyl-1,3,2-dioxaborolan-2-yl)-3,4-dihydroisoquinolin-1(2H)-one. LCMS (M+H)$^+$=484.1/486.0.

Example 10

6-[6-(2,6-Dichloro-3,5-dimethoxyphenyl)-1H-pyrazolo[3,4-d]pyrimidin-3-yl]-2-ethyl-3,4-dihydroisoquinolin-1(2H)-one

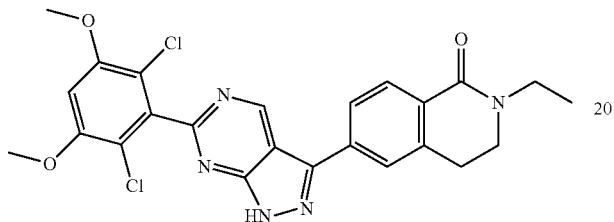

Step 1: 2-ethyl-6-(4,4,5,5-tetramethyl-1,3,2-dioxaborolan-2-yl)-3,4-dihydroisoquinolin-1(2H)-one This compound was prepared by using procedures analogous to those described for the synthesis of Example 9, Step 1 starting from 6-(4,4,5,5-tetramethyl-1,3,2-dioxaborolan-2-yl)-3,4-dihydroisoquinolin-1(2H)-one and iodoethane. LCMS (M+H)$^+$=302.1.

Step 2: 6-[6-(2,6-dichloro-3,5-dimethoxyphenyl)-1H-pyrazolo[3,4-d]pyrimidin-3-yl]-2-ethyl-3,4-dihydroisoquinolin-1(2H)-one This compound was prepared by using procedures analogous to those described for the synthesis of Example 8, Step 2 starting from 6-(2,6-dichloro-3,5-dimethoxyphenyl)-3-iodo-1H-pyrazolo[3,4-d]pyrimidine and 2-ethyl-6-(4,4,5,5-tetramethyl-1,3,2-dioxaborolan-2-yl)-3,4-dihydroisoquinolin-1(2H)-one. LCMS (M+H)$^+$=498.1/500.0.

Example 11

6-[6-(2,6-Dichloro-3,5-dimethoxyphenyl)-1H-pyrazolo[3,4-d]pyrimidin-3-yl]-2-isopropyl-3,4-dihydroisoquinolin-1(2H)-one

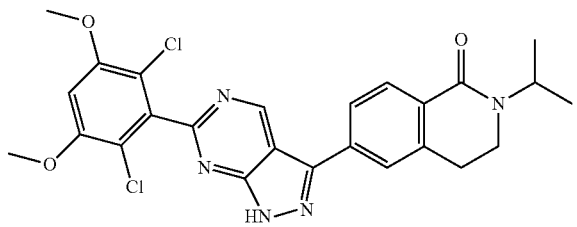 [SMILES: COc1cc(OC)c(Cl)c(-c2ncc3c(-c4ccc5c(c4)CCN(C(C)C)C5=O)n[nH]c3n2)c1Cl]

Step 1: 2-isopropyl-6-(4,4,5,5-tetramethyl-1,3,2-dioxaborolan-2-yl)-3,4-dihydroisoquinolin-1(2H)-one This compound was prepared by using procedures analogous to those described for the synthesis of Example 9, Step 1 starting from 6-(4,4,5,5-tetramethyl-1,3,2-dioxaborolan-2-yl)-3,4-dihydroisoquinolin-1(2H)-one and isopropyl iodide. LCMS (M+H)+=316.1.

Step 2: 6-[6-(2,6-dichloro-3,5-dimethoxyphenyl)-1H-pyrazolo[3,4-d]pyrimidin-3-yl]-2-isopropyl-3,4-dihydroisoquinolin-1(2H)-one This compound was prepared by using procedures analogous to those described for the synthesis of Example 8, Step 2 starting from 6-(2,6-dichloro-3,5-dimethoxyphenyl)-3-iodo-1H-pyrazolo[3,4-d]pyrimidine and 2-isopropyl-6-(4,4,5,5-tetramethyl-1,3,2-dioxaborolan-2-yl)-3,4-dihydroisoquinolin-1(2H)-one. LCMS (M+H)$^+$=511.9/514.0.

Example 12

6-[6-(2,6-Difluoro-3,5-dimethoxyphenyl)-1H-pyrazolo[3,4-d]pyrimidin-3-yl]-3,4-dihydroisoquinolin-1(2H)-one

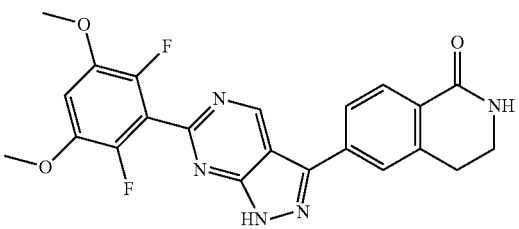 [SMILES: COc1cc(OC)c(F)c(-c2ncc3c(-c4ccc5c(c4)CCNC5=O)n[nH]c3n2)c1F]

This compound was prepared as a TFA salt by using procedures analogous to those described for the synthesis of Example 7, Step 3 starting from 6-(2,6-difluoro-3,5-dimethoxyphenyl)-3-iodo-1H-pyrazolo[3,4-d]pyrimidine and 6-(4,4,5,5-tetramethyl-1,3,2-dioxaborolan-2-yl)-3,4-dihydroisoquinolin-1(2H)-one. LCMS (M+H)$^+$=438.0.

Example 13

6-[6-(2,6-Difluoro-3,5-dimethoxyphenyl)-1H-pyrazolo[3,4-d]pyrimidin-3-yl]-2-(methylsulfonyl)-1,2,3,4-tetrahydroisoquinoline

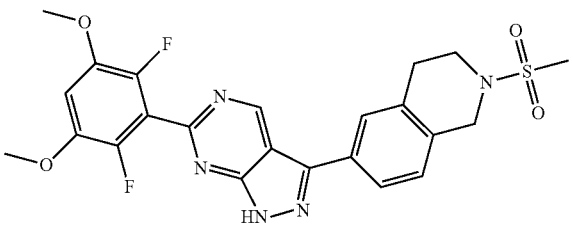

Step 1: tert-butyl 6-(4,4,5,5-tetramethyl-1,3,2-dioxaborolan-2-yl)-3,4-dihydroisoquinoline-2(1H)-carboxylate This compound was prepared by using procedures analogous to those described for the synthesis of Example 1, Step 2 starting from tert-butyl 6-bromo-3,4-dihydroisoquinoline-2(1H)-carboxylate (J&W PharmLab, Cat. No. 50-0272) and 4,4,5,5,4',4',5',5'-octamethyl-[2,2']bi[[1,3,2]dioxaborolanyl]. LCMS (M+H-56)$^+$=304.1.

Step 2: tert-butyl 6-[6-(2,6-difluoro-3,5-dimethoxyphenyl)-1H-pyrazolo[3,4-d]pyrimidin-3-yl]-3,4-dihydroisoquinoline-2(1H)-carboxylate

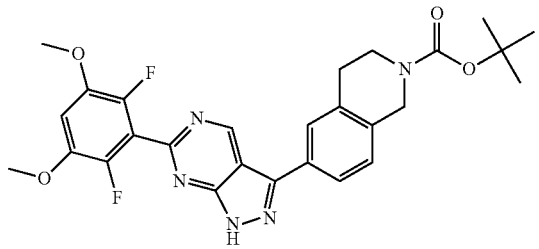 [SMILES: COc1cc(OC)c(F)c(-c2ncc3c(-c4ccc5c(c4)CCN(C(=O)OC(C)(C)C)C5)n[nH]c3n2)c1F]

This compound was prepared by using procedures analogous to those described for the synthesis of Example 4, Step 2 starting from 6-(2,6-difluoro-3,5-dimethoxyphenyl)-3-iodo-1H-pyrazolo[3,4-d]pyrimidine and tert-butyl 6-(4,4,5,5-tetramethyl-1,3,2-dioxaborolan-2-yl)-3,4-dihydroisoquinoline-2(1H)-carboxylate. LCMS (M+H)$^+$=524.1.

Step 3: 6-[6-(2,6-difluoro-3,5-dimethoxyphenyl)-1H-pyrazolo[3,4-d]pyrimidin-3-yl]-2-(methylsulfonyl)-1,2,3,4-tetrahydroisoquinoline tert-Butyl 6-[6-(2,6-difluoro-3,5-dimethoxyphenyl)-1H-pyrazolo[3,4-d]pyrimidin-3-yl]-3,4-dihydroisoquinoline-2(1H)-carboxylate (10.0 mg, 0.0191 mmol) in methanol (0.10 mL) was treated at r.t. with HCl solution previously prepared from acetyl chloride (0.1 mL) and methanol (0.1 mL) at 0° C. The mixture was stirred at r.t. for 1 h. The volatiles were evaporated. The residue was dissolved in acetonitrile (0.5 mL) and N,N-diisopropylethylamine (30.0 μL, 0.172 mmol). To the mixture was added methanesulfonyl chloride (2.0 μL, 0.026 mmol). The mixture was stirred at r.t. for 1 h. The volatiles were removed. The residue was dissolved in methanol (0.5 mL) and treated with sodium methoxide (25%, 0.060 mL). After 1 h, the mixture was diluted with methanol, and purified by RP-HPLC (pH=10) to afford the desired product. LCMS (M+H)$^+$=502.1. $^1$H NMR (300 MHz, DMSO-d$_6$) δ: 9.39 (s, 1H), 7.91 (d, J=7.8 Hz, 1H), 7.89 (s, 1H), 7.25 (d, J=7.8 Hz, 1H), 7.07 (t, J=8.1 Hz, 1H), 4.40 (s, 2H), 3.92 (s, 6H), 3.48 (t, J=5.7 Hz, 2H), 3.04 (d, J=5.7 Hz, 3H), 2.97 (s, 3H).

Example 14

6-(2,6-Difluoro-3,5-dimethoxyphenyl)-3-[(4-methoxyphenyl)ethynyl]-1H-pyrazolo[3,4-d]pyrimidine

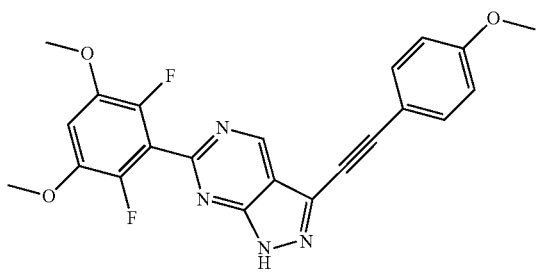

6-(2,6-Difluoro-3,5-dimethoxyphenyl)-3-iodo-1H-pyrazolo[3,4-d]pyrimidine (20.9 mg, 0.0500 mmol) was mixed with 1-ethynyl-4-methoxybenzene (8.26 mg, 0.0625 mmol) (Aldrich, cat. No. 206490), copper(I) iodide (0.48 mg, 0.0025 mmol), triethylamine (0.010 mL, 0.075 mmol) and bis(triphenylphosphine)palladium(II) chloride (1.8 mg, 0.0025 mmol) in N,N-dimethylformamide (0.10 mL). The reaction mixture was stirred at 60° C. overnight. The mixture was diluted with methanol, and purified by RP-HPLC (pH=2) to afford the desired product as TFA salt. LCMS (M+H)$^+$=423.0.

Example 15

5-[6-(2,6-Difluoro-3,5-dimethoxyphenyl)-1H-pyrazolo[3,4-d]pyrimidin-3-yl]-2-(trans-4-hydroxycyclohexyl)isoindolin-1-one

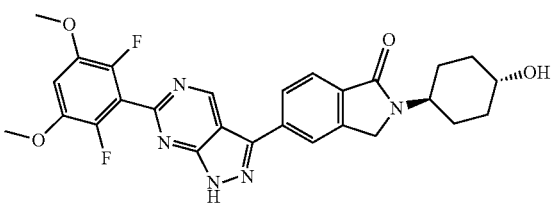 [SMILES: COc1cc(OC)c(F)c(-c2ncc3c(-c4ccc5c(c4)CN([C@H]4CC[C@H](O)CC4)C5=O)n[nH]c3n2)c1F]

Step 1: 5-bromo-2-(trans-4-hydroxycyclohexyl)isoindolin-1-one

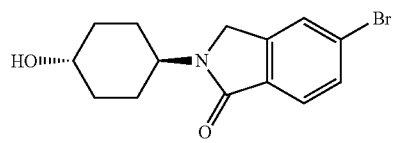 [SMILES: O=C1c2ccc(Br)cc2CN1[C@H]1CC[C@H](O)CC1]

A mixture of methyl 4-bromo-2-(bromomethyl)benzoate (0.500 g, 1.62 mmol), trans-4-aminocyclohexanol hydrochloride (0.295 g, 1.95 mmol), and potassium carbonate (0.44 g, 3.2 mmol) in ethanol (5.0 mL) was stirred in a sealed vial at 50° C. for 4 h. After cooling, the mixture was diluted with ethyl acetate (10 mL), and was filtered. The filtrate was concentrated under reduced pressure. The residue was triturated with ethyl ether (3 mL). The precipitates were collected by filtration and washed with ethyl ether to afford the desired product. LCMS (M+H)$^+$=309.9/312.0.

Step 2: 2-(trans-4-hydroxycyclohexyl)-5-(4,4,5,5-tetramethyl-1,3,2-dioxaborolan-2-yl)isoindolin-1-one This compound was prepared by using procedures analogous to those described for the synthesis of Example 1, Step 2 starting from 5-bromo-2-(trans-4-hydroxycyclohexyl)isoindolin-1-one and 4,4,5,5,4',4',5',5'-octamethyl-[2,2']bi[[1,3,2]dioxaborolanyl]. LCMS (M+H)$^+$=358.1.

Step 3: 5-[6-(2,6-difluoro-3,5-dimethoxyphenyl)-1H-pyrazolo[3,4-d]pyrimidin-3-yl]-2-(trans-4-hydroxycyclohexyl)isoindolin-1-one This compound was prepared by using procedures analogous to those described for the synthesis of Example 4, Step 2 starting from 6-(2,6-difluoro-3,5-dimethoxyphenyl)-3-iodo-1H-pyrazolo[3,4-d]pyrimidine and 2-(trans-4-hydroxycyclohexyl)-5-(4,4,5,5-tetramethyl-1,3,2-dioxaborolan-2-yl)isoindolin-1-one. LCMS (M+H)$^+$=522.0.

Example 16

5-[6-(2,6-Difluoro-3,5-dimethoxyphenyl)-1H-pyrazolo[3,4-d]pyrimidin-3-yl]-2-(cis-4-hydroxycyclohexyl)isoindolin-1-one

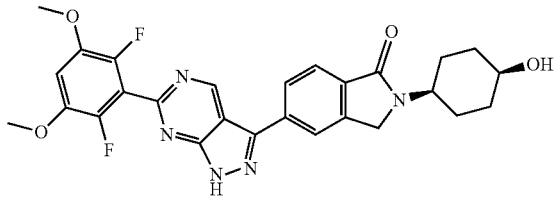 [SMILES: COc1cc(OC)c(F)c(-c2ncc3c(-c4ccc5c(c4)CN([C@H]4CC[C@@H](O)CC4)C5=O)n[nH]c3n2)c1F]

Step 1: 5-bromo-2-(cis-4-hydroxycyclohexyl)isoindolin-1-one

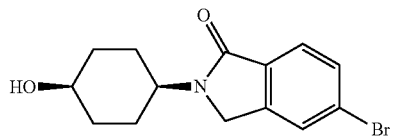 [SMILES: O=C1c2ccc(Br)cc2CN1[C@H]1CC[C@@H](O)CC1]

This compound was prepared by using procedures analogous to those described for the synthesis of Example 15, Step 1 starting from methyl 4-bromo-2-(bromomethyl)benzoate and cis-4-aminocyclohexanol hydrochloride. LCMS (M+H)⁺=310.0/312.0.

Step 2: 2-(cis-4-hydroxycyclohexyl)-5-(4,4,5,5-tetramethyl-1,3,2-dioxaborolan-2-yl)isoindolin-1-one This compound was prepared by using procedures analogous to those described for the synthesis of Example 1, Step 2 starting from 5-bromo-2-(cis-4-hydroxycyclohexyl)isoindolin-1-one and 4,4,5,5,4',4',5',5'-octamethyl-[2,2']bi[[1,3,2]dioxaborolanyl]. LCMS (M+H)⁺=358.1.

Step 3: 5-[6-(2,6-difluoro-3,5-dimethoxyphenyl)-1H-pyrazolo[3,4-d]pyrimidin-3-yl]-2-(cis-4-hydroxycyclohexyl)isoindolin-1-one This compound was prepared by using procedures analogous to those described for the synthesis of Example 4, Step 2 starting from 6-(2,6-difluoro-3,5-dimethoxyphenyl)-3-iodo-1H-pyrazolo[3,4-d]pyrimidine and 2-(cis-4-hydroxycyclohexyl)-5-(4,4,5,5-tetramethyl-1,3,2-dioxaborolan-2-yl)isoindolin-1-one. LCMS (M+H)⁺=522.1.

Example 17

6-(2,6-Difluoro-3,5-dimethoxyphenyl)-3-[4-(4-methylpiperazin-1-yl)phenyl]-1H-pyrazolo[3,4-d]pyrimidine

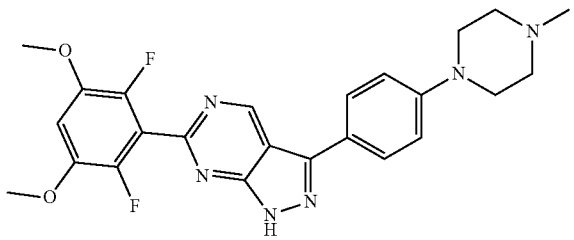

This compound was prepared as a TFA salt by using procedures analogous to those described for the synthesis of Example 7, Step 3 starting from 6-(2,6-difluoro-3,5-dimethoxyphenyl)-3-iodo-1H-pyrazolo[3,4-d]pyrimidine and 1-methyl-4-[4-(4,4,5,5-tetramethyl-1,3,2-dioxaborolan-2-yl)phenyl]piperazine. LCMS (M+H)⁺=467.0.

Example 18

6-(2,6-Difluoro-3,5-dimethoxyphenyl)-3-[6-(4-methylpiperazin-1-yl)pyridin-3-yl]-1H-pyrazolo[3,4-d]pyrimidine

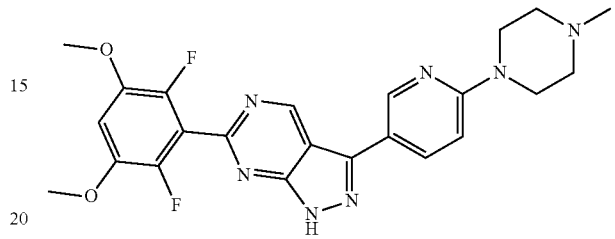

This compound was prepared by using procedures analogous to those described for the synthesis of Example 4, Step 2 starting from 6-(2,6-difluoro-3,5-dimethoxyphenyl)-3-iodo-1H-pyrazolo[3,4-d]pyrimidine and 1-methyl-4-[5-(4,4,5,5-tetramethyl-1,3,2-dioxaborolan-2-yl)pyridin-2-yl]piperazine. LCMS (M+H)⁺=468.0.

Example 19

6-(2,6-Difluoro-3,5-dimethoxyphenyl)-3-[2-(4-methylpiperazin-1-yl)pyridin-4-yl]-1H-pyrazolo[3,4-d]pyrimidine

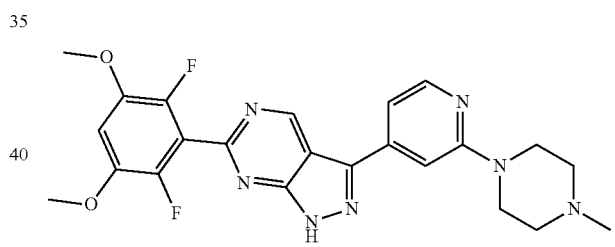

This compound was prepared as TFA salt by using procedures analogous to those described for the synthesis of Example 7, Step 3 starting from 6-(2,6-difluoro-3,5-dimethoxyphenyl)-3-iodo-1H-pyrazolo[3,4-d]pyrimidine and 1-methyl-4-[4-(4,4,5,5-tetramethyl-1,3,2-dioxaborolan-2-yl)pyridin-2-yl]piperazine. LCMS (M+H)⁺=468.1.

Example 20

2-{4-[6-(2,6-Difluoro-3,5-dimethoxyphenyl)-1H-pyrazolo[3,4-d]pyrimidin-3-yl]phenoxy}-N,N-dimethylethanamine

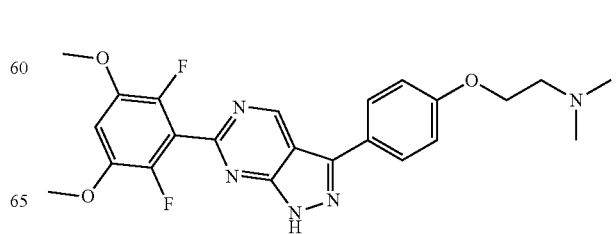

This compound was prepared as TFA salt by using procedures analogous to those described for the synthesis of Example 7, Step 3 starting from 6-(2,6-difluoro-3,5-dimethoxyphenyl)-3-iodo-1H-pyrazolo[3,4-d]pyrimidine and N,N-dimethyl-2-[4-(4,4,5,5-tetramethyl-1,3,2-dioxaborolan-2-yl)phenoxy]ethanamine (Combi-Blocks, Cat. No. PN-3972). LCMS (M+H)+=456.1.

Example 21

2-Cyclopropyl-5-[6-(2,6-difluoro-3,5-dimethoxyphenyl)-1H-pyrazolo[3,4-d]pyrimidin-3-yl]isoindolin-1-one

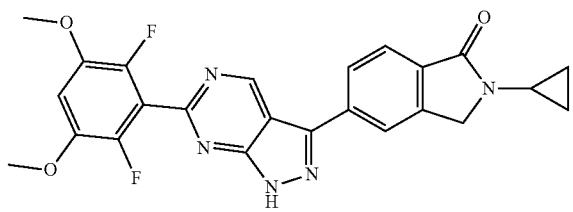 [SMILES: COc1cc(OC)c(F)c(-c2ncc3c(-c4ccc5c(c4)CN(C4CC4)C5=O)n[nH]c3n2)c1F]

Step 1: 5-bromo-2-cyclopropylisoindolin-1-one

A mixture of methyl 4-bromo-2-(bromomethyl)benzoate (Ark Pharm, Cat. No. AK-26333) (0.5 g, 0.002 mol), cyclopropylamine (0.17 mL, 0.0024 mol) and potassium carbonate (0.45 g, 0.0032 mol) in ethanol (5 mL) was stirred at 40° C. for 3 h. The reaction mixture was quenched with water and extracted with ethyl acetate. The organic layers were washed with brine, dried with Na$_2$SO$_4$, filtered, and concentrated under reduced pressure to give a crude product which was directly used in nest step reaction without further purification. LCMS (M+H)+=252.0/254.0.

Step 2: 2-cyclopropyl-5-(4,4,5,5-tetramethyl-1,3,2-dioxaborolan-2-yl)isoindolin-1-one To a solution of 5-bromo-2-cyclopropylisoindolin-1-one (0.51 g, 0.0020 mol) and 4,4,5,5,4',4',5',5'-octamethyl-[2,2']bi[[1,3,2]dioxaborolanyl] (0.56 g, 0.0022 mol) in 1,4-dioxane (5 mL) was added [1,1'-bis(diphenylphosphino)ferrocene]dichloropalladium(II) complex with dichloromethane (1:1) (0.08 g, 0.0001 mol), potassium acetate (0.60 g, 0.0061 mol), and 1,1'-bis(diphenylphosphino)ferrocene (0.06 g, 0.0001 mol) under an atmosphere of nitrogen. The reaction mixture was stirred at 80° C. overnight. After cooled to r.t., the mixture was filtered through a pad of Celite, washed with ethyl acetate, and concentrated. The residue was purified by flash chromatography on a silica gel column with ethyl acetate in hexanes (0-40%) to afford the desired product. LCMS (M+H)+=300.1.

Step 3: 2-cyclopropyl-5-[6-(2,6-difluoro-3,5-dimethoxyphenyl)-1H-pyrazolo[3,4-d]pyrimidin-3-yl]isoindolin-1-one This compound was prepared by using procedures analogous to those described for the synthesis of Example 4, Step 2 starting from 6-(2,6-difluoro-3,5-dimethoxyphenyl)-3-iodo-1H-pyrazolo[3,4-d]pyrimidine and 2-cyclopropyl-5-(4,4,5,5-tetramethyl-1,3,2-dioxaborolan-2-yl)isoindolin-1-one. LCMS (M+H)+=464.1. $^1$H NMR (300 MHz, DMSO-d$_6$) δ: 9.86 (s, 1H), 8.34 (s, 1H), 8.27 (d, J=8.0 Hz, 1H), 7.80 (d, J=8.0 Hz, 1H), 7.18 (t, J=8.3 Hz, 1H), 4.52 (s, 2H), 3.94 (s, 6H), 3.07-2.90 (m, 1H), 0.97-0.76 (m, 4H).

Example 22

5-[6-(2,6-Dichloro-3,5-dimethoxyphenyl)-1H-pyrazolo[3,4-d]pyrimidin-3-yl]-2-(cis-4-hydroxycyclohexyl)isoindolin-1-one

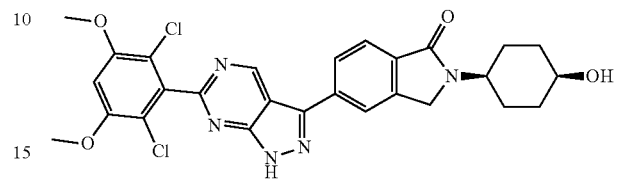

This compound was prepared by using procedures analogous to those described for the synthesis of Example 1, Step 7 starting from 6-(2,6-dichloro-3,5-dimethoxyphenyl)-3-iodo-1H-pyrazolo[3,4-d]pyrimidine and 2-(cis-4-hydroxycyclohexyl)-5-(4,4,5,5-tetramethyl-1,3,2-dioxaborolan-2-yl)isoindolin-1-one. LCMS (M+H)+=553.9/555.9. $^1$H NMR (300 MHz, DMSO-d$_6$) δ: 9.90 (s, 1H), 8.40 (s, 1H), 8.28 (d, J=7.9 Hz, 1H), 7.83 (d, J=7.9 Hz, 1H), 7.08 (s, 1H), 4.57 (s, 2H), 4.48 (d, J=3.1 Hz, 1H), 4.13-4.01 (m, 1H), 4.00 (s, 6H), 3.91-3.85 (m, 1H), 2.03-1.91 (m, 2H), 1.85-1.73 (m, 2H), 1.67-1.42 (m, 4H).

Example 23

5-[6-(2,6-Dichloro-3,5-dimethoxyphenyl)-1H-pyrazolo[3,4-d]pyrimidin-3-yl]-2-(trans-4-hydroxycyclohexyl)isoindolin-1-one

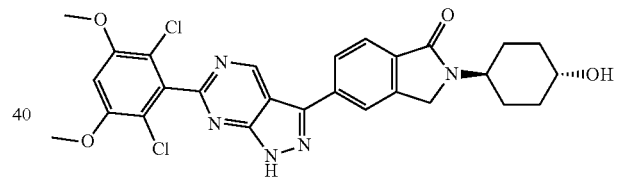

This compound was prepared by using procedures analogous to those described for the synthesis of Example 1, Step 7 starting from 6-(2,6-dichloro-3,5-dimethoxyphenyl)-3-iodo-1H-pyrazolo[3,4-d]pyrimidine and 2-(trans-4-hydroxycyclohexyl)-5-(4,4,5,5-tetramethyl-1,3,2-dioxaborolan-2-yl)isoindolin-1-one. LCMS (M+H)+=554.1/556.0.

Example 24

6-(2,6-Difluoro-3,5-dimethoxyphenyl)-3-{2-[(4-methylpiperazin-1-yl)carbonyl]-2,3-dihydro-1-benzofuran-5-yl}-1H-pyrazolo[4,3-c]pyridine

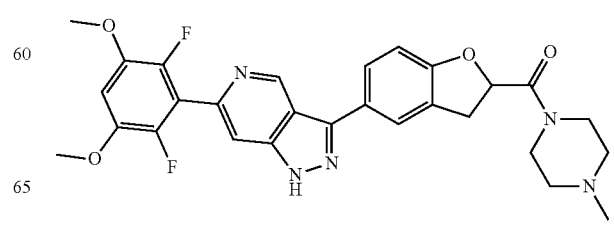

Step 1: 6-chloro-1-(tetrahydro-2H-pyran-2-yl)-1H-pyrazolo[4,3-c]pyridine

At r.t. to a suspension of 6-chloro-1H-pyrazolo[4,3-c]pyridine (0.5 g, 3 mmol) (Frontier Cat. No. Z13659) in methylene chloride (3 mL) and THF (1 mL) was added methanesulfonic acid (42 µL, 0.65 mmol), followed by dihydropyran (0.89 mL, 9.8 mmol). The mixture was stirred at r.t. for 2 h., and then at 50° C. overnight. After cooling the mixture was concentrated under reduced pressure. The residue was purified by flash chromatography on a silica gel column with ethyl acetate in hexanes (0-50%) to afford the desired product (0.8 g). LCMS (M+H)$^+$=238.0; LCMS (M-84+H)$^+$=154.0/156.0.

Step 2: 6-(2,6-difluoro-3,5-dimethoxyphenyl)-1-(tetrahydro-2H-pyran-2-yl)-1H-pyrazolo[4,3-c]pyridine A mixture of 6-chloro-1-(tetrahydro-2H-pyran-2-yl)-1H-pyrazolo[4,3-c]pyridine (333 mg, 1.40 mmol), 2-(2,6-difluoro-3,5-dimethoxyphenyl)-4,4,5,5-tetramethyl-1,3,2-dioxaborolane (400.0 mg, 1.333 mmol), dicyclohexyl(2',4',6'-triisopropylbiphenyl-2-yl)phosphine-(2'-aminobiphenyl-2-yl)(chloro)palladium (1:1) (21.0 mg, 0.0266 mmol), and potassium phosphate (566 mg, 2.66 mmol) in tetrahydrofuran (3 mL) and water (5.5 mL) in a reaction vial was degassed and sealed. The mixture was stirred at r.t. for 30 min. The mixture was extracted with ethyl acetate. The organic layer was dried over MgSO$_4$, filtered and concentrated under reduced pressure. The residue was purified by flash chromatography on a silica gel column with ethyl acetate in hexanes (gradient: 0-50%) to afford the desired product (0.38 g, 76%). LCMS (M+H)$^+$=376.1.

Step 3: 6-(2,6-difluoro-3,5-dimethoxyphenyl)-3-iodo-1H-pyrazolo[4,3-c]pyridine This compound was prepared by using procedures analogous to those described for the synthesis of Example 1, Step 5-6 starting from 6-(2,6-difluoro-3,5-dimethoxyphenyl)-1-(tetrahydro-2H-pyran-2-yl)-1H-pyrazolo[4,3-c]pyridine and N-iodosuccinimide. LCMS (M+H)$^+$=418.0.

Step 4: 6-(2,6-Difluoro-3,5-dimethoxyphenyl)-3-{2-[(4-methylpiperazin-1-yl)carbonyl]-2,3-dihydro-1-benzofuran-5-yl}-1H-pyrazolo[4,3-c]pyridine This compound was prepared by using procedures analogous to those described for the synthesis of Example 4, Step 2 starting from 6-(2,6-difluoro-3,5-dimethoxyphenyl)-3-iodo-1H-pyrazolo[4,3-c]pyridine and 1-methyl-4-{[5-(4,4,5,5-tetramethyl-1,3,2-dioxaborolan-2-yl)-2,3-dihydro-1-benzofuran-2-yl]carbonyl}piperazine. LCMS (M+H)$^+$=536.2.

Example 25

6-(2,6-Difluoro-3,5-dimethoxyphenyl)-3-[4-(4-methylpiperazin-1-yl)phenyl]-1H-pyrazolo[4,3-c]pyridine

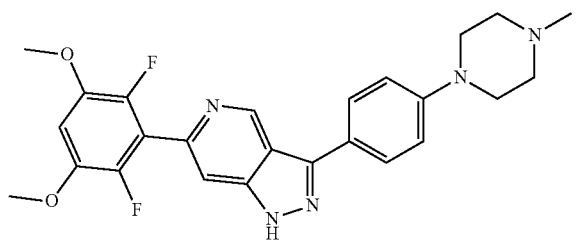

This compound was prepared as TFA salt by using procedures analogous to those described for the synthesis of Example 7, Step 3 starting from 6-(2,6-difluoro-3,5-dimethoxyphenyl)-3-iodo-1H-pyrazolo[4,3-c]pyridine and 1-methyl-4-[4-(4,4,5,5-tetramethyl-1,3,2-dioxaborolan-2-yl)phenyl]piperazine. LCMS (M+H)$^+$=466.2.

Example 26

6-(2,6-Difluoro-3,5-dimethoxyphenyl)-3-[6-(4-methylpiperazin-1-yl)pyridin-3-yl]-1H-pyrazolo[4,3-c]pyridine

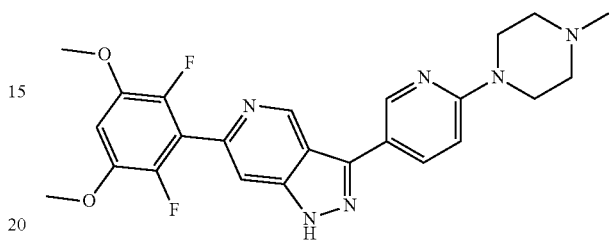

This compound was prepared as TFA salt by using procedures analogous to those described for the synthesis of Example 7, Step 3 starting from 6-(2,6-difluoro-3,5-dimethoxyphenyl)-3-iodo-1H-pyrazolo[4,3-c]pyridine and 1-methyl-4-[5-(4,4,5,5-tetramethyl-1,3,2-dioxaborolan-2-yl)pyridin-2-yl]piperazine. LCMS (M+H)$^+$=467.2.

Example 27

6-(2,6-Difluoro-3,5-dimethoxyphenyl)-3-[2-(4-methylpiperazin-1-yl)pyridin-4-yl]-1H-pyrazolo[4,3-c]pyridine

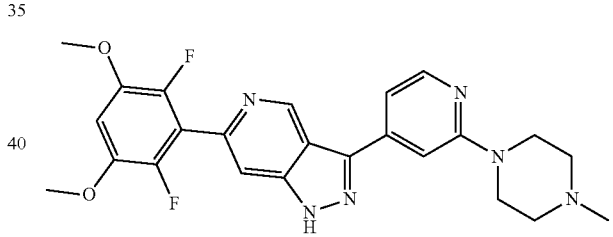

This compound was prepared by using procedures analogous to those described for the synthesis of Example 4, Step 2 starting from 6-(2,6-difluoro-3,5-dimethoxyphenyl)-3-iodo-1H-pyrazolo[4,3-c]pyridine and 1-methyl-4-[4-(4,4,5,5-tetramethyl-1,3,2-dioxaborolan-2-yl)pyridin-2-yl]piperazine. LCMS (M+H)$^+$=467.2.

Example 28

2-Cyclopropyl-5-[6-(2,6-dichloro-3,5-dimethoxyphenyl)-1H-pyrazolo[4,3-c]pyridin-3-yl]isoindolin-1-one

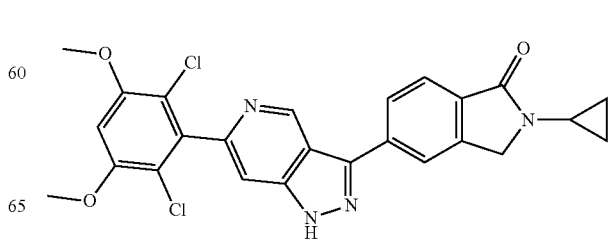

Step 1: 6-(3,5-dimethoxyphenyl)-1-(tetrahydro-2H-pyran-2-yl)-1H-pyrazolo[4,3-c]pyridine A mixture of 6-chloro-1-(tetrahydro-2H-pyran-2-yl)-1H-pyrazolo[4,3-c]pyridine (0.80 g, 3.4 mmol) (Example 24, Step 1), 2-(3,5-dimethoxyphenyl)-4,4,5,5-tetramethyl-1,3,2-dioxaborolane (1.1 g, 4.0 mmol), [1,1'-bis(diphenylphosphino)ferrocene]dichloropalladium(II) complexed with dichloromethane (1:1) (200 mg, 0.3 mmol), and potassium phosphate (1400 mg, 6.7 mmol) in 1,4-dioxane (7 mL) and water (1 mL) in a reaction vial was degassed and sealed. It was stirred at 90° C. for 2 h. After cooling it was concentrated under reduced pressure. The residue was purified by flash chromatography on a silica gel column with ethyl acetate in hexanes (0-50%) to afford the desired product (660 mg). LCMS (M+H)$^+$=340.1.

Step 2: 6-(2,6-dichloro-3,5-dimethoxyphenyl)-1-(tetrahydro-2H-pyran-2-yl)-1H-pyrazolo[4,3-c]pyridine At r.t. to a solution of 6-(3,5-dimethoxyphenyl)-1-(tetrahydro-2H-pyran-2-yl)-1H-pyrazolo[4,3-c]pyridine (0.66 g, 1.9 mmol) in methylene chloride (10 mL) with stirring was added drop-wise sulfuryl chloride (300 µL, 3.7 mmol)(Acros Organics, Cat. No. 37815). The mixture was stirred at r.t. for 2 h. LCMS showed 25% product formed, and 75% was monochlorinated product. Additional sulfuryl chloride (100 µL) was added to the mixture. It was stirred at r.t. for 5 h, and then concentrated under reduced pressure. The residue was purified by flash chromatography on a silica gel column with ethyl acetate in hexanes (0-50%) to afford the desired product (0.78 g). LCMS (M+H)$^+$=408.0.

Step 3: 6-(2,6-dichloro-3,5-dimethoxyphenyl)-1H-pyrazolo[4,3-c]pyridine

At 0° C. (with ice-bath) to a stirring solution of 6-(2,6-dichloro-3,5-dimethoxyphenyl)-1-(tetrahydro-2H-pyran-2-yl)-1H-pyrazolo[4,3-c]pyridine (0.78 g, 1.9 mmol) in methanol (10 mL) was added drop-wise a pre-cooled (with ice-bath) HCl solution prepared from acetyl chloride (2.72 mL, 38.2 mmol) in methanol (15 mL). After the addition, the ice-bath was removed. The mixture was stirred at r.t. for 2 h, and then concentrated under reduced pressure. The residue was purified by flash chromatography on a silica gel column with ethyl acetate in hexanes (0-50%) to afford the desired product (0.62 g). LC/MS (M+H)$^+$=324.0.

Step 4: 6-(2,6-dichloro-3,5-dimethoxyphenyl)-3-iodo-1H-pyrazolo[4,3-c]pyridine At r.t. to a stirring solution of 6-(2,6-dichloro-3,5-dimethoxyphenyl)-1H-pyrazolo[4,3-c]pyridine (0.62 g, 1.9 mmol) in methylene chloride (10 mL) was added N-iodosuccinimide (0.47 g, 2.1 mmol). The mixture was stirred at r.t. for 2 h. It was concentrated under reduced pressure. The residue was purified by flash chromatography on a silica gel column with ethyl acetate in hexanes (0-50%) to afford the desired product 0.50 g.

Step 5: 2-Cyclopropyl-5-[6-(2,6-dichloro-3,5-dimethoxyphenyl)-1H-pyrazolo[4,3-c]pyridin-3-yl]isoindolin-1-one This compound was prepared by using procedures analogous to those described for the synthesis of Example 4, Step 2 starting from 6-(2,6-dichloro-3,5-dimethoxyphenyl)-3-iodo-1H-pyrazolo[4,3-c]pyridine and 2-cyclopropyl-5-(4,4,5,5-tetramethyl-1,3,2-dioxaborolan-2-yl)isoindolin-1-one (Example 21, Step 2). LCMS (M+H)$^+$=495.1/497.1.

Example 29

2-{4-[6-(2,6-Dichloro-3,5-dimethoxyphenyl)-1H-pyrazolo[4,3-c]pyridin-3-yl]-2-methylphenoxy}-N,N-dimethylacetamide

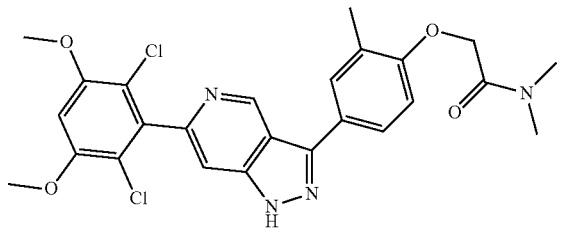

Step 1: 2-(4-bromo-2-methylphenoxy)-N,N-dimethylacetamide

The reaction mixture of 4-bromo-2-methylphenol (Aldrich, Cat. No. 681121) (0.50 g, 2.7 mmol), 2-chloro-N,N-dimethylacetamide (Aldrich, Cat. No. 24350) (0.27 mL, 2.7 mmol) and potassium carbonate (1.1 g, 8.0 mmol) in DMF (4 mL) was stirred at 60° C. overnight. After cooling to r.t., the mixture was adjusted to pH~2 with aqueous HCl, and extracted with ethyl acetate (3×20 mL). The combined organic layers were dried over MgSO$_4$, filtered, and concentrated under reduced pressure to afford the product which was directly used in nest step reaction without further purification. LCMS (M+H)$^+$=272.2/274.2.

Step 2: N,N-dimethyl-2-[2-methyl-4-(4,4,5,5-tetramethyl-1,3,2-dioxaborolan-2-yl)phenoxy]acetamide This compound was prepared by using procedures analogous to those described for the synthesis of Example 1, Step 2 starting from 2-(4-bromo-2-methylphenoxy)-N,N-dimethylacetamide and 4,4,5,5,4',4',5',5'-octamethyl-[2,2']bi[[1,3,2]dioxaborolanyl]. LCMS (M+H)$^+$=320.4.

Step 3: 2-{4-[6-(2,6-dichloro-3,5-dimethoxyphenyl)-1H-pyrazolo[4,3-c]pyridin-3-yl]-2-methylphenoxy}-N,N-dimethylacetamide This compound was prepared using procedures analogous to those described for the synthesis of Example 4, Step 2 starting from 6-(2,6-dichloro-3,5-dimethoxyphenyl)-3-iodo-1H-pyrazolo[4,3-c]pyridine and N,N-dimethyl-2-[2-methyl-4-(4,4,5,5-tetramethyl-1,3,2-dioxaborolan-2-yl)phenoxy]acetamide. LCMS (M+H)$^+$=515.1/517.1.

Example 30

6-[6-(2,6-Dichloro-3,5-dimethoxyphenyl)-1H-pyrazolo[4,3-c]pyridin-3-yl]-2H-1,4-benzoxazin-3(4H)-one

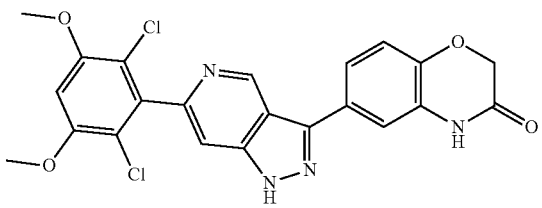 [SMILES: COc1cc(OC)c(Cl)c(-c2cc3[nH]nc(-c4ccc5c(c4)NC(=O)CO5)c3cn2)c1Cl]

Step 1: 6-(4,4,5,5-tetramethyl-1,3,2-dioxaborolan-2-yl)-2H-1,4-benzoxazin-3(4H)-one This compound was prepared using procedures analogous to those described in Example 1, Step 2 starting from 6-bromo-2H-1,4-benzoxazin-3(4H)-one (Aldrich, Cat. No. 662348) and 4,4,5,5,4',4',5',5'-octamethyl-[2,2']bi[[1,3,2]dioxaborolanyl]. LCMS (M+H)$^+$=276.3.

Step 2: 6-[6-(2,6-dichloro-3,5-dimethoxyphenyl)-1H-pyrazolo[4,3-c]pyridin-3-yl]-2H-1,4-benzoxazin-3(4H)-one This compound was prepared by using procedures analogous to those described for the synthesis of Example 4, Step 2 starting from 6-(2,6-dichloro-3,5-dimethoxyphenyl)-3-iodo-1H-pyrazolo[4,3-c]pyridine and 6-(4,4,5,5-tetramethyl-1,3,2-dioxaborolan-2-yl)-2H-1,4-benzoxazin-3(4H)-one. LCMS (M+H)$^+$=471.0/473.0.

Example 31

6-[6-(2,6-Dichloro-3,5-dimethoxyphenyl)-1H-pyrazolo[4,3-c]pyridin-3-yl]-4-methyl-2H-1,4-benzoxazin-3(4H)-one

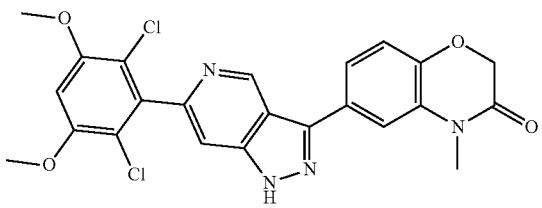 [SMILES: COc1cc(OC)c(Cl)c(-c2cc3[nH]nc(-c4ccc5c(c4)N(C)C(=O)CO5)c3cn2)c1Cl]

Step 1: 6-bromo-4-methyl-2H-1,4-benzoxazin-3(4H)-one

Sodium hydride (0.10 g, 2.6 mmol) was added to a solution of 6-bromo-2H-1,4-benzoxazin-3(4H)-one (0.49 g, 2.1 mmol) in N,N-dimethylformamide (3 mL) under nitrogen. After the mixture was stirred at r.t. for 10 min, methyl iodide (0.27 mL, 4.3 mmol) was added. The reaction mixture was stirred at r.t. for 1 h. Then 10 mL of water was added to the mixture, and a white precipitate was removed by filtration, washed with water, and dried under vacuum to afford the product which was directly used in next step reaction without further purification. LCMS (M+H)$^+$=242.2/244.2.

Step 2: 4-methyl-6-(4,4,5,5-tetramethyl-1,3,2-dioxaborolan-2-yl)-2H-1,4-benzoxazin-3(4H)-one This compound was prepared by using procedures analogous to those described for the synthesis of Example 1, Step 2 starting from 6-bromo-4-methyl-2H-1,4-benzoxazin-3(4H)-one and 4,4,5,5,4',4',5',5'-octamethyl-[2,2']bi[[1,3,2]dioxaborolanyl]. LCMS (M+H)$^+$=290.3.

Step 3: 6-[6-(2,6-dichloro-3,5-dimethoxyphenyl)-1H-pyrazolo[4,3-c]pyridin-3-yl]-4-methyl-2H-1,4-benzoxazin-3(4H)-one This compound was prepared by using procedures analogous to those described for the synthesis of Example 4, Step 2 starting from 6-(2,6-dichloro-3,5-dimethoxyphenyl)-3-iodo-1H-pyrazolo[4,3-c]pyridine and 4-methyl-6-(4,4,5,5-tetramethyl-1,3,2-dioxaborolan-2-yl)-2H-1,4-benzoxazin-3(4H)-one. LCMS (M+H)$^+$=485.0/487.0.

Example 32

5-[6-(2,6-Dichloro-3,5-dimethoxyphenyl)-1H-pyrazolo[4,3-c]pyridin-3-yl]-2-benzofuran-1(3H)-one

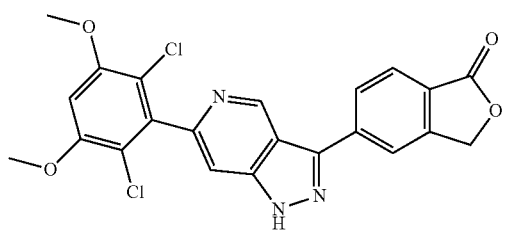 [SMILES: COc1cc(OC)c(Cl)c(-c2cc3[nH]nc(-c4ccc5c(c4)COC5=O)c3cn2)c1Cl]

Step 1: 5-(4,4,5,5-tetramethyl-1,3,2-dioxaborolan-2-yl)-2-benzofuran-1(3H)-one This compound was prepared by using procedures analogous to those described for the synthesis of Example 1, Step 2 starting from 5-bromo-2-benzofuran-1(3H)-one (Aldrich, Cat. No. 647187) and 4,4,5,5,4',4',5',5'-octamethyl-[2,2']bi[[1,3,2]dioxaborolanyl].

Step 2: 5-[6-(2,6-dichloro-3,5-dimethoxyphenyl)-1H-pyrazolo[4,3-c]pyridin-3-y]-2-benzofuran-1(3H)-one This compound was prepared by using procedures analogous to those described for the synthesis of Example 4, Step 2 starting from 6-(2,6-dichloro-3,5-dimethoxyphenyl)-3-iodo-1H-pyrazolo[4,3-c]pyridine and 5-(4,4,5,5-tetramethyl-1,3,2-dioxaborolan-2-yl)-2-benzofuran-1(3H)-one. LCMS (M+H)$^+$: 456.0/458.0.

Example 33

2-{4-[6-(2,6-Dichloro-3,5-dimethoxyphenyl)-1H-pyrazolo[4,3-c]pyridin-3-yl]-1H-pyrazol-1-yl}propanenitrile

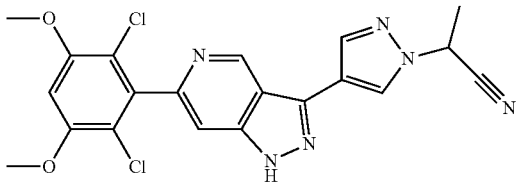 [SMILES: COc1cc(OC)c(Cl)c(-c2cc3[nH]nc(-c4cnn(C(C)C#N)c4)c3cn2)c1Cl]

Step 1: 2-[4-(4,4,5,5-tetramethyl-1,3,2-dioxaborolan-2-yl)-1H-pyrazol-1-yl]propanenitrile A mixture of 4-(4,4,5,5-tetramethyl-1,3,2-dioxaborolan-2-yl)-1H-pyrazole (Aldrich, Cat. No. 525057)(0.22 g, 1.1 mmol), 2-chloropropanenitrile (Aldrich, Cat. No. 192406) (0.12 g, 1.4 mmol), and cesium carbonate (0.82 g, 2.5 mmol) in acetonitrile (4.0 mL) was stirred at 80° C. for 2 h. The reaction mixture was diluted with water, extracted with ethyl acetate, washed with brine. The combined organic layers were dried over MgSO$_4$, filtered and concentrated under reduced pressure. The residue was purified by flash chromatography on a silica gel column with ethyl acetate in hexanes (0-40%) to afford the desired product. LCMS (M+H)$^+$=248.1.

Step 2: 2-{4-[6-(2,6-dichloro-3,5-dimethoxyphenyl)-1H-pyrazolo[4,3-c]pyridin-3-yl]-1H-pyrazol-1-yl}propanenitrile This compound was prepared by using procedures analogous to those described for the synthesis of Example 4, Step 2 starting from 6-(2,6-dichloro-3,5-dimethoxyphenyl)-3-iodo-1H-pyrazolo[4,3-c]pyridine and 2-[4-(4,4,5,5-tetramethyl-1,3,2-dioxaborolan-2-yl)-1H-pyrazol-1-yl]propanenitrile. LCMS (M+H)$^+$=443.0/445.0. $^1$H NMR (300 MHz, DMSO-d$_6$) δ: 9.39 (s, 1H), 8.66 (s, 1H), 8.27 (s, 1H), 7.42 (s, 1H), 7.00 (s, 1H), 5.91 (q, J=7.1 Hz, 1H), 3.96 (s, 6H), 1.88 (d, J=7.1 Hz, 3H).

Example 34

2-{4-[6-(2,6-Dichloro-3,5-dimethoxyphenyl)-1H-pyrazolo[4,3-c]pyridin-3-yl]-2-fluorophenyl}-2-hydroxy-N,N-dimethylacetamide

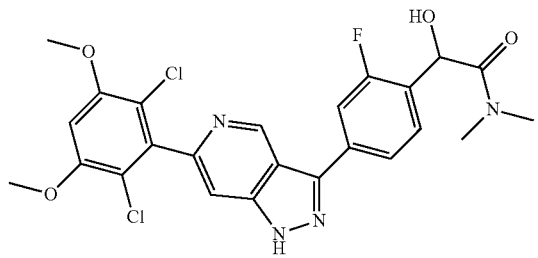

Step 1: 2-(4-bromo-2-fluorophenyl)-2-hydroxy-N,N-dimethylacetamide

N,N-Diisopropylethylamine (0.8 g, 0.006 mol) was added to a mixture of (4-bromo-2-fluorophenyl)(hydroxy)acetic acid (Oakwood, Cat. No. 019267) (0.5 g, 0.002 mol), dimethylamine in THF (2.4 mmol, 2.0 M, 1.2 mL), and benzotriazol-1-yloxytris(dimethylamino)phosphonium hexafluorophosphate (1.1 g, 0.0024 mol) in methylene chloride (10 mL). The mixture was stirred at r.t. overnight, and concentrated under reduced pressure. The residue was purified by flash chromatography on a silica gel column with ethyl acetate in hexanes (0-40%) to afford the desired product. LCMS (M+H)$^+$=276.2/278.2. $^1$H NMR (300 MHz, DMSO-d$_6$) δ: 9.50 (d, J=1.1 Hz, 1H), 7.97 (dd, J=8.0, 1.5 Hz, 1H), 7.83 (dd, J=11.4, 1.5 Hz, 1H), 7.54 (d, J=8.0 Hz, 1H), 7.51 (d, J=1.1 Hz, 1H), 7.01 (s, 1H), 5.70 (s, 1H), 5.65 (s, 1H), 3.96 (s, 6H), 2.94 (s, 3H), 2.88 (s, 3H).

Step 2: 2-[2-fluoro-4-(4,4,5,5-tetramethyl-1,3,2-dioxaborolan-2-yl)phenyl]-2-hydroxy-N,N-dimethylacetamide This compound was prepared by using procedures analogous to those described for the synthesis of Example 1, Step 2 starting from 2-(4-bromo-2-fluorophenyl)-2-hydroxy-N,N-dimethylacetamide and 4,4,5,5,4',4',5',5'-octamethyl-[2,2']bi[[1,3,2]dioxaborolanyl]. LCMS (M+H)$^+$=324.2.

Step 3: 2-{4-[6-(2,6-dichloro-3,5-dimethoxyphenyl)-1H-pyrazolo[4,3-c]pyridin-3-yl]-2-fluorophenyl}-2-hydroxy-N,N-dimethylacetamide This compound was prepared by using procedures analogous to those described for the synthesis of Example 4, Step 2 starting from 6-(2,6-dichloro-3,5-dimethoxyphenyl)-3-iodo-1H-pyrazolo[4,3-c]pyridine and {4-[2-(dimethylamino)-1-hydroxy-2-oxoethyl]-3-fluorophenyl}boronic acid. LCMS (M+H)$^+$=519.0/521.0.

Example 35

2-{4-[6-(2,6-Dichloro-3,5-dimethoxyphenyl)-1H-pyrazolo[4,3-c]pyridin-3-yl]phenoxy}-N,N-dimethylethanamine

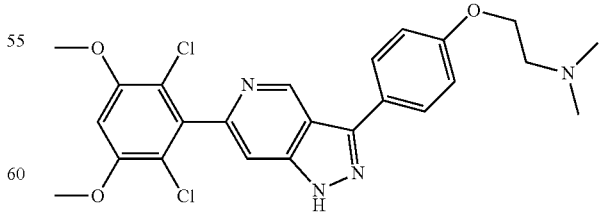

This compound was prepared by using procedures analogous to those described for the synthesis of Example 4, Step 2 starting from 6-(2,6-dichloro-3,5-dimethoxyphenyl)-3-iodo-1H-pyrazolo[4,3-c]pyridine and N,N-dimethyl-2-[4-(4, 4,5,5-tetramethyl-1,3,2-dioxaborolan-2-yl)phenoxy]ethanamine (Combi-Blocks, Cat. No. PN-3972). LCMS (M+H)$^+$=487.0/489.0.

Example 36

2-{4-[6-(2,6-Dichloro-3,5-dimethoxyphenyl)-1H-pyrazolo[4,3-c]pyridin-3-yl]-1H-pyrazol-1-yl}-N-methylacetamide

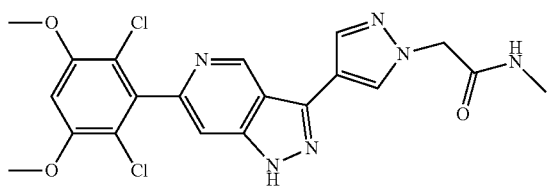

Step 1: {4-[6-(2,6-dichloro-3,5-dimethoxyphenyl)-1H-pyrazolo[4,3-c]pyridin-3-yl]-1H-pyrazol-1-yl}acetic acid

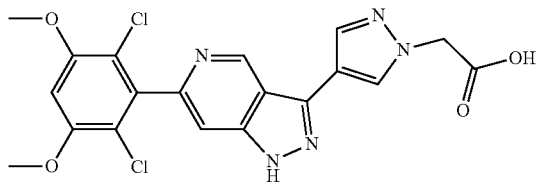 [SMILES: COc1cc(OC)c(Cl)c(-c2cc3[nH]nc(-c4cnn(CC(=O)O)c4)c3cn2)c1Cl]

A mixture of 6-(2,6-dichloro-3,5-dimethoxyphenyl)-3-iodo-1H-pyrazolo[4,3-c]pyridine (0.20 g, 0.44 mmol), ethyl [4-(4,4,5,5-tetramethyl-1,3,2-dioxaborolan-2-yl)-1H-pyrazol-1-yl]acetate (Aldrich, Cat. No. 683566) (0.14 g, 0.49 mmol), [1,1'-bis(diphenylphosphino)ferrocene]dichloropalladium(II) complexed with dichloromethane (1:1) (18 mg, 0.022 mmol), and potassium carbonate (0.184 g, 1.33 mmol) in 1,4-dioxane (10 mL) and water (5 mL) was degassed and recharged with nitrogen three times. The reaction mixture was stirred at 85° C. for 6 h. The reaction mixture was adjusted to pH~4 with 1N HCl. The precipitates formed were filtered, washed with water and ether, and dried under vacuum to afford the desired product (0.10 g, 50%). LCMS (M+H)$^+$=448.0/450.0.

Step 2: 2-{4-[6-(2,6-dichloro-3,5-dimethoxyphenyl)-1H-pyrazolo[4,3-c]pyridin-3-yl]-1H-pyrazol-1-yl}-N-methylacetamide N,N-Diisopropylethylamine (9.3 µL, 0.054 mmol) was added to a mixture of {4-[6-(2,6-dichloro-3,5-dimethoxyphenyl)-1H-pyrazolo[4,3-c]pyridin-3-yl]-1H-pyrazol-1-yl}acetic acid (8.0 mg, 0.018 mmol), 2.0 M methylamine in THF (9.8 µL, 0.020 mmol) and benzotriazol-1-yloxytris(dimethylamino)phosphonium hexafluorophosphate (8.7 mg, 0.020 mmol) in N,N-dimethylformamide (0.5 mL). The reaction mixture was stirred at r.t. for 3 h, and purified by RP-HPLC (pH=10) to afford the desired product. LCMS (M+H)$^+$=461.0/463.0.

Example 37

2-{4-[6-(2,6-Dichloro-3,5-dimethoxyphenyl)-1H-pyrazolo[4,3-c]pyridin-3-yl]-1H-pyrazol-1-yl}-N,N-dimethylacetamide

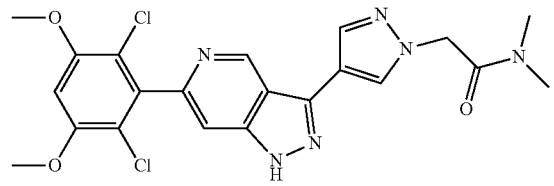

This compound was prepared by using procedures analogous to those described for the synthesis of Example 36, Step 2, starting from {4-[6-(2,6-dichloro-3,5-dimethoxyphenyl)-1H-pyrazolo[4,3-c]pyridin-3-yl]-1H-pyrazol-1-yl}acetic acid and 2.0 M dimethylamine in THF. LCMS (M+H)$^+$=475.0/477.0.

Example 38

N-Cyclopropyl-2-{4-[6-(2,6-dichloro-3,5-dimethoxyphenyl)-1H-pyrazolo[4,3-c]pyridin-3-yl]-1H-pyrazol-1-yl}acetamide

This compound was prepared by using procedures analogous to those described for the synthesis of Example 36, Step 2, starting from {4-[6-(2,6-dichloro-3,5-dimethoxyphenyl)-1H-pyrazolo[4,3-c]pyridin-3-yl]-1H-pyrazol-1-yl}acetic acid and cyclopropylamine. LCMS (M+H)$^+$=487.1/489.1.

Example 39

1-({4-[6-(2,6-Dichloro-3,5-dimethoxyphenyl)-1H-pyrazolo[4,3-c]pyridin-3-yl]-1H-pyrazol-1-yl}acetyl)azetidin-3-ol

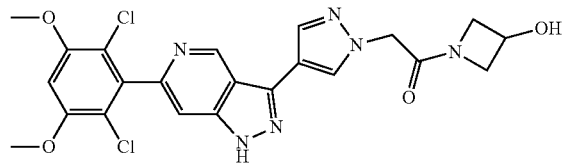 [SMILES: COc1cc(OC)c(Cl)c(-c2cc3[nH]nc(-c4cnn(CC(=O)N5CC(O)C5)c4)c3cn2)c1Cl]

This compound was prepared by using procedures analogous to those described for the synthesis of Example 36, Step 2, starting from {4-[6-(2,6-dichloro-3,5-dimethoxyphenyl)-1H-pyrazolo[4,3-c]pyridin-3-yl]-1H-pyrazol-1-yl}acetic acid and azetidin-3-ol hydrochloride (Aldrich, Cat. No. 680079). LCMS (M+H)⁺=503.1/505.3.

Example 40

6-(2,6-Dichloro-3,5-dimethoxyphenyl)-3-[1-(2-morpholin-4-yl-2-oxoethyl)-1H-pyrazol-4-yl]-1H-pyrazolo[4,3-c]pyridine

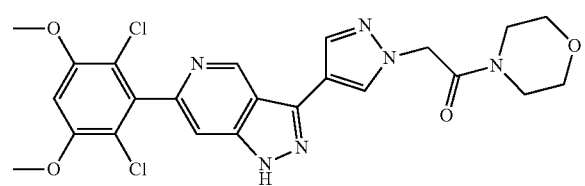 [SMILES: COc1cc(OC)c(Cl)c(-c2cc3[nH]nc(-c4cnn(CC(=O)N5CCOCC5)c4)c3cn2)c1Cl]

This compound was prepared by using procedures analogous to those described for the synthesis of Example 36, Step 2, starting from {4-[6-(2,6-dichloro-3,5-dimethoxyphenyl)-1H-pyrazolo[4,3-c]pyridin-3-yl]-1H-pyrazol-1-yl}acetic acid and morpholine. LCMS (M+H)⁺=517.0/519.0.

Example 41

6-(2,6-Dichloro-3,5-dimethoxyphenyl)-3-{1-[2-(4-methylpiperazin-1-yl)-2-oxoethyl]-1H-pyrazol-4-yl}-1H-pyrazolo[4,3-c]pyridine

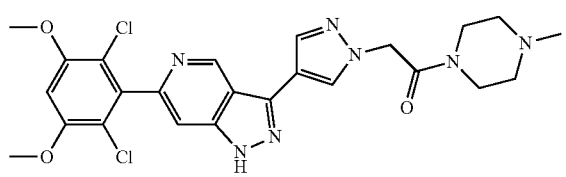

This compound was prepared by using procedures analogous to those described for the synthesis of Example 36, Step 2, starting from {4-[6-(2,6-dichloro-3,5-dimethoxyphenyl)-1H-pyrazolo[4,3-c]pyridin-3-yl]-1H-pyrazol-1-yl}acetic acid and 1-methyl piperazine. LCMS (M+H)⁺=530.1/532.1.

Example 42

2-{4-[6-(2,6-Dichloro-3,5-dimethoxyphenyl)-1H-pyrazolo[4,3-c]pyridin-3-yl]-1H-pyrazol-1-yl}-N-(1-methylpiperidin-4-yl)acetamide

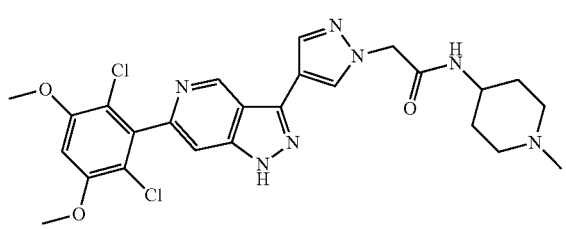

This compound was prepared by using procedures analogous to those described for the synthesis of Example 36, Step 2, starting from {4-[6-(2,6-dichloro-3,5-dimethoxyphenyl)-1H-pyrazolo[4,3-c]pyridin-3-yl]-1H-pyrazol-1-yl}acetic acid and 1-methylpiperidin-4-amine. LCMS (M+H)⁺=544.1/546.1.

Example 43

1-({4-[6-(2,6-Dichloro-3,5-dimethoxyphenyl)-1H-pyrazolo[4,3-c]pyridin-3-yl]-1H-pyrazol-1-yl}acetyl)pyrrolidin-3-ol

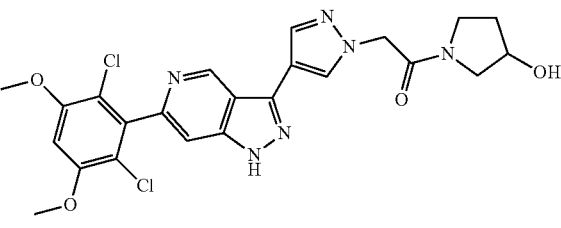 [SMILES: COc1cc(OC)c(Cl)c(-c2cc3[nH]nc(-c4cnn(CC(=O)N5CCC(O)C5)c4)c3cn2)c1Cl]

This compound was prepared by using procedures analogous to those described for the synthesis of Example 36, Step 2, starting from {4-[6-(2,6-dichloro-3,5-dimethoxyphenyl)-1H-pyrazolo[4,3-c]pyridin-3-yl]-1H-pyrazol-1-yl}acetic acid and 3-pyrrolidinol. LCMS (M+H)⁺=517.1/519.0.

Example 44

1-({4-[6-(2,6-Dichloro-3,5-dimethoxyphenyl)-1H-pyrazolo[4,3-c]pyridin-3-yl]-1H-pyrazol-1-yl}acetyl)-N,N-dimethylpyrrolidin-3-amine

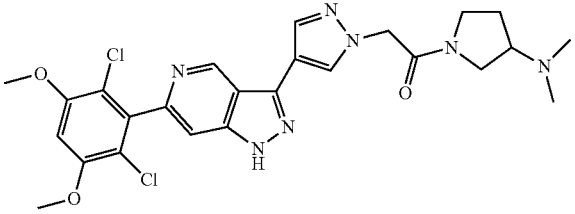

This compound was prepared by using procedures analogous to those described for the synthesis of Example 36, Step 2, starting from {4-[6-(2,6-dichloro-3,5-dimethoxyphenyl)-1H-pyrazolo[4,3-c]pyridin-3-yl]-1H-pyrazol-1-yl}acetic acid and N,N-dimethylpyrrolidin-3-amine. LCMS (M+H)⁺=544.2/546.3.

Example 45

6-(2,6-Dichloro-3,5-dimethoxyphenyl)-3-{1-[2-(3-methoxypyrrolidin-1-yl)-2-oxoethyl]-1H-pyrazol-4-yl}-1H-pyrazolo[4,3-c]pyridine

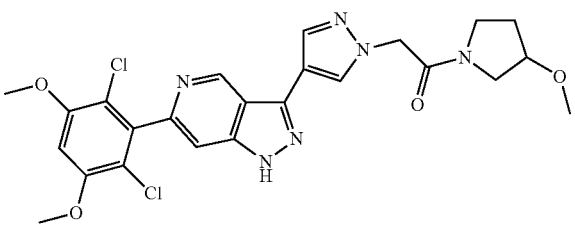

This compound was prepared by using procedures analogous to those described for the synthesis of Example 36, Step 2, starting from {4-[6-(2,6-dichloro-3,5-dimethoxyphenyl)-1H-pyrazolo[4,3-c]pyridin-3-yl]-1H-pyrazol-1-yl}acetic acid and 3-methoxypyrrolidine. LCMS (M+H)⁺=531.2/533.2.

Example 46

2-{4-[6-(2,6-Dichloro-3,5-dimethoxyphenyl)-1H-pyrazolo[4,3-c]pyridin-3-yl]-1H-pyrazol-1-yl}-N-(2-methoxyethyl)acetamide

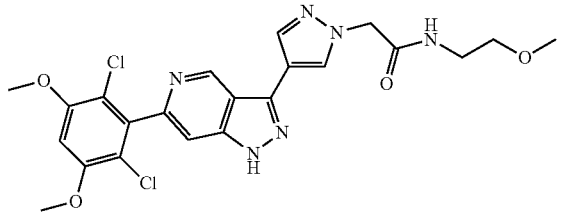

This compound was prepared by using procedures analogous to those described for the synthesis of Example 36, Step 2, starting from {4-[6-(2,6-dichloro-3,5-dimethoxyphenyl)-1H-pyrazolo[4,3-c]pyridin-3-yl]-1H-pyrazol-1-yl}acetic acid and 2-Methoxyethylamine. LCMS (M+H)⁺=505.1/507.1.

Example 47

1-({4-[6-(2,6-Dichloro-3,5-dimethoxyphenyl)-1H-pyrazolo[4,3-c]pyridin-3-yl]-1H-pyrazol-1-yl}acetyl)pyrrolidine-3-carbonitrile

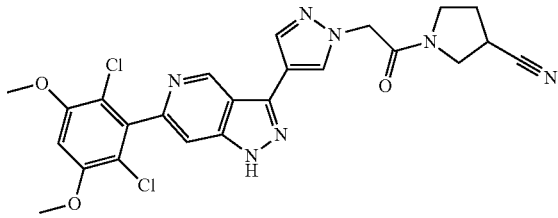 [SMILES: COc1cc(OC)c(Cl)c(-c2cc3[nH]nc(-c4cnn(CC(=O)N5CCC(C#N)C5)c4)c3cn2)c1Cl]

This compound was prepared by using procedures analogous to those described for the synthesis of Example 36, Step 2, starting from {4-[6-(2,6-dichloro-3,5-dimethoxyphenyl)-1H-pyrazolo[4,3-c]pyridin-3-yl]-1H-pyrazol-1-yl}acetic acid and pyrrolidine-3-carbonitrile hydrochloride. LCMS (M+H)⁺=526.2/528.1.

Example 48

6-(2,6-Dichloro-3,5-dimethoxyphenyl)-3-(1-{2-[(3S)-3-fluoropyrrolidin-1-yl]-2-oxoethyl}-1H-pyrazol-4-yl)-1H-pyrazolo[4,3-c]pyridine

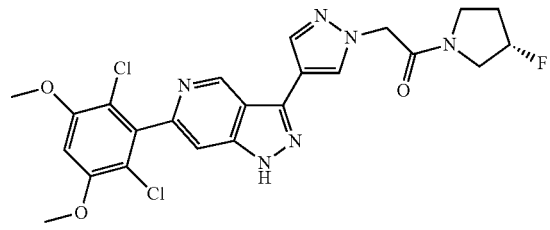 [SMILES: COc1cc(OC)c(Cl)c(-c2cc3[nH]nc(-c4cnn(CC(=O)N5CC[C@H](F)C5)c4)c3cn2)c1Cl]

This compound was prepared by using procedures analogous to those described for the synthesis of Example 36, Step 2, starting from {4-[6-(2,6-dichloro-3,5-dimethoxyphenyl)-1H-pyrazolo[4,3-c]pyridin-3-yl]-1H-pyrazol-1-yl}acetic acid and (3S)-3-fluoropyrrolidine hydrochloride. LCMS (M+H)⁺=519.1/521.1.

Example 49

6-(2,6-Dichloro-3,5-dimethoxyphenyl)-3-[(E)-2-(1-methyl-1H-pyrazol-4-yl)vinyl]-1H-pyrazolo[4,3-c]pyridine

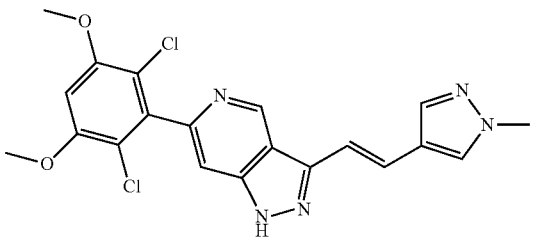

Step 1: 6-(2,6-dichloro-3,5-dimethoxyphenyl)-3-iodo-1-(tetrahydro-2H-pyran-2-yl)-1H-pyrazolo[4,3-c]pyridine A mixture of 6-(2,6-dichloro-3,5-dimethoxyphenyl)-3-iodo-1H-pyrazolo[4,3-c]pyridine (0.45 g, 1.0 mmol) (Example 28, Step 4), dihydropyran (270 μL, 3.0 mmol) and methanesulfonic acid (13 μL, 0.20 mmol) in methylene chloride (9 mL) and tetrahydrofuran (3 mL) in reaction flask was stirred at r.t. overnight. The mixture was concentrated under reduced pressure. The residue was purified by flash chromatography on a silica gel column with ethyl acetate in hexanes (0-50%) to afford the desired product (0.34 g, 64%). LC/MS (M+H)⁺=534.0.

Step 2: 6-(2,6-dichloro-3,5-dimethoxyphenyl)-1-(tetrahydro-2H-pyran-2-yl)-3-vinyl-1H-pyrazolo[4,3-c]pyridine A mixture of 6-(2,6-dichloro-3,5-dimethoxyphenyl)-3-iodo-1-(tetrahydro-2H-pyran-2-yl)-1H-pyrazolo[4,3-c]pyridine (100 mg, 0.2 mmol), 4,4,5,5-tetramethyl-2-vinyl-1,3,2-dioxaborolane (44 μL, 0.26 mmol) (Aldrich Cat. No. 633348), tributylamine (54 μL, 0.22 mmol) and dichloro[bis(triphenylphosphoranyl)]palladium (5 mg, 0.007 mmol) in N,N-dimethylformamide (1 mL) in a reaction vial was degassed and sealed. The mixture was stirred at 95° C. for 15 h. After cooling it was equally split into two parts. The material was used in the next step without further purification.

Step 3: 6-(2,6-dichloro-3,5-dimethoxyphenyl)-3-[(E)-2-(1-methyl-1H-pyrazol-4-yl)vinyl]-1-(tetrahydro-2H-pyran-2-yl)-1H-pyrazolo[4,3-c]pyridine

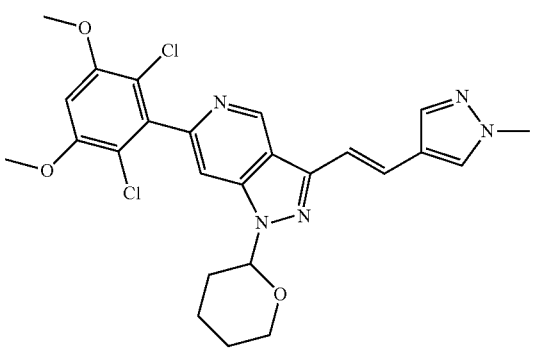

67

To a solution of 6-(2,6-dichloro-3,5-dimethoxyphenyl)-1-(tetrahydro-2H-pyran-2-yl)-3-vinyl-1H-pyrazolo[4,3-c]pyridine (0.1 mmol) in N,N-dimethylformamide (0.5 mL) was added 4-iodo-1-methyl-1H-pyrazole (22 mg, 0.10 mmol) (Aldrich Cat. No. 683531), barium hydroxide (36 mg, 0.21 mmol) and [1,1'-bis(diphenylphosphino)ferrocene]dichloropalladium(II) complexed with dichloromethane (1:1) (5.6 mg, 0.0069 mmol), and water (0.05 mL). The mixture was degassed and sealed. The mixture was stirred at 95° C. overnight. After cooling the solid was filtered off, washed with acetonitrile. The filtrate was concentrated under reduced pressure to afford the crude product which was directly used in next step reaction without further purification. LCMS (M+H)$^+$=514.2/516.1.

Step 4: 6-(2,6-dichloro-3,5-dimethoxyphenyl)-3-[(E)-2-(1-methyl-1H-pyrazol-4-yl)vinyl]-1H-pyrazolo[4,3-c]pyridine 6-(2,6-Dichloro-3,5-dimethoxyphenyl)-3-[(E)-2-(1-methyl-1H-pyrazol-4-yl)vinyl]-1-(tetrahydro-2H-pyran-2-yl)-1H-pyrazolo[4,3-c]pyridine was dissolved in methanol (0.8 mL). To the solution was added HCl solution previously prepared from acetyl chloride (0.5 mL) and methanol (0.5 mL). The mixture was stirred at r.t. for 2 h. The solvent was removed. The residue was dissolved in methanol, and purified by RP-HPLC (pH=10) to afford the desired product (4.9 mg). LCMS (M+H)$^+$=430.1.

Example 50

2-(4-{(E)-2-[6-(2,6-Dichloro-3,5-dimethoxyphenyl)-1H-pyrazolo[4,3-c]pyridin-3-yl]vinyl}-1H-pyrazol-1-yl)ethanol

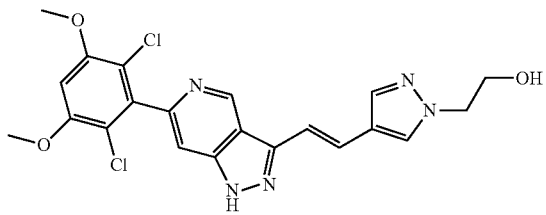 [SMILES: COc1cc(OC)c(Cl)c(-c2cc3[nH]nc(/C=C/c4cnn(CCO)c4)c3cn2)c1Cl]

Step 1: 4-iodo-1-[2-(tetrahydro-2H-pyran-2-yloxy)ethyl]-1H-pyrazole

At r.t. to a solution of 2-(2-bromoethoxy)tetrahydro-2H-pyran (210 μL, 1.4 mmol) (Aldrich Cat. No. 475394) in acetonitrile (6 mL) was added 4-iodo-1H-pyrazole (0.25 g, 1.3 mmol) (Aldrich Cat. No. 213993), followed by cesium carbonate (0.63 g, 1.9 mmol). The mixture was stirred at r.t. over a weekend. The solid was filtered off, then washed with acetonitrile. The filtrate was concentrated under reduced pressure. The residue was purified by flash chromatography on a silica gel column with ethyl acetate in hexanes (0-50%) to afford the desired product (0.12 g). LCMS (M-84)$^+$=239.0.

68

Step 2: 6-(2,6-dichloro-3,5-dimethoxyphenyl)-1-(tetrahydro-2H-pyran-2-yl)-3-((E)-2-{1-[2-(tetrahydro-2H-pyran-2-yloxy)ethyl]-1H-pyrazol-4-yl}vinyl)-1H-pyrazolo[4,3-c]pyridine

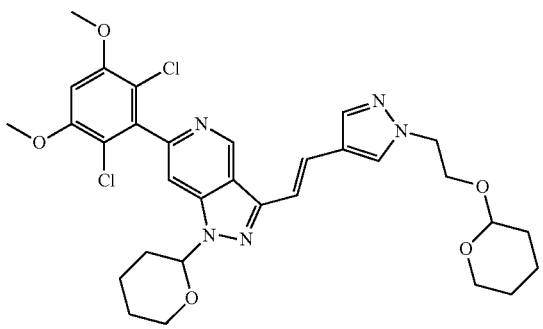 [SMILES: COc1cc(OC)c(Cl)c(-c2cc3c(cn2)c(/C=C/c2cnn(CCOC4CCCCO4)c2)nn3C2CCCCO2)c1Cl]

To a solution of 6-(2,6-dichloro-3,5-dimethoxyphenyl)-1-(tetrahydro-2H-pyran-2-yl)-3-vinyl-1H-pyrazolo[4,3-c]pyridine (0.1 mmol) in DMF (0.5 mL) was added 4-iodo-1-[2-(tetrahydro-2H-pyran-2-yloxy)ethyl]-1H-pyrazole (44 mg, 0.14 mmol), [1,1'-bis(diphenylphosphino)ferrocene]dichloropalladium(II) complexed with dichloromethane (1:1) (7.5 mg, 0.0092 mmol), and water (0.05 mL). The mixture was degassed and sealed. It was stirred at 95° C. for 3 h. After cooling the solid was filtered off, washed with acetonitrile. The filtrate was concentrated under reduced pressure. The residue was purified by flash chromatography on a silica gel column with ethyl acetate in hexanes (0-50%) to afford the desired product (32 mg). LCMS (M+H)$^+$=628.2/630.3.

Step 3: 2-(4-{(E)-2-[6-(2,6-dichloro-3,5-dimethoxyphenyl)-1H-pyrazolo[4,3-c]pyridin-3-yl]vinyl}-1H-pyrazol-1-yl)ethanol 6-(2,6-Dichloro-3,5-dimethoxyphenyl)-1-(tetrahydro-2H-pyran-2-yl)-3-((E)-2-{1-[2-(tetrahydro-2H-pyran-2-yloxy)ethyl]-1H-pyrazol-4-yl}vinyl)-1H-pyrazolo[4,3-c]pyridine (32 mg) was dissolved in methanol (1 mL). To the solution was added HCl solution previously prepared from acetyl chloride (0.5 mL) and methanol (0.5 mL). The mixture was stirred at r.t. for 30 min. The solvent was removed. The residue was dissolved in methanol, purified by RP-HPLC (pH=2) to afford the desired product as TFA salt. LCMS (M+H)$^+$=460.0.

Example 51

(2S)-1-{4-[6-(2,6-Dichloro-3,5-dimethoxyphenyl)-1H-pyrazolo[4,3-c]pyridin-3-yl]-1H-pyrazol-1-yl}propan-2-ol

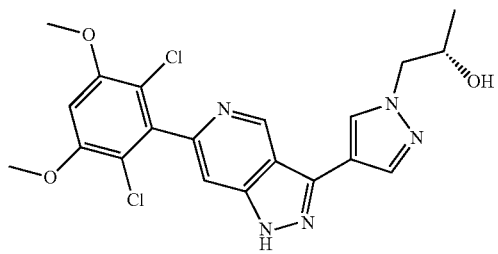 [SMILES: COc1cc(OC)c(Cl)c(-c2cc3[nH]nc(-c4cnn(C[C@H](C)O)c4)c3cn2)c1Cl]

Step 1: (2S)-1-[4-(4,4,5,5-tetramethyl-1,3,2-dioxaborolan-2-yl)-1H-pyrazol-1-yl]propan-2-ol A mixture of 4-(4,4,5,5-tetramethyl-1,3,2-dioxaborolan-2-yl)-1H-pyrazole (300 mg, 1.5 mmol)(Aldrich Cat. No. 525057), (S)-(–)-methyloxirane (130 µL, 1.9 mmol) and triethylamine (0.45 mL, 3.2 mmol) in acetonitrile (1.0 mL) in a reaction vial was stirred at 50° C. for 2 h. After cooling it was concentrated under reduced pressure. The residue was purified by flash chromatography on a silica gel column with ethyl acetate in hexanes (0-50%) to afford the desired product (0.35 g). LCMS (M+H)$^+$=253.0.

Step 2: (2S)-1-{4-[6-(2,6-dichloro-3,5-dimethoxyphenyl)-1H-pyrazolo[4,3-c]pyridin-3-yl]-1H-pyrazol-1-yl}propan-2-ol A mixture of 6-(2,6-dichloro-3,5-dimethoxyphenyl)-3-iodo-1H-pyrazolo[4,3-c]pyridine (15 mg, 0.033 mmol) (Example 28, Step 4), (2S)-1-[4-(4,4,5,5-tetramethyl-1,3,2-dioxaborolan-2-yl)-1H-pyrazol-1-yl]propan-2-ol (10 mg, 0.04 mmol), [1,1'-bis(diphenylphosphino)ferrocene]-dichloropalladium(II) complexed with dichloromethane (1:1) (2 mg, 0.003 mmol), and potassium phosphate (14 mg, 0.067 mmol) in 1,4-dioxane (0.3 mL) and water (0.05 mL) in a reaction vial was degassed and sealed. It was stirred at 90° C. overnight. After cooling it was diluted with methanol, purified by RP-HPLC (pH=2) to afford the desired product (2.5 mg) as TFA salt. LCMS (M+H)$^+$=448.1.

Example 52

5-[6-(2,6-Difluoro-3,5-dimethoxyphenyl)-1H-pyrazolo[4,3-c]pyridin-3-yl]-2-ethylisoindolin-1-one

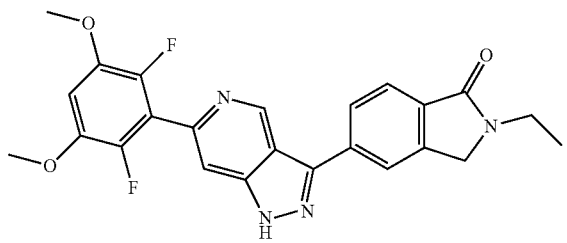 [SMILES: CCN1Cc2cc(-c3n[nH]c4cc(-c5c(F)c(OC)cc(OC)c5F)ncc34)ccc2C1=O]

Step 1:
6-(3,5-dimethoxyphenyl)-1H-pyrazolo[4,3-c]pyridine

A mixture of 6-chloro-1H-pyrazolo[4,3-c]pyridine (500 mg, 3.2 mmol) (Frontier Cat. No. Z13659), (3,5-dimethoxyphenyl)boronic acid (890 mg, 4.9 mmol) (TCI Cat. No. D3513), [1,1'-bis(diphenylphosphino)ferrocene]dichloropalladium(II) complexed with dichloromethane (1:1) (200 mg, 0.3 mmol), and sodium carbonate (1.0 g, 9.8 mmol) in 1,2-dimethoxyethane (4 mL) and water (0.6 mL) was degassed, and sealed. The mixture was stirred at 110° C. overnight. After cooling it was partitioned between ethyl acetate and water. After separation the aqueous solution was extracted with ethyl acetate twice. The combined organic layers were dried over Na$_2$SO$_4$, filtered, and concentrated under reduced pressure. The residue was purified by flash chromatography on a silica gel column with ethyl acetate in hexanes (0-50%) to afford the desired product (0.80 g). LCMS (M+H)$^+$=256.0.

Step 2: 6-(3,5-dimethoxyphenyl)-3-iodo-1H-pyrazolo[4,3-c]pyridine

A mixture of 6-(3,5-dimethoxyphenyl)-1H-pyrazolo[4,3-c]pyridine (0.80 g, 3.1 mmol) and N-iodosuccinimide (0.78 g, 3.4 mmol) in N,N-dimethylformamide (10 mL) was stirred at r.t. over weekend. Water was added to the mixture with stirring. The light brown solid precipitated and was collected by filtration to afford the desired product (0.83 g) which was directly used in next step reaction without further purification. LCMS (M+H)$^+$=382.0.

Step 3: 6-(3,5-dimethoxyphenyl)-3-iodo-1-(tetrahydro-2H-pyran-2-yl)-1H-pyrazolo[4,3-c]pyridine A mixture of 6-(3,5-dimethoxyphenyl)-3-iodo-1H-pyrazolo[4,3-c]pyridine (0.50 g, 1.3 mmol), dihydropyran (360 µL, 3.9 mmol), and methanesulfonic acid (17 µL, 0.26 mmol) in tetrahydrofuran (3 mL) and methylene chloride (7.5 mL) was stirred at 80° C. for 2 days. After cooling, to the mixture was added some triethylamine, and concentrated under reduced pressure. The residue was purified by flash chromatography on a silica gel column with ethyl acetate in hexanes (0-50%) to afford the desired product (0.55 g). LCMS (M+H)$^+$=466.0.

Step 4: 6-(2-fluoro-3,5-dimethoxyphenyl)-3-iodo-1-(tetrahydro-2H-pyran-2-yl)-1H-pyrazolo[4,3-c]pyridine 1-(Chloromethyl)-4-fluoro-1,4-diazoniabicyclo[2.2.2]octane ditetrafluoroborate (0.84 g, 2.4 mmol) (Alfa Aesar Cat. No. L17003) was added to a stirring solution of 6-(3,5-dimethoxyphenyl)-3-iodo-1-(tetrahydro-2H-pyran-2-yl)-1H-pyrazolo[4,3-c]pyridine (0.55 g, 1.2 mmol) in acetonitrile (15 mL). The mixture was stirred at r.t. for 1 h. The solid was filtered out. The filtrate was concentrated under reduced pressure. The residue was purified by flash chromatography on a silica gel column with ethyl acetate in hexanes (0-50%) to afford the desired product (0.52 g) which contained some amount of the corresponding di-fluoride analogue, and was directly used in next step reaction without further purification. LCMS (M+H)$^+$=484.0

Step 5: 6-(2,6-difluoro-3,5-dimethoxyphenyl)-3-iodo-1-(tetrahydro-2H-pyran-2-yl)-1H-pyrazolo[4,3-c]pyridine 1-(Chloromethyl)-4-fluoro-1,4-diazoniabicyclo[2.2.2]octane ditetrafluoroborate (97 mg, 0.27 mmol) was added a stirring solution of 6-(2-fluoro-3,5-dimethoxyphenyl)-3-iodo-1-(tetrahydro-2H-pyran-2-yl)-1H-pyrazolo[4,3-c]pyridine (88 mg, 0.18 mmol) in acetonitrile (5 mL). The mixture was stirred at r.t. for 1 h then concentrated. The solid was filtered out and the filtrate was purified by flash chromatography on a silica gel column with ethyl acetate in hexanes (0-50%) to afford the desired product (30 mg). LCMS (M+H)$^+$=502.0.

Step 6: 5-bromo-2-ethylisoindolin-1-one

A mixture of methyl 4-bromo-2-(bromomethyl)benzoate (0.5 g, 2 mmol) (AstaTech Cat. No. 27012), ethylamine in THF (1.0 mL, 2.0 M) (Aldrich Cat. No. 395072), and potassium carbonate (0.34 g, 2.4 mmol) in ethanol (5 mL) in a sealed vial was stirred at 40° C. overnight. The solid was filtered off. The filtrate was concentrated under reduced pressure. The residue was purified by flash chromatography on a silica gel column with ethyl acetate in hexanes (0-50%) to afford the desired product (0.28 g). LCMS (M+H)+=240.0/242.0.

Step 7: 2-ethyl-5-(4,4,5,5-tetramethyl-1,3,2-dioxaborolan-2-yl)isoindolin-1-one

A mixture of 5-bromo-2-ethylisoindolin-1-one (300 mg, 1.2 mmol), 4,4,5,5,4',4',5',5'-octamethyl-[2,2']bi[[1,3,2]dioxaborolanyl] (310 mg, 1.2 mmol) (Aldrich Cat. No. 473294), potassium acetate (300 mg, 3.1 mmol), and [1,1'-bis(diphenylphosphino)ferrocene]-dichloropalladium(II) complexed with dichloromethane (1:1) (30 mg, 0.04 mmol) in 1,4-dioxane (10 mL) was degassed and stirred at 100° C. for 3 h. After cooling it was concentrated under reduced pressure. The residue was purified by flash chromatography on a silica gel column with ethyl acetate in hexanes (0-50%) to afford the desired product (0.26 g). LCMS (M+H)+=288.2.

Step 8: 5-[6-(2,6-difluoro-3,5-dimethoxyphenyl)-1H-pyrazolo[4,3-c]pyridin-3-yl]-2-ethylisoindolin-1-one A mixture of 6-(2,6-difluoro-3,5-dimethoxyphenyl)-3-iodo-1-(tetrahydro-2H-pyran-2-yl)-1H-pyrazolo[4,3-c]pyridine (9 mg, 0.02 mmol), 2-ethyl-5-(4,4,5,5-tetramethyl-1,3,2-dioxaborolan-2-yl)isoindolin-1-one (7.7 mg, 0.027 mmol), [1,1'-bis(diphenylphosphino)-ferrocene]dichloropalladium (II) complex with dichloromethane (1:1) (1 mg, 0.001 mmol), and sodium carbonate (5.7 mg, 0.054 mmol) in 1,4-dioxane (0.2 mL) and water (0.03 mL) was degassed and recharged with nitrogen three times. The mixture was stirred at 110° C. for 3 h. After cooling the solid was filtered off. The filtrate was concentrated. The residue was dissolved in methanol (0.5 mL). At r.t. to the solution was added HCl solution prepared previously from acetyl chloride (0.30 mL) and methanol (0.30 mL). The mixture was stirred at r.t. for 2 h, and purified by RP-HPLC (pH=10) to afford the desired product (5.6 mg). LCMS (M+H)+=451.1.

Example 53

5-[6-(2,6-Difluoro-3,5-dimethoxyphenyl)-1H-pyrazolo[4,3-c]pyridin-3-yl]-2-isopropylisoindolin-1-one

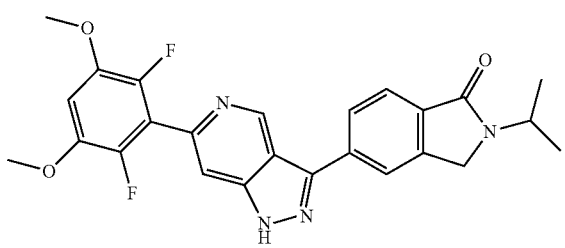 [SMILES: COc1cc(OC)c(F)c(-c2cc3[nH]nc(-c4ccc5c(c4)CN(C(C)C)C5=O)c3cn2)c1F]

Step 1: 5-bromo-2-isopropylisoindolin-1-one

This compound was prepared by using procedures analogous to those described for the synthesis of Example 52, Step 6 starting from 4-bromo-2-(bromomethyl)benzoate (AstaTech Cat. No. 27012) and isopropylamine (Aldrich Cat No. 471291). LCMS (M+H)+=254.0/256.0.

Step 2: 2-isopropyl-5-(4,4,5,5-tetramethyl-1,3,2-dioxaborolan-2-yl)isoindolin-1-one This compound was prepared by using procedures analogous to those described for the synthesis of Example 52, Step 7 starting from 5-bromo-2-isopropylisoindolin-1-one and 4,4,5,5,4',4',5',5'-octamethyl-[2,2']bi[[1,3,2]dioxaborolanyl]. LCMS (M+H)+=302.2.

Step 3: 5-[6-(2,6-difluoro-3,5-dimethoxyphenyl)-1H-pyrazolo[4,3-c]pyridin-3-yl]-2-isopropylisoindolin-1-one This compound was prepared by using procedures analogous to those described for the synthesis of Example 52, Step 8 starting from 6-(2,6-difluoro-3,5-dimethoxyphenyl)-3-iodo-1-(tetrahydro-2H-pyran-2-yl)-1H-pyrazolo[4,3-c]pyridine and 2-isopropyl-5-(4,4,5,5-tetramethyl-1,3,2-dioxaborolan-2-yl)isoindolin-1-one. LCMS (M+H)+=465.2.

Example 54

2-Cyclopropyl-5-[6-(2,6-difluoro-3,5-dimethoxyphenyl)-1H-pyrazolo[4,3-c]pyridin-3-yl]isoindolin-1-one

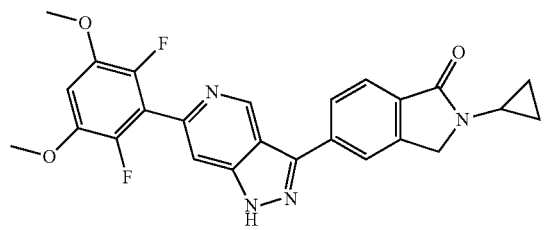 [SMILES: COc1cc(OC)c(F)c(-c2cc3[nH]nc(-c4ccc5c(c4)CN(C4CC4)C5=O)c3cn2)c1F]

This compound was prepared by using procedures analogous to those described for the synthesis of Example 52, Step 8 starting from 6-(2,6-difluoro-3,5-dimethoxyphenyl)-3-iodo-1-(tetrahydro-2H-pyran-2-yl)-1H-pyrazolo[4,3-c]pyridine and 2-cyclopropyl-5-(4,4,5,5-tetramethyl-1,3,2-dioxaborolan-2-yl)isoindolin-1-one (Example 21, Step 2) LCMS (M+H)+=463.2.

Example 55

3-[6-(2,6-Difluoro-3,5-dimethoxyphenyl)-1H-pyrazolo[4,3-c]pyridin-3-yl]-6-ethyl-5,6-dihydro-7H-pyrrolo[3,4-b]pyridin-7-one

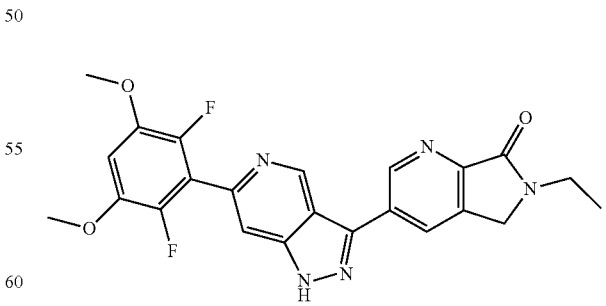

Step 1: methyl 5-bromo-3-(bromomethyl)pyridine-2-carboxylate

Methyl 5-bromo-3-methylpyridine-2-carboxylate (800 mg, 3.5 mmol)(Combi-Blocks Cat. No. SS-3016) in methylene chloride (15 mL) was treated with N-bromosuccinimide (620 mg, 3.5 mmol) and AIBN [2,2'-azobis(isobutyronitrile)] (14 mg, 0.087 mmol). The mixture was stirred and irradiated with a 250W tungsten halogen lamp overnight. LCMS showed most starting material was consumed. The mixture was concentration under reduced pressure. The residue was purified by flash chromatography on a silica gel column with ethyl acetate in hexanes (0-50%) to afford the desired product (1.0 g). LCMS (M+H)$^+$=309.9.

Step 2: 3-bromo-6-ethyl-5,6-dihydro-7H-pyrrolo[3,4-b]pyridin-7-one

A mixture of methyl 5-bromo-3-(bromomethyl)pyridine-2-carboxylate (0.39 g, 1.3 mmol), ethylamine in THF (0.88 mL, 2.0 M, 1.8 mmol) and potassium carbonate (0.26 g, 1.9 mmol) in ethanol (5 mL) in a sealed reaction vial was stirred at 40° C. for 2 h. The solid was filtered off. The filtrate was concentrated under reduced pressure. The residue was purified by flash chromatography on a silica gel column with ethyl acetate in hexanes (0-50%) to afford the desired product (0.24 g). LCMS (M+H)$^+$=240.9/242.9.

Step 3: (6-ethyl-7-oxo-6,7-dihydro-5H-pyrrolo[3,4-b]pyridin-3-yl)boronic acid

A mixture of 3-bromo-6-ethyl-5,6-dihydro-7H-pyrrolo[3,4-b]pyridin-7-one (240 mg, 1.0 mmol), 4,4,5,5,4',4',5',5'-octamethyl-[2,2']bi[[1,3,2]dioxaborolanyl] (250 mg, 1.0 mmol), potassium acetate (290 mg, 3.0 mmol), and [1,1'-bis(diphenylphosphino)ferrocene]-dichloropalladium(II) complexed with dichloromethane (1:1) (30 mg, 0.04 mmol) in 1,4-dioxane (10 mL) was degassed and stirred at 100° C. for 6 h. After cooling it was concentrated under reduced pressure. The residue was purified by flash chromatography on a silica gel column with ethyl acetate in hexanes (0-50%) to afford the desired product (0.11 g). LCMS (M+H)$^+$=207.1.

Step 4: 3-[6-(2,6-difluoro-3,5-dimethoxyphenyl)-1H-pyrazolo[4,3-c]pyridin-3-yl]-6-ethyl-5,6-dihydro-7H-pyrrolo[3,4-b]pyridin-7-one This compound was prepared by using procedures analogous to those described for the synthesis of Example 52, Step 8 starting from 6-(2,6-difluoro-3,5-dimethoxyphenyl)-3-iodo-1-(tetrahydro-2H-pyran-2-yl)-1H-pyrazolo[4,3-c]pyridine and (6-ethyl-7-oxo-6,7-dihydro-5H-pyrrolo[3,4-b]pyridin-3-yl)boronic acid. LCMS (M+H)$^+$=452.1.

Example 56

6-[6-(2,6-Difluoro-3,5-dimethoxyphenyl)-1H-pyrazolo[4,3-c]pyridin-3-yl]-3,4-dihydroisoquinolin-1(2H)-one

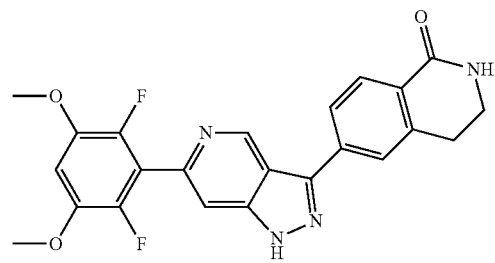 [SMILES: COc1cc(OC)c(F)c(-c2cc3[nH]nc(-c4ccc5c(c4)CCNC5=O)c3cn2)c1F]

This compound was prepared by using procedures analogous to those described for the synthesis of Example 52, Step 8 starting from 6-(2,6-difluoro-3,5-dimethoxyphenyl)-3-iodo-1-(tetrahydro-2H-pyran-2-yl)-1H-pyrazolo[4,3-c]pyridine and 6-(4,4,5,5-tetramethyl-1,3,2-dioxaborolan-2-yl)-3,4-dihydroisoquinolin-1(2H)-one (Example 8, Step 1). LCMS (M+H)$^+$=437.2.

Example 57

6-[6-(2,6-Difluoro-3,5-dimethoxyphenyl)-1H-pyrazolo[4,3-c]pyridin-3-yl]-N,N-dimethylchromane-2-carboxamide

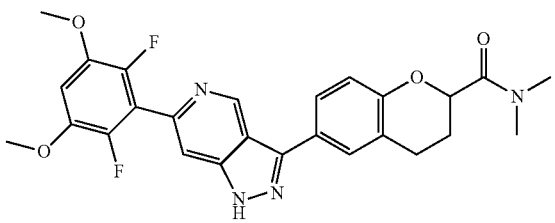

This compound was prepared by using procedures analogous to those described for the synthesis of Example 52, Step 8 starting from 6-(2,6-difluoro-3,5-dimethoxyphenyl)-3-iodo-1-(tetrahydro-2H-pyran-2-yl)-1H-pyrazolo[4,3-c]pyridine and N,N-dimethyl-6-(4,4,5,5-tetramethyl-1,3,2-dioxaborolan-2-yl)chromane-2-carboxamide (Example 2, Step 2). LCMS (M+H)$^+$=495.4.

Example 58

5-[6-(2,6-Difluoro-3,5-dimethoxyphenyl)-1H-pyrazolo[4,3-c]pyridin-3-yl]-2-(2-methoxyethyl)isoindolin-1-one

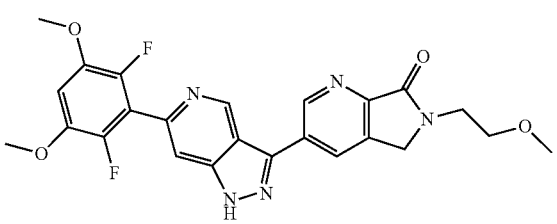

Step 1: 5-bromo-2-(2-methoxyethyl)isoindolin-1-one

This compound was prepared by using procedures analogous to those described for the synthesis of Example 52, Step 6 starting from 4-bromo-2-(bromomethyl)benzoate (AstaTech Cat. No. 27012) and 2-methoxyethylamine (Aldrich Cat No. 241067). LCMS (M+H)$^+$=270.0/272.0.

Step 2: 2-(2-methoxyethyl)-5-(4,4,5,5-tetramethyl-1,3,2-dioxaborolan-2-yl)isoindolin-1-one This compound was prepared by using procedures analogous to those described for the synthesis of Example 52, Step 7 starting from 5-bromo-2-(2-methoxyethyl)isoindolin-1-one and 4,4,5,5,4',4',5',5'-octamethyl-[2,2']bi[[1,3,2]dioxaborolanyl]. LCMS (M+H)$^+$=318.1.

Step 3: 5-[6-(2,6-difluoro-3,5-dimethoxyphenyl)-1H-pyrazolo[4,3-c]pyridin-3-yl]-2-(2-methoxyethyl)isoindolin-1-one This compound was prepared by using procedures analogous to those described for the synthesis of Example 52, Step 8 starting from 6-(2,6-difluoro-3,5-dimethoxyphenyl)-3-iodo-1-(tetrahydro-2H-pyran-2-yl)-1H-pyrazolo[4,3-c]pyridine and 2-(2-methoxyethyl)-5-(4,4,5,5-tetramethyl-1,3,2-dioxaborolan-2-yl)isoindolin-1-one. LCMS (M+H)$^+$=481.2.

Example 59

5-[6-(2,6-Difluoro-3,5-dimethoxyphenyl)-1H-pyrazolo[4,3-c]pyridin-3-yl]-2-(tetrahydro-2H-pyran-4-yl)isoindolin-1-one

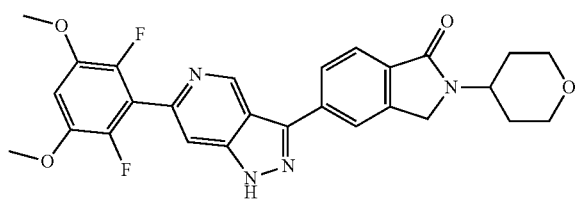 [SMILES: COc1cc(OC)c(F)c(-c2cc3[nH]nc(-c4ccc5c(c4)CN(C4CCOCC4)C5=O)c3cn2)c1F]

Step 1: 5-bromo-2-(tetrahydro-2H-pyran-4-yl)isoindolin-1-one

This compound was prepared by using procedures analogous to those described for the synthesis of Example 52, Step 6 starting from 4-bromo-2-(bromomethyl)benzoate (AstaTech Cat. No. 27012) and 4-aminotetrahydropyran (Aldrich Cat No. 711357). LCMS (M+H)$^+$=296.0/298.0.

Step 2: 2-(tetrahydro-2H-pyran-4-yl)-5-(4,4,5,5-tetramethyl-1,3,2-dioxaborolan-2-yl)isoindolin-1-one This compound was prepared by using procedures analogous to those described for the synthesis of Example 52, Step 7 starting from 5-bromo-2-(tetrahydro-2H-pyran-4-yl)isoindolin-1-one and 4,4,5,5,4',4',5',5'-octamethyl-[2,2']bi[[1,3,2]dioxaborolanyl]. LCMS (M+H)$^+$=344.2.

Step 3: 5-[6-(2,6-difluoro-3,5-dimethoxyphenyl)-1H-pyrazolo[4,3-c]pyridin-3-yl]-2-(tetrahydro-2H-pyran-4-yl)isoindolin-1-one This compound was prepared by using procedures analogous to those described for the synthesis of Example 52, Step 8 starting from 6-(2,6-difluoro-3,5-dimethoxyphenyl)-3-iodo-1-(tetrahydro-2H-pyran-2-yl)-1H-pyrazolo[4,3-c]pyridine and 2-(tetrahydro-2H-pyran-4-yl)-5-(4,4,5,5-tetramethyl-1,3,2-dioxaborolan-2-yl)isoindolin-1-one. LCMS (M+H)$^+$=507.2.

Example 60

5-[6-(2,6-Difluoro-3,5-dimethoxyphenyl)-1H-pyrazolo[4,3-c]pyridin-3-yl]-2-(2,2,2-trifluoroethyl)isoindolin-1-one

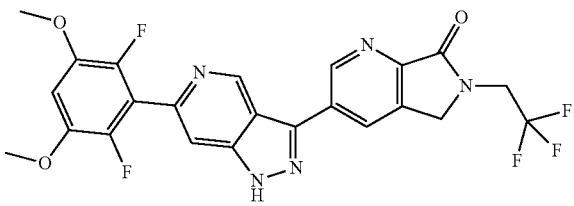

Step 1: 5-bromo-2-(2,2,2-trifluoroethyl)isoindolin-1-one

This compound was prepared by using procedures analogous to those described for the synthesis of Example 52, Step 6 starting from 4-bromo-2-(bromomethyl)benzoate and 2,2,2-trifluoroethylamine (Aldrich Cat No. 269042). LCMS (M+H)$^+$=294.0/296.0.

Step 2: 5-(4,4,5,5-tetramethyl-1,3,2-dioxaborolan-2-yl)-2-(2,2,2-trifluoroethyl)isoindolin-1-one This compound was prepared by using procedures analogous to those described for the synthesis of Example 52, Step 7 starting from 5-bromo-2-(2,2,2-trifluoroethyl)isoindolin-1-one and 4,4,5,5,4',4',5',5'-octamethyl-[2,2']bi[[1,3,2]dioxaborolanyl]. LCMS (M+H)$^+$=342.2.

Step 3: 5-[6-(2,6-difluoro-3,5-dimethoxyphenyl)-1H-pyrazolo[4,3-c]pyridin-3-yl]-2-(2,2,2-trifluoroethyl)isoindolin-1-one This compound was prepared by using procedures analogous to those described for the synthesis of Example 52, Step 8 starting from 6-(2,6-difluoro-3,5-dimethoxyphenyl)-3-iodo-1-(tetrahydro-2H-pyran-2-yl)-1H-pyrazolo[4,3-c]pyridine and 5-(4,4,5,5-tetramethyl-1,3,2-dioxaborolan-2-yl)-2-(2,2,2-trifluoroethyl)isoindolin-1-one. LCMS (M+H)$^+$=505.0.

Example 61

5-[6-(2,6-Difluoro-3,5-dimethoxyphenyl)-1H-pyrazolo[4,3-c]pyridin-3-yl]-2-(cis-4-hydroxycyclohexyl)isoindolin-1-one

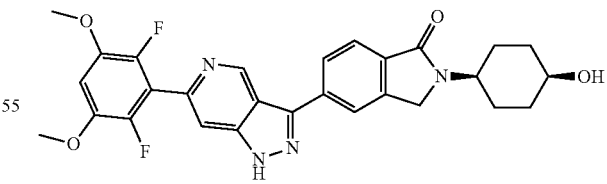

This compound was prepared by using procedures analogous to those described for the synthesis of Example 52, Step 8 starting from 5-[6-(2,6-difluoro-3,5-dimethoxyphenyl)-1-(tetrahydro-2H-pyran-2-yl)-1H-pyrazolo[4,3-c]pyridin-3-yl]-2-(tetrahydro-2H-pyran-4-yl)isoindolin-1-one and 2-(cis-4-hydroxycyclohexyl)-5-(4,4,5,5-tetramethyl-1,3,2-dioxaborolan-2-yl)isoindolin-1-one (Example 16, Step 2). LCMS (M+H)$^+$=521.2.

Example 62

5-[6-(2,6-Difluoro-3,5-dimethoxyphenyl)-1H-pyrazolo[4,3-c]pyridin-3-yl]-2-(trans-4-hydroxycyclohexyl)isoindolin-1-one

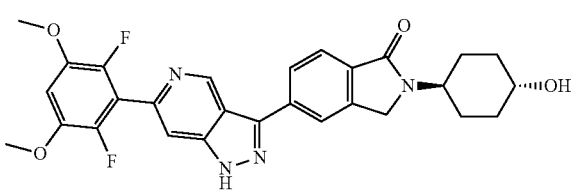 [SMILES: COc1cc(OC)c(F)c(-c2cc3[nH]nc(-c4ccc5c(c4)CN([C@H]4CC[C@H](O)CC4)C5=O)c3cn2)c1F]

This compound was prepared by using procedures analogous to those described for the synthesis of Example 52, Step 8 starting from 5-[6-(2,6-difluoro-3,5-dimethoxyphenyl)-1-(tetrahydro-2H-pyran-2-yl)-1H-pyrazolo[4,3-c]pyridin-3-yl]-2-(tetrahydro-2H-pyran-4-yl)isoindolin-1-one and 2-(trans-4-hydroxycyclohexyl)-5-(4,4,5,5-tetramethyl-1,3,2-dioxaborolan-2-yl)isoindolin-1-one (Example 15, Step 2). LCMS (M+H)$^+$=521.2.

Example 63

5-[6-(2,6-Difluoro-3,5-dimethoxyphenyl)-1H-pyrazolo[4,3-c]pyridin-3-yl]-2-(2-hydroxy-1-methylethyl)isoindolin-1-one

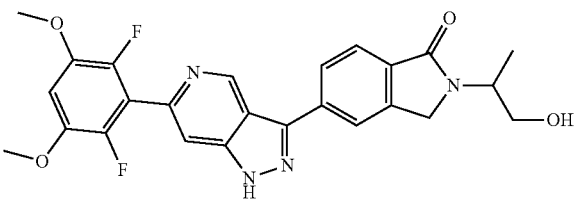 [SMILES: COc1cc(OC)c(F)c(-c2cc3[nH]nc(-c4ccc5c(c4)CN(C(C)CO)C5=O)c3cn2)c1F]

Step 1: 5-bromo-2-(2-hydroxy-1-methylethyl)isoindolin-1-one

This compound was prepared by using procedures analogous to those described for the synthesis of Example 52, Step 6 starting from 4-bromo-2-(bromomethyl)benzoate and 2-aminopropanol (Aldrich Cat No. 192171). LCMS (M+H)$^+$=270.1.

Step 2: 2-(2-hydroxy-1-methylethyl)-5-(4,4,5,5-tetramethyl-1,3,2-dioxaborolan-2-yl)isoindolin-1-one This compound was prepared by using procedures analogous to those described for the synthesis of Example 52, Step 7 starting from 5-bromo-2-(2-hydroxy-1-methylethyl)isoindolin-1-one and 4,4,5,5,4',4',5',5'-octamethyl-[2,2']bi[[1,3,2]dioxaborolanyl]. LCMS (M+H)$^+$=318.1.

Step 3: 5-[6-(2,6-difluoro-3,5-dimethoxyphenyl)-1H-pyrazolo[4,3-c]pyridin-3-yl]-2-(2-hydroxy-1-methylethyl)isoindolin-1-one This compound was prepared by using procedures analogous to those described for the synthesis of Example 52, Step 8 starting from 6-(2,6-difluoro-3,5-dimethoxyphenyl)-3-iodo-1-(tetrahydro-2H-pyran-2-yl)-1H-pyrazolo[4,3-c]pyridine and 2-(2-hydroxy-1-methylethyl)-5-(4,4,5,5-tetramethyl-1,3,2-dioxaborolan-2-yl)isoindolin-1-one. LCMS (M+H)$^+$=481.1.

Example 64

5-[6-(2,6-Difluoro-3,5-dimethoxyphenyl)-1H-pyrazolo[4,3-c]pyridin-3-yl]-2-(2-hydroxypropyl)isoindolin-1-one

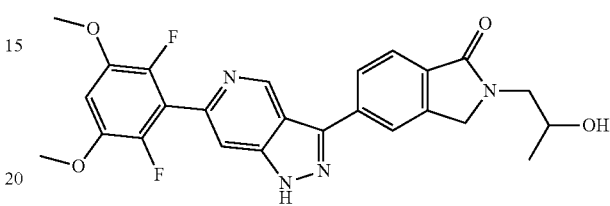

Step 1:
5-bromo-2-(2-hydroxypropyl)isoindolin-1-one

This compound was prepared using procedures analogous to those described for the synthesis of Example 52, Step 6 starting from 4-bromo-2-(bromomethyl)benzoate and 1-amino-2-propanol (Aldrich Cat No. 110248). LCMS (M+H)$^+$=270.0/272.0.

Step 2: 2-(2-hydroxypropyl)-5-(4,4,5,5-tetramethyl-1,3,2-dioxaborolan-2-yl)isoindolin-1-one This compound was prepared using procedures analogous to those described for the synthesis of Example 52, Step 7 starting from 5-bromo-2-(2-hydroxypropyl)isoindolin-1-one and 4,4,5,5,4',4',5',5'-octamethyl-[2,2']bi[[1,3,2]dioxaborolanyl]. LCMS (M+H)$^+$=318.1.

Step 3: 5-[6-(2,6-difluoro-3,5-dimethoxyphenyl)-1H-pyrazolo[4,3-c]pyridin-3-yl]-2-(2-hydroxypropyl)isoindolin-1-one This compound was prepared using procedures analogous to those described for the synthesis of Example 52, Step 8 starting from 6-(2,6-difluoro-3,5-dimethoxyphenyl)-3-iodo-1-(tetrahydro-2H-pyran-2-yl)-1H-pyrazolo[4,3-c]pyridine and 2-(2-hydroxypropyl)-5-(4,4,5,5-tetramethyl-1,3,2-dioxaborolan-2-yl)isoindolin-1-one. LCMS (M+H)$^+$=481.1.

Example 65

5-[6-(2,6-Difluoro-3,5-dimethoxyphenyl)-1H-pyrazolo[4,3-c]pyridin-3-yl]-6-fluoro-2-isopropylisoindolin-1-one

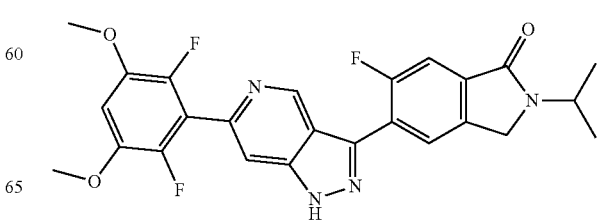

Step 1: Methyl 4-bromo-2-(bromomethyl)-5-fluorobenzoate

A mixture of methyl 4-bromo-5-fluoro-2-methylbenzoate (1.0 g, 4.0 mmol) (Ellanoval Laboratories Cat. No. 38-0304), N-bromosuccinimide (900. mg, 5.06 mmol) and benzoyl peroxide (50 mg, 0.2 mmol) in carbon tetrachloride (50 mL) was refluxed under a nitrogen atmosphere for 4 h. After cooling the mixture was diluted with methylene chloride. The organic solution was washed with brine, then dried over $Na_2SO_4$. After filtration the filtrate was concentrated under reduced pressure. The residue was purified by flash chromatography on a silica gel column with ethyl acetate in hexanes (0-50%) to afford the desired product (1.2 g).

Step 2: 5-bromo-6-fluoro-2-isopropylisoindolin-1-one

This compound was prepared using procedures analogous to those described for the synthesis of Example 52, Step 6 starting from methyl 4-bromo-2-(bromomethyl)-5-fluorobenzoate and isopropylamine. LC/MS: $(M+H)^+=271.9/273.9$.

Step 3: (6-fluoro-2-isopropyl-1-oxo-2,3-dihydro-1H-isoindol-5-yl)boronic acid This compound was prepared by using procedures analogous to those described for the synthesis of Example 52, Step 7 starting from 5-bromo-6-fluoro-2-isopropylisoindolin-1-one and 4,4,5,5,4',4',5',5'-octamethyl-[2,2']bi[[1,3,2]dioxaborolanyl]. LCMS: $(M+H)^+=238.1$.

Step 4: 5-[6-(2,6-difluoro-3,5-dimethoxyphenyl)-1H-pyrazolo[4,3-c]pyridin-3-yl]-6-fluoro-2-isopropyl-isoindolin-1-one This compound was prepared by using procedures analogous to those described for the synthesis of Example 52, Step 8 starting from 6-(2,6-difluoro-3,5-dimethoxyphenyl)-3-iodo-1-(tetrahydro-2H-pyran-2-yl)-1H-pyrazolo[4,3-c]pyridine and (6-fluoro-2-isopropyl-1-oxo-2,3-dihydro-1H-isoindol-5-yl)boronic acid. LCMS $(M+H)^+=483.1$.

Example 66

5-[6-(2,6-Difluoro-3,5-dimethoxyphenyl)-1H-pyrazolo[4,3-c]pyridin-3-yl]-2-(1-methylpiperidin-4-yl)isoindolin-1-one

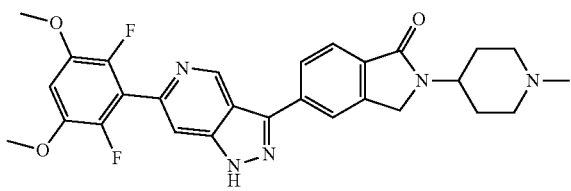

Step 1: 5-bromo-2-(1-methylpiperidin-4-yl)isoindolin-1-one

A mixture of methyl 4-bromo-2-(bromomethyl)benzoate (0.3 g, 1 mmol; AstaTech Cat. No. 27012), 1-methylpiperidin-4-amine (0.14 g, 1.3 mmol)(Combi-blocks Cat. No. 4003460), and potassium carbonate (0.19 g, 1.4 mmol) in ethanol (5 mL) in a sealed reaction vial was stirred at 80° C. for 1 h. After cooling the solid was filtered off. The filtrate was concentrated under reduced pressure. The residue was purified by flash chromatography on a silica gel column with ethyl acetate in hexanes (0-50%) to afford the desired product (0.1 g). LCMS $(M+H)^+=309.0/311.0$.

Step 2: 2-(1-methylpiperidin-4-yl)-5-(4,4,5,5-tetramethyl-1,3,2-dioxaborolan-2-yl)isoindolin-1-one This compound was prepared by using procedures analogous to those described for the synthesis of Example 52, Step 7 starting from 5-bromo-2-(1-methylpiperidin-4-yl)isoindolin-1-one and 4,4,5,5,4',4',5',5'-octamethyl-[2,2']bi[[1,3,2]dioxaborolanyl]. LCMS $(M+H)^+=357.3$.

Step 3: 5-[6-(2,6-difluoro-3,5-dimethoxyphenyl)-1H-pyrazolo[4,3-c]pyridin-3-yl]-2-(1-methylpiperidin-4-yl)isoindolin-1-one This compound was prepared by using procedures analogous to those described for the synthesis of Example 52, Step 8 starting from 6-(2,6-difluoro-3,5-dimethoxyphenyl)-3-iodo-1-(tetrahydro-2H-pyran-2-yl)-1H-pyrazolo[4,3-c]pyridine and 2-(1-methylpiperidin-4-yl)-5-(4,4,5,5-tetramethyl-1,3,2-dioxaborolan-2-yl)isoindolin-1-one. LCMS $(M+H)^+=520.2$.

Example 67

5-[6-(2,6-Difluoro-3,5-dimethoxyphenyl)-1H-pyrazolo[4,3-c]pyridin-3-yl]-2-[2-(dimethylamino)ethyl]isoindolin-1-one

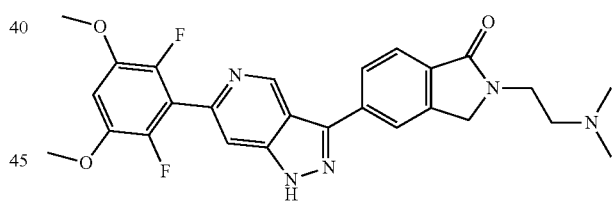

Step 1: 5-bromo-2-[2-(dimethylamino)ethyl]isoindolin-1-one

This compound was prepared by using procedures analogous to those described for the synthesis of Example 52, Step 6 starting from 4-bromo-2-(bromomethyl)benzoate and N,N-dimethylethylenediamine (Aldrich Cat No. D158003). LCMS $(M+H)^+=283.1$.

Step 2: 2-[2-(dimethylamino)ethyl]-5-(4,4,5,5-tetramethyl-1,3,2-dioxaborolan-2-yl)isoindolin-1-one This compound was prepared by using procedures analogous to those described for the synthesis of Example 52, Step 7 starting from 5-bromo-2-[2-(dimethylamino)ethyl]isoindolin-1-one and 4,4,5,5,4',4',5',5'-octamethyl-[2,2']bi[[1,3,2]dioxaborolanyl]. LCMS $(M+H)^+=331.3$.

Step 3: 5-[6-(2,6-difluoro-3,5-dimethoxyphenyl)-1H-pyrazolo[4,3-c]pyridin-3-yl]-2-[2-(dimethylamino)ethyl]isoindolin-1-one This compound was prepared by using procedures analogous to those described for the synthesis of Example 52, Step 8 starting from 6-(2,6-difluoro-3,5-dimethoxyphenyl)-3-iodo-1-(tetrahydro-2H-pyran-2-yl)-1H-pyrazolo[4,3-c]pyridine and 2-[2-(dimethylamino)ethyl]-5-(4,4,5,5-tetramethyl-1,3,2-dioxaborolan-2-yl)isoindolin-1-one. LCMS (M+H)$^+$=494.3.

Example 68

5-[6-(2,6-Difluoro-3,5-dimethoxyphenyl)-1H-pyrazolo[4,3-c]pyridin-3-yl]-2-[2-(1-methylpyrrolidin-2-yl)ethyl]isoindolin-1-one

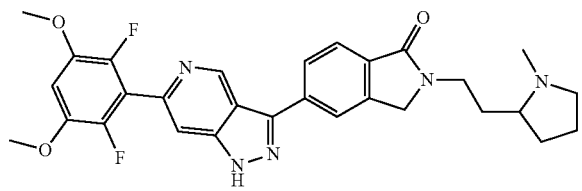 [SMILES: COc1cc(OC)c(F)c(-c2cc3[nH]nc(-c4ccc5c(c4)CN(CCC4CCCN4C)C5=O)c3cn2)c1F]

Step 1: 5-bromo-2-[2-(1-methylpyrrolidin-2-yl)ethyl]isoindolin-1-one

This compound was prepared by using procedures analogous to those described for the synthesis of Example 52, Step 6 starting from 4-bromo-2-(bromomethyl)benzoate and 2-(2-aminoethyl)-1-methylpyrrolidine (Aldrich Cat No. D139505). LCMS (M+H)$^+$=323.0.

Step 2: 2-[2-(1-methylpyrrolidin-2-yl)ethyl]-5-(4,4,5,5-tetramethyl-1,3,2-dioxaborolan-2-yl)isoindolin-1-one This compound was prepared by using procedures analogous to those described for the synthesis of Example 52, Step 7 starting from 5-bromo-2-[2-(1-methylpyrrolidin-2-yl)ethyl]isoindolin-1-one and 4,4,5,5,4',4',5',5'-octamethyl-[2,2']bi[[1,3,2]dioxaborolanyl]. LCMS (M+H)$^+$=371.3.

Step 3: 5-[6-(2,6-difluoro-3,5-dimethoxyphenyl)-1H-pyrazolo[4,3-c]pyridin-3-yl]-2-[2-(1-methylpyrrolidin-2-yl)ethyl]isoindolin-1-one This compound was prepared by using procedures analogous to those described for the synthesis of Example 52, Step 8 starting from 6-(2,6-difluoro-3,5-dimethoxyphenyl)-3-iodo-1-(tetrahydro-2H-pyran-2-yl)-1H-pyrazolo[4,3-c]pyridine and 2-[2-(1-methylpyrrolidin-2-yl)ethyl]-5-(4,4,5,5-tetramethyl-1,3,2-dioxaborolan-2-yl)isoindolin-1-one. LCMS (M+H)$^+$=534.3.

Example 69

5-[6-(2-chloro-6-fluoro-3,5-dimethoxyphenyl)-1H-pyrazolo[4,3-c]pyridin-3-yl]-2-ethylisoindolin-1-one

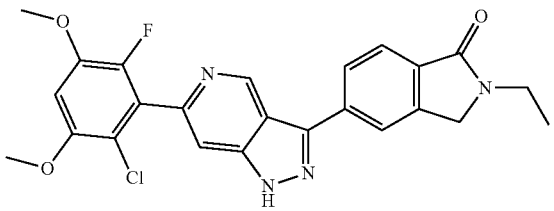 [SMILES: CCN1Cc2cc(-c3n[nH]c4cc(-c5c(F)c(OC)cc(OC)c5Cl)ncc34)ccc2C1=O]

Step 1: 6-(2-chloro-6-fluoro-3,5-dimethoxyphenyl)-3-iodo-1-(tetrahydro-2H-pyran-2-yl)-1H-pyrazolo[4,3-c]pyridine At r.t. to a solution of 6-(2-fluoro-3,5-dimethoxyphenyl)-3-iodo-1-(tetrahydro-2H-pyran-2-yl)-1H-pyrazolo[4,3-c]pyridine (35 mg, 0.072 mmol) (Example 52, Step 4) in methylene chloride (3 mL) was added sulfuryl chloride (7.0 μL, 0.087 mmol). The mixture was stirred at r.t. for 20 min then concentrated. The solid was filtered out and the crude material was purified by flash chromatography on a silica gel column with ethyl acetate in hexanes (0-50%) to afford the desired product (0.025 g). LCMS (M+H)$^+$=518.1.

Step 2: 5-[6-(2-chloro-6-fluoro-3,5-dimethoxyphenyl)-1H-pyrazolo[4,3-c]pyridin-3-yl]-2-ethylisoindolin-1-one This compound was prepared using procedures analogous to those described in Example 52, Step 8 starting from 6-(2-chloro-6-fluoro-3,5-dimethoxyphenyl)-3-iodo-1-(tetrahydro-2H-pyran-2-yl)-1H-pyrazolo[4,3-c]pyridine and 2-ethyl-5-(4,4,5,5-tetramethyl-1,3,2-dioxaborolan-2-yl)isoindolin-1-one. LCMS (M+H)$^+$=466.1.

Example 70

6-(2,6-dichloro-3,5-dimethoxyphenyl)-3-(1-methyl-1H-pyrazol-4-yl)-1H-pyrazolo[4,3-b]pyridine

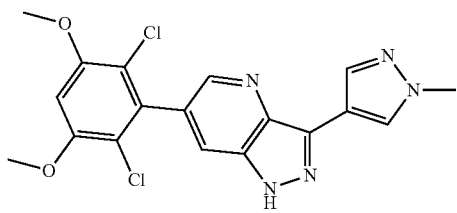

Step 1: 6-(3,5-dimethoxyphenyl)-1H-pyrazolo[4,3-b]pyridine

A mixture of 6-bromo-1H-pyrazolo[4,3-b]pyridine (0.3 g, 2 mmol)(Annova Chem Cat. No. L05238), (3,5-dimethoxyphenyl)boronic acid (0.33 g, 1.8 mmol), [1,1'-bis(diphenylphosphino)ferrocene]dichloropalladium(II) complexed with dichloromethane (1:1) (100 mg, 0.1 mmol), and potassium phosphate (0.64 g, 3.0 mmol) in 1,4-dioxane (1 mL) and water (0.12 mL) was degassed and sealed. It was stirred at 85° C. overnight. After cooling it was concentrated under reduced pressure. The residue was purified by flash chromatography on a silica gel column with ethyl acetate in hexanes (0-50%) to afford the desired product (0.38 g). LCMS (M+H)$^+$=256.2.

Step 2: 6-(3,5-dimethoxyphenyl)-3-iodo-1H-pyrazolo[4,3-b]pyridine

At r.t. to a solution of 6-(3,5-dimethoxyphenyl)-1H-pyrazolo[4,3-b]pyridine (0.38 g, 1.5 mmol) in methylene chloride (5 mL) was added N-iodosuccinimide (0.352 g, 1.56 mmol) with stirring. The mixture was stirred at r.t. overnight. Then the solvent was removed, the residue was treated with methanol. The solid was collected by filtration to afford the desired product (0.54 g) which was directly used in next step reaction without further purification. LCMS (M+H)$^+$=382.1.

Step 3: 6-(3,5-dimethoxyphenyl)-3-iodo-1-(tetrahydro-2H-pyran-2-yl)-1H-pyrazolo[4,3-b]pyridine A mixture of 6-(3,5-dimethoxyphenyl)-3-iodo-1H-pyrazolo[4,3-b]pyridine (0.54 g, 1.4 μmmol), dihydropyran (0.39 mL, 4.2 mmol) and methanesulfonic acid (18 μL, 0.28 mmol) in methylene chloride (6 mL) and tetrahydrofuran (2 mL) in a sealed reaction vial was stirred at 50° C. for 3 h. After cooling it was concentrated under reduced pressure. The residue was purified by flash chromatography on a silica gel column with ethyl acetate in hexanes (0-50%) to afford the desired product (0.60 g). LCMS (M+H)$^+$=465.9.

Step 4: 6-(2,6-dichloro-3,5-dimethoxyphenyl)-3-iodo-1-(tetrahydro-2H-pyran-2-yl)-1H-pyrazolo[4,3-b]pyridine Sulfuryl chloride (0.20 mL, 2.4 mmol) was added dropwise to stirring a solution of 6-(3,5-dimethoxyphenyl)-3-iodo-1-(tetrahydro-2H-pyran-2-yl)-1H-pyrazolo[4,3-b]pyridine (0.60 g, 1.3 mmol) in methylene chloride (10 mL). The mixture was stirred at r.t. for 2 h. LCMS showed about 30% product formed and 70% mono-chlorinated product formed. To the mixture another 70 μL of sulfuryl chloride was added. The mixture was stirred at r.t. for an additional 3 h then concentrated under reduced pressure. The residue was purified by flash chromatography on a silica gel column with ethyl acetate in hexanes (0-50%) to afford the desired product (0.56 g). LCMS (M+H)$^+$=533.9.

Step 5: 6-(2,6-dichloro-3,5-dimethoxyphenyl)-3-(1-methyl-1H-pyrazol-4-yl)-1H-pyrazolo[4,3-b]pyridine A mixture of 6-(2,6-dichloro-3,5-dimethoxyphenyl)-3-iodo-1-(tetrahydro-2H-pyran-2-yl)-1H-pyrazolo[4,3-b]pyridine (25 mg, 0.047 mmol), 1-methyl-4-(4,4,5,5-tetramethyl-1,3,2-dioxaborolan-2-yl)-1H-pyrazole (12 mg, 0.056 mmol), tetrakis(triphenylphosphine)palladium(0) (3 mg, 0.002 mmol), and cesium carbonate (46 mg, 0.14 mmol) in 1,4-dioxane (0.5 mL) and water (0.07 mL) in a reaction vial was degassed, sealed, and stirred at 85° C. for 3 h. After cooling the mixture was concentrated and the residue was dissolved in methanol (0.4 mL, 10 mmol). To the solution was added HCl solution previously prepared from acetyl chloride (0.3 mL) in methanol (0.3 mL). The mixture was stirred at r.t. for 1 h then concentrated, diluted with methanol, and purified by RP-HPLC (pH=2) to afford the desired product (3.9 mg) as a TFA salt. LCMS (M+H)$^+$=404.1.

Example 71

3-{4-[6-(2,6-Dichloro-3,5-dimethoxyphenyl)-1H-pyrazolo[4,3-b]pyridin-3-yl]-1H-pyrazol-1-yl}propan-1-ol

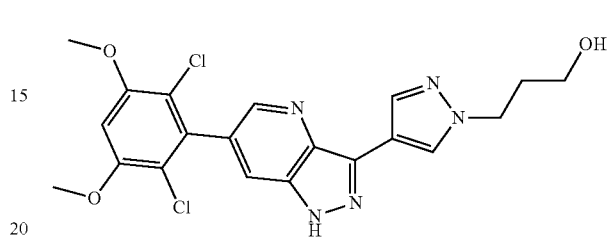

Step 1: 6-(2,6-dichloro-3,5-dimethoxyphenyl)-3-(1H-pyrazol-4-yl)-1-(tetrahydro-2H-pyran-2-yl)-1H-pyrazolo[4,3-b]pyridine

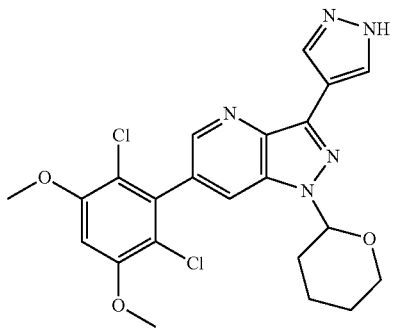 [SMILES: COc1cc(OC)c(Cl)c(-c2cnc3c(-c4cn[nH]c4)nn(C4CCCCO4)c3c2)c1Cl]

A mixture of 6-(2,6-dichloro-3,5-dimethoxyphenyl)-3-iodo-1-(tetrahydro-2H-pyran-2-yl)-1H-pyrazolo[4,3-b]pyridine (60 mg, 0.1 mmol), tert-butyl 4-(4,4,5,5-tetramethyl-1,3,2-dioxaborolan-2-yl)-1H-pyrazole-1-carboxylate (40. mg, 0.13 mmol), [1,1'-bis(diphenylphosphino)ferrocene]dichloropalladium(II) complexed with dichloromethane (1:1) (7 mg, 0.009 mmol), and potassium phosphate (48 mg, 0.22 mmol) in 1,4-dioxane (0.5 mL) and water (0.07 mL) in a reaction vial was degassed and sealed. It was stirred at 85° C. overnight. After cooling it was concentrated under reduced pressure. The residue was purified by flash chromatography on a silica gel column with ethyl acetate in hexanes (0-50%) to afford the desired product (50 mg).

Step 2: 3-{4-[6-(2,6-dichloro-3,5-dimethoxyphenyl)-1H-pyrazolo[4,3-b]pyridin-3-yl]-1H-pyrazol-1-yl}propan-1-ol A mixture of 3-bromo-1-propanol (5.7 μL, 0.063 mmol), 6-(2,6-dichloro-3,5-dimethoxyphenyl)-3-(1H-pyrazol-4-yl)-1-(tetrahydro-2H-pyran-2-yl)-1H-pyrazolo[4,3-b]pyridine (15 mg, 0.032 mmol), and cesium carbonate (14 mg, 0.044 mmol) in acetonitrile (0.5 mL) was stirred at 50° C. for 2 h. After cooling the solid was filtered out and washed with acetonitrile. The filtrate was concentrated and the residue was dissolved in methanol (0.3 mL). To the solution was added 0.5 mL of HCL solution previously prepared from acetyl chloride (0.25 mL) and methanol (0.25 mL). The mixture was stirred at r.t. for 2 h. It was concentrated and the resulting residue was dissolved in methanol, and purified by RP-HPLC (pH=2) to afford the desired product as TFA salt. LCMS (M+H)$^+$=448.0.

Example 72

6-(2,6-Difluoro-3,5-dimethoxyphenyl)-3-(1-methyl-1H-pyrazol-4-yl)-1H-pyrazolo[3,4-b]pyridine

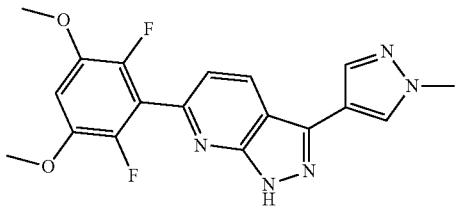

Step 1: 6-chloro-3-iodo-1H-pyrazolo[3,4-b]pyridine

A mixture of 6-chloro-1H-pyrazolo[3,4-b]pyridine (0.40 g, 2.6 mmol)(Ark Pharm Cat. No. AK-32412) and N-iodosuccinimide (0.64 g, 2.9 mmol) in methylene chloride (6 mL) and acetonitrile (3 mL) was stirred at 70° C. for 3 h. After cooling it was concentrated and the residue was treated with water. The precipitate was collected by filtration to afford the desired product (0.70 g). LCMS (M+H)$^+$=279.9.

Step 2: 6-chloro-3-iodo-1-(tetrahydro-2H-pyran-2-yl)-1H-pyrazolo[3,4-b]pyridine

A mixture of 6-chloro-3-iodo-1H-pyrazolo[3,4-b]pyridine (0.70 g, 2.5 mmol), dihydropyran (690 µL, 7.5 mmol) and methanesulfonic acid (33 µL, 0.50 mmol) in methylene chloride (30 mL) and tetrahydrofuran (10 mL) in reaction flask was stirred at r.t. overnight. It was concentrated under reduced pressure. The residue was purified by flash chromatography on a silica gel column with ethyl acetate in hexanes (0-50%) to afford the desired product (0.80 g). LCMS (M-84+H)$^+$=279.9.

Step 3: 6-chloro-3-(1-methyl-1H-pyrazol-4-yl)-1-(tetrahydro-2H-pyran-2-yl)-1H-pyrazolo[3,4-b]pyridine A mixture of 6-chloro-3-iodo-1-(tetrahydro-2H-pyran-2-yl)-1H-pyrazolo[3,4-b]pyridine (200 mg, 0.6 mmol), 1-methyl-4-(4,4,5,5-tetramethyl-1,3,2-dioxaborolan-2-yl)-1H-pyrazole (110 mg, 0.55 mmol), tetrakis(triphenylphosphine) palladium(0) (30 mg, 0.03 mmol), and cesium carbonate (540 mg, 1.6 mmol) in 1,4-dioxane (1 mL) and water (0.12 mL) was degassed and sealed. It was stirred at 80° C. for 3 h. After cooling it was concentrated under reduced pressure. The residue was purified by flash chromatography on a silica gel column with ethyl acetate in hexanes (0-50%) to afford the desired product (0.12 g). LCMS (M+H)$^+$=318.0.

Step 4: 6-(3,5-dimethoxyphenyl)-3-(1-methyl-1H-pyrazol-4-yl)-1-(tetrahydro-2H-pyran-2-yl)-1H-pyrazolo[3,4-b]pyridine

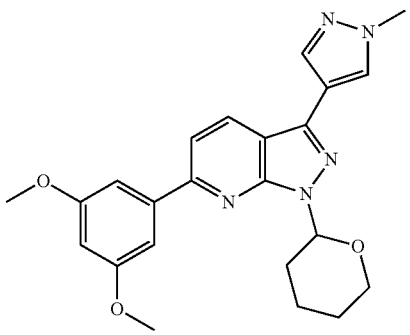

A mixture of (3,5-dimethoxyphenyl)boronic acid (0.13 g, 0.71 mmol), 6-chloro-3-(1-methyl-1H-pyrazol-4-yl)-1-(tetrahydro-2H-pyran-2-yl)-1H-pyrazolo[3,4-b]pyridine (0.15 g, 0.47 mmol), [1,1'-bis(diphenylphosphino)ferrocene]dichloropalladium(II) complexed with dichloromethane (1:1) (30 mg, 0.04 mmol) and potassium phosphate (200 mg, 0.94 mmol) in 1,4-dioxane (1.0 mL) and water (0.13 mL) in a reaction vial was degassed and sealed. The mixture was stirred at 90° C. for 2 h. After cooling it was concentrated under reduced pressure. The residue was purified by flash chromatography on a silica gel column with ethyl acetate in hexanes (0-50%) to afford the desired product (180 mg). LCMS (M+H)$^+$=420.1.

Step 5: 6-(2,6-difluoro-3,5-dimethoxyphenyl)-3-(1-methyl-1H-pyrazol-4-yl)-1H-pyrazolo[3,4-b]pyridine At r.t. to a stirring solution of 6-(3,5-dimethoxyphenyl)-3-(1-methyl-1H-pyrazol-4-yl)-1-(tetrahydro-2H-pyran-2-yl)-1H-pyrazolo[3,4-b]pyridine (40 mg, 0.1 mmol) in acetonitrile (3 mL) was added 1-(chloromethyl)-4-fluoro-1,4-diazoniabicyclo[2.2.2]octane ditetrafluoroborate (68 mg, 0.19 mmol). The mixture was stirred at 40° C. for 40 min. After cooling it was treated with methanol. After concentration, the residue was treated with methanol, the solid was filtered off. The filtrate was concentrated. The residue was dissolved in methanol (1 mL). To the solution was added HCl solution previously prepared from acetyl chloride (0.5 mL) and methanol (0.5 mL). The mixture was stirred at r.t. for 30 min. The product was purified by RP-HPLC (pH=10) to afford the desired product. LCMS (M+H)$^+$=372.2.

Example 73

2-{4-[6-(2,6-Dichloro-3,5-dimethoxyphenyl)-1H-pyrazolo[3,4-d]pyrimidin-3-yl]-1H-pyrazol-1-yl}propanenitrile

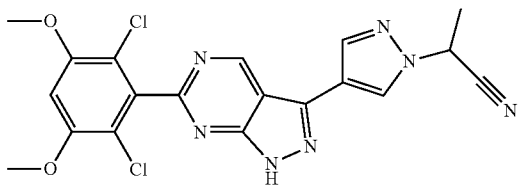 [SMILES: COc1cc(OC)c(Cl)c(-c2ncc3c(-c4cnn(C(C)C#N)c4)n[nH]c3n2)c1Cl]

This compound was prepared by using procedures analogous to those described for the synthesis of Example 4, Step 2 starting from 6-(2,6-dichloro-3,5-dimethoxyphenyl)-3-iodo-1H-pyrazolo[3,4-d]pyrimidine and 2-[4-(4,4,5,5-tetramethyl-1,3,2-dioxaborolan-2-yl)-1H-pyrazol-1-yl]propanenitrile (Example 34, Step 1). LCMS (M+H)$^+$=444.0/446.0. $^1$H NMR (300 MHz, DMSO-d$_6$) δ: 9.72 (s, 1H), 8.72 (s, 1H), 8.33 (s, 1H), 7.04 (s, 1H), 5.92 (q, J=7.1 Hz, 1H), 3.97 (s, 6H), 1.88 (d, J=7.1 Hz, 3H).

Example 74

2-Cyclopropyl-5-[6-(2,6-dichloro-3,5-dimethoxyphenyl)-1H-pyrazolo[3,4-d]pyrimidin-3-yl]isoindolin-1-one

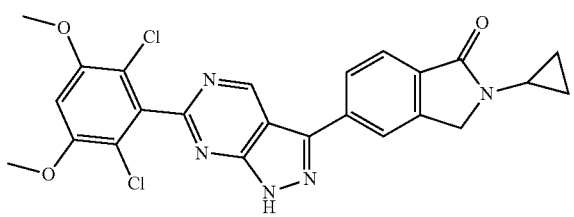 [SMILES: COc1cc(OC)c(Cl)c(-c2ncc3c(-c4ccc5c(c4)CN(C4CC4)C5=O)n[nH]c3n2)c1Cl]

This compound was prepared by using procedures analogous to those described for the synthesis of Example 4, Step 2 starting from 6-(2,6-dichloro-3,5-dimethoxyphenyl)-3-iodo-1H-pyrazolo[3,4-d]pyrimidine and 2-cyclopropyl-5-(4,4,5,5-tetramethyl-1,3,2-dioxaborolan-2-yl)isoindolin-1-one. LCMS (M+H)$^+$=496.0/498.0

Example 75

6-(2,6-Dichloro-3,5-dimethoxyphenyl)-3-[4-(4-methylpiperazin-1-yl)phenyl]-1H-pyrazolo[3,4-d]pyrimidine

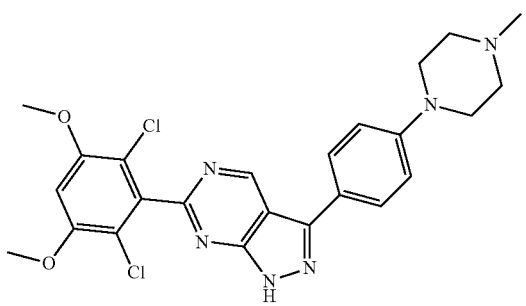

This compound was prepared by using procedures analogous to those described for the synthesis of Example 4, Step 2 starting from 6-(2,6-dichloro-3,5-dimethoxyphenyl)-3-iodo-1H-pyrazolo[3,4-d]pyrimidine and 1-methyl-4-(4-(4,4,5,5-tetramethyl-1,3,2-dioxaborolan-2-yl)phenyl)piperazine (Alfa Aesar, Cat. No. H51659). LCMS (M+H)$^+$=499.1/501.1. $^1$H NMR (300 MHz, DMSO-d$_6$) δ: 9.61 (s, 1H), 7.91 (d, J=8.8 Hz, 2H), 7.01 (d, J=8.8 Hz, 2H), 6.98 (s, 1H), 3.92 (s, 6H), 3.30-3.14 (m, 8H), 2.17 (s, 3H).

Example 76

2-{4-[6-(2,6-Difluoro-3,5-dimethoxyphenyl)-1H-pyrazolo[3,4-d]pyrimidin-3-yl]-1H-pyrazol-1-yl}propanenitrile

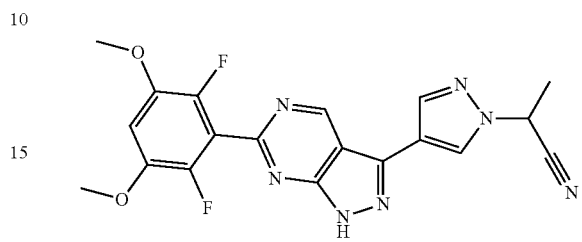

This compound was prepared as a TFA salt by using procedures analogous to those described for the synthesis of Example 7, Step 3 starting from 6-(2,6-difluoro-3,5-dimethoxyphenyl)-3-iodo-1H-pyrazolo[3,4-d]pyrimidine and 2-[4-(4,4,5,5-tetramethyl-1,3,2-dioxaborolan-2-yl)-1H-pyrazol-1-yl]propanenitrile. LCMS (M+H)$^+$=412.0.

Example 77

3-[6-(2,6-Dichloro-3,5-dimethoxyphenyl)-1H-pyrazolo[3,4-d]pyrimidin-3-yl]-6-ethyl-5,6-dihydro-7H-pyrrolo[3,4-b]pyridin-7-one

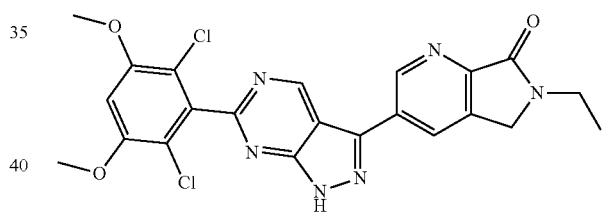

This compound was prepared as a TFA salt by using procedures analogous to those described for the synthesis of Example 1, Step 7 starting from 6-(2,6-dichloro-3,5-dimethoxyphenyl)-3-iodo-1H-pyrazolo[3,4-d]pyrimidine and 6-ethyl-3-(4,4,5,5-tetramethyl-1,3,2-dioxaborolan-2-yl)-5,6-dihydro-7H-pyrrolo[3,4-b]pyridin-7-one (Example 55, Step 3). LCMS (M+H)$^+$=485.0/487.0.

Example 78

5-[6-(2,6-Difluoro-3,5-dimethoxyphenyl)-1H-pyrazolo[3,4-d]pyrimidin-3-yl]-2-isopropylisoindolin-1-one

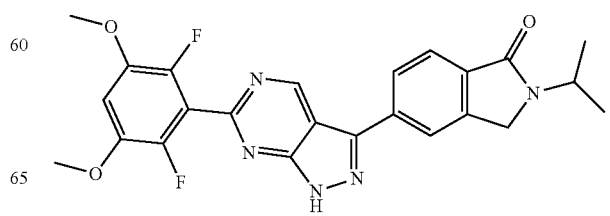

This compound was prepared by using procedures analogous to those described for the synthesis of Example 1, Step 7 starting from 6-(2,6-difluoro-3,5-dimethoxyphenyl)-3-iodo-1H-pyrazolo[3,4-d]pyrimidine and 2-isopropyl-5-(4,4,5,5-tetramethyl-1,3,2-dioxaborolan-2-yl)isoindolin-1-one. LCMS (M+H)+=466.0.

Example 79

5-[6-(2,6-Difluoro-3,5-dimethoxyphenyl)-1H-pyrazolo[3,4-d]pyrimidin-3-yl]-2-(1-methylpiperidin-4-yl)isoindolin-1-one

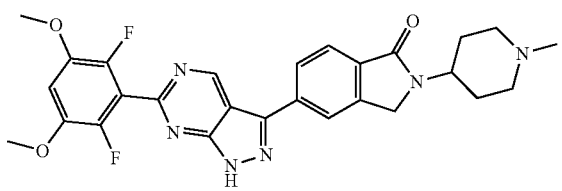

This compound was prepared by using procedures analogous to those described for the synthesis of Example 4, Step 2 starting from 6-(2,6-difluoro-3,5-dimethoxyphenyl)-3-iodo-1H-pyrazolo[3,4-d]pyrimidine and 2-(1-methylpiperidin-4-yl)-5-(4,4,5,5-tetramethyl-1,3,2-dioxaborolan-2-yl)isoindolin-1-one. LCMS (M+H)+=521.1. $^1$H NMR (300 MHz, DMSO-$d_6$) δ: 14.57 (s, 1H), 9.86 (s, 1H), 8.39 (s, 1H), 8.27 (d, J=8.0 Hz, 1H), 7.82 (d, J=8.0 Hz, 1H), 7.18 (t, J=8.2 Hz, 1H), 4.58 (s, 2H), 3.94 (s, 6H), 2.92-2.84 (m, 5H), 2.21 (s, 3H), 2.08-1.66 (m, 4H).

Example 80

5-[6-(2,6-Difluoro-3,5-dimethoxyphenyl)-1H-pyrazolo[3,4-d]pyrimidin-3-yl]-2-[2-(dimethylamino)ethyl]isoindolin-1-one

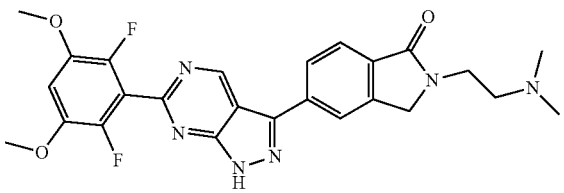

This compound was prepared by using procedures analogous to those described for the synthesis of Example 4, Step 2 starting from 6-(2,6-difluoro-3,5-dimethoxyphenyl)-3-iodo-1H-pyrazolo[3,4-d]pyrimidine and 2-[2-(dimethylamino)ethyl]-5-(4,4,5,5-tetramethyl-1,3,2-dioxaborolan-2-yl)isoindolin-1-one. LCMS (M+H)+=495.1.

Example 81

5-[6-(2,6-Difluoro-3,5-dimethoxyphenyl)-1H-pyrazolo[3,4-d]pyrimidin-3-yl]-2-(2-hydroxy-1-methylethyl)isoindolin-1-one

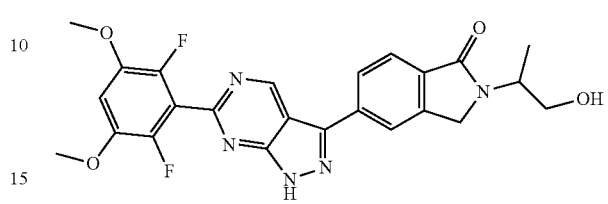

This compound was prepared by using procedures analogous to those described for the synthesis of Example 4, Step 2 starting from 6-(2,6-difluoro-3,5-dimethoxyphenyl)-3-iodo-1H-pyrazolo[3,4-d]pyrimidine and 2-(2-hydroxy-1-methylethyl)-5-(4,4,5,5-tetramethyl-1,3,2-dioxaborolan-2-yl)isoindolin-1-one. LCMS (M+H)+=482.0.

Example 82

5-[6-(2,6-Difluoro-3,5-dimethoxyphenyl)-1H-pyrazolo[3,4-d]pyrimidin-3-yl]-2-(2-hydroxypropyl)isoindolin-1-one

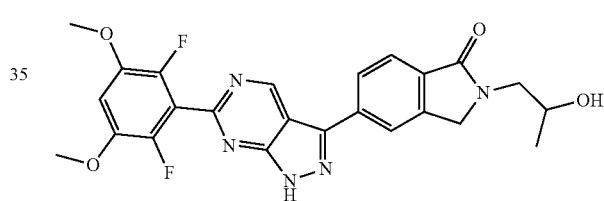

This compound was prepared by using procedures analogous to those described for the synthesis of Example 4, Step 2 starting from 6-(2,6-difluoro-3,5-dimethoxyphenyl)-3-iodo-1H-pyrazolo[3,4-d]pyrimidine and 2-(2-hydroxypropyl)-5-(4,4,5,5-tetramethyl-1,3,2-dioxaborolan-2-yl)isoindolin-1-one. LCMS (M+H)+=482.1.

Example 83

5-[6-(2,6-Difluoro-3,5-dimethoxyphenyl)-1H-pyrazolo[4,3-c]pyridin-3-yl]-N,N-dimethyl-2,3-dihydro-1-benzofuran-2-carboxamide (Enantiomer I)

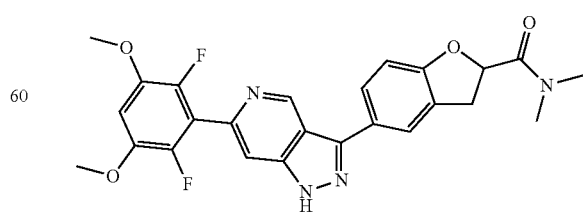

A mixture of 6-(2,6-difluoro-3,5-dimethoxyphenyl)-3-iodo-1-(tetrahydro-2H-pyran-2-yl)-1H-pyrazolo[4,3-c]pyridine (17.9 mg, 0.0357 mmol) (Example 52, Step 5), N,N-dimethyl-5-(4,4,5,5-tetramethyl-1,3,2-dioxaborolan-2-yl)-2,3-dihydro-1-benzofuran-2-carboxamide (13.6 mg, 0.0429 mmol) (Peak I from chiral separation, Example 4, Step 1), [1,1'-bis(diphenylphosphino)ferrocene]dichloropalladium (II) complexed with dichloromethane (1:1) (0.0018 g, 0.0021 mmol), and potassium phosphate (0.0228 g, 0.107 mmol) in 1,4-dioxane (0.48 mL) and water (0.24 mL) in a reaction vial was sealed, and degassed and recharged with nitrogen three times. The mixture was stirred at 90° C. for 3 h. After cooling, the mixture was diluted with ethyl acetate (2 mL). The mixture was filtered. The filtrate was concentrated under reduced pressure. The residue was dissolved in methanol (0.3 mL). To the solution was added a solution of acetyl chloride (0.2 mL) in methanol (0.2 mL) which was previously prepared at 0° C. The mixture was stirred at r.t. for 2 h, diluted with methanol, and purified by RP-HPLC (pH=2) to afford the desired product as a TFA salt. LCMS (M+H)$^+$=481.0. $^1$H NMR (300 MHz, DMSO-$d_6$) δ: 13.62 (s, 1H), 9.47 (d, J=1.1 Hz, 1H), 7.95 (s, 1H), 7.86 (d, J=8.4 Hz, 1H), 7.70 (s, 1H), 7.12 (t, J=8.2 Hz, 1H), 6.97 (d, J=8.4 Hz, 1H), 5.81-5.70 (m, 1H), 3.93 (s, 6H), 3.57-3.48 (m, 2H), 3.13 (s, 3H), 2.90 (s, 3H).

Example 84

5-[6-(2,6-Difluoro-3,5-dimethoxyphenyl)-1H-pyrazolo[4,3-c]pyridin-3-yl]-N,N-dimethyl-2,3-dihydro-1-benzofuran-2-carboxamide (Enantiomer II)

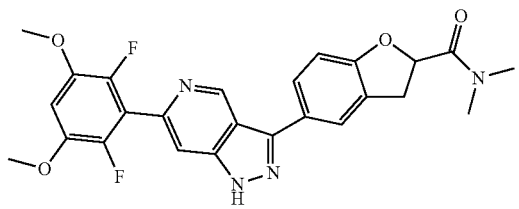

This compound was prepared as a TFA salt by using procedures analogous to those described for the synthesis of Example 83 starting from 6-(2,6-difluoro-3,5-dimethoxyphenyl)-3-iodo-1-(tetrahydro-2H-pyran-2-yl)-1H-pyrazolo[4,3-c]pyridine (Example 52, Step 5) and N,N-dimethyl-5-(4,4,5,5-tetramethyl-1,3,2-dioxaborolan-2-yl)-2,3-dihydro-1-benzofuran-2-carboxamide (Peak II from chiral separation, Example 4, Step 1). LCMS (M+H)$^+$=481.0.

Example 85

7-[6-(2,6-Difluoro-3,5-dimethoxyphenyl)-1H-pyrazolo[3,4-d]pyrimidin-3-yl]-2-(methylsulfonyl)-1,2,3,4-tetrahydroisoquinoline

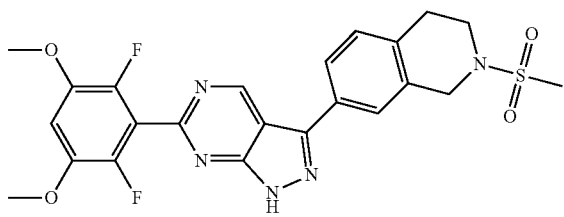

Step 1: tert-butyl 7-(4,4,5,5-tetramethyl-1,3,2-dioxaborolan-2-yl)-3,4-dihydroisoquinoline-2(1H)-carboxylate This compound was prepared as by using procedures analogous to those described for the synthesis of Example 1, Step 2 starting from tert-butyl 7-bromo-3,4-dihydroisoquinoline-2(1H)-carboxylate and 4,4,5,5,4',4',5',5'-octamethyl-[2,2']bi[[1,3,2]dioxaborolanyl]. LCMS (M+H-56)$^+$=304.1.

Step 2: tert-butyl 7-[6-(2,6-difluoro-3,5-dimethoxyphenyl)-1H-pyrazolo[3,4-d]pyrimidin-3-yl]-3,4-dihydroisoquinoline-2(1H)-carboxylate

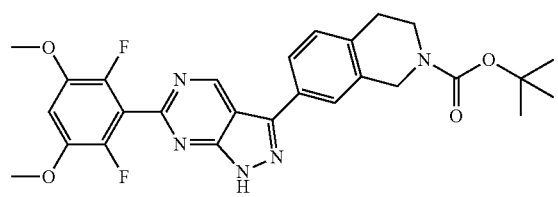 [SMILES: COc1cc(OC)c(F)c(-c2ncc3c(-c4ccc5c(c4)CN(C(=O)OC(C)(C)C)CC5)n[nH]c3n2)c1F]

A mixture of 6-(2,6-difluoro-3,5-dimethoxyphenyl)-3-iodo-1H-pyrazolo[3,4-d]pyrimidine (16.7 mg, 0.0400 mmol), tert-butyl 7-(4,4,5,5-tetramethyl-1,3,2-dioxaborolan-2-yl)-3,4-dihydroisoquinoline-2(1H)-carboxylate (17.96 mg, 0.05000 mmol), [1,1'-bis(diphenylphosphino)ferrocene]dichloropalladium(II) complex with dichloromethane (1:1) (2.0 mg, 0.0024 mmol) and potassium phosphate (25.5 mg, 0.120 mmol) in 1,4-dioxane (0.50 mL) and water (0.15 mL) in a reaction vial was sealed, and degassed and recharged with nitrogen for three times. The mixture was stirred at 115° C. for 3 h. After cooling, the mixture was diluted with methanol, and purified by RP-HPLC (pH=10) to afford the desired product. LCMS (M+H)$^+$=524.1.

Step 3: 7-[6-(2,6-difluoro-3,5-dimethoxyphenyl)-1H-pyrazolo[3,4-d]pyrimidin-3-yl]-2-(methylsulfonyl)-1,2,3,4-tetrahydroisoquinoline tert-Butyl 7-[6-(2,6-difluoro-3,5-dimethoxyphenyl)-1H-pyrazolo[3,4-d]pyrimidin-3-yl]-3,4-dihydroisoquinoline-2(1H)-carboxylate (10.0 mg, 0.0191 mmol) in dichloromethane (0.10 mL) was treated with TFA (0.10 mL). The mixture was stirred at r.t. for 1 h. The volatiles were evaporated. The residue was dissolved in acetonitrile (0.5 mL) and N,N-diisopropylethylamine (30.0 µL). To the mixture was added methanesulfonyl chloride (2.0 µL, 0.026 mmol). The mixture was stirred at r.t. for 30 min, and then diluted with methanol, and purified by RP-HPLC (pH=10) to afford the desired product. LCMS (M+H)$^+$=502.1.

Example 86

6-(2,6-Dichloro-3,5-dimethoxyphenyl)-3-(2,3-dihydro-1-benzofuran-5-yl)-1H-pyrazolo[3,4-d]pyrimidine

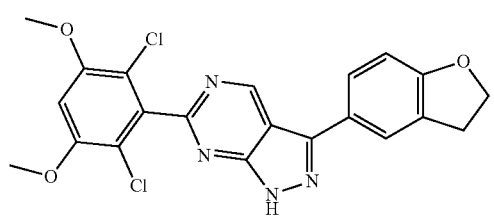

This compound was prepared as TFA salt by using procedures analogous to those described for the synthesis of Example 7, Step 3 starting from 6-(2,6-dichloro-3,5-dimethoxyphenyl)-3-iodo-1H-pyrazolo[3,4-d]pyrimidine and 2,3-dihydro-1-benzofuran-5-ylboronic acid. LCMS (M+H)⁺=443.0/445.0.

Example 87

6-(2,6-Difluoro-3,5-dimethoxyphenyl)-3-(1-methyl-1H-pyrazol-4-yl)-1H-pyrazolo[3,4-d]pyrimidine

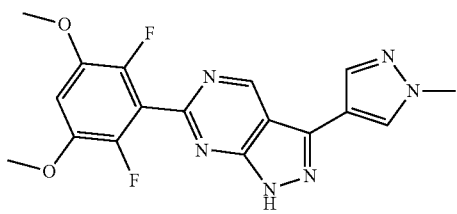

This compound was prepared as a TFA salt by using procedures analogous to those described for the synthesis of Example 7, Step 3 starting from 6-(2,6-difluoro-3,5-dimethoxyphenyl)-3-iodo-1H-pyrazolo[3,4-d]pyrimidine and 1-methyl-4-(4,4,5,5-tetramethyl-1,3,2-dioxaborolan-2-yl)-1H-pyrazole. LCMS (M+H)⁺=373.0. ¹H NMR (300 MHz, DMSO-d₆) δ: 14.11 (s, 1H), 9.74 (s, 1H), 8.56 (s, 1H), 8.17 (s, 1H), 7.17 (t, J=8.1 Hz, 1H), 3.95 (s, 3H), 3.93 (s, 3H).

Example 88

2-{4-[6-(2,6-Difluoro-3,5-dimethoxyphenyl)-1H-pyrazolo[4,3-c]pyridin-3-yl]-1H-pyrazol-1-yl}ethanol

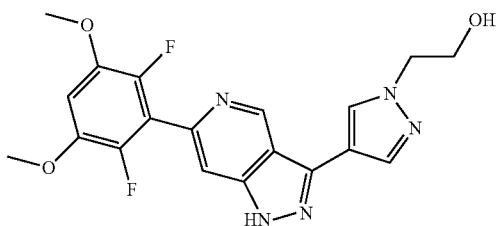 [SMILES: COc1cc(OC)c(F)c(-c2cc3[nH]nc(-c4cnn(CCO)c4)c3cn2)c1F]

Step 1: 1-[2-(tetrahydro-2H-pyran-2-yloxy)ethyl]-4-(4,4,5,5-tetramethyl-1,3,2-dioxaborolan-2-yl)-1H-pyrazole A mixture of 4-(4,4,5,5-tetramethyl-1,3,2-dioxaborolan-2-yl)-1H-pyrazole (0.20 g, 1.0 mmol) (Aldrich Cat. No. 525057), 2-(2-bromoethoxy)tetrahydro-2H-pyran (170 µL, 1.1 mmol) (Aldrich Cat. No. 475394) and potassium carbonate (0.21 g, 1.5 mmol) in acetonitrile (2 mL) was stirred at r.t. overnight. After filtration the filtrate was concentrated under reduced pressure. The residue was purified by flash chromatography on a silica gel column with ethyl acetate in hexanes (0-50%) to afford the desired product.

Step 2: 2-{4-[6-(2,6-difluoro-3,5-dimethoxyphenyl)-1H-pyrazolo[4,3-c]pyridin-3-yl]-1H-pyrazol-1-yl}ethanol This compound was prepared by using procedures analogous to those described for the synthesis of Example 52, Step 8 starting from 6-(2,6-difluoro-3,5-dimethoxyphenyl)-3-iodo-1-(tetrahydro-2H-pyran-2-yl)-1H-pyrazolo[4,3-c]pyridine and 1-[2-(tetrahydro-2H-pyran-2-yloxy)ethyl]-4-(4,4,5,5-tetramethyl-1,3,2-dioxaborolan-2-yl)-1H-pyrazole. LCMS (M+H)⁺=402.1.

Example 89

5-[6-(2-Chloro-6-fluoro-3,5-dimethoxyphenyl)-1H-pyrazolo[3,4-b]pyridin-3-yl]-2-cyclopropylisoindolin-1-one

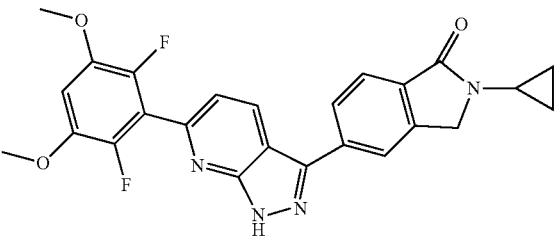 [SMILES: COc1cc(OC)c(F)c(-c2ccc3c(-c4ccc5c(c4)CN(C4CC4)C5=O)n[nH]c3n2)c1F]

Step 1: 5-[6-chloro-1-(tetrahydro-2H-pyran-2-yl)-1H-pyrazolo[3,4-b]pyridin-3-yl]-2-cyclopropylisoindolin-1-one

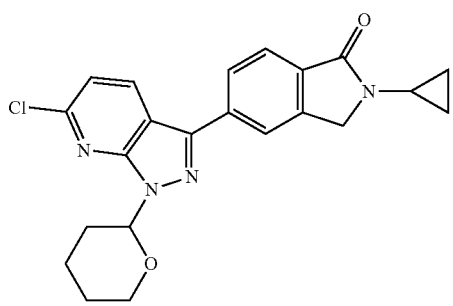 [SMILES: O=C1c2ccc(-c3nn(C4CCCCO4)c4nc(Cl)ccc34)cc2CN1C1CC1]

This compound was prepared by using procedures analogous to those described for the synthesis of Example 72, Step 3 starting from 6-chloro-3-iodo-1-(tetrahydro-2H-pyran-2-yl)-1H-pyrazolo[3,4-b]pyridine (Example 72, Step 2) and 2-cyclopropyl-5-(4,4,5,5-tetramethyl-1,3,2-dioxaborolan-2-yl)isoindolin-1-one. LCMS (M+H)⁺=409.1.

Step 2: 2-cyclopropyl-5-[6-(3,5-dimethoxyphenyl)-1-(tetrahydro-2H-pyran-2-yl)-1H-pyrazolo[3,4-b]pyridin-3-yl]isoindolin-1-one

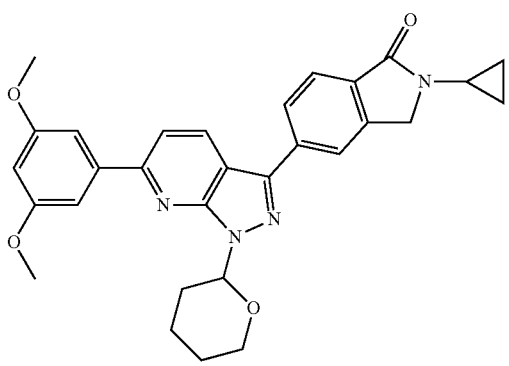 [SMILES: COc1cc(OC)cc(-c2ccc3c(-c4ccc5c(c4)CN(C4CC4)C5=O)nn(C4CCCCO4)c3n2)c1]

This compound was prepared by using procedures analogous to those described for the synthesis of Example 72, Step 4 starting from 5-[6-chloro-1-(tetrahydro-2H-pyran-2-yl)-1H-pyrazolo[3,4-b]pyridin-3-yl]-2-cyclopropylisoindolin-1-one and 2-(3,5-dimethoxyphenyl)-4,4,5,5-tetramethyl-1,3,2-dioxaborolane. LCMS (M+H)⁺=511.2.

Step 3: 2-cyclopropyl-5-[6-(2-fluoro-3,5-dimethoxyphenyl)-1-(tetrahydro-2H-pyran-2-yl)-1H-pyrazolo[3,4-b]pyridin-3-yl]isoindolin-1-one

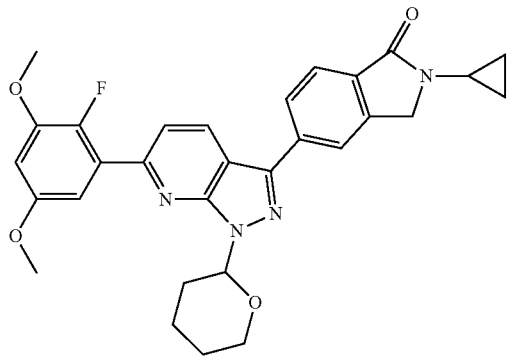 [SMILES: COc1cc(OC)c(F)c(-c2ccc3c(-c4ccc5c(c4)CN(C4CC4)C5=O)nn(C4CCCCO4)c3n2)c1]

1-(Chloromethyl)-4-fluoro-1,4-diazoniabicyclo[2.2.2]octane ditetrafluoroborate (0.21 g, 0.59 mmol) was added to a stirring solution of 2-cyclopropyl-5-[6-(3,5-dimethoxyphenyl)-1-(tetrahydro-2H-pyran-2-yl)-1H-pyrazolo[3,4-b]pyridin-3-yl]isoindolin-1-one (0.15 g, 0.29 mmol) in acetonitrile (3 mL). The mixture was stirred at r.t. for 2 h. Then it was concentrated under reduced pressure. The residue was purified by flash chromatography on a silica gel column with ethyl acetate in hexanes (0-50%) to afford the desired product (0.12 g). LCMS (M+H)⁺=529.2.

Step 4: 5-[6-(2-chloro-6-fluoro-3,5-dimethoxyphenyl)-1H-pyrazolo[3,4-b]pyridin-3-yl]-2-cyclopropylisoindolin-1-one Sulfuryl chloride (10. µL, 0.12 mmol) was added to a stirring solution of 2-cyclopropyl-5-[6-(2-fluoro-3,5-dimethoxyphenyl)-1-(tetrahydro-2H-pyran-2-yl)-1H-pyrazolo[3,4-b]pyridin-3-yl]isoindolin-1-one (65 mg, 0.12 mmol) in methylene chloride (1 mL). The mixture was stirred at r.t. for 30 min. It was concentrated to dryness. The solid was dissolved in methanol (0.3 mL). To the solution was added a solution of HCl previously prepared from acetyl chloride (0.15 mL) and methanol (0.15 mL). The mixture was stirred at r.t. for 1 h and then diluted with methanol, and purified by RP-HPLC (pH=10) to afford the desired product. LCMS (M+H)⁺=479.1.

Example 90

6-(2,6-Dichloro-3,5-dimethoxyphenyl)-3-(1-methyl-1H-pyrazol-4-yl)-1H-pyrazolo[4,3-c]pyridine

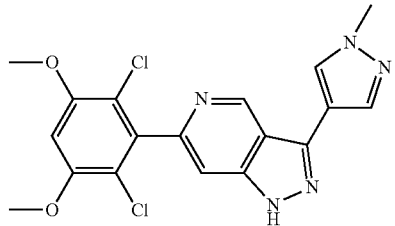

Step 1: 6-chloro-3-iodo-1H-pyrazolo[4,3-c]pyridine

A mixture of 6-chloro-1H-pyrazolo[4,3-c]pyridine (0.3 g, 2 mmol) (Frontier Cat. No. Z13659) and N-iodosuccinimide (0.53 g, 2.3 mmol) in N,N-dimethylformamide (2 mL) was stirred at 80° C. for 1 h. After cooling it was concentrated and the residue was treated with methanol. The white solid was collected by filtration to afford the desired product (0.5 g). LCMS (M+H)⁺=279.9.

Step 2: 6-chloro-3-iodo-1-(tetrahydro-2H-pyran-2-yl)-1H-pyrazolo[4,3-c]pyridine

At r.t. to a suspension of 6-chloro-3-iodo-1H-pyrazolo[4,3-c]pyridine (0.55 g, 2.0 mmol) in methylene chloride (6 mL) and tetrahydrofuran (3 mL) was added methanesulfonic acid (20 µL, 0.4 mmol), followed by dihydropyran (0.54 mL, 5.9 mmol) (Aldrich, Cat. #: D106208). The mixture was stirred at r.t. overnight. Then, it was stirred at 60° C. for 4 h. After cooling it was concentrated under reduced pressure. The residue was purified by flash chromatography on a silica gel column with ethyl acetate in hexanes (0-50%) to afford the desired product (0.72 g).

Step 3: 6-chloro-3-(1-methyl-1H-pyrazol-4-yl)-1-(tetrahydro-2H-pyran-2-yl)-1H-pyrazolo[4,3-c]pyridine

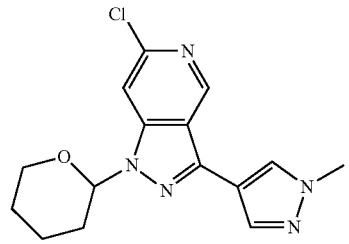 [SMILES: Cn1cc(-c2nn(C3CCCCO3)c3cc(Cl)ncc23)cn1]

A mixture of 6-chloro-3-iodo-1-(tetrahydro-2H-pyran-2-yl)-1H-pyrazolo[4,3-c]pyridine (120 mg, 0.33 mmol), 1-methyl-4-(4,4,5,5-tetramethyl-1,3,2-dioxaborolan-2-yl)-1H-pyrazole (100 mg, 0.50 mmol), tetrakis(triphenylphosphine)palladium(0) (20 mg, 0.02 mmol) and cesium carbonate (320 mg, 0.99 mmol) in 1,4-dioxane (1 mL) and water (0.12 mL) was degassed and sealed. It was stirred at 85° C. for 3 h. After cooling it was concentrated under reduced pressure. The residue was purified by flash chromatography on a silica gel column with ethyl acetate in hexanes (0-50%) to afford the desired product (0.10 g). LCMS (M+H)⁺=318.1.

Step 4: 6-(3,5-dimethoxyphenyl)-3-(1-methyl-1H-pyrazol-4-yl)-1-(tetrahydro-2H-pyran-2-yl)-1H-pyrazolo[4,3-c]pyridine

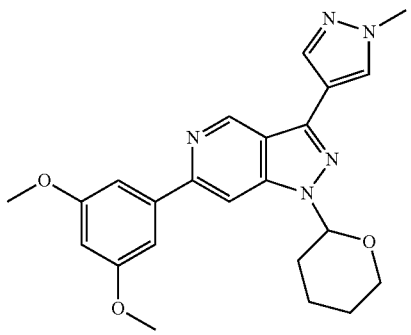

A mixture of 6-chloro-3-(1-methyl-1H-pyrazol-4-yl)-1-(tetrahydro-2H-pyran-2-yl)-1H-pyrazolo[4,3-c]pyridine (0.06 g, 0.2 mmol), 2-(3,5-dimethoxyphenyl)-4,4,5,5-tetramethyl-1,3,2-dioxaborolane (0.060 g, 0.23 mmol), [1,1'-bis(diphenylphosphino)ferrocene]-dichloropalladium(II) complex with dichloromethane (1:1) (10 mg, 0.02 mmol), and potassium phosphate (80. mg, 0.38 mmol) in 1,4-dioxane (0.5 mL) and water (0.07 mL) in a reaction vial was degassed and sealed. The mixture was stirred at 90° C. for 2 h. After cooling it was concentrated under reduced pressure. The residue was purified by flash chromatography on a silica gel column with ethyl acetate in hexanes (0-50%) to afford the desired product (80 mg). LCMS (M+H)$^+$=420.2.

Step 5: 6-(2,6-dichloro-3,5-dimethoxyphenyl)-3-(1-methyl-1H-pyrazol-4-yl)-1H-pyrazolo[4,3-c]pyridine At 0° C. to a stirring solution of 6-(3,5-dimethoxyphenyl)-3-(1-methyl-1H-pyrazol-4-yl)-1-(tetrahydro-2H-pyran-2-yl)-1H-pyrazolo[4,3-c]pyridine (80 mg, 0.2 mmol) in methylene chloride (3 mL) was added dropwise a solution of sulfuryl chloride (31 µL, 0.38 mmol)(Acros Organics, Cat. #: 37815) in methylene chloride (1 mL). The mixture was stirred at r.t. overnight. To the mixture was added acetonitrile (2 mL) and it was stirred at r.t. for 1 h. Then, to the mixture was added another 31 µL of sulfuryl chloride and it was stirred at r.t. for 4 h. The solvent was removed under reduced pressure and the residue was treated with methylene chloride and sat'd NaHCO$_3$ solution. After separation the aq. layer was extracted with methylene chloride. The combined organic layers were dried over Na$_2$SO$_4$. After filtration the filtrate was concentrated under reduced pressure. The residue was purified by flash chromatography on a silica gel column with ethyl acetate in hexanes (0-50%) to afford an intermediate which was dissolved in methanol (3 mL), and cooled to 0° C. To the solution was added a pre-cooled HCl solution prepared from acetyl chloride (700 µL, 10 mmol) and methanol (1 mL). The mixture was stirred at r.t. for 4 h and then the solvents were removed. The residue was dissolved in methanol, and purified by RP-HPLC (pH=2) to afford the desired product (4.8 mg) as a TFA salt. LCMS (M+H)$^+$=404.1.

Example 91

6-(2,6-Difluoro-3,5-dimethoxyphenyl)-3-(1-methyl-1H-pyrazol-4-yl)-1H-pyrazolo[4,3-c]pyridine

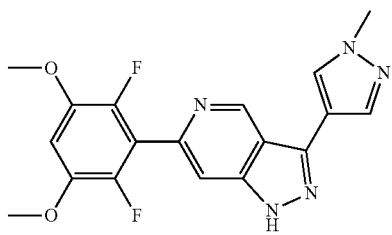 [SMILES: COc1cc(OC)c(F)c(-c2cc3[nH]nc(-c4cnn(C)c4)c3cn2)c1F]

At 0° C. to a stirring solution of 6-(3,5-dimethoxyphenyl)-3-(1-methyl-1H-pyrazol-4-yl)-1-(tetrahydro-2H-pyran-2-yl)-1H-pyrazolo[4,3-c]pyridine (70 mg, 0.2 mmol) in acetonitrile (1 mL) was added a suspension of 1-(chloromethyl)-4-fluoro-1,4-diazoniabicyclo[2.2.2]octane ditetrafluoroborate (120 mg, 0.33 mmol) in acetonitrile (2 mL). The mixture was stirred at r.t. for 3 h. To the mixture another portion of 1-(chloromethyl)-4-fluoro-1,4-diazoniabicyclo[2.2.2]octane ditetrafluoroborate (100 mg) was added and then the mixture was stirred at r.t. overnight. Then another portion of 1-(chloromethyl)-4-fluoro-1,4-diazoniabicyclo[2.2.2]octane ditetrafluoroborate (60 mg) was added. The mixture was stirred at 40° C. for 1 h. After cooling it was treated with sat'd NaHCO$_3$ solution and filtered. After filtration the filtrate was concentrated to dryness and the residue was dissolved in methanol. At r.t. to the mixture was added HCl solution previously prepared from acetyl chloride (0.5 mL) and methanol (0.5 mL). The mixture was stirred at r.t. for 1 h. and purified by RP-HPLC (pH=10) to afford the desired product 0.8 mg. LCMS (M+H)$^+$=372.2. $^1$H-NMR (500 MHz, DMSO-d$_6$) δ: 9.31 (s, 1H), 8.39 (s, 1H), 8.03 (s, 1H), 7.54 (s, 1H), 7.06 (t, J=8.0 Hz, 1H), 3.93 (s, 3H), 3.90 (s, 6H).

Example 92

Methyl 5-[6-(2,6-difluoro-3,5-dimethoxyphenyl)-1H-pyrazolo[4,3-c]pyridin-3-yl]-1-benzofuran-2-carboxylate

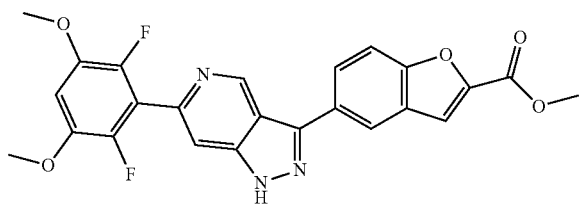

Step 1: ethyl 5-(4,4,5,5-tetramethyl-1,3,2-dioxaborolan-2-yl)-1-benzofuran-2-carboxylate

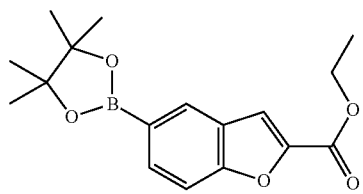 [SMILES: CCOC(=O)c1cc2cc(B3OC(C)(C)C(C)(C)O3)ccc2o1]

This compound was prepared by using procedures analogous to those described for the synthesis of Example 52, Step 7 starting from ethyl (5-bromobenzofuran)-2-carboxylate (Maybridge Cat. No. CC 31223) and 4,4,5,5,4',4',5',5'-octamethyl-[2,2']bi[[1,3,2]dioxaborolanyl] (Aldrich Cat. No. 473294).

Step 2: methyl 5-[6-(2,6-difluoro-3,5-dimethoxyphenyl)-1H-pyrazolo[4,3-c]pyridin-3-yl]-1-benzofuran-2-carboxylate This compound was prepared by using procedures analogous to those described for the synthesis of Example 52, Step 8 starting from 6-(2,6-difluoro-3,5-dimethoxyphenyl)-3-iodo-1-(tetrahydro-2H-pyran-2-yl)-1H-pyrazolo[4,3-c]pyridine (9 mg, 0.02 mmol; from step 6) and ethyl 5-(4,4,5,5- tetramethyl-1,3,2-dioxaborolan-2-yl)-1-benzofuran-2-carboxylate. LCMS (M+H)⁺: m/z=466.2.

Example 93

6-(2,6-Difluoro-3,5-dimethoxyphenyl)-3-imidazo[1,2-a]pyridin-6-yl-1H-pyrazolo[3,4-d]pyrimidine

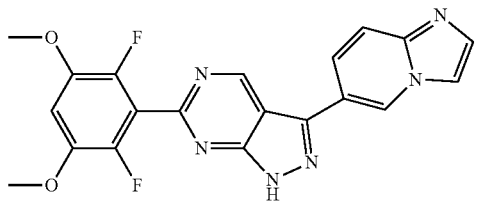 [SMILES: COc1cc(OC)c(F)c(-c2ncc3c(-c4ccc5nccn5c4)n[nH]c3n2)c1F]

This compound was prepared by using procedures analogous to those described for the synthesis of Example 4, Step 2 starting from 6-(2,6-difluoro-3,5-dimethoxyphenyl)-3-iodo-1H-pyrazolo[3,4-d]pyrimidine (16.7 mg, 0.0400 mmol) (Example 3, Step 4) and imidazo[1,2-a]pyridin-6-ylboronic acid (Combi-Blocks, Cat. No. BB-3457). LCMS (M+H)⁺=409.0.

Example 94

6-[6-(2,6-Difluoro-3,5-dimethoxyphenyl)-1H-pyrazolo[3,4-d]pyrimidin-3-yl]quinoline

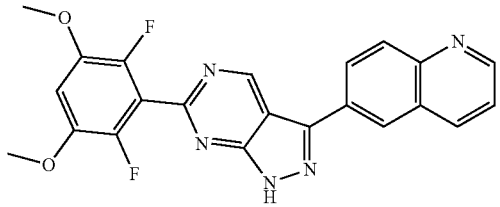 [SMILES: COc1cc(OC)c(F)c(-c2ncc3c(-c4ccc5ncccc5c4)n[nH]c3n2)c1F]

This compound was prepared using procedures analogous to those described for the synthesis of Example 4, Step 2 starting from 6-(2,6-difluoro-3,5-dimethoxyphenyl)-3-iodo-1H-pyrazolo[3,4-d]pyrimidine and quinolin-6-ylboronic acid (Combi-Blocks, Cat. No. BB-5182). LCMS (M+H)⁺=420.1.

Example A

FGFR Enzymatic Assay

The inhibitor potency of the Example compounds was measured in an enzyme assay that measures peptide phosphorylation using FRET measurements to detect product formation. Inhibitors were serially diluted in DMSO and a volume of 0.5 µL was transferred to the wells of a 384-well plate. For FGFR3, a 10 µL volume of FGFR3 enzyme (Millipore) diluted in assay buffer (50 mM HEPES, 10 mM MgCl$_2$, 1 mM EGTA, 0.01% Tween-20, 5 mM DTT, pH 7.5) was added to the plate and pre-incubated for 5-10 minutes. Appropriate controls (enzyme blank and enzyme with no inhibitor) were included on the plate. The assay was initiated by the addition of a 10 µL solution containing biotinylated EQEDEPEGDYFEWLE peptide substrate (SEQ ID NO: 1) and ATP (final concentrations of 500 nM and 140 µM respectively) in assay buffer to the wells. The plate was incubated at 25° C. for 1 hr. The reactions were ended with the addition of 10 µL/well of quench solution (50 mM Tris, 150 mM NaCl, 0.5 mg/mL BSA, pH~7.8, 30 mM EDTA with Perkin Elmer Lance Detection Reagents at 3.75 nM Eu-antibody PY20 and 180 nM APC-Streptavidin). The plate was allowed to equilibrate for 1 hour before scanning the wells on a PheraStar plate reader (BMG Labtech). The enzymes were purchased from Millipore or Invitrogen.

FGFR1 and FGFR2 were measured under equivalent conditions with the following changes in enzyme and ATP concentrations: FGFR1, 0.02 nM and 210 µM, respectively and FGFR2, 0.01 nM and 100 µM, respectively.

GraphPad prism3 was used to analyze the data. The IC$_{50}$ values were derived by fitting the data to the equation for a sigmoidal dose-response with a variable slope. Y=Bottom+(Top−Bottom)/(1+10^((Log IC$_{50}$−X)*HillSlope)) where X is the logarithm of concentration and Y is the response. Compounds having an IC$_{50}$ of 1 µM or less are considered active.

The compounds of the Examples were found to be inhibitors of one or more of FGFR1, FGFR2, and FGFR3 according to the above-described assay. IC$_{50}$ data is provided below in Table 1. The symbol "+" indicates an IC$_{50}$ less than 100 nM and the symbol "++" indicates an IC$_{50}$ of 100 to 500 nM.

TABLE 1

| Example No. | FGFR1 IC50 (nM) | FGFR2 IC50 (nM) | FGFR3 IC50 (nM) |
| --- | --- | --- | --- |
| 1 | + | + | + |
| 2 | + | + | + |
| 3 | + | + | + |
| 4 | + | + | + |
| 5 | + | + | + |
| 6 | + | + | + |
| 7 | + | + | + |
| 8 | + | + | + |
| 9 | + | + | + |
| 10 | + | + | + |
| 11 | + | + | + |
| 12 | + | + | + |
| 13 | + | + | + |
| 14 | + | + | + |
| 15 | + | + | + |
| 16 | + | + | + |
| 17 | + | + | + |
| 18 | + | + | + |
| 19 | + | + | + |
| 20 | + | + | + |
| 21 | + | + | + |
| 22 | + | + | + |
| 23 | + | + | + |
| 24 | + | + | + |
| 25 | + | + | + |
| 26 | + | + | + |
| 27 | + | + | + |
| 28 | + | + | + |
| 29 | + | + | + |
| 30 | + | + | + |
| 31 | + | ++ | + |
| 32 | + | + | + |
| 33 | + | + | + |
| 34 | + | + | + |
| 35 | + | + | + |
| 36 | + | + | + |
| 37 | + | + | + |
| 38 | + | + | + |
| 39 | + | + | + |
| 40 | + | + | + |
| 41 | + | + | + |
| 42 | + | + | + |
| 43 | + | + | + |
| 44 | + | + | + |

TABLE 1-continued

| Example No. | FGFR1 IC50 (nM) | FGFR2 IC50 (nM) | FGFR3 IC50 (nM) |
|---|---|---|---|
| 45 | + | + | + |
| 46 | + | + | + |
| 47 | + | + | + |
| 48 | + | + | + |
| 49 | + | + | + |
| 50 | + | + | + |
| 51 | + | + | + |
| 52 | + | + | + |
| 53 | + | + | + |
| 54 | + | + | + |
| 55 | + | + | + |
| 56 | + | + | + |
| 57 | + | + | + |
| 58 | + | + | + |
| 59 | + | + | + |
| 60 | + | + | + |
| 61 | + | + | + |
| 62 | + | + | + |
| 63 | + | + | + |
| 64 | + | + | + |
| 65 | + | + | + |
| 66 | + | + | + |
| 67 | + | + | + |
| 68 | + | + | + |
| 69 | + | + | + |
| 70 | + | + | + |
| 71 | + | + | + |
| 72 | + | + | + |
| 73 | + | + | + |
| 74 | + | + | + |
| 75 | + | + | + |
| 76 | + | + | + |
| 77 | + | + | + |
| 78 | + | + | + |
| 79 | + | + | + |
| 80 | + | + | + |
| 81 | + | + | + |
| 82 | + | + | + |
| 83 | + | + | + |
| 84 | + | + | + |
| 85 | + | + | + |
| 86 | + | + | + |
| 87 | + | + | + |
| 88 | + | + | + |
| 89 | + | + | + |
| 90 | + | + | + |
| 91 | + | + | + |
| 92 | + | + | + |
| 93 | + | + | + |
| 94 | + | + | + |

Example B

FGFR3 Cell Proliferation/Survival Assays

A recombinant cell line over-expressing human FGFR3 was developed by stable transfection of the mouse pro-B Ba/F3 cells (obtained from the Deutsche Sammlung von Mikroorganismen and Zellkulturen) with a plasmid encoding the full length human FGFR3. Cells were sequentially selected for puromycin resistance and proliferation in the presence of heparin and FGF1. A single cell clone was isolated and characterized for functional expression of FGFR3. This Ba/F3-FGFR3 clone is used in cell proliferation assays, and compounds are screened for their ability to inhibit cell proliferation/survival. The Ba/F3-FGFR3 cells are seeded into 96 well, black cell culture plates at 3500 cells/well in RPMI1640 media containing 2% FBS, 20 ug/mL Heparin and 5 ng/mL FGF1. The cells were treated with 10 µL of 10× concentrations of serially diluted compounds (diluted with medium lacking serum from 5 mM DSMO dots) to a final volume of 100 µL/well. After 72 hour incubation, 100 µL of Cell Titer Glo® reagent (Promega Corporation) that measures cellular ATP levels is added to each well. After 20 minute incubation with shaking, the luminescence is read on a plate reader. The luminescent readings are converted to percent inhibition relative to DMSO treated control wells, and the $IC_{50}$ values are calculated using GraphPad Prism software. Compounds having an $IC_{50}$ of 10 µM or less are considered active. Other non-recombinant cancer cell lines representing a variety of tumor types including KMS-11 (multiple myeloma), RT112 (bladder cancer), KatoIII (gastric cancer), and H-1581 (lung) are used in similar proliferation assays. In some experiments, MTS reagent, Cell Titer 96® AQueous One Solution Reagent (Promega Corporation) is added to a final concentration of 333 µg/mL in place Cell Titer Glo and read at 490/650 nm on a plate reader. Compounds having an $IC_{50}$ of 5 µM or less are considered active.

Example C

Cell-Based FGFR Phosphorylation Assays

The inhibitory effect of compounds on FGFR phosphorylation in relevant cell lines (Ba/F3-FGFR3, KMS-11, RT112, KatoIII, H-1581 cancer cell lines and HUVEC cell line) can be assessed using immunoassays specific for FGFR phosphorylation. Cells are starved in media with reduced serum (0.5%) and no FGF1 for 4 to 48 h depending upon the cell line then treated with various concentrations of individual inhibitors for 1-4 hours. For some cell lines, such as Ba/F3-FGFR3 and KMS-11, cells are stimulated with Heparin (20 µg/mL) and FGF1 (10 ng/mL) for 10 min. Whole cell protein extracts are prepared by incubation in lysis buffer with protease and phosphatase inhibitors [50 mM HEPES (pH 7.5), 150 mM NaCl, 1.5 mM $MgCl_2$, 10% Glycerol, 1% Triton X-100, 1 mM sodium orthovanadate, 1 mM sodium fluoride, aprotinin (2 µg/mL), leupeptin (2 µg/mL), pepstatin A (2 µg/mL), and phenylmethylsulfonyl fluoride (1 mM)] at 4° C. Protein extracts are cleared of cellular debris by centrifugation at 14,000×g for 10 minutes and quantified using the BCA (bicinchoninic acid) microplate assay reagent (Thermo Scientific).

Phosphorylation of FGFR receptor in protein extracts was determined using immunoassays including western blotting, enzyme-linked immunoassay (ELISA) or bead-based immunoassays (Luminex). For detection of phosphorylated FGFR2, a commercial ELISA kit DuoSet IC Human Phospho-FGF R2α ELISA assay (R&D Systems, Minneapolis, Minn.) can be used. For the assay KATO111 cells are plated in 0.2% FBS supplemented Iscove's medium (50,000 cells/well/per 100 µL) into 96-well flat-bottom tissue culture treated plates (Corning, Corning, N.Y.), in the presence or absence of a concentration range of test compounds and incubated for 4 hours at 37° C., 5% $CO_2$. The assay is stopped with addition of 200 µL of cold PBS and centrifugation. The washed cells are lysed in Cell Lysis Buffer (Cell Signaling, #9803) with Protease Inhibitor (Calbiochem, #535140) and PMSF (Sigma, #P7626) for 30 min on wet ice. Cell lysates were frozen at −80° C. before testing an aliquot with the DuoSet IC Human Phospho-FGF R2α ELISA assay kit. GraphPad prism3 was used to analyze the data. The $IC_{50}$ values were derived by fitting the data to the equation for a sigmoidal dose-response with a variable slope.

For detection of phosphorylated FGFR3, a bead based immunoassay was developed. An anti-human FGFR3 mouse mAb (R&D Systems, cat#MAB7661) was conjugated to Luminex MAGplex microspheres, bead region 20 and used as the capture antibody. RT-112 cells were seeded into multi-well tissue culture plates and cultured until 70% confluence.

Cells were washed with PBS and starved in RPMI+0.5% FBS for 18 hr. The cells were treated with 10 μL of 10× concentrations of serially diluted compounds for 1 hr at 37° C., 5% $CO_2$ prior to stimulation with 10 ng/mL human FGF1 and 20 μg/mL Heparin for 10 min. Cells were washed with cold PBS and lysed with Cell Extraction Buffer (Invitrogen) and centrifuged. Clarified supernatants were frozen at −80° C. until analysis.

For the assay, cell lysates are diluted 1:10 in Assay Diluent and incubated with capture antibody-bound beads in a 96-well filter plate for 2 hours at room temperature on a plate shaker. Plates are washed three times using a vacuum manifold and incubated with anti-phospho-FGF R1-4 (Y653/Y654) rabbit polyclonal antibody (R&D Systems cat# AF3285) for 1 hour at RT with shaking Plates are washed three times. The diluted reporter antibody, goat anti-rabbit-RPE conjugated antibody (Invitrogen Cat. # LHB0002) is added and incubated for 30 minutes with shaking Plates are washed three times. The beads are suspended in wash buffer with shaking at room temperature for 5 minutes and then read on a Luminex 200 instrument set to count 50 events per sample, gate settings 7500-13500. Data is expressed as mean fluorescence intensity (MFI). MFI from compound treated samples are divided by MFI values from DMSO controls to determine the percent inhibition, and the $IC_{50}$ values are calculated using the GraphPad Prism software. Compounds having an $IC_{50}$ of 1 μM or less are considered active.

Example D

FGFR Cell-Based Signaling Assays

Activation of FGFR leads to phosphorylation of Erk proteins. Detection of pErk is monitored using the Cellu'Erk HTRF (Homogeneous Time Resolved Flurorescence) Assay (CisBio) according to the manufacturer's protocol. KMS-11 cells are seeded into 96-well plates at 40,000 cells/well in RPMI medium with 0.25% FBS and starved for 2 days. The medium is aspirated and cells are treated with 30 μL of 1× concentrations of serially diluted compounds (diluted with medium lacking serum from 5 mM DSMO dots) to a final volume of 30 μL/well and incubated for 45 min at room temperature. Cells are stimulated by addition of 10 μL of Heparin (100 μg/mL) and FGF1 (50 ng/mL) to each well and incubated for 10 min at room temperature. After lysis, an aliquot of cell extract is transferred into 384-well low volume plates, and 4 μL of detection reagents are added followed by incubation for 3 hr at room temperature. The plates are read on a PheraStar instrument with settings for HTRF. The normalized fluorescence readings are converted to percent inhibition relative to DMSO treated control wells, and the $IC_{50}$ values are calculated using the GraphPad Prism software. Compounds having an $IC_{50}$ of 1 μM or less are considered active.

Example E

VEGFR2 Kinase Assay

40 μL Enzyme reactions are run in black 384 well polystyrene plates for 1 hour at 25° C. Wells are dotted with 0.8 μL of test compound in DMSO. The assay buffer contains 50 mM Tris, pH~7.5, 0.01% Tween-20, 10 mM $MgCl_2$, 1 mM EGTA, 5 mM DTT, 0.5 μM Biotin-labeled EQEDEPEGDYFEWLE peptide substrate (SEQ ID NO: 1), 1 mM ATP, and 0.1 nM enzyme (Millipore catalogue number 14-630). Reactions are stopped by addition of 20 μL Stop Buffer (50 mM Tris, pH=7.8, 150 mM NaCl, 0.5 mg/mL BSA, 45 mM EDTA) with 225 nM LANCE Streptavidin Surelight® APC (PerkinElmer catalogue number CR130-100) and 4.5 nM LANCE Eu-W1024 anti phosphotyrosine (PY20) antibody (PerkinElmer catalogue number AD0067). After 20 minutes of incubation at room temperature, the plates are read on a PheraStar FS plate reader (BMG Labtech). $IC_{50}$ values can be calculated using GraphPad Prism. Compounds having an $IC_{50}$ of 1 μM or less are considered active.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:
1. A compound of Formula I:

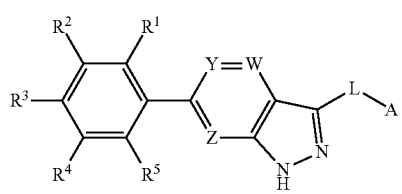

or a pharmaceutically acceptable salt thereof, wherein:
W is N or $CR^6$;
Y is N or $CR^7$;
Z is N or $CR^8$;
wherein one or two of W, Y, and Z is N;

L is absent or selected from $C_{2-6}$ alkenylene, $C_{3-6}$ heteroalkenylene, $C_{2-6}$ alkynylene, and $C_{3-6}$ heteroalkynylene, wherein said $C_{2-6}$ alkenylene, $C_{3-6}$ heteroalkenylene, $C_{2-6}$ alkynylene, and $C_{3-6}$ heteroalkynylene are each optionally substituted with 1, 2, or 3 substituents independently selected from halo, CN, $NO_2$, $OR^B$, $C_{1-4}$ alkyl, $C_{1-4}$ haloalkyl, $C_{1-4}$ cyanoalkyl, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

A is selected from Formulas [aa], [bb], and [cc]:

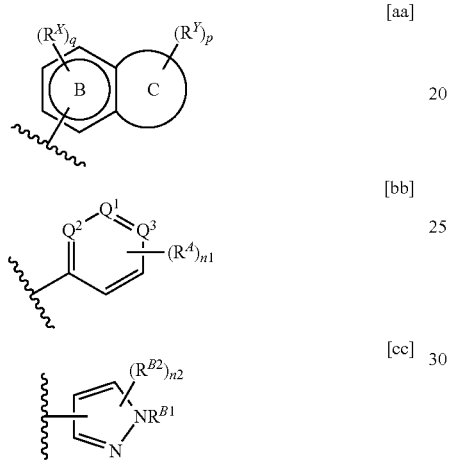

rings B and C in Formula [aa] together form a fused bicyclic heterocycle, wherein ring B is a six-membered aromatic ring selected from phenyl, pyridyl, pyrimidinyl, pyrazinyl, pyridazinyl, and triazinyl, wherein ring C is a 5- or 6-membered carbocycle or a 5- or 6-membered heterocycle, wherein 0, 1, or 2 ring-forming carbon or nitrogen atoms in ring C can be substituted by oxo, and wherein the fused bicyclic heterocycle comprising rings B and C is attached to L in Formula I via a ring atom in ring B;

$Q^1$, $Q^2$, and $Q^3$ are each independently selected from N and CH, wherein at least one of $Q^1$, $Q^2$, and $Q^3$ is CH;

each $R^X$ is a substituent on ring B and is independently selected from halo, $C_{1-4}$ alkyl, $C_{1-4}$ haloalkyl, and $C_{1-4}$ cyanoalkyl;

each $R^Y$ is a substituent on ring C and is independently selected from $C_{1-6}$ alkyl, $C_{1-6}$ haloalkyl, $Cy^1$, $OR^{a1}$, $C(O)R^{b1}$, $C(O)NR^{c1}R^{d1}$, $C(O)OR^{a1}$, $C(=NR^{e1})R^{b1}$, $C(=NR^{e1})NR^{c1}R^{d1}$, $S(O)R^{b1}$, $S(O)NR^{c1}R^{d1}$, $S(O)_2R^{b1}$, and $S(O)_2NR^{c1}R^{d1}$, wherein said $C_{1-6}$ alkyl, is optionally substituted with 1, 2, 3, 4, or 5 substituents independently selected from $R^{Ya}$;

each $R^{Ya}$ is independently selected from $Cy^1$, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl of $R^{Ya}$ are each optionally substituted with 1, 2, or 3 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{di}$;

each $R^A$ is independently selected from halo, $C_{1-6}$ alkyl, $C_{2-6}$ alkenyl, $C_{2-6}$ alkynyl, $Cy^2$, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{2-6}$ alkenyl, and $C_{2-6}$ alkynyl are each optionally substituted with 1, 2, 3, 4, or 5 substituents independently selected from $R^{AZ}$;

each $R^{AZ}$ is independently selected from $Cy^2$, halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$, wherein said $C_{1-6}$ alkyl, $C_{2-6}$ alkenyl, and $C_{2-6}$ alkynyl of $R^{AZ}$ are each optionally substituted with 1, 2, or 3 substituents independently selected from $Cy^2$, halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

$R^{B1}$ is H, $C_{1-6}$ alkyl, $Cy^3$, $C(O)R^{b3}$, $C(O)NR^{c3}R^{d3}$, $C(O)OR^{a3}$, $C(=NR^{e3})R^{b3}$, or $C(=NR^{e3})NR^{c3}R^{d3}$; wherein said $C_{1-6}$ alkyl, is optionally substituted with 1, 2, 3, 4, or 5 substituents independently selected from $R^{BZ}$;

each $R^{BZ}$ is independently selected from $Cy^3$, halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$, wherein said $C_{1-6}$ alkyl, $C_{2-6}$ alkenyl, and $C_{2-6}$ alkynyl of $R^{BZ}$ are each optionally substituted with 1, 2, or 3 substituents independently selected from $Cy^3$, halo, CN, $NO_2$, $OR^{a3}$, $SR^{a2}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

each $R^{B2}$ is independently selected from halo, $C_{1-6}$ alkyl, $C_{2-6}$ alkenyl, $C_{2-6}$ alkynyl, $Cy^3$, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, and $C_{2-6}$ alkynyl are each optionally substituted with 1, 2, 3, 4, or 5 substituents independently selected from $R^{BZ}$;

$R^1$, $R^2$, $R^4$, and $R^5$ are each independently selected from halo, $C_{1-4}$ alkyl, $C_{1-4}$ haloalkyl, CN, $OR^{a4}$, $SR^{a4}$, $C(O)NR^{c4}R^{d4}$, $N^{c4}R^{d4}$, $NR^{c4}C(O)R^{b4}$, $NR^{c4}S(O)R^{b4}$, $NR^{c4}S(O)_2R^{b4}$, $S(O)R^{b4}$, $S(O)N^{c4}R^{d4}$, $S(O)_2R^{b4}$, and $S(O)_2N^{c4}R^{d4}$; wherein said $C_{1-4}$ alkyl is optionally substituted with 1, 2, or 3 substituents independently selected from halo, CN, $OR^{a4}$, $SR^{a4}$, $C(O)NR^{c4}R^{d4}$, $N^{c4}R^{d4}$, $NR^{c4}C(O)R^{b4}$, $NR^{c4}S(O)R^{b4}$, $NR^{c4}S(O)_2R^{b4}$, $S(O)R^{b4}$, $S(O)N^{c4}R^{d4}$, $S(O)_2R^{b4}$, and $S(O)_2NR^{c4}R^{d4}$;

$R^3$ is H, halo, $C_{1-4}$ alkyl, $C_{1-4}$ haloalkyl, CN, $OR^{a4}$, $SR^{a4}$, $C(O)N^{c4}R^{d4}$, $N^{c4}R^{d4}$, $NR^{c4}C(O)R^{b4}$, $NR^{c4}S(O)R^{b4}$, $NR^{c4}S(O)_2R^{b4}$, $S(O)R^{b4}$, $S(O)NR^{c4}R^{d4}$, $S(O)_2R^{b4}$, and $S(O)_2N^{c4}R^{d4}$; wherein said $C_{1-4}$ alkyl is optionally substituted with 1, 2, or 3 substituents independently selected from halo, CN, $OR^{a4}$, $SR^{a4}$, $C(O)N^{c4}R^{d4}$, $N^{c4}R^{d4}$, $NR^{c4}C(O)R^{b4}$, $NR^{c4}S(O)R^{b4}$, $NR^{c4}S(O)_2R^{b4}$, $S(O)R^{b4}$, $S(O)N^{c4}R^{d4}$, $S(O)_2R^{b4}$, and $S(O)_2NR^{c4}R^{d4}$;

$R^6$, $R^7$, and $R^8$ are each independently selected from H, halo, $C_{1-4}$ alkyl, $C_{1-4}$ haloalkyl, and $C_{1-4}$ cyanoalkyl;

$Cy^1$, $Cy^2$, and $Cy^3$ are each independently selected from $C_{6-10}$ aryl, $C_{3-10}$ cycloalkyl, 5-10 membered heteroaryl, 4-10 membered heterocycloalkyl, each of which is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$, wherein said $C_{1-6}$ alkyl, $C_{2-6}$ alkenyl, $C_{2-6}$ alkynyl, $C_{3-10}$ cycloalkyl, 5-10 membered heteroaryl, and 4-10 membered heterocycloalkyl are each optionally substituted with 1, 2, or 3 substituents independently selected from halo, $C_{1-4}$ haloalkyl, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $c(=NR^{e5})NR^{c5}R^{d5}$, $NR^{c5}C(=NR^{e5})NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$;

each $R^a$, $R^b$, $R^c$, $R^d$, $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, $R^{d3}$, $R^{a5}$, $R^{b5}$, $R^{c5}$, and $R^{d5}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, or (4-10 membered heterocycloalkyl)-$C_{1-4}$ alkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl is optionally substituted with 1, 2, 3, 4, or 5 substituents independently selected from $C_{1-4}$ alkyl, $C_{1-4}$ haloalkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})N^{e6}R^{d6}$, $NR^{c6}C(=NR^{e6})NR^{c6}R^{d6}$, $S(O)R^{b6}$, $S(O)N^{e6}R^{d6}$, $S(O)_2R^{b6}$, $NR^{c6}S(O)_2R^{b6}$, $NR^{c6}S(O)_2N^{e6}R^{d6}$, and $S(O)_2NR^{c6}R^{d6}$;

each $R^{a4}$, $R^{b4}$, $R^{c4}$, and $R^{d4}$ is independently selected from H, $C_{1-4}$ alkyl, $C_{1-4}$ haloalkyl, $C_{1-4}$ hydroxyalkyl, and $C_{1-4}$ cyanoalkyl;

or any $R^c$ and $R^d$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, $C_{1-4}$ alkyl, $C_{1-4}$ haloalkyl, $C_{1-4}$ cyanoalkyl, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

or any $R^{c1}$ and $R^{d1}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 3-7 membered heterocycloalkyl, $C_{6-10}$ aryl, 5-6 membered heteroaryl, $C_{1-6}$ haloalkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, $C_{1-4}$ alkyl, $C_{1-4}$ haloalkyl, $C_{1-4}$ cyanoalkyl, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$ $NR^{c6}S(O)_2R^{b6}$, $NR^{c6}S(O)_2NR^{c6}R^{d6}$, and $S(O)_2NR^{c6}R^{d6}$;

or any $R^{c2}$ and $R^{d2}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, and 5-6 membered heteroaryl, $C_{1-6}$ haloalkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $NR^{c6}R^{d6}$, $S(O)R^{b6}$, $S(O)NR^{c6}R^{d6}$, $S(O)_2R^{b6}$, $NR^{c6}S (O)$_2$R$^{b6}$, NR$^{c6}$S(O)$_2$NR$^{c6}$R$^{d6}$, and S(O)$_2$NR$^{c6}$R$^{d6}$, wherein said C$_{1-6}$ alkyl, C$_{3-7}$ cycloalkyl, 4-7 membered heterocycloalkyl, C$_{6-10}$ aryl, and 5-6 membered heteroaryl are optionally substituted by 1, 2, or 3 substituents independently selected from halo, C$_{1-4}$ alkyl, C$_{1-4}$ haloalkyl, C$_{1-4}$ cyanoalkyl, CN, OR$^{a6}$, SR$^{a6}$, C(O)R$^{b6}$, C(O)NR$^{c6}$R$^{d6}$, C(O)OR$^{a6}$, OC(O)R$^{b6}$, OC(O)NR$^{c6}$R$^{d6}$, NR$^{c6}$R$^{d6}$, NR$^{c6}$C(O)R$^{b6}$, NR$^{c6}$C(O)NR$^{c6}$R$^{d6}$, NR$^{c6}$C(O)OR$^{a6}$, C(=NR$^{e6}$)NR$^{c6}$R$^{d6}$, NR$^{c6}$C(=NR$^{e6}$)NR$^{c6}$R$^{d6}$, S(O)R$^{b6}$, S(O)NR$^{c6}$R$^{d6}$, S(O)$_2$R$^{b6}$, NR$^{c6}$S(O)$_2$R$^{b6}$, NR$^{c6}$S(O)$_2$NR$^{c6}$R$^{d6}$, and S(O)$_2$NR$^{c6}$R$^{d6}$;

or any R$^{c3}$ and R$^{d3}$ together with the N atom to which they are attached form a 4-, 5-, 6-, or 7-membered heterocycloalkyl group optionally substituted with 1, 2, or 3 substituents independently selected from C$_{1-6}$ alkyl, C$_{3-7}$ cycloalkyl, 4-7 membered heterocycloalkyl, C$_{6-10}$ aryl, 5-6 membered heteroaryl, C$_{1-6}$ haloalkyl, halo, CN, OR$^{a6}$, SR$^{a6}$, C(O)R$^{b6}$, C(O)NR$^{c6}$R$^{d6}$, C(O)OR$^{a6}$, OC(O)R$^{b6}$, OC(O)NR$^{c6}$R$^{d6}$, NR$^{c6}$R$^{d6}$, NR$^{c6}$C(O)R$^{b6}$, NR$^{c6}$C(O)NR$^{c6}$R$^{d6}$, NR$^{c6}$C(O)OR$^{a6}$, C(=NR$^{e6}$)NR$^{c6}$R$^{d6}$, NR$^{c6}$C(=NR$^{e6}$)NR$^{c6}$R$^{d6}$, S(O)R$^{b6}$, S(O)NR$^{c6}$R$^{d6}$, S(O)$_2$R$^{b6}$, NR$^{c6}$S(O)$_2$R$^{b6}$, NR$^{c6}$S(O)$_2$NR$^{c6}$R$^{d6}$, and S(O)$_2$NR$^{c6}$R$^{d6}$, wherein said C$_{1-6}$ alkyl, C$_{3-7}$ cycloalkyl, 4-7 membered heterocycloalkyl, C$_{6-10}$ aryl, and 5-6 membered heteroaryl are optionally substituted by 1, 2, or 3 substituents independently selected from halo, C$_{1-4}$ alkyl, C$_{1-4}$ haloalkyl, C$_{1-4}$ cyanoalkyl, CN, OR$^{a6}$, SR$^{a6}$, C(O)R$^{b6}$, C(O)NR$^{c6}$R$^{d6}$, C(O) OR$^{a6}$, OC(O)R$^{b6}$, OC(O)NR$^{c6}$R$^{d6}$, NR$^{c6}$R$^{d6}$, NR$^{c6}$C(O)R$^{b6}$, NR$^{c6}$C(O)NR$^{c6}$R$^{d6}$, NR$^{c6}$C(O)OR$^{a6}$, C(=NR$^{e6}$)NR$^{c6}$R$^{d6}$, NR$^{c6}$C(=NR$^{e6}$)NR$^{c6}$R$^{d6}$, S(O)R$^{b6}$, S(O)NR$^{c6}$R$^{d6}$, S(O)$_2$R$^{b6}$ NR$^{c6}$S(O)$_2$R$^{b6}$, NR$^{c6}$S(O)$_2$NR$^{c6}$R$^{d6}$, and S(O)$_2$NR$^{c6}$R$^{d6}$;

or any R$^{c5}$ and R$^{d5}$ together with the N atom to which they are attached form a 4-, 5-, 6-, or 7-membered heterocycloalkyl group optionally substituted with 1, 2, or 3 substituents independently selected from C$_{1-6}$ alkyl, C$_{3-7}$ cycloalkyl, 4-7 membered heterocycloalkyl, C$_{6-10}$ aryl, 5-6 membered heteroaryl, C$_{1-6}$ haloalkyl, halo, CN, OR', SR$^{a6}$, C(O)R$^{b6}$, C(O)NR$^{c6}$R$^{d6}$, C(O)OR$^{a6}$, OC(O)R$^{b6}$, OC(O)NR$^{c6}$R$^{d6}$, NR$^{c6}$R$^{d6}$, NR$^{c6}$C(O)R$^{b6}$, NR$^{c6}$C(O)NR$^{c6}$R$^{d6}$, NR$^{c6}$C(O)OR$^{a6}$, C(=NR$^{e6}$)NR$^{c6}$R$^{d6}$, NR$^{c6}$C(=NR$^{e6}$)NR$^{c6}$R$^{d6}$, S(O)R$^{b6}$, S(O)NR$^{c6}$R$^{d6}$, S(O)$_2$R$^{b6}$, NR$^{c6}$S(O)$_2$R$^{b6}$, NR$^{c6}$S(O)$_2$NR$^{c6}$R$^{d6}$, and S(O)$_2$NR$^{c6}$R$^{d6}$, wherein said C$_{1-6}$ alkyl, C$_{3-7}$ cycloalkyl, 4-7 membered heterocycloalkyl, C$_{6-10}$ aryl, and 5-6 membered heteroaryl are optionally substituted by 1, 2, or 3 substituents independently selected from halo, C$_{1-4}$ alkyl, C$_{1-4}$ haloalkyl, C$_{1-4}$ cyanoalkyl, CN, OR$^{a6}$, SR$^{a6}$, C(O)R$^{b6}$, C(O)NR$^{c6}$R$^{d6}$, C(O)OR$^{a6}$, OC(O)R$^{b6}$, OC(O)NR$^{c6}$R$^{d6}$, NR$^{c6}$R$^{d6}$, NR$^{c6}$C(O)R$^{b6}$, NR$^{c6}$C(O)NR$^{c6}$R$^{d6}$, NR$^{c6}$C(O)OR$^{a6}$, C(=NR$^{e6}$)NR$^{c6}$R$^{d6}$, NR$^{c6}$C(=NR$^{e6}$)NR$^{c6}$R$^{d6}$, S(O)R$^{b6}$, S(O)NR$^{c6}$R$^{d6}$, S(O)$_2$R$^{b6}$, NR$^{c6}$S(O)$_2$R$^{b6}$, NR$^{c6}$S(O)$_2$NR$^{c6}$R$^{d6}$, and S(O)$_2$NR$^{c6}$R$^{d6}$;

each R$^{a6}$, R$^{b6}$, R$^{c6}$, and R$^{d6}$ is independently selected from H, C$_{1-4}$ alkyl, C$_{1-4}$ haloalkyl, C$_{2-4}$ alkenyl, and C$_{2-4}$ alkynyl, wherein said C$_{1-4}$ alkyl, C$_{2-4}$ alkenyl, and C$_{2-4}$ alkynyl, is optionally substituted with 1, 2, or 3 substituents independently selected from OH, CN, amino, halo, C$_{1-4}$ alkyl, C$_{1-4}$ alkoxy, C$_{1-4}$ alkylthio, C$_{1-4}$ alkylamino, di(C$_{1-4}$ alkyl)amino, C$_{1-4}$ haloalkyl, and C$_{1-4}$ haloalkoxy;

or any R$^{c6}$ and R$^{d6}$ together with the N atom to which they are attached form a 3-, 4-, 5-, 6-, or 7-membered heterocycloalkyl group optionally substituted with 1, 2, or 3 substituents independently selected from OH, CN, amino, halo, C$_{1-6}$ alkyl, C$_{1-4}$ alkoxy, C$_{1-4}$ alkylthio, C$_{1-4}$ alkylamino, di(C$_{1-4}$ alkyl)amino, C$_{1-4}$ haloalkyl, and C$_{1-4}$ haloalkoxy; and each R$^e$, R$^{e1}$, R$^{e2}$, R$^{e3}$, R$^{e5}$, and R$^{e6}$ is independently selected from H, C$_{1-4}$ alkyl, and CN;

n1 is 0, 1, 2, 3, 4, or 5;

n2 is 0, 1, or 2;

p is 0, 1, 2, or 3; and q is 0, 1, 2, or 3.

2. The compound of claim 1, or a pharmaceutically acceptable salt thereof, wherein:

W is CR$^6$;

Y is N; and

Z is N.

3. The compound of claim 1, or a pharmaceutically acceptable salt thereof, wherein:

W is CR$^6$;

Y is N; and

Z is CR$^8$.

4. The compound of claim 1, or a pharmaceutically acceptable salt thereof, wherein:

W is CR$^6$;

Y is CR$^7$; and

Z is N.

5. The compound of claim 1, or a pharmaceutically acceptable salt thereof, wherein:

W is N;

Y is CR$^7$; and

Z is CR$^8$.

6. The compound of claim 1, or a pharmaceutically acceptable salt thereof, wherein L is absent.

7. The compound of claim 1, or a pharmaceutically acceptable salt thereof, wherein L is selected from C$_{2-6}$ alkenylene, C$_{3-6}$ heteroalkenylene, C$_{2-6}$ alkynylene, and C$_{3-6}$ heteroalkynylene, wherein said C$_{2-6}$ alkenylene, C$_{3-6}$ heteroalkenylene, C$_{2-6}$ alkynylene, and C$_{3-6}$ heteroalkynylene are each optionally substituted with 1, 2, or 3 substituents independently selected from halo, CN, NO$_2$, ORB, C$_{1-4}$ alkyl, C$_{1-4}$ haloalkyl, C$_{1-4}$ cyanoalkyl, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$-C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$.

8. The compound of claim 1, or a pharmaceutically acceptable salt thereof, wherein L is selected from C$_{2-6}$ alkenylene and C$_{2-6}$ alkynylene, wherein said C$_{2-6}$ alkenylene and C$_{2-6}$ alkynylene are each optionally substituted with 1, 2, or 3 substituents independently selected from halo, CN, NO$_2$, ORB, C$_{1-4}$ alkyl, C$_{1-4}$ haloalkyl, C$_{1-4}$ cyanoalkyl, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$.

9. The compound of claim 1, or a pharmaceutically acceptable salt thereof, wherein L is selected from C$_{2-6}$ alkenylene and C$_{2-6}$ alkynylene.

10. The compound of claim 1, or a pharmaceutically acceptable salt thereof, wherein R$^3$ is H.

11. The compound of claim 1, or a pharmaceutically acceptable salt thereof, wherein R$^1$, R$^2$, R$^4$, and R$^5$ are each independently selected from halo, C$_{1-4}$ alkyl, C$_{1-4}$ halo alkyl, CN, and OR$^{a4}$.

12. The compound of claim 1, or a pharmaceutically acceptable salt thereof, wherein $R^1$, $R^2$, $R^4$, and $R^5$ are each independently selected from F, Cl, and methoxy.

13. The compound of claim 1, or a pharmaceutically acceptable salt thereof, wherein $R^1$ and $R^5$ are each independently selected from F and Cl, and $R^2$ and $R^4$ are each methoxy.

14. The compound of claim 1, or a pharmaceutically acceptable salt thereof, wherein $R^6$, $R^7$, and $R^8$ are each independently selected from H and halo.

15. The compound of claim 1, or a pharmaceutically acceptable salt thereof, wherein $R^6$, $R^7$, and $R^8$ are each H.

16. The compound of claim 1, or a pharmaceutically acceptable salt thereof, wherein A is a group represented by Formula [aa].

17. The compound of claim 16, or a pharmaceutically acceptable salt thereof, wherein Ring B is phenyl or pyridyl.

18. The compound of claim 16, or a pharmaceutically acceptable salt thereof, wherein Ring C is a 5-membered carbocycle or a 5-membered heterocycle.

19. The compound of claim 16, or a pharmaceutically acceptable salt thereof, wherein Ring C is a 6-membered carbocycle or a 6-membered heterocycle.

20. The compound of claim 16, or a pharmaceutically acceptable salt thereof, wherein Formula [aa] is a structure selected from:

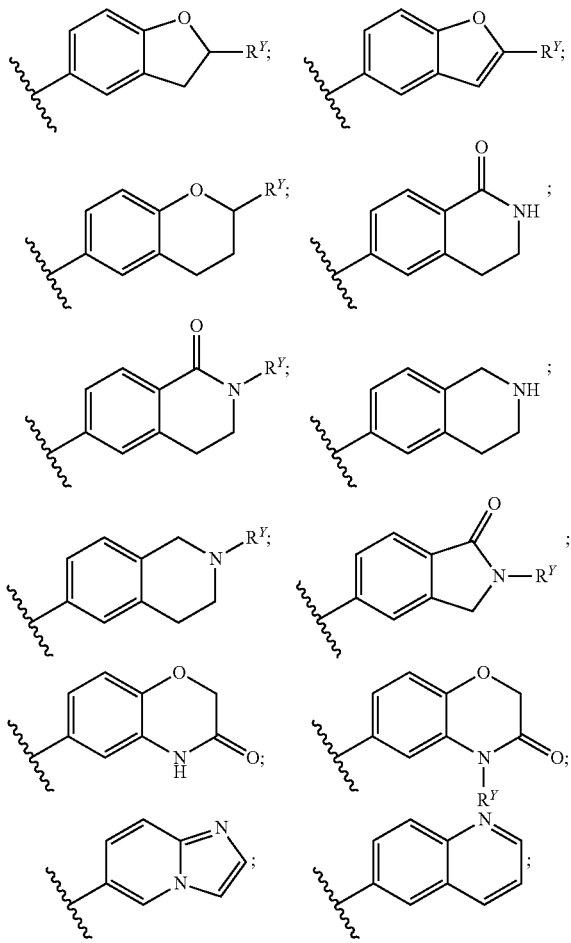

-continued

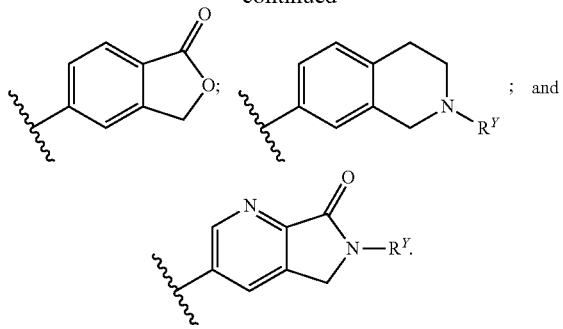

21. The compound of claim 16, or a pharmaceutically acceptable salt thereof, wherein each $R^Y$ is independently selected from $C_{1-6}$ alkyl, $Cy^1$, $C(O)NR^{c1}R^{d1}C(O)OR^{a1}$, and $S(O)_2R^{b1}$, wherein said $C_{1-6}$ alkyl is optionally substituted with halo, $OR^{a1}$, $NR^{c1}R^{d1}$, $Cy^1$.

22. The compound of claim 1, or a pharmaceutically acceptable salt thereof, wherein A is a group represented by Formula [bb].

23. The compound of claim 22, or a pharmaceutically acceptable salt thereof, wherein $Q^1$, $Q^2$, and $Q^3$ are each CH.

24. The compound of claim 22, or a pharmaceutically acceptable salt thereof, wherein $Q^1$ is N and $Q^2$, and $Q^3$ are each CH.

25. The compound of claim 22, or a pharmaceutically acceptable salt thereof, wherein $Q^1$ and $Q^2$ are both CH and $Q^3$ is N.

26. The compound of claim 22, or a pharmaceutically acceptable salt thereof, wherein each $R^A$ is independently selected from halo, $C_{1-6}$ alkyl, $Cy^2$, and $OR^{a2}$; wherein said $C_{1-6}$ alkyl is optionally substituted with 1, 2, or 3 substituents independently selected from $R^{AZ}$.

27. The compound of claim 22, or a pharmaceutically acceptable salt thereof, wherein n1 is 0, 1, or 2.

28. The compound of claim 1, or a pharmaceutically acceptable salt thereof, wherein A is a group represented by Formula [cc].

29. The compound of claim 28, or a pharmaceutically acceptable salt thereof, wherein A is a group represented by Formula [cc1]:

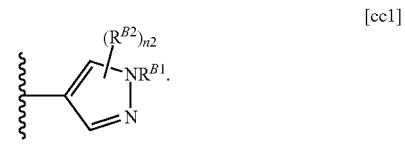

[cc1]

30. The compound of claim 28, or a pharmaceutically acceptable salt thereof, wherein $R^{B1}$ is $C_{1-6}$ alkyl optionally substituted with 1 or 2 substituents independently selected from $R^{BZ}$.

31. The compound of claim 28, or a pharmaceutically acceptable salt thereof, wherein each $R^{BZ}$ is independently selected from CN, $OR^{a3}$, and $C(O)NR^{c3}R^{d3}$.

32. The compound of claim 28, or a pharmaceutically acceptable salt thereof, wherein n2 is 0.

33. The compound of claim 1, or a pharmaceutically acceptable salt thereof, having Formula IIa, IIb, IIc, or IId:

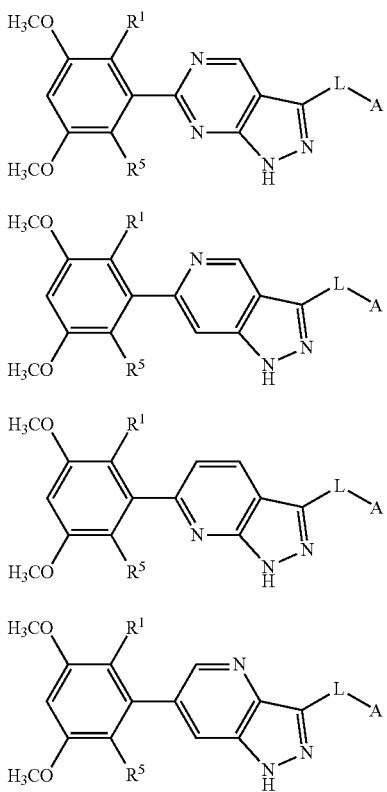

wherein R¹ and R⁵ are independently selected from F and Cl.

34. The compound of claim 1, or a pharmaceutically acceptable salt thereof, selected from:
- 5-[6-(2,6-Dichloro-3,5-dimethoxyphenyl)-1H-pyrazolo[3,4-d]pyrimidin-3-yl]-N,N-dimethyl-2,3-dihydro-1-benzofuran-2-carboxamide;
- 6-[6-(2,6-Dichloro-3,5-dimethoxyphenyl)-1H-pyrazolo[3,4-d]pyrimidin-3-yl]-N,N-dimethylchromane-2-carboxamide;
- 5-[6-(2,6-Difluoro-3,5-dimethoxyphenyl)-1H-pyrazolo[3,4-d]pyrimidin-3-yl]-N,N-dimethyl-2,3-dihydro-1-benzofuran-2-carboxamide;
- 5-[6-(2,6-Difluoro-3,5-dimethoxyphenyl)-1H-pyrazolo[3,4-d]pyrimidin-3-yl]-N,N-dimethyl-2,3-dihydro-1-benzofuran-2-carboxamide;
- 6-[6-(2,6-Difluoro-3,5-dimethoxyphenyl)-1H-pyrazolo[3,4-d]pyrimidin-3-yl]-N,N-dimethylchromane-2-carboxamide;
- 6-(2,6-Difluoro-3,5-dimethoxyphenyl)-3-{2-[(4-methylpiperazin-1-yl)carbonyl]-2,3-dihydro-1-benzofuran-5-yl}-1H-pyrazolo[3,4-d]pyrimidine;
- 6-[6-(2,6-Dichloro-3,5-dimethoxyphenyl)-1H-pyrazolo[3,4-d]pyrimidin-3-yl]-3,4-dihydroisoquinolin-1(2H)-one;
- 6-[6-(2,6-Dichloro-3,5-dimethoxyphenyl)-1H-pyrazolo[3,4-d]pyrimidin-3-yl]-2-methyl-3,4-dihydroisoquinolin-1(2H)-one;
- 6-[6-(2,6-Dichloro-3,5-dimethoxyphenyl)-1H-pyrazolo[3,4-d]pyrimidin-3-yl]-2-ethyl-3,4-dihydroisoquinolin-1(2H)-one;
- 6-[6-(2,6-Dichloro-3,5-dimethoxyphenyl)-1H-pyrazolo[3,4-d]pyrimidin-3-yl]-2-isopropyl-3,4-dihydroisoquinolin-1(2H)-one;
- 6-[6-(2,6-Difluoro-3,5-dimethoxyphenyl)-1H-pyrazolo[3,4-d]pyrimidin-3-yl]-3,4-dihydroisoquinolin-1(2H)-one;
- 6-[6-(2,6-Difluoro-3,5-dimethoxyphenyl)-1H-pyrazolo[3,4-d]pyrimidin-3-yl]-2-(methylsulfonyl)-1,2,3,4-tetrahydroisoquinoline;
- 6-(2,6-Difluoro-3,5-dimethoxyphenyl)-3-[(4-methoxyphenyl)ethynyl]-1H-pyrazolo[3,4-d]pyrimidine;
- 5-[6-(2,6-Difluoro-3,5-dimethoxyphenyl)-1H-pyrazolo[3,4-d]pyrimidin-3-yl]-2-(trans-4-hydroxycyclohexyl)isoindolin-1-one;
- 5-[6-(2,6-Difluoro-3,5-dimethoxyphenyl)-1H-pyrazolo[3,4-d]pyrimidin-3-yl]-2-(cis-4-hydroxycyclohexyl)isoindolin-1-one;
- 6-(2,6-Difluoro-3,5-dimethoxyphenyl)-3-[4-(4-methylpiperazin-1-yl)phenyl]-1H-pyrazolo[3,4-d]pyrimidine;
- 6-(2,6-Difluoro-3,5-dimethoxyphenyl)-3-[6-(4-methylpiperazin-1-yl)pyridin-3-yl]-1H-pyrazolo[3,4-d]pyrimidine;
- 6-(2,6-Difluoro-3,5-dimethoxyphenyl)-3-[2-(4-methylpiperazin-1-yl)pyridin-4-yl]-1H-pyrazolo[3,4-d]pyrimidine;
- 2-{4-[6-(2,6-Difluoro-3,5-dimethoxyphenyl)-1H-pyrazolo[3,4-d]pyrimidin-3-yl]phenoxy}-N,N-dimethylethanamine;
- 2-Cyclopropyl-5-[6-(2,6-difluoro-3,5-dimethoxyphenyl)-1H-pyrazolo[3,4-d]pyrimidin-3-yl]isoindolin-1-one;
- 5-[6-(2,6-Dichloro-3,5-dimethoxyphenyl)-1H-pyrazolo[3,4-d]pyrimidin-3-yl]-2-(cis-4-hydroxycyclohexyl)isoindolin-1-one;
- 5-[6-(2,6-Dichloro-3,5-dimethoxyphenyl)-1H-pyrazolo[3,4-d]pyrimidin-3-yl]-2-(trans-4-hydroxycyclohexyl)isoindolin-1-one;
- 6-(2,6-Difluoro-3,5-dimethoxyphenyl)-3-{2-[(4-methylpiperazin-1-yl)carbonyl]-2,3-dihydro-1-benzofuran-5-yl}-1H-pyrazolo[4,3-c]pyridine;
- 6-(2,6-Difluoro-3,5-dimethoxyphenyl)-3-[4-(4-methylpiperazin-1-yl)phenyl]-1H-pyrazolo[4,3-c]pyridine;
- 6-(2,6-Difluoro-3,5-dimethoxyphenyl)-3-[6-(4-methylpiperazin-1-yl)pyridin-3-yl]-1H-pyrazolo[4,3-c]pyridine;
- 6-(2,6-Difluoro-3,5-dimethoxyphenyl)-3-[2-(4-methylpiperazin-1-yl)pyridin-4-yl]-1H-pyrazolo[4,3-c]pyridine;
- 2-Cyclopropyl-5-[6-(2,6-dichloro-3,5-dimethoxyphenyl)-1H-pyrazolo[4,3-c]pyridin-3-yl]isoindolin-1-one;
- 2-{4-[6-(2,6-Dichloro-3,5-dimethoxyphenyl)-1H-pyrazolo[4,3-c]pyridin-3-yl]-2-methylphenoxy}-N,N-dimethylacetamide;
- 6-[6-(2,6-Dichloro-3,5-dimethoxyphenyl)-1H-pyrazolo[4,3-c]pyridin-3-yl]-2H-1,4-benzoxazin-3(4H)-one;
- 6-[6-(2,6-Dichloro-3,5-dimethoxyphenyl)-1H-pyrazolo[4,3-c]pyridin-3-yl]-4-methyl-2H-1,4-benzoxazin-3(4H)-one;
- 5-[6-(2,6-Dichloro-3,5-dimethoxyphenyl)-1H-pyrazolo[4,3-c]pyridin-3-yl]-2-benzofuran-1(3H)-one;
- 2-{4-[6-(2,6-Dichloro-3,5-dimethoxyphenyl)-1H-pyrazolo[4,3-c]pyridin-3-yl]-1H-pyrazol-1-yl}propanenitrile;
- 2-{4-[6-(2,6-Dichloro-3,5-dimethoxyphenyl)-1H-pyrazolo[4,3-c]pyridin-3-yl]-2-fluorophenyl}-2-hydroxy-N,N-dimethylacetamide;
- 2-{4-[6-(2,6-Dichloro-3,5-dimethoxyphenyl)-1H-pyrazolo[4,3-c]pyridin-3-yl]phenoxy}-N,N-dimethylethanamine;

2-{4-[6-(2,6-Dichloro-3,5-dimethoxyphenyl)-1H-pyrazolo[4,3-c]pyridin-3-yl]-1H-pyrazol-1-yl}-N-methylacetamide;
2-{4-[6-(2,6-Dichloro-3,5-dimethoxyphenyl)-1H-pyrazolo[4,3-c]pyridin-3-yl]-1H-pyrazol-1-yl}-N,N-dimethylacetamide;
N-Cyclopropyl-2-{4-[6-(2,6-dichloro-3,5-dimethoxyphenyl)-1H-pyrazolo[4,3-c]pyridin-3-yl]-1H-pyrazol-1-yl}acetamide;
1-({4-[6-(2,6-Dichloro-3,5-dimethoxyphenyl)-1H-pyrazolo[4,3-c]pyridin-3-yl]-1H-pyrazol-1-yl}acetyl)azetidin-3-ol;
6-(2,6-Dichloro-3,5-dimethoxyphenyl)-3-[1-(2-morpholin-4-yl-2-oxoethyl)-1H-pyrazol-4-yl]-1H-pyrazolo[4,3-c]pyridine;
6-(2,6-Dichloro-3,5-dimethoxyphenyl)-3-{1-[2-(4-methylpiperazin-1-yl)-2-oxoethyl]-1H-pyrazol-4-yl}-1H-pyrazolo[4,3-c]pyridine;
2-{4-[6-(2,6-Dichloro-3,5-dimethoxyphenyl)-1H-pyrazolo[4,3-c]pyridin-3-yl]-1H-pyrazol-1-yl}-N-(1-methylpiperidin-4-yl)acetamide;
1-({4-[6-(2,6-Dichloro-3,5-dimethoxyphenyl)-1H-pyrazolo[4,3-c]pyridin-3-yl]-1H-pyrazol-1-yl}acetyl)pyrrolidin-3-ol;
1-({4-[6-(2,6-Dichloro-3,5-dimethoxyphenyl)-1H-pyrazolo[4,3-c]pyridin-3-yl]-1H-pyrazol-1-yl}acetyl)-N,N-dimethylpyrrolidin-3-amine;
6-(2,6-Dichloro-3,5-dimethoxyphenyl)-3-{1-[2-(3-methoxypyrrolidin-1-yl)-2-oxoethyl]-1H-pyrazol-4-yl}-1H-pyrazolo[4,3-c]pyridine;
2-{4-[6-(2,6-Dichloro-3,5-dimethoxyphenyl)-1H-pyrazolo[4,3-c]pyridin-3-yl]-1H-pyrazol-1-yl}-N-(2-methoxyethyl)acetamide;
1-({4-[6-(2,6-Dichloro-3,5-dimethoxyphenyl)-1H-pyrazolo[4,3-c]pyridin-3-yl]-1H-pyrazol-1-yl}acetyl)pyrrolidine-3-carbonitrile;
6-(2,6-Dichloro-3,5-dimethoxyphenyl)-3-(1-{2-[(3S)-3-fluoropyrrolidin-1-yl]-2-oxoethyl}-1H-pyrazol-4-yl)-1H-pyrazolo[4,3-c]pyridine;
6-(2,6-Dichloro-3,5-dimethoxyphenyl)-3-[(E)-2-(1-methyl-1H-pyrazol-4-yl)vinyl]-1H-pyrazolo[4,3-c]pyridine;
2-(4-{(E)-2-[6-(2,6-Dichloro-3,5-dimethoxyphenyl)-1H-pyrazolo[4,3-c]pyridin-3-yl]vinyl}-1H-pyrazol-1-yl)ethanol;
(2S)-1-{4-[6-(2,6-Dichloro-3,5-dimethoxyphenyl)-1H-pyrazolo[4,3-c]pyridin-3-yl]-1H-pyrazol-1-yl}propan-2-ol;
5-[6-(2,6-Difluoro-3,5-dimethoxyphenyl)-1H-pyrazolo[4,3-c]pyridin-3-yl]-2-ethylisoindolin-1-one;
5-[6-(2,6-Difluoro-3,5-dimethoxyphenyl)-1H-pyrazolo[4,3-c]pyridin-3-yl]-2-isopropylisoindolin-1-one;
2-Cyclopropyl-5-[6-(2,6-difluoro-3,5-dimethoxyphenyl)-1H-pyrazolo[4,3-c]pyridin-3-yl]isoindolin-1-one;
3-[6-(2,6-Difluoro-3,5-dimethoxyphenyl)-1H-pyrazolo[4,3-c]pyridin-3-yl]-6-ethyl-5,6-dihydro-7H-pyrrolo[3,4-b]pyridin-7-one;
6-[6-(2,6-Difluoro-3,5-dimethoxyphenyl)-1H-pyrazolo[4,3-c]pyridin-3-yl]-3,4-dihydroisoquinolin-1(2H)-one;
6-[6-(2,6-Difluoro-3,5-dimethoxyphenyl)-1H-pyrazolo[4,3-c]pyridin-3-yl]-N,N-dimethylchromane-2-carboxamide;
5-[6-(2,6-Difluoro-3,5-dimethoxyphenyl)-1H-pyrazolo[4,3-c]pyridin-3-yl]-2-(2-methoxyethyl)isoindolin-1-one;
5-[6-(2,6-Difluoro-3,5-dimethoxyphenyl)-1H-pyrazolo[4,3-c]pyridin-3-yl]-2-(tetrahydro-2H-pyran-4-yl)isoindolin-1-one;
5-[6-(2,6-Difluoro-3,5-dimethoxyphenyl)-1H-pyrazolo[4,3-c]pyridin-3-yl]-2-(2,2,2-trifluoroethyl)isoindolin-1-one;
5-[6-(2,6-Difluoro-3,5-dimethoxyphenyl)-1H-pyrazolo[4,3-c]pyridin-3-yl]-2-(cis-4-hydroxycyclohexyl)isoindolin-1-one;
5-[6-(2,6-Difluoro-3,5-dimethoxyphenyl)-1H-pyrazolo[4,3-c]pyridin-3-yl]-2-(trans-4-hydroxycyclohexyl)isoindolin-1-one;
5-[6-(2,6-Difluoro-3,5-dimethoxyphenyl)-1H-pyrazolo[4,3-c]pyridin-3-yl]-2-(2-hydroxy-1-methylethyl)isoindolin-1-one;
5-[6-(2,6-Difluoro-3,5-dimethoxyphenyl)-1H-pyrazolo[4,3-c]pyridin-3-yl]-2-(2-hydroxypropyl)isoindolin-1-one;
5-[6-(2,6-Difluoro-3,5-dimethoxyphenyl)-1H-pyrazolo[4,3-c]pyridin-3-yl]-6-fluoro-2-isopropylisoindolin-1-one;
5-[6-(2,6-Difluoro-3,5-dimethoxyphenyl)-1H-pyrazolo[4,3-c]pyridin-3-yl]-2-(1-methylpiperidin-4-yl)isoindolin-1-one;
5-[6-(2,6-Difluoro-3,5-dimethoxyphenyl)-1H-pyrazolo[4,3-c]pyridin-3-yl]-2-[2-(dimethylamino)ethyl]isoindolin-1-one;
5-[6-(2,6-Difluoro-3,5-dimethoxyphenyl)-1H-pyrazolo[4,3-c]pyridin-3-yl]-2-[2-(1-methylpyrrolidin-2-yl)ethyl]isoindolin-1-one;
5-[6-(2-chloro-6-fluoro-3,5-dimethoxyphenyl)-1H-pyrazolo[4,3-c]pyridin-3-yl]-2-ethylisoindolin-1-one;
6-(2,6-dichloro-3,5-dimethoxyphenyl)-3-(1-methyl-1H-pyrazol-4-yl)-1H-pyrazolo[4,3-b]pyridine;
3-{4-[6-(2,6-Dichloro-3,5-dimethoxyphenyl)-1H-pyrazolo[4,3-b]pyridin-3-yl]-1H-pyrazol-1-yl}propan-1-ol;
6-(2,6-Difluoro-3,5-dimethoxyphenyl)-3-(1-methyl-1H-pyrazol-4-yl)-1H-pyrazolo[3,4-b]pyridine;
2-{4-[6-(2,6-Dichloro-3,5-dimethoxyphenyl)-1H-pyrazolo[3,4-d]pyrimidin-3-yl]-1H-pyrazol-1-yl}propanenitrile;
2-Cyclopropyl-5-[6-(2,6-dichloro-3,5-dimethoxyphenyl)-1H-pyrazolo[3,4-d]pyrimidin-3-yl]isoindolin-1-one;
6-(2,6-Dichloro-3,5-dimethoxyphenyl)-3-[4-(4-methylpiperazin-1-yl)phenyl]-1H-pyrazolo[3,4-d]pyrimidine;
2-{4-[6-(2,6-Difluoro-3,5-dimethoxyphenyl)-1H-pyrazolo[3,4-d]pyrimidin-3-yl]-1H-pyrazol-1-yl}propanenitrile;
3-[6-(2,6-Dichloro-3,5-dimethoxyphenyl)-1H-pyrazolo[3,4-d]pyrimidin-3-yl]-6-ethyl-5,6-dihydro-7H-pyrrolo[3,4-b]pyridin-7-one;
5-[6-(2,6-Difluoro-3,5-dimethoxyphenyl)-1H-pyrazolo[3,4-d]pyrimidin-3-yl]-2-isopropylisoindolin-1-one;
5-[6-(2,6-Difluoro-3,5-dimethoxyphenyl)-1H-pyrazolo[3,4-d]pyrimidin-3-yl]-2-(1-methylpiperidin-4-yl)isoindolin-1-one;
5-[6-(2,6-Difluoro-3,5-dimethoxyphenyl)-1H-pyrazolo[3,4-d]pyrimidin-3-yl]-2-[2-(dimethylamino)ethyl]isoindolin-1-one;
5-[6-(2,6-Difluoro-3,5-dimethoxyphenyl)-1H-pyrazolo[3,4-d]pyrimidin-3-yl]-2-(2-hydroxy-1-methylethyl)isoindolin-1-one;
5-[6-(2,6-Difluoro-3,5-dimethoxyphenyl)-1H-pyrazolo[3,4-d]pyrimidin-3-yl]-2-(2-hydroxypropyl)isoindolin-1-one;

5-[6-(2,6-Difluoro-3,5-dimethoxyphenyl)-1H-pyrazolo[4,3-c]pyridin-3-yl]-N,N-dimethyl-2,3-dihydro-1-benzofuran-2-carboxamide;
7-[6-(2,6-Difluoro-3,5-dimethoxyphenyl)-1H-pyrazolo[3,4-d]pyrimidin-3-yl]-2-(methylsulfonyl)-1,2,3,4-tetrahydroisoquinoline;
6-(2,6-Dichloro-3,5-dimethoxyphenyl)-3-(2,3-dihydro-1-benzofuran-5-yl)-1H-pyrazolo[3,4-d]pyrimidine;
6-(2,6-Difluoro-3,5-dimethoxyphenyl)-3-(1-methyl-1H-pyrazol-4-yl)-1H-pyrazolo[3,4-d]pyrimidine;
2-{4-[6-(2,6-Difluoro-3,5-dimethoxyphenyl)-1H-pyrazolo[4,3-c]pyridin-3-yl]-1H-pyrazol-1-yl}ethanol;
5-[6-(2-Chloro-6-fluoro-3,5-dimethoxyphenyl)-1H-pyrazolo[3,4-b]pyridin-3-yl]-2-cyclopropylisoindolin-1-one;
6-(2,6-Dichloro-3,5-dimethoxyphenyl)-3-(1-methyl-1H-pyrazol-4-yl)-1H-pyrazolo[4,3-c]pyridine;
6-(2,6-Difluoro-3,5-dimethoxyphenyl)-3-(1-methyl-1H-pyrazol-4-yl)-1H-pyrazolo[4,3-c]pyridine;
Methyl 5-[6-(2,6-difluoro-3,5-dimethoxyphenyl)-1H-pyrazolo[4,3-c]pyridin-3-yl]-1-benzofuran-2-carboxylate;
6-(2,6-Difluoro-3,5-dimethoxyphenyl)-3-imidazo[1,2-a]pyridin-6-yl-1H-pyrazolo[3,4-d]pyrimidine; and
6-[6-(2,6-Difluoro-3,5-dimethoxyphenyl)-1H-pyrazolo[3,4-d]pyrimidin-3-yl]quinolone.

35. A pharmaceutical composition comprising a compound of claim 1, or a pharmaceutically acceptable salt thereof, and at least one pharmaceutically acceptable carrier.

36. A method of inhibiting an FGFR enzyme comprising contacting the FGFR enzyme with a compound of claim 1, or a pharmaceutically acceptable salt thereof.

37. A method of treating cancer in a patient comprising administering to said patient a therapeutically effective amount of a compound of claim 1, or a pharmaceutically acceptable salt thereof.

38. The method of claim 37 wherein said cancer is selected from bladder cancer, breast cancer, cervical cancer, colorectal cancer, endometrial cancer, gastric cancer, head and neck cancer, kidney cancer, liver cancer, lung cancer, ovarian cancer, prostate cancer, esophageal cancer, gall bladder cancer, pancreatic cancer, thyroid cancer, skin cancer. leukemia, multiple myeloma, chronic lymphocytic lymphoma, adult T cell leukemia, B-cell lymphoma, acute myelogenous leukemia, Hodgkin's or non-Hodgkin's lymphoma, Waldenstrom's Macroglubulinemia, hairy cell lymphoma, Burkett's lymphoma, glioblastoma, melanoma, and rhabdosarcoma.

39. A method of treating a myeloproliferative disorder in a patient comprising administering to said patient a therapeutically effective amount of a compound of claim 1, or a pharmaceutically acceptable salt thereof.

40. The method of claim 39 wherein said myeloproliferative disorder is selected from polycythemia vera (PV), essential thrombocythemia (ET), and primary myelofibrosis (PMF).

* * * * *

UNITED STATES PATENT AND TRADEMARK OFFICE
CERTIFICATE OF CORRECTION

PATENT NO. : 9,266,892 B2  Page 1 of 1
APPLICATION NO. : 14/132653
DATED : February 23, 2016
INVENTOR(S) : Jincong Zhuo, Meizhong Xu and Ding-Quan Qian It is certified that error appears in the above-identified patent and that said Letters Patent is hereby corrected as shown below:

Claims

Col. 105, Line 7, in Claim 1, delete "ORB," and insert -- $OR^a$, --.

Col. 105, Line 64, in Claim 1, delete the second "$NR^{c1}S(O)R^{b1}$," and insert -- $NR^{c1}S(O)_2R^{b1}$, --.

Col. 106, Line 8, in Claim 1, delete "$S(O)_2NR^{c1}R^{di}$;" and insert -- $S(O)_2NR^{c1}R^{d1}$; --.

Col. 107, Line 20, in Claim 1, delete "$S(O)_2N^{c4}R^{d4}$;" and insert -- $S(O)_2NR^{c4}R^{d4}$; --.

Col. 107, Lines 22-23, in Claim 1, delete "$C(O)N^{c4}R^{d4}$," and insert -- $C(O)_2NR^{c4}R^{d4}$, --.

Col. 107, Line 23, in Claim 1, delete "$N^{c4}R^{d4}$," and insert -- $NR^{c4}R^{d4}$, --.

Col. 107, Line 24, in Claim 1, delete "$S(O)N^{c4}R^{d4}$," and insert -- $S(O)NR^{c4}R^{d4}$, --.

Col. 107, Line 48, in Claim 1, delete "$c(=NR^{e5})NR^{c5}R^{d5}$," and insert -- $C(=NR^{e5})NR^{c5}R^{d5}$, --.

Col. 108, Line 5, in Claim 1, delete "$C(=NR^{e6})N^{e6}R^{d6}$," and insert -- $C(=NR^{e6})NR^{c6}R^{d6}$, --.

Col. 108, Line 6, in Claim 1, delete "$S(O)N^{e6}R^{d6}$" and insert -- $S(O)NR^{c6}R^{d6}$ --.

Col. 109, Line 31, in Claim 1, delete "$C(O) OR^{a6}$," and insert -- $C(O)OR^{a6}$, --.

Col. 109, Line 43, in Claim 1, delete "OR'," and insert -- $OR^{a6}$, --.

Col. 112, Line 18, in Claim 21, delete "$C(O)NR^{c1}R^{d1}$" and insert -- $C(O)NR^{c1}R^{d1}$, --.

Col. 118, Line 13, in Claim 38, delete "cancer." and insert -- cancer, --.

Col. 118, Line 17, in Claim 38, delete "Macroglubulinemia," and insert -- Macroglobulinemia, --.

Col. 118, Line 18, in Claim 38, delete "rhabdosarcoma." and insert -- rhabdomyosarcoma. --.

Signed and Sealed this
Tenth Day of May, 2016

Michelle K. Lee
*Director of the United States Patent and Trademark Office*

```
SEQUENCE LISTING

<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: synthetic peptide

<400> SEQUENCE: 1

Glu Gln Glu Asp Glu Pro Glu Gly Asp Tyr Phe Glu Trp Leu Glu
 1               5                  10                  15
```